United States Patent
Lim et al.

(10) Patent No.: US 10,093,683 B2
(45) Date of Patent: Oct. 9, 2018

(54) FACTOR XIA INHIBITORS

(71) Applicant: Merck Sharp & Dohme Corp., Rahway, NJ (US)

(72) Inventors: Yeon-Hee Lim, Piscataway, NJ (US); Zhuyan Guo, Scotch Plains, NJ (US); Amjad Ali, Freehold, NJ (US); Scott D. Edmondson, Clark, NJ (US); Weiguo Liu, Princeton, NJ (US); Gioconda V. Gallo-Etienne, Union, NJ (US); Heping Wu, Edison, NJ (US); Ying-Duo Gao, Holmdel, NJ (US); Andrew W. Stamford, Chatham, NJ (US); Younong Yu, East Brunswick, NJ (US); Nancy J. Kevin, East Brunswick, NJ (US); Rajan Anand, Fanwood, NJ (US); Deyou Sha, Yardley, PA (US); Santhosh F. Neelamkavil, Edison, NJ (US); Zahid Hussain, Dayton, NJ (US); Puneet Kumar, Woodbridge, NJ (US); Remond Moningka, Jersey City, NJ (US); Joseph L. Duffy, Cranford, NJ (US); Jiayi Xu, Marlboro, NJ (US); Yu Jiang, East Windsor, NJ (US); Anjan Chakrabarti, Singapore (SG); Hiroki Sone, Singapore (SG)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/305,421

(22) PCT Filed: Apr. 21, 2015

(86) PCT No.: PCT/US2015/026774
§ 371 (c)(1),
(2) Date: Oct. 20, 2016

(87) PCT Pub. No.: WO2015/164308
PCT Pub. Date: Oct. 29, 2015

(65) Prior Publication Data
US 2017/0044183 A1   Feb. 16, 2017

Related U.S. Application Data

(60) Provisional application No. 61/982,420, filed on Apr. 22, 2014.

(51) Int. Cl.
| C07D 498/20 | (2006.01) |
| C07F 9/6561 | (2006.01) |
| C07D 487/10 | (2006.01) |
| C07D 498/10 | (2006.01) |
| C07D 471/10 | (2006.01) |

(52) U.S. Cl.
CPC ........ C07D 498/20 (2013.01); C07D 471/10 (2013.01); C07D 487/10 (2013.01); C07D 498/10 (2013.01); C07F 9/6561 (2013.01)

(58) Field of Classification Search
None
See application file for complete search history.

(56) References Cited

U.S. PATENT DOCUMENTS

| 5,536,716 A | 7/1996 | Chen et al. |
| 6,291,469 B1 | 9/2001 | Fisher et al. |
| 7,696,201 B2 | 4/2010 | Makings et al. |
| 2005/0282858 A1 | 12/2005 | Yao et al. |

FOREIGN PATENT DOCUMENTS

| WO | WO2009080682 A1 | 7/2009 |
| WO | WO2013055984 A1 | 4/2013 |
| WO | WO2013056060 A1 | 4/2013 |

OTHER PUBLICATIONS

Chemical Abstract Registry No. 869976-71-6, indexed in the Registry File on STN CAS Online Dec. 15, 2005.*
Wong et al., A small-molecule factor XIa inhibitor produces antithrombotic efficacy with minimal bleeding time prolongation in rabbits. Journal of Thrombosis and Thrombolysis, 2011, 32, 129-137.*
International Search Report and Written Opinion for PCT/US15/026774, dated Jul. 13, 2015, 7 pages.
Supplementary European Search Report for 15783339.3, dated Dec. 1, 2017; 6 pages.

* cited by examiner

*Primary Examiner* — Po-Chih Chen
(74) *Attorney, Agent, or Firm* — Nicole M. Beeler; John C. Toadaro

(57) ABSTRACT

The present invention provides a compound of Formula (I)

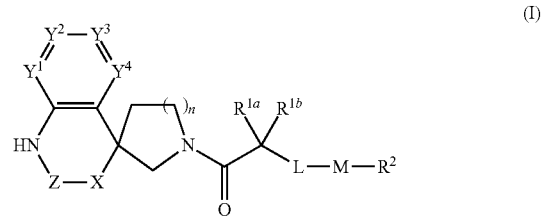

and pharmaceutical compositions comprising one or more compounds of Formula (I), and methods for using the compounds of Formula (I) for treating or preventing thromboses, embolisms, hypercoagulability or fibrotic changes. The compounds are selective Factor XIa inhibitors or dual inhibitors of Factor XIa and plasma kallikrein.

13 Claims, No Drawings

FACTOR XIA INHIBITORS

CROSS REFERENCE TO RELATED APPLICATIONS

This application is a U.S. National Phase application under 35 U.S.C. § 371 of PCT Application No. PCT/US15/26774 filed Apr. 21, 2015, which claims priority from U.S. Provisional Application Ser. No. 61/982,420, filed Apr. 22, 2014.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor 25 XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolyticactivation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on Cl-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2013022814, WO 2013022814, WO 2013022818, WO 2013055984, WO2013056034, WO2013056060, WO2013118805, WO2013093484, WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

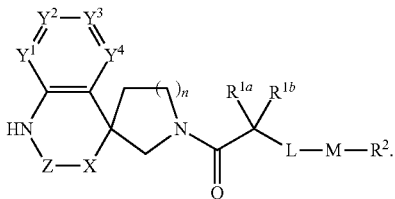

I or pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I.

DETAILED DESCRIPTION OF THE INVENTION

The present invention relates to compounds of Formula I:

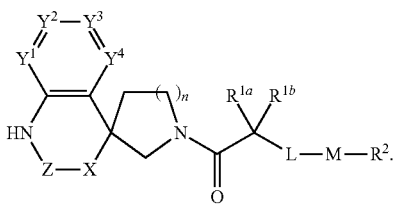

I wherein X is $CH_2$, O or NH;
$Y^1$ is $CR^3$ or N,
$Y^2$ is $CR^3$ or N,
$Y^3$ is $CR^3$ or N,
$Y^4$ is $CR^3$ or N, with the proviso that three of $Y^1$, $Y^2$, $Y^3$ and $Y^4$ are not simultaneously, N and all four of $Y^1$, $Y^2$, $Y^3$ and $Y^4$ are not simultaneously N;

Z is S, SO, $SO_2$ or C=O;

L is a bond, C(=O)NH, NHC(=O), NHC(=O)NH, $NHSO_2$, $CHR^8$ or $R^9$;

M is aryl, $C_{3-6}$ cycloalkyl, heteroaryl or $CH_2$, wherein said aryl cycloalkyl and heteroaryl groups are optionally substituted with one to three substituents independently selected from halo, cyano, hydroxy, oxo, $C_{1-6}$ alkyl or $NR^6R^7$;

$R^{1a}$ is hydrogen, halo, cyano, hydroxy, $C_{1-4}$ alkyl, $C_{3-6}$ cycloalkyl, aryl, heteroaryl, heterocyclyl, $C_{1-4}$ alkyl-$C_{3-6}$ cycloalkyl, $C_{1-4}$ alkyl-aryl, $C_{1-4}$ alkyl-heteroaryl or $C_{1-4}$ alkyl-heterocyclyl, wherein said alkyl groups are optionally substituted with one to three substituents independently selected from halo or hydroxy, and said cycloalkyl, aryl, heteraryl and heterocyclyl groups are optionally substituted with one to three groups independently selected from halo, hydroxy, $C_{1-4}$ alkyl, C(=O)$NR^6R^7$, C(O)$R^9$, $OR^9$, $NHSO_2R^4$, $SO_2R^4$ or $NR^6R^7$;

$R^{1b}$ is hydrogen, halo, cyano, hydroxy or $C_{1-4}$ alkyl, wherein said alkyl is optionally substituted with one to three groups independently selected from halo or hydroxy;

or $R^{1a}$ and $R^{1b}$ can be taken together with the atom between them to form a $C_{3-6}$ cycloalkyl, aryl, heteroaryl or heterocyclyl ring system which is optionally substituted with one to three groups independently selected from halo, hydroxy or aryl;

$R^2$ is hydrogen, halo, cyano, $OR^4$, $R^4$, $R^9$, C(=O)$OR^4$, $C_{1-3}$ alkyl-C(=O)$OR^5$, $NR^6R^7$, $NR^6R^9$, NHC(=O)$R^4$, NHC(=O)$OR^4$, NHC(=O)O—$C_{1-3}$ alkyl-$OR^5$, NHC(=O)O($C_{1-3}$ alkyl)$R^9$, NHC(=O)O($R^4$)C(=O)OH, $C_{1-3}$ alkyl-NHC(=O)$OR^5$, NHC(=O)$NR^6R^7$, NH(C=NH)$NR^6R^7$, C(O)$NR^6R^7$, $CH_2$C(=O)$NR^6R^7$, $C(CH_3)(NR^6R^7)$C(=O)$R^4$, NHC(=O)NH—$C_{1-3}$ alkyl-$R^9$, $SO_2R^4$, $NHSO_2R^4$, $NHSO_2R^9$ or $SO_2NR^6R^7$;

each $R^3$ is independently hydrogen, $C_{1-3}$ alkyl, $C_{3-6}$ cycloalkyl, halo, cyano or hydroxy, wherein said alkyl and cycloalkyl groups are optionally substituted with one to three groups independently selected from halo or hydroxy;

each $R^4$ is independently hydrogen or $C_{1-6}$ alkyl, wherein said alkyl is optionally substituted with one to three halo or hydroxy;

each $R^5$ is independently hydrogen or $C_{1-6}$ alkyl, wherein said alkyl is optionally substituted with one to three halo;

each $R^6$ is independently hydrogen or $C_{1-6}$ alkyl;

each $R^7$ is independently hydrogen or $C_{1-6}$ alkyl;

each $R^8$ is independently hydrogen, halo or methyl;

each $R^9$ is independently aryl, heteroaryl, heterocyclyl or $C_{3-8}$ cycloalkyl, wherein said aryl, heteroaryl, heterocyclyl and cycloalkyl groups are optionally substituted with one to three substituents independently selected from the group consisting of halo, cyano, hydroxy, oxo, $C_{1-6}$ alkyl, C(=O)$OR^4$ or $NR^6R^7$;

n is an integer from zero to three;

or a pharmaceutically acceptable salt thereof.

The present invention further relates to compounds of Formula I:

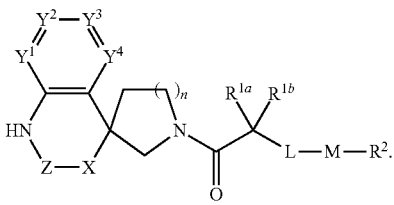

wherein X is absent, CH$_2$, CH$_2$O, O or NH;
Y$^1$ is CR$^3$ or N,
Y$^2$ is CR$^3$ or N,
Y$^3$ is CR$^3$ or N,
Y$^4$ is CR$^3$ or N,
with the proviso that three of Y$^1$, Y$^2$, Y$^3$ and Y$^4$ are not simultaneously N, and all four of Y$^1$, Y$^2$, Y$^3$ and Y$^4$ are not simultaneously N;
Z is S, SO, SO$_2$ or C=O;
L is a bond, C(=O)NH, NHC(=O), NHC(=O)NH, NHSO$_2$, NHCHR$^4$, CHR$^8$ or R$^9$;
M is aryl, C$_{3-6}$ cycloalkyl, heteroaryl or CH$_2$, wherein said aryl, cycloalkyl and heteroaryl groups are optionally substituted with one to three substituents independently selected from halo, cyano, hydroxy, oxo, C$_{1-6}$ alkyl or NR$^6$R$^7$;
R$^{1a}$ is hydrogen, halo, cyano, hydroxy, C$_{1-4}$ alkyl, C$_{3-6}$ cycloalkyl, aryl, heteroaryl, heterocyclyl, C$_{1-4}$ alkyl-C$_{3-6}$ cycloalkyl, C$_{1-4}$ alkyl-aryl, C$_{1-4}$ alkyl-heteroaryl or C$_{1-4}$ alkyl-heterocyclyl, wherein said alkyl groups are optionally substituted with one to three substituents independently selected from halo, hydroxy, methoxy, SR$^4$, SOR$^4$, SO$_2$R$^4$, C(=O)R$^9$, C(=O)NHR$^9$, C(=O)NHCH$_2$R$^9$, C(=O)NHSO$_2$R$^9$ or NHC(=O)R$^4$, and said cycloalkyl, aryl, heteraryl and heterocyclyl groups are optionally substituted with one to three groups independently selected from halo, hydroxy, oxo, cyano, C$_{1-4}$ alkyl, C$_{2-4}$ alkenyl-OR$^4$, OR$^4$, C(=O)NR$^6$R$^7$, NHC(=O)R$^4$, NHC(=O)R$^9$, NHC(=O)OR$^9$, C(=O)R$^9$, R$^9$, OR$^9$, NHSO$_2$R$^4$, SO$_2$R$^4$ or NR$^6$R$^7$;
R$^{1b}$ is hydrogen, halo, cyano, hydroxy or C$_{1-4}$ alkyl, wherein said alkyl is optionally substituted with one to three groups independently selected from halo or hydroxy;
or R$^{1a}$ and R$^{1b}$ can be taken together with the atom between them to form a C$_{3-6}$ cycloalkyl, aryl, heteroaryl or heterocyclyl ring system wherein said cycloalkyl, aryl, heteroaryl or heterocyclyl ring systems are are optionally substituted with one to three groups independently selected from halo, hydroxy or aryl;
R$^2$ is hydrogen, halo, cyano, OR$^4$, R$^4$, R$^9$, C(=O)OR$^4$, C$_{1-3}$ alkyl-C(=O)OR$^5$, NR$^4$R$^7$, NR$^6$R$^9$, NHC(=O)R$^4$, NHC(=O)OR$^4$, NHC(=O)O—C$_{1-3}$ alkyl-OR$^5$, NHC(=O)O(C$_{1-3}$ alkyl)R$^9$, NHC(=O)O(R$^4$)C(=O)OH, C$_{1-3}$ alkyl-NHC(=O)OR$^5$, NHC(=O)NR$^6$R$^7$, NH(C=NH)NR$^6$R$^7$, C(=O)NR$^6$R$^7$, CH$_2$C(=O)NR$^6$R$^7$, C(CH$_3$)(NR$^6$R$^7$)C(=O)R$^4$, NHC(=O)NH—C$_{1-3}$ alkyl-R$^9$, SO$_2$R$^4$, NHSO$_2$R$^4$, NHSO$_2$R$^9$, SO$_2$NR$^6$R$^7$, P(=O)(OCH$_2$CH$_3$)$_2$, P(=O)(OH)$_2$; or B(OH)$_2$;
each R$^3$ is independently hydrogen, R$^4$, C$_{3-6}$ cycloalkyl, halo, cyano or OR$^4$, wherein said alkyl and cycloalkyl groups are optionally substituted with one to three groups independently selected from halo or hydroxy;
each R$^4$ is independently hydrogen or C$_{1-6}$ alkyl, wherein said alkyl is optionally substituted with one to three halo or hydroxy;
each R$^5$ is independently hydrogen or C$_{1-6}$ alkyl, wherein said alkyl is optionally substituted with one to three halo;
each R$^6$ is independently hydrogen or C$_{1-6}$ alkyl;
each R$^7$ is independently hydrogen or C$_{1-6}$ alkyl;
each R$^8$ is independently hydrogen, halo or methyl;
each R$^9$ is independently aryl, heteroaryl, heterocyclyl or C$_{3-8}$ cycloalkyl, wherein said aryl, heteroaryl, heterocyclyl and cycloalkyl groups are optionally substituted with one to three substituents independently selected from the group consisting of halo, cyano, oxo, cyclopropyl, R$^4$, OR$^4$, C(=O)OR$^4$ or NR$^6$R$^7$;
n is an integer from zero to three;
or a pharmaceutically acceptable salt thereof.

An embodiment of the present invention relates to compounds of the following formula:

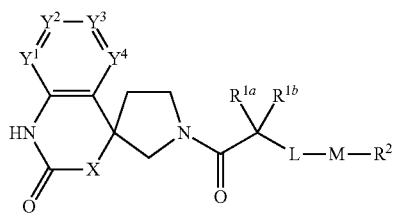

Y$^1$ is CR$^3$ or N,
Y$^2$ is CR$^3$ or N,
Y$^3$ is CR$^3$ or N,
Y$^4$ is CR$^3$ or N,
with the proviso that three of Y$^1$, Y$^2$, Y$^3$ and Y$^4$ are not simultaneously N, and all four of Y$^1$, Y$^2$, Y$^3$ and Y$^4$ are not simultaneously N;
L is a bond, C(=O)NH, NHC(=O), NHC(=O)NH, NHSO$_2$, NHCHR$^4$, CHR$^8$ or R$^9$;
M is aryl, C$_{3-6}$ cycloalkyl, heteroaryl or CH$_2$, wherein said aryl, cycloalkyl and heteroaryl groups are optionally substituted with one to three substituents independently selected from halo, cyano, hydroxy, oxo, C$_{1-6}$ alkyl or NR$^6$R$^7$;
R$^{1a}$ is hydrogen, halo, cyano, hydroxy, C$_{1-4}$ alkyl, C$_{3-6}$ cycloalkyl, aryl, heteroaryl, heterocyclyl, C$_{1-4}$ alkyl-C$_{3-6}$ cycloalkyl, C$_{1-4}$ alkyl-aryl, C$_{1-4}$ alkyl-heteroaryl or C$_{1-4}$ alkyl-heterocyclyl, wherein said alkyl groups are optionally substituted with one to three substituents independently selected from halo, hydroxy, methoxy, SR$^4$, SOR$^4$, SO$_2$R$^4$, C(O)R$^9$, C(=O)NHR$^9$, C(=O)NHCH$_2$R$^9$, C(=O)NHSO$_2$R$^9$ or NHC(=O)R$^4$, and said cycloalkyl, aryl, heteraryl and heterocyclyl groups are optionally substituted with one to three groups independently selected from halo, hydroxy, oxo, cyano, C$_{1-4}$ alkyl, C$_{2-4}$ alkenyl-OR$^4$, OR$^4$, C(=O)NR$^6$R$^7$, NHC(=O)R$^4$, NHC(=O)R$^9$, NHC(=O)OR$^9$, C(=O)R$^9$, R$^9$, OR$^9$, NHSO$_2$R$^4$, SO$_2$R$^4$ or NR$^6$R$^7$;
R$^{1b}$ is hydrogen, halo, cyano, hydroxy or C$_{1-4}$ alkyl, wherein said alkyl is optionally substituted with one to three groups independently selected from halo or hydroxy;
or R$^{1a}$ and R$^{1b}$ can be taken together with the atom between them to form a C$_{3-6}$ cycloalkyl, aryl, heteroaryl or heterocyclyl ring system wherein said cycloalkyl, aryl, heteroaryl or heterocyclyl ring systems are are optionally substituted with one to three groups independently selected from halo, hydroxy or aryl;
R$^2$ is hydrogen, halo, cyano, OR$^4$, R$^4$, R$^9$, C(=O)OR$^4$, C$_{1-3}$ alkyl-C(=O)OR$^5$, NR$^4$R$^7$, NR$^6$R$^9$, NHC(=O)R$^4$, NHC(=O)OR$^4$, NHC(=O)O—C$_{1-3}$ alkyl-OR$^5$, NHC(=O)O ($C_{1-3}$ alkyl)$R^9$, NHC(=O)O($R^4$)C(=O)OH, $C_{1-3}$ alkyl-NHC(=O)O$R^5$, NHC(=O)N$R^6R^7$, NH(C=NH)N$R^6R^7$, C(=O)N$R^6R^7$, $CH_2$C(=O)N$R^6R^7$, C($CH_3$)(N$R^6R^7$)C(=O)$R^4$, NHC(=O)NH—$C_{1-3}$ alkyl-$R^9$, $SO_2R^4$, NHSO$_2R^4$, NHSO$_2R^9$, $SO_2$N$R^6R^7$, P(=O)(OCH$_2$CH$_3$)$_2$, P(=O)(OH)$_2$; or B(OH)$_2$;

each $R^3$ is independently hydrogen, $R^4$, $C_{3-6}$ cycloalkyl, halo, cyano or O$R^4$, wherein said alkyl and cycloalkyl groups are optionally substituted with one to three groups independently selected from halo or hydroxy;

each $R^4$ is independently hydrogen or $C_{1-6}$ alkyl, wherein said alkyl is optionally substituted with one to three halo or hydroxy;

each $R^5$ is independently hydrogen or $C_{1-6}$ alkyl, wherein said alkyl is optionally substituted with one to three halo;

each $R^6$ is independently hydrogen or $C_{1-6}$ alkyl;

each $R^7$ is independently hydrogen or $C_{1-6}$ alkyl;

each $R^8$ is independently hydrogen, halo or methyl;

each $R^9$ is independently aryl, heteroaryl, heterocyclyl or $C_{3-8}$ cycloalkyl, wherein said aryl, heteroaryl, heterocyclyl and cycloalkyl groups are optionally substituted with one to three substituents independently selected from the group consisting of halo, cyano, oxo, cyclopropyl, $R^4$, O$R^4$, C(=O)O$R^4$ or N$R^6R^7$;

or a pharmaceutically acceptable salt thereof.

Another embodiment of the invention relates to compounds of the formula:

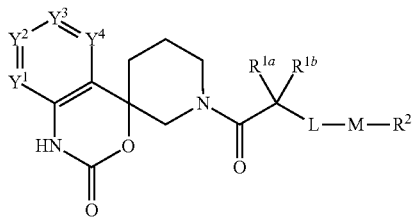

wherein $Y^1$ is C$R^3$ or N,
$Y^2$ is C$R^3$ or N,
$Y^3$ is C$R^3$ or N,
$Y^4$ is C$R^3$ or N,
with the proviso that three of $Y^1$, $Y^2$, $Y^3$ and $Y^4$ are not simultaneously N, and all four of $Y^1$, $Y^2$, $Y^3$ and $Y^4$ are not simultaneously N;

Z is S, SO, SO$_2$ or C=O;

L is a bond, C(=O)NH, NHC(=O), NHC(=O)NH, NHSO$_2$, NHCH$R^4$, CH$R^8$ or $R^9$;

M is aryl, $C_{3-6}$ cycloalkyl, heteroaryl or CH$_2$, wherein said aryl, cycloalkyl and heteroaryl groups are optionally substituted with one to three substituents independently selected from halo, cyano, hydroxy, oxo, $C_{1-6}$ alkyl or N$R^6R^7$;

$R^{1a}$ is hydrogen, halo, cyano, hydroxy, $C_{1-4}$ alkyl, $C_{3-6}$ cycloalkyl, aryl, heteroaryl, heterocyclyl, $C_{1-4}$ alkyl-$C_{3-6}$ cycloalkyl, $C_{1-4}$ alkyl-aryl, $C_{1-4}$ alkyl-heteroaryl or $C_{1-4}$ alkyl-heterocyclyl, wherein said alkyl groups are optionally substituted with one to three substituents independently selected from halo, hydroxy, methoxy, S$R^4$, SO$R^4$, SO$_2R^4$, C(=O)$R^9$, C(=O)NH$R^9$, C(=O)NHCH$_2R^9$, C(=O)NHSO$_2R^9$ or NHC(=O)$R^4$, and said cycloalkyl, aryl, heteraryl and heterocyclyl groups are optionally substituted with one to three groups independently selected from halo, hydroxy, oxo, cyano, $C_{1-4}$ alkyl, $C_{2-4}$ alkenyl-O$R^4$, O$R^4$, C(=O)N$R^6R^7$, NHC(=O)$R^4$, NHC(=O)$R^9$, NHC(=O)O$R^9$, C(=O)$R^9$, $R^9$, O$R^9$, NHSO$_2R^4$, SO$_2R^4$ or N$R^6R^7$;

$R^{1b}$ is hydrogen, halo, cyano, hydroxy or $C_{1-4}$ alkyl, wherein said alkyl is optionally substituted with one to three groups independently selected from halo or hydroxy;

or $R^{1a}$ and $R^{1b}$ can be taken together with the atom between them to form a $C_{3-6}$ cycloalkyl, aryl, heteroaryl or heterocyclyl ring system wherein said cycloalkyl, aryl, heteroaryl or heterocyclyl ring systems are are optionally substituted with one to three groups independently selected from halo, hydroxy or aryl;

$R^2$ is hydrogen, halo, cyano, O$R^4$, $R^4$, $R^9$, C(=O)O$R^4$, $C_{1-3}$ alkyl-C(=O)O$R^5$, N$R^4R^7$, N$R^6R^9$, NHC(=O)$R^4$, NHC(=O)O$R^4$, NHC(=O)O—$C_{1-3}$ alkyl-O$R^5$, NHC(=O)O($C_{1-3}$ alkyl)$R^9$, NHC(=O)O($R^4$)C(=O)OH, $C_{1-3}$ alkyl-NHC(=O)O$R^5$, NHC(=O)N$R^6R^7$, NH(C=NH)N$R^6R^7$, C(=O)N$R^6R^7$, $CH_2$C(=O)N$R^6R^7$, C($CH_3$)(N$R^6R^7$)C(=O)$R^4$, NHC(=O)NH—$C_{1-3}$ alkyl-$R^9$, $SO_2R^4$, NHSO$_2R^4$, NHSO$_2R^9$, $SO_2$N$R^6R^7$, P(=O)(OCH$_2$CH$_3$)$_2$, P(=O)(OH)$_2$; or B(OH)$_2$;

each $R^3$ is independently hydrogen, $R^4$, $C_{3-6}$ cycloalkyl, halo, cyano or O$R^4$, wherein said alkyl and cycloalkyl groups are optionally substituted with one to three groups independently selected from halo or hydroxy;

each $R^4$ is independently hydrogen or $C_{1-6}$ alkyl, wherein said alkyl is optionally substituted with one to three halo or hydroxy;

each $R^5$ is independently hydrogen or $C_{1-6}$ alkyl, wherein said alkyl is optionally substituted with one to three halo;

each $R^6$ is independently hydrogen or $C_{1-6}$ alkyl;

each $R^7$ is independently hydrogen or $C_{1-6}$ alkyl;

each $R^8$ is independently hydrogen, halo or methyl;

each $R^9$ is independently aryl, heteroaryl, heterocyclyl or $C_{3-8}$ cycloalkyl, wherein said aryl, heteroaryl, heterocyclyl and cycloalkyl groups are optionally substituted with one to three substituents independently selected from the group consisting of halo, cyano, oxo, cyclopropyl, $R^4$, O$R^4$, C(=O)O$R^4$ or N$R^6R^7$;

n is an integer from zero to three;

or a pharmaceutically acceptable salt thereof.

Another embodiment of the invention relates to compounds of the formula:

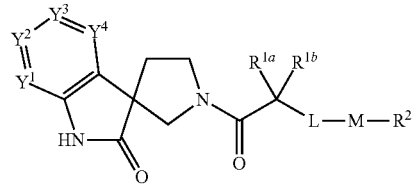

wherein $Y^1$ is C$R^3$ or N,
$Y^2$ is C$R^3$ or N,
$Y^3$ is C$R^3$ or N,
$Y^4$ is C$R^3$ or N,
with the proviso that three of $Y^1$, $Y^2$, $Y^3$ and $Y^4$ are not simultaneously N, and all four of $Y^1$, $Y^2$, $Y^3$ and $Y^4$ are not simultaneously N;

Z is S, SO, SO$_2$ or C=O;

L is a bond, C(=O)NH, NHC(=O), NHC(=O)NH, NHSO$_2$, NHCH$R^4$, CH$R^8$ or $R^9$;

M is aryl, $C_{3-6}$ cycloalkyl, heteroaryl or CH$_2$, wherein said aryl, cycloalkyl and heteroaryl groups are optionally substituted with one to three substituents independently selected from halo, cyano, hydroxy, oxo, $C_{1-6}$ alkyl or $NR^6R^7$;

$R^{1a}$ is hydrogen, halo, cyano, hydroxy, $C_{1-4}$ alkyl, $C_{3-6}$ cycloalkyl, aryl, heteroaryl, heterocyclyl, $C_{1-4}$ alkyl-$C_{3-6}$ cycloalkyl, $C_{1-4}$ alkyl-aryl, $C_{1-4}$ alkyl-heteroaryl or $C_{1-4}$ alkyl-heterocyclyl, wherein said alkyl groups are optionally substituted with one to three substituents independently selected from halo, hydroxy, methoxy, $SR^4$, $SOR^4$, $SO_2R^4$, $C(O)R^9$, $C(=O)NHR^9$, $C(=O)NHCH_2R^9$, $C(=O)NHSO_2R^9$ or $NHC(=O)R^4$, and said cycloalkyl, aryl, heteraryl and heterocyclyl groups are optionally substituted with one to three groups independently selected from halo, hydroxy, oxo, cyano, $C_{1-4}$ alkyl, $C_{2-4}$ alkenyl-$OR^4$, $OR^4$, $C(=O)NR^6R^7$, $NHC(=O)R^4$, $NHC(=O)R^9$, $NHC(=O)OR^9$, $C(=O)R^9$, $R^9$, $OR^9$, $NHSO_2R^4$, $SO_2R^4$ or $NR^6R^7$;

$R^{1b}$ is hydrogen, halo, cyano, hydroxy or $C_{1-4}$ alkyl, wherein said alkyl is optionally substituted with one to three groups independently selected from halo or hydroxy;

or $R^{1a}$ and $R^{1b}$ can be taken together with the atom between them to form a $C_{3-6}$ cycloalkyl, aryl, heteroaryl or heterocyclyl ring system wherein said cycloalkyl, aryl, heteroaryl or heterocyclyl ring systems are are optionally substituted with one to three groups independently selected from halo, hydroxy or aryl;

$R^2$ is hydrogen, halo, cyano, $OR^4$, $R^4$, $R^9$, $C(=O)OR^4$, $C_{1-3}$ alkyl-$C(=O)OR^5$, $NR^4R^7$, $NR^6R^9$, $NHC(=O)R^4$, $NHC(=O)OR^4$, $NHC(=O)O-C_{1-3}$ alkyl-$OR^5$, $NHC(=O)O(C_{1-3}$ alkyl)$R^9$, $NHC(=O)O(R^4)C(=O)OH$, $C_{1-3}$ alkyl-$NHC(=O)OR^5$, $NHC(=O)NR^6R^7$, $NH(C=NH)NR^6R^7$, $C(=O)NR^6R^7$, $CH_2C(=O)NR^6R^7$, $C(CH_3)(NR^6R^7)C(=O)R^4$, $NHC(=O)NH-C_{1-3}$ alkyl-$R^9$, $SO_2R^4$, $NHSO_2R^4$, $NHSO_2R^9$, $SO_2NR^6R^7$, $P(=O)(OCH_2CH_3)_2$, $P(=O)(OH)_2$; or $B(OH)_2$;

each $R^3$ is independently hydrogen, $R^4$, $C_{3-6}$ cycloalkyl, halo, cyano or $OR^4$, wherein said alkyl and cycloalkyl groups are optionally substituted with one to three groups independently selected from halo or hydroxy;

each $R^4$ is independently hydrogen or $C_{1-6}$ alkyl, wherein said alkyl is optionally substituted with one to three halo or hydroxy;

each $R^5$ is independently hydrogen or $C_{1-6}$ alkyl, wherein said alkyl is optionally substituted with one to three halo;

each $R^6$ is independently hydrogen or $C_{1-6}$ alkyl;

each $R^7$ is independently hydrogen or $C_{1-6}$ alkyl;

each $R^8$ is independently hydrogen, halo or methyl;

each $R^9$ is independently aryl, heteroaryl, heterocyclyl or $C_{3-8}$ cycloalkyl, wherein said aryl, heteroaryl, heterocyclyl and cycloalkyl groups are optionally substituted with one to three substituents independently selected from the group consisting of halo, cyano, oxo, cyclopropyl, $R^4$, $OR^4$, $C(=O)OR^4$ or $NR^6R^7$;

n is an integer from zero to three;

or a pharmaceutically acceptable salt thereof.

In an embodiment of the invention, X is $CH_2$. In another embodiment of the invention, X is O. In another embodiment of the invention, X is NH.

In an embodiment of the invention, $Y^1$ is $CR^3$. In another embodiment of the invention, $Y^1$ is N.

In an embodiment of the invention, $Y^2$ is $CR^3$. In another embodiment of the invention, $Y^2$ is N.

In an embodiment of the invention, $Y^3$ is $CR^3$. In another embodiment of the invention, $Y^3$ is N.

In an embodiment of the invention, $Y^4$ is $CR^3$. In another embodiment of the invention, $Y^4$ is N.

In an embodiment of the invention, Z is S. In another embodiment of the invention, Z is SO. In another embodiment of the invention, Z is $SO_2$. In another embodiment of the invention, Z is $C=O$.

In an embodiment of the invention, L is a bond. In another embodiment of the invention, L is $C(=O)NH$. In another embodiment of the invention, L is $NH(C=)O$. In another embodiment of the invention, L is $NHC(=O)NH$. In another embodiment of the invention, L is $NHSO_2$. In another embodiment of the invention, L is $CHR^8$. In another embodiment of the invention, L is $R^9$.

In an embodiment of the invention, M is aryl, which is optionally substituted with one to three substituents independently selected from halo, cyano, hydroxy, $C_{1-6}$ alkyl or $NR^6R^7$. In a class of the invention, M is phenyl. In another embodiment of the invention, M is $C_{3-6}$ cycloalkyl, which is optionally substituted with one to three substituents independently selected from halo, cyano, hydroxy, $C_{1-6}$ alkyl or $NR^6R^7$. In another embodiment of the invention, M is heteroaryl, which is optionally substituted with one to three substituents independently selected from halo, cyano, hydroxy, $C_{1-6}$ alkyl, oxo or $NR^6R^7$. In another embodiment of the invention, M is $CH_2$.

In an embodiment of the invention, $R^{1a}$ is $C_{1-4}$ alkyl-aryl. In a class of the invention, $R^{1a}$ is $CH_2$-phenyl.

In an embodiment of the invention, $R^{1b}$ is hydrogen. In another embodiment of the invention, $R^{1b}$ is $CH_3$.

In an embodiment of the invention, $R^2$ is $NHC(=O)OR^4$. In a class of the invention, $R^2$ is $NHC(=O)OCH_3$.

In an embodiment of the invention, $R^3$ is halo.

In an embodiment of the invention, n is 0. In another embodiment of the invention, n is 1. In another embodiment of the invention, n is 2. In another embodiment of the invention, n is 3.

Reference to the preferred classes and subclasses set forth above is meant to include all combinations of particular and preferred groups unless stated otherwise.

Specific embodiments of the present invention include, but are not limited to the compounds identified herein as Examples 1 to 297, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO$^-$ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

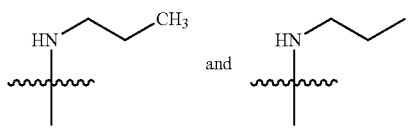

have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms. Cycloalkyl can include fused ring systems. For example, "cycloalkyl" includes cyclopropyl, cyclobutyl, cyclopentyl, cyclohexyl, bicyclo[1.1.1]pentanyl, bicycle[2.2.2]octanyl, and so on.

Except where noted, the term "halogen" means fluorine, chlorine, bromine or iodine.

Except where noted, the term "heteroaryl", as used herein, represents a stable monocyclic, bicyclic or tricyclic ring of up to 10 atoms in each ring, wherein at least one ring is aromatic, and at least one ring contains from 1 to 4 heteroatoms selected from the group consisting of O, N and S. Heteroaryl can include bicyclic fused ring systems, with at least one ring contains from 1 to 4 heteroatoms selected from the group consisting of O, N and S, and wherein one ring is aromatic and one is saturated. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline, tetrahydrobenzo[b]azepinyl and 3-oxo-3,4dihydro-2Nbenzo[b][1,4]thiazine. If the heteroaryl contains nitrogen atoms, it is understood that the corresponding N-oxides thereof are also encompassed by this definition.

Except where noted, the term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or SO$_2$ and includes bicyclic groups. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Aryl can include bicyclic fused ring systems, wherein one ring is aromatic and one is saturated. Examples of such aryl elements include phenyl, naphthyl, tetrahydronaphthyl and indanyl.

"Celite®" (Fluka) diatomite is diatomaceous earth, and can be referred to as "Celite".

Except where noted herein, structures containing substituent variables such as variable "R" below:

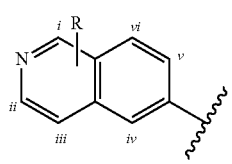

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema, diabetic retinopathy and/or diabetic macular edema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula (I) can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:
List of Abbreviations:
ACN=acetonitrile
Aq.=aqueous
DMF=dimethylformamide
DMS=dimethyl sulfide
DCM=dichloromethane
DEA=Diethanolamine
DIBAL-H=Diisobutylaluminium hydride
DIEA=N,N-Diisopropylethylamine
DIPEA=N,N-Diisopropylethylamine
DMAP=4-Dimethylaminopyridine.
DMPU=N,N'-dimethyl-N,N'-propylene urea
DMSO=Dimethyl sulfoxide
DMT=N,N-Dimethyltryptamine
DPPA=Diphenylphosphoryl azide
EtOAc=ethyl acetate
$Et_3N$=Triethyl amine
EDC=N-(3-Dimethylaminopropyl)-N'-ethylcarbodiimide hydrochloride
DCE=1,2-dichloroethane
RP HPLC=Reverse Phase High Pressure Liquid Chromatography
Hex=hexanes
HOBT=Hydroxybenzotriazole
IPA=iso-Propanol
LCMS=Liquid Chromatography Mass Spectrometry
LiHMDS=Lithium bis(trimethylsilyl)amide
LiOH=lithium hydroxide
Me=methyl
mCPBA=meta-chloroperoxybenzoic acid
$MgSO_4$=magnesium sulfate
MP-cyanoborohydride=macroporous polymer-supported cyanoborohydride
rt or RT=room temperature
THF=tetrahydrofuran nBu₄LI=Tetra-n-butylammonium iodide
NMP=N-Methyl-2-pyrrolidone
NBS=N-Bromosuccinimide
NCS=N-Chlorosuccinimide
ODS=Octadecylsilane
PCC=Pyridinium Chlorochromate
PPA=Poly Phosphoric acid
PPT=Precipitate
RuPhos=2-Dicyclohexylphosphino-2',6'-diisopropoxybiphenyl
sat.=saturated
SEM=2-Trimethylsilylethoxymethoxy
SFC=supercritical fluid chromatography
SM=Starting material
tBuBrettPhos=2-(Di-tert-butylphosphino)-2',4',6'-triisopropyl-3,6-dimethoxy-1,1'-biphenyl
TEA=triethylamine
TEMPO=(2,2,6,6-tetramethylpiperidin-1-yl)oxidanyl
TFA=Trifluoroacetic acid
Vac=Vacuum
Xphos=2-Dicyclohexylphosphino-2',4',6'-triisopropylbiphenyl
HATU=2-(1H-7-Azabenzotriazol-1-yl)-1,1,3,3-tetramethyluronium hexafluorophosphate Methanaminium
LAH=lithium Aluminum Hydride Also, TLC is thin layer chromatography; Ts is tosyl; UV is ultraviolet; W is watts; wt. % is percentage by weight; ×g is times gravity; $\alpha_D$ is the specific rotation of polarized light at 589 nm; ° C. is degrees Celsius; % w/v is percentage in weight of the former agent relative to the volume of the latter agent.

LCMS conditions: column: SUPELCO Ascentis Express C18 3×100 mm, 2.7 um.
Solvent system: A—0.05% TFA in water and B—0.05% TFA in Acetonitrile.
Gradient condition: 10% B to 99% B in 3.5 min.

SCHEME 1

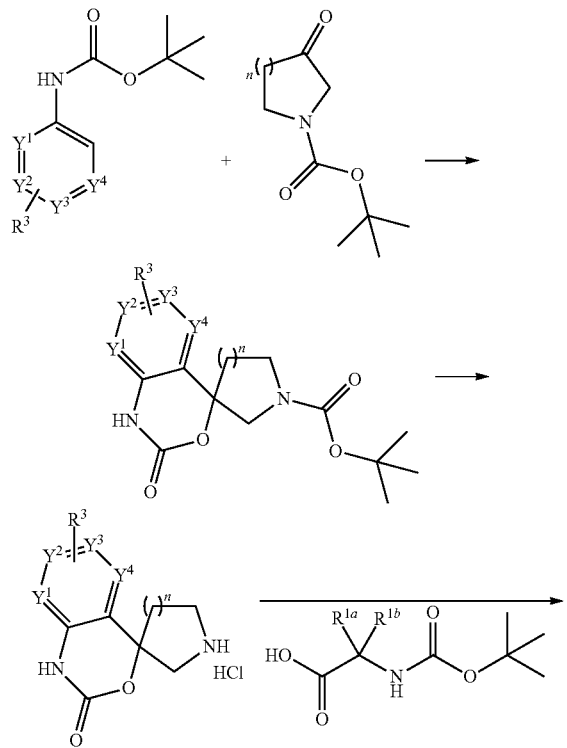

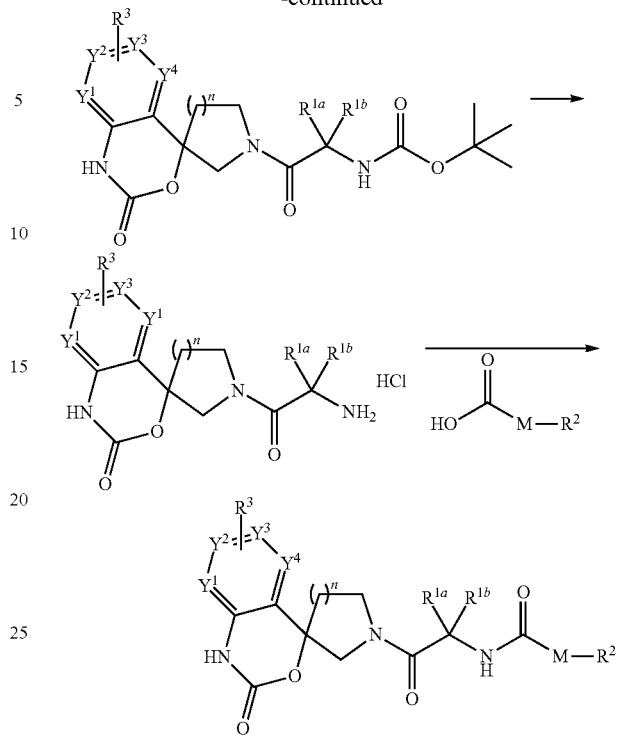

Example 1

Methyl (4-(((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate

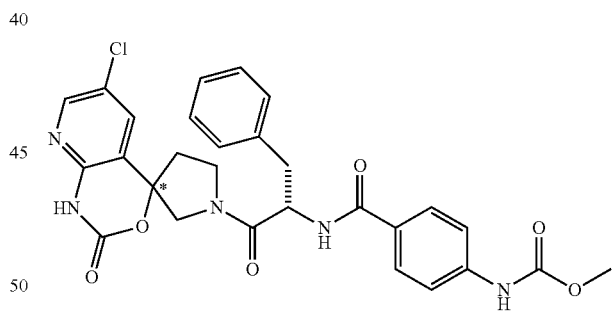

Ex-1a and Ex-1b

Methyl (4-(((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate was prepared by using a procedure described in *J. Am. Chem. Soc.* 2008, 47, 3690-3699.

Step A: Tert-butyl 6-chloro-2-oxo-1,2-dihydrospiro[pyrido[2,3-d][1,3]oxazine-4,3'-pyrrolidine]-1'-carboxylate To a stirred solution of tert-butyl (5-chloropyridin-2-yl)carbamate (685 mg, 3.00 mmol) in THF (10 ml) was added tert-buthyllithium (4.23 ml, 7.19 mmol) (1.7 M in pentane)

dropwise at −40° C. The reaction mixture was stirred below −10° C. for 3.5 hrs. After it cooled down to −78° C., lanthanum trichloride-lithium chloride complex (5.49 ml, 3.30 mmol) (0.6M in THF) was added dropwise into the reaction mixture. After 5 min at −78° C., a solution of tert-butyl 3-oxopyrrolidine-1-carboxylate (666 mg, 3.59 mmol) in THF (3.6 ml) was added rapidly into the reaction mixture. The reaction mixture was warmed to RT over 1 hr. Potassium tert-butoxide (33.6 mg, 0.300 mmol) was added into the reaction mixture and the reaction mixture was heated to 70° C. for overnight. After it cooled down to RT, the reaction mixture was diluted with EtOAc. The organic layer was washed with 1N HCl, sat. NH$_4$Cl (aq) and sat. NaHCO$_3$ (aq) and brine solution. The organic layer was dried over MgSO$_4$, filtered and concentrated in vacuo. The crude product was purified by flash silica gel column chromatography (EtOAc/Hex=1/1) to afford tert-butyl6-chloro-2-oxo-1,2-dihydrospiro[pyrido[2,3-d][1,3]oxazine-4,3'-pyrrolidine]-1'-carboxylate. LC/MS=284 [M−55].

Step B: 6-chlorospiro[pyrido[2,3-d][1,3]oxazine-4,3'-pyrrolidin]-2(1H)-one hydrochloride To a round bottom flask charged with tert-butyl6-chloro-2-oxo-1,2-dihydrospiro[pyrido[2,3-d][1,3]oxazine-4,3'-pyrrolidine]-1'-carboxylate (274 mg, 0.806 mmol) added 4N HCl in 1,4-dioxane (2.1 ml, 8.40 mmol) and stirred at RT for 2 hrs. The reaction mixture was concentrated by a rotary evaporator. The crude product was dried over vac. oven overnight and used for the next step without further purification. LC/MS=240 [M+1].

Step C: Tert-butyl ((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl)carbamate To a stirred solution of 6-chlorospiro[pyrido[2,3-d][1,3]oxazine-4,3'-pyrrolidin]-2(1H)-one hydrochloride (151 mg, 0.547 mmol) in DMF (5.5 mL) was added (S)-2-((tert-butoxycarbonyl)amino)-3-phenylpropanoic acid (218 mg, 0.820 mmol), EDC (157 mg, 0.820 mmol), HOBT (126 mg, 0.820 mmol) and DIPEA (458 µl, 2.62 mmol) at RT. The reaction mixture was stirred at RT overnight. The reaction mixture was diluted with EtOAc and sat. NaHCO$_3$ (aq) was added. The organic layer was washed with brine, dried over MgSO$_4$, filtered and concentrated in vacuo. The crude product was purified by flash silica gel column chromatography (0-100% EtOAc in Hexanes) to afford tert-butyl ((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl)carbamate. LC/MS=487 [M+1].

Step D: 1'-((S)-2-amino-3-phenylpropanoyl)-6-chlorospiro[pyrido[2,3-d][1,3]oxazine-4,3'-pyrrolidin]-2(1H)-one hydrochloride To a round bottom flask charged with tert-butyl ((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl) carbamate (224 mg, 0.460 mmol) was added 4N HCl in 1,4-dioxane (2.00 mL, 8.00 mmol) at RT. The reaction mixture was stirred at RT for. The reaction mixture was concentrated by a rotary evaporator. The crude product was dried over vac. oven overnight and used for the next step without further purification. LC/MS=387 [M+1].

Step E: Methyl (4-(((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate To a stirred solution of 1'-((S)-2-amino-3-phenylpropanoyl)-6-chlorospiro[pyrido[2,3-d][1,3]oxazine-4,3'-pyrrolidin]-2(1H)-one hydrochloride (187 mg, 0.407 mmol) in DMF (4.0 mL) was added 4-((methoxycarbonyl)amino) benzoic acid (119 mg, 0.610 mmol), EDC (117 mg, 0.610 mmol), HOBT (93 mg, 0.610 mmol) and DIPEA (107 µl, 0.610 mmol) at RT. The reaction mixture was stirred at RT overnight. The reaction mixture was diluted with EtOAc and sat. NaHCO$_3$ (aq) was added. The organic layer was washed with brine, dried over MgSO$_4$, filtered and concentrated in vacuo. The crude product was purified by flash silica gel column chromatography (0-100% EtOAc in Hexanes and 1-10% MeOH in DCM) to afford methyl (4-(((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate (Ex-1a and Ex-1b). LC/MS=564 [M+1]. The mixture of the two stereoisomers was purified by chiral SFC (IC-H column, 60% 2:1 IPA:MeCN/CO$_2$) to afford Ex-1a (faster eluting) and Ex-1b (slower eluting).

By using procedures similar to those described in Example 1 with appropriate starting materials, including appropriate "left-side" reagents, the following compounds were synthesized. These compounds were characterized by LC/MS.

| Example | Structure | LCMS [M + 1] | FXIa Ki (nM) |
|---|---|---|---|
| 1a (isomer A) | methyl (4-(((S)-1-((S)-6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate | 564 | 3472 |
| 1b (isomer B) | methyl (4-(((S)-1-((R)-6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate | 564 | 246 |
| 2 | methyl (4-(((S)-1-oxo-1-((R)-2-oxo-1,2-dihydrospiro[benzo[d][1,3]oxazine-4,3'-pyrrolidin]-1'-yl)-3-phenylpropan-2-yl)carbamoyl)phenyl)carbamate | 528 | 220 |
| 3a (isomer A) | methyl (4-(((S)-1-((S)-6-chloro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 577 | 815 |
| 3b (isomer B) | methyl (4-(((S)-1-((R)-6-chloro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 577 | 1.5 |

| Example | Structure | LCMS [M + 1] | FXIa Ki (nM) |
|---|---|---|---|
| 4 (racemate) | methyl (4-(((2S)-1-(6'-chloro-2'-oxo-1',2'-dihydrospiro[azepane-3,4'-benzo[d][1,3]oxazin]-1-yl)-1-oxo-3-phenylpropan-2-yl)carbamoyl)phenyl)carbamate | 591 | 4597 |
| 5 (racemate) | (S)-methyl (4-((1-(6'-chloro-2'-oxo-1',2'-dihydrospiro[azetidine-3,4'-benzo[d][1,3]oxazin]-1-yl)-1-oxo-3-phenylpropan-2-yl)carbamoyl)phenyl)carbamate | 549 | >5000 |
| 6 | methyl (4-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 563 | 4.7 |
| 7 | methyl (4-(((S)-1-((R)-6-chloro-5-fluoro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 581 | 4.44 |
| 8a Isomer A | methyl (4-(((S)-1-((R)-6-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 560.5 | 12.8 |
| 8b Isomer B | methyl (4-(((S)-1-((S)-6-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 560.6 | 5000 |
| 9 | methyl (4-(((S)-1-((R)-6-methoxy-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 573.6 | 2.0 |
| 10 | methyl (4-(((S)-1-oxo-1-((R)-2-oxo-6-(trifluoromethyl)-1,2-dihydrospiro[benzo[d][1,3]oxazine-4,3'-piperidin]-1'-yl)-3-phenylpropan-2-yl)carbamoyl)phenyl)carbamate | 611.5 | 8439 |
| 11 | methyl (4-(((S)-1-((R)-6-chloro-5,7-difluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 614.0 | 51.0 |
| 12 | methyl (4-(((S)-1-((R)-6-chloro-8-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 596.0 | 109 |
| 13 | methyl (4-(((2S)-1-(6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 596 | 1.8 |

Example 14

Methyl (4-(((2S)-1-(6-methyl-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate

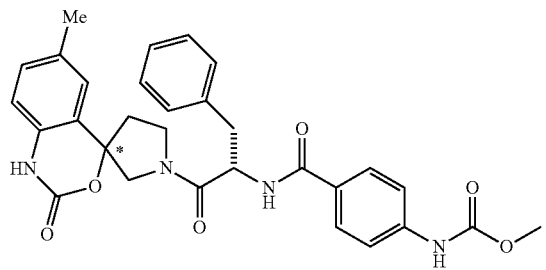 [SMILES: COC(=O)Nc1ccc(C(=O)N[C@@H](Cc2ccccc2)C(=O)N2CCC3(CC(=O)Nc4ccc(Cl)cc43)C2)cc1]

Ex-14b and Ex-14b

Step A: Tert-butyl 6-chloro-2-oxo-1,2-dihydrospiro[benzo[d][1,3]oxazine-4,3'-pyrrolidine]-1'-carboxylate To a stirred solution of tert-butyl 2-oxo-1,2-dihydrospiro[benzo[d][1,3]oxazine-4,3'-pyrrolidine]-1'-carboxylate (5.87 g, 19.29 mmol) in DMF (129 mL) was added NCS (2.83 g, 21.22 mmol) at RT. The reaction mixture was stirred at RT overnight. The reaction mixture was diluted with sat. NaHCO₃ (aq) and EtOAc. The organic layer was washed with brine, dried over MgSO₄, filtered and concentrated in vacuo. The crude product was purified by flash silica gel column chromatography (1/1=EtOAc/Hex) to afford tert-butyl 6-chloro-2-oxo-1,2-dihydrospiro[benzo[d][1,3]oxazine-4,3'-pyrrolidine]-1'-carboxylate. LC/MS=283 [M−55].

Step B: Tert-butyl 6-methyl-2-oxo-1,2-dihydrospiro[benzo[d][1,3]oxazine-4,3'-pyrrolidine]-1'-carboxylate To a stirred solution of tert-butyl 6-chloro-2-oxo-1,2-dihydrospiro[benzo[d][1,3]oxazine-4,3'-pyrrolidine]-1'-carboxylate (500 mg, 1.476 mmol) in THF (7379 µL) was added bis(tri-tert-buthylphosphine)palladium(0) (75 mg, 0.148 mmol) and methylzinc chloride (3.7 mL, 7.38 mmol) at 0° C. The reaction mixture was warmed to RT for 3 hrs and then the reaction mixture was heated to 50° C. overnight. The reaction mixture was diluted with EtOAc and the organic layer was washed with sat. NaHCO₃ (aq) and brine, dried over MgSO₄, filtered and concentrated in vacuo. The crude product was purified by flash silica gel column chromatography (1/1=EtOAc/Hex) to afford tert-butyl 6-methyl-2-oxo-1,2-dihydrospiro[benzo[d][1,3]oxazine-4,3'-pyrrolidine]-1'-carboxylate. LC/MS=263 [M−55].

Step C: 6-Methylspiro[benzo[d][1,3]oxazine-4,3'-pyrrolidin]-2(1H)-one hydrochloride To a round bottom flask charged with tert-butyl 6-methyl-2-oxo-1,2-dihydrospiro[benzo[d][1,3]oxazine-4,3'-pyrrolidine]-1'-carboxylate (330 mg, 1.037 mmol) was added 4N HCl in 1,4-dioxame (2.6 mL, 10.37 mmol) at RT. The reaction mixture was stirred at RT for 2 hrs. The reaction mixture was concentrated by a rotary evaporator. The crude product was dried over vac. oven overnight and used for the next step without further purification. LC/MS=219 [M+1]

Step D: Tert-butyl ((2S)-1-(6-methyl-2-oxo-1,2-dihydrospiro[benzo[d][1,3]oxazine-4,3'-pyrrolidin]-1'-yl)-1-oxo-3-phenylpropan-2-yl)carbamate To a stirred solution of 6-Methylspiro[benzo[d][1,3]oxazine-4,3'-pyrrolidin]-2(1H)-one hydrochloride (89 mg, 0.349 mmol) in DMF (1747 µl) was added (S)-2-((tert-butoxycarbonyl)amino)-3-phenylpropanoic acid (185 mg, 0.699 mmol), HATU (266 mg, 0.699 mmol) and DIPEA (244 µl, 1.398 mmol) at RT. The reaction mixture was stirred at RT for 5 hrs. The reaction mixture was diluted with sat. NaHCO₃ (aq) and EtOAc. The organic layer was washed with brine, dried over MgSO₄, filtered and concentrated in vacuo. The crude product was purified by flash silica gel column chromatography (1/1=EtOAc/Hex) to give tert-butyl ((2S)-1-(6-methyl-2-oxo-1,2-dihydrospiro[benzo[d][1,3]oxazine-4,3'-pyrrolidin]-1'-yl)-1-oxo-3-phenylpropan-2-yl)carbamate. LC/MS=366 [M–100]

Step E: 1'-((S)-2-Amino-3-phenylpropanoyl)-6-methylspiro[benzo[d][1,3]oxazine-4,3'-pyrrolidin]-2(1H)-one hydrochloride To a round bottom flask charged with tert-butyl ((2S)-1-(6-methyl-2-oxo-1,2-dihydrospiro[benzo[d][1,3]oxazine-4,3'-pyrrolidin]-1'-yl)-1-oxo-3-phenylpropan-2-yl)carbamate (150 mg, 0.322 mmol) was added 4N HCl in 1,4-dioxane (0.806 ml, 3.22 mmol) at RT. The reaction mixture was stirred for 5 hr at RT. The reaction mixture was concentrated by a rotary evaporator. The crude product was dried over vac. oven overnight and used for the next step without further purification. LC/MS=366 [M+1]

Step F: Methyl (4-(((2S)-1-(6-methyl-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate To a stirred solution of 1'-((S)-2-Amino-3-phenylpropanoyl)-6-methylspiro[benzo[d][1,3]oxazine-4,3'-pyrrolidin]-2(1H)-one hydrochloride (129 mg, 0.321 mmol) was added 4-((methoxycarbonyl)amino)benzoic acid (125 mg, 0.642 mmol), HATU (244 mg, 0.642 mmol) and DIPEA (224 µl, 1.284 mmol) at RT. The reaction mixture was stirred at RT overnight. The reaction mixture was diluted with sat. NaHCO₃ (aq) and EtOAc. The organic layer was washed with brine and dried over MgSO₄, filtered and concentrated in vacuo. The crude product was purified by flash silica gel column chromatography (0-100% EtOAc in hexames) to afford Methyl (4-(((2S)-1-(6-methyl-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate (Ex-14). LC/MS=542 [M+1]. The mixture of the two stereoisomers was purified by chiral SFC (AS-H column, 30% MeOH (0.2% DEA)/CO₂) to afford Ex-14a (faster eluting) and Ex-14b (slower eluting):

By using procedures silimiar to those described above with appropriate starting materials, the following compounds were synthesized. These compounds were characterized by LC/MS.

| Example | Structure | LCMS [M + 1] | FXIa Ki (nM) |
|---|---|---|---|
| 14a (isomer A) | methyl (4-(((S)-1-((S)-6-methyl-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 542 | 5000 |
| 14b (isomer B) | methyl (4-(((S)-1-((R)-6-methyl-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 542 | 9.5 |
| 15 | methyl (4-(((S)-1-((R)-6-methyl-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 557.6 | 5.5 |
| 16 | methyl (4-(((S)-1-((R)-5-fluoro-6-methyl-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 575.6 | 3.85 |
| 17 | methyl (4-(((S)-1-((R)-6-cyclopropyl-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 601.6 | 37.4 |

Example 18

Methyl (4-(((2S)-1-(6'-chloro-2'-oxo-2',3'-dihydro-1'H-spiro[pyrrolidine-3,4'-quinolin]-1-yl)-1-oxo-3-phenylpropan-2-yl)carbamoyl)phenyl)carbamate

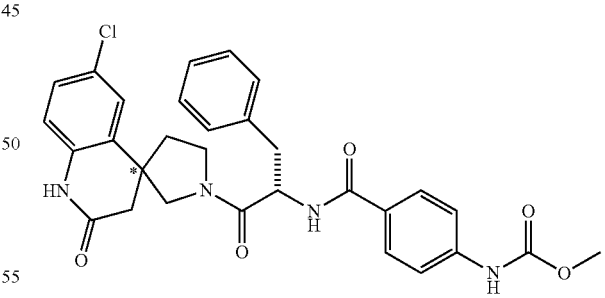

tert-butyl 6-chloro-2,3-dihydrospiro[indene-1,3'-pyrrolidine]-1'-carboxylate tert-butyl 6-chloro-2,3-dihydrospiro[indene-1,3'-pyrrolidine]-1'-carboxylate was prepared by using a procedure described in WO2007125061.

Step A: Tert-butyl 6-chloro-3-oxo-2,3-dihydrospiro[indene-1,3'-pyrrolidine]-1'-carboxylate To a stirred solution of tert-butyl 6-chloro-2,3-dihydrospiro[indene-1,3'-pyrrolidine]-1'-carboxylate (139 mg, 0.45 mmol) in acetone (2.0 mL) were added MgSO$_4$ (0.40 ml, 0.60 mmol) (1.5 M in H$_2$O) and KMnO$_4$ (164 mg, 1.04 mmol) and the resulting mixture was stirred at RT for 18 hrs. Acetone was removed in vacuo and the resulting aqueous layer was diluted with DCM (50 mL). The resulting mixture was stirred for 10 min, filtered, and the filtrate was concentrated in vacuo. The crude product was purified by flash silica gel column chromatography (0 to 50% EtOAc in Hexanes) to afford tert-butyl 6-chloro-3-oxo-2,3-dihydrospiro[indene-1,3'-pyrrolidine]-1'-carboxylate. LC/MS=322 [M+1].

Step B: Tert-butyl 6'-chloro-2'-oxo-2',3'-dihydro-1'H-spiro[pyrrolidine-3,4'-quinoline]-1-carboxylate To a stirred solution of tert-butyl 6-chloro-3-oxo-2,3-dihydrospiro[indene-1,3'-pyrrolidine]-1'-carboxylate (49.0 mg, 0.15 mmol) in EtOH (0.5 mL) were added hydroxylamine hydrochloride (21.2 mg, 0.30 mmol) and NaOAc (22.5 mg, 0.27 mmol) at RT under nitrogen atmosphere. The resulting mixture was refluxed for 1.5 hrs and cooled to RT. The reaction mixture was concentrated in vacuo. The resulting residue was diluted with H$_2$O (10 mL) and the mixture was extracted with DCM (50 mL). The organic layer was dried over Na$_2$SO$_4$, filtered and concentrated in vacuo. The crude product was purified by flash ODS column chromatography (10-100% CH$_3$CN in H$_2$O) to afford tert-butyl 6'-chloro-2'-oxo-2',3'-dihydro-1'H-spiro[pyrrolidine-3,4'-quinoline]-1-carboxylate. LC/MS=337 [M+1].

Step C: 6'-chloro-1'H-spiro[pyrrolidine-3,4'-quinolin]-2'(3'H)-one hydrochloride To a round bottom flask charged with tert-butyl 6'-chloro-2'-oxo-2',3'-dihydro-1'H-spiro[pyrrolidine-3,4'-quinoline]-1-carboxylate (25.6 mg, 0.08 mmol) was added 4N HCl in 1,4-dioxane (0.8 mL, 3.20 mmol) at RT under nitrogen atmosphere and the resulting mixture was stirred at RT for 4 hrs. The reaction mixture was concentrated, dried, and used for the next step without further purification. LC/MS=237 [M+1].

Step D: Tert-butyl ((2S)-1-(6'-chloro-2'-oxo-2',3'-dihydro-1'H-spiro[pyrrolidine-3,4'-quinolin]-1-yl)-1-oxo-3-phenylpropan-2-yl)carbamate To a stirred solution of 6'-chloro-1'H-spiro[pyrrolidine-3,4'-quinolin]-2'(3'H)-one hydrochloride (21.3 mg, 0.08 mmol) in DMF (0.8 mL) were added (S)-2-((tert-butoxycarbonyl)amino)-3-phenylpropanoic acid (31.0 mg, 0.12 mmol), EDC.HCl (22.4 mg, 0.12 mmol), HOBT (16.0 mg, 0.12 mmol) and DIPEA (70.0 µl, 0.37 mmol) at RT under nitrogen atmosphere. The resulting mixture was stirred at RT for 17 hrs and concentrated in vacuo. The crude product was purified by flash silica gel column chromatography (0-10% MeOH in DCM) followed by flash ODS column chromatography (10-100% CH$_3$CN in H$_2$O) to afford tert-butyl ((2S)-1-(6'-chloro-2'-oxo-2',3'-dihydro-1'H-spiro[pyrrolidine-3,4'-quinolin]-1-yl)-1-oxo-3-phenylpropan-2-yl)carbamate. LC/MS=484 [M+1].

Step E: 1-((S)-2-amino-3-phenylpropanoyl)-6'-chloro-1'H-spiro[pyrrolidine-3,4'-quinolin]-2'(3'H)-one hydrochloride To a round bottom flask charged with tert-butyl ((2S)-1-(6'-chloro-2'-oxo-2',3'-dihydro-1'H-spiro[pyrrolidine-3,4'-quinolin]-1-yl)-1-oxo-3-phenylpropan-2-yl)carbamate (15.7 mg, 0.03 mmol) was added 4N HCl in 1,4-dioxane (1.00 mL, 4.00 mmol) at RT under nitrogen atmosphere and the resulting mixture was stirred at RT for 4 hrs. The reaction mixture was concentrated, dried, and used for the next step without further purification. LC/MS=384 [M+1].

Step F: Methyl (4-(((2S)-1-(6'-chloro-2'-oxo-2',3'-dihydro-1'H-spiro[pyrrolidine-3,4'-quinolin]-1-yl)-1-oxo-3-phenylpropan-2-yl)carbamoyl)phenyl)carbamate To a stirred solution of 1-((S)-2-amino-3-phenylpropanoyl)-6'-chloro-1'H-spiro[pyrrolidine-3,4'-quinolin]-2'(3'H)-one hydrochloride (14.1 mg, 0.03 mmol) in DMF (0.5 mL) were added 4-((methoxycarbonyl)amino)benzoic acid (10.0 mg, 0.05 mmol), EDC.HCl (10.0 mg, 0.05 mmol), HOBT (8.0 mg, 0.05 mmol) and DIPEA (30 µl, 0.16 mmol) at RT under nitrogen atmosphere. The resulting mixture was stirred at RT for 17 hrs and concentrated in vacuo. The crude product was purified by flash silica gel column chromatography (0-10% MeOH in DCM) followed by flash OBS column chromatography (10-100% CH$_3$CN in H$_2$O) to afford methyl (4-(((2S)-1-(6'-chloro-2'-oxo-2',3'-dihydro-1'H-spiro[pyrrolidine-3,4'-quinolin]-1-yl)-1-oxo-3-phenylpropan-2-yl)carbamoyl)phenyl)carbamate (Ex-18). LC/MS=561 [M+1].

| Example | Structure | LCMS [M + 1] | FXIa Ki (nM) |
|---|---|---|---|
| 18 (racemate) | methyl (4-(((2S)-1-(6'-chloro-2'-oxo-2',3'-dihydro-1'H-spiro[pyrrolidine-3,4'-quinolin]-1-yl)-1-oxo-3-phenylpropan-2-yl)carbamoyl)phenyl)carbamate | 561 | 5000 |

Example 19

Methyl (4-(((2S)-1-(6'-chloro-2'-oxo-2',3'-dihydro-1'H-spiro[pyrrolidine-3,4'-quinazolin]-1-yl)-1-oxo-3-phenylpropan-2-yl)carbamoyl)phenyl)carbamate

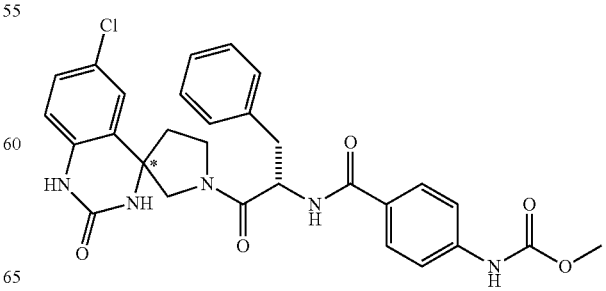

Step A: Ethyl 2-(2-nitrophenyl)acrylate

To a stirred solution of ethyl 2-(2-nitrophenyl)acetate (500 mg, 2.39 mmol) in toluene (3.1 ml) was added paraformaldehyde (200 mg, 6.69 mmol), nBu$_4$NI (17.0 mg, 0.05 mmol) and K$_2$CO$_3$ (990 mg, 7.17 mmol) at RT under nitrogen atmosphere. The resulting mixture was stirred at 80° C. for 16 hrs. After it cooled down to RT, the reaction mixture was diluted with EtOAc. The organic layer was washed with water, brine, dried over Na$_2$SO$_4$, filtered and concentrated in vacuo. The crude product was purified by flash silica gel column chromatography (0-8% EtOAc in Hexanes) to afford ethyl 2-(2-nitrophenyl)acrylate. LC/MS=222 [M+1].

Step B: Ethyl 1-benzyl-3-(2-nitrophenyl)pyrrolidine-3-carboxylate

To a stirred solution of ethyl 2-(2-nitrophenyl)acrylate (208 mg, 0.94 mmol) in THF (1.5 mL) was added N-(methoxymethyl)-N-(trimethylsilylmethyl)benzylamine (360 µL, 1.41 mmol) and TFA (7 µL, 0.09 mmol) at 0° C. under nitrogen atmosphere. The resulting mixture was stirred at 0° C. for 1 hr and at RT for 1.5 hrs. The reaction mixture was concentrated in vacuo. The crude product was purified by flash silica gel column chromatography (0-10% EtOAc in Hexanes) to afford ethyl 1-benzyl-3-(2-nitrophenyl)pyrrolidine-3-carboxylate. LC/MS=355 [M+1].

Step C: 1-benzyl-3-(2-nitrophenyl)pyrrolidine-3-carboxylic acid

To a stirred solution of ethyl 1-benzyl-3-(2-nitrophenyl)pyrrolidine-3-carboxylate (3.31 g, 9.34 mmol) in MeOH/H$_2$O (1:1, 30 mL) was added KOH (5.24 g, 80.1 mmol) at RT. The reaction mixture was stirred at 110° C. for 9 hrs. MeOH was removed in vacuo. The resulting aqueous layer was acidified to pH 3 and extracted with CH$_2$Cl$_2$. The organic layer was dried over Na$_2$SO$_4$, filtered and concentrated in vacuo. The crude product was purified by flash silica gel column chromatography (0-6% MeOH in CH$_2$Cl$_2$) to afford 1-benzyl-3-(2-nitrophenyl)pyrrolidine-3-carboxylic acid. LC/MS=327 [M+1].

Step D: (1-benzyl-3-(2-nitrophenyl)pyrrolidin-3-yl) carbamoyl azide

To a stirred solution of 1-benzyl-3-(2-nitrophenyl)pyrrolidine-3-carboxylic acid (1.0 g, 3.06 mmol) in CH$_2$Cl$_2$ (40 mL) was added DPPA (1.65 mL, 7.66 mmol) and triethylamine (555 µL, 3.98 mmol) at 0° C. under nitrogen atmosphere. The resulting mixture was stirred at RT for 16 hrs. The reaction mixture was concentrated in vacuo. The crude product was dissolved in toluene (40 mL) and refluxed for 4 hrs. The reaction mixture was concentrated in vacuo. The crude product was used for the next step without further purification. LC/MS=367 [M+1].

Step E: 1-benzyl-1'H-spiro[pyrrolidine-3,4'-quinazolin]-2'(3'H)-one

To a stirred solution of (1-benzyl-3-(2-nitrophenyl)pyrrolidin-3-yl)carbamoyl azide (1.12 g, 3.06 mmol) in EtOH/H$_2$O (4:1, 20 mL) was added Fe powder (1.87 g, 33.6 mmol) and concentrated HCl (aq) (2.51 mL, 30.1 mmol). The resulting mixture was stirred at 75° C. for 1 hr in a sealed tube. EtOH was removed in vacuo. The resulting aqueous layer was basified to pH 8 with sat. NaHCO$_3$ (aq) and extracted with EtOAc. The combined organic layers were washed with brine, dried over Na$_2$SO$_4$, filtered and concentrated in vacuo. The crude product was purified by flash silica gel column chromatography (0-3% MeOH in CH$_2$Cl$_2$) to afford 1-benzyl-1'H-spiro[pyrrolidine-3,4'-quinazolin]-2'(3'H)-one. LC/MS=294 [M+1].

Step F: 1'H-spiro[pyrrolidine-3,4'-quinazolin]-2'(3'H)-one

To a stirred solution of 1-benzyl-1'H-spiro[pyrrolidine-3,4'-quinazolin]-2'(3'H)-one (291 mg, 0.99 mmol) in EtOH (5.0 mL) was added Pd(OH)$_2$ (41.8 mg, 0.30 mmol) at RT under nitrogen atmosphere. The resulting mixture was stirred at RT for 44 hrs under hydrogen atmosphere (balloon). The reaction mixture was filtered and the filtrate was concentrated in vacuo. The crude product was used for the next step without further purification. LC/MS=204 [M+1].

Step G: Tert-butyl 2'-oxo-2',3'-dihydro-1'H-spiro[pyrrolidine-3,4'-quinazoline]-1-carboxylate To a stirred solution of 1'H-spiro[pyrrolidine-3,4'-quinazolin]-2'(3'H)-one (172 mg, 0.85 mmol) in MeOH (1.7 mL) was added di-tert-butyl dicarbonate (240 mg, 1.10 mmol) and triethylamine (176 µL, 1.27 mmol) at RT under nitrogen atmosphere. The resulting mixture was stirred at RT for 16 hrs. The reaction mixture was concentrated in vacuo. The crude product was purified by flash ODS column chromatography (0-55% CH$_3$CN in H$_2$O) to afford tert-butyl 2'-oxo-2',3'-dihydro-1'H-spiro[pyrrolidine-3,4'-quinazoline]-1-carboxylate. $^1$H NMR (400 MHz, CDCl$_3$) δ 7.73 (br s, 1H), 7.22 (td, 1H, J=7.5, 1.1 Hz), 7.15 (br d, 1H, J=7.5 Hz), 7.01 (td, 1H, J=7.5, 1.1 Hz), 6.76 (dd, 1H, J=7.5, 1.1 Hz), 5.59 (br s, 0.6H), 5.46 (br s, 0.4H), 3.82-3.50 (m, 4H), 2.42-2.15 (m, 2H), 1.48 (br s, 9H).

Step H: Tert-butyl 6'-chloro-2'-oxo-2',3'-dihydro-1'H-spiro[pyrrolidine-3,4'-quinazoline]-1-carboxylate To a stirred solution of tert-butyl 2'-oxo-2',3'-dihydro-1'H-spiro[pyrrolidine-3,4'-quinazoline]-1-carboxylate (183 mg, 0.60 mmol) in DMF (2.0 mL) was added NCS (80.5 mg, 0.60 mmol) at RT under nitrogen atmosphere. The resulting mixture was stirred at RT for 16 hrs and concentrated in vacuo. The crude product was purified by flash silica gel column chromatography (0-30% acetone in CH$_2$Cl$_2$) to afford tert-butyl 6'-chloro-2'-oxo-2',3'-dihydro-1'H-spiro[pyrrolidine-3,4'-quinazoline]-1-carboxylate. $^1$H NMR (400 MHz, CDCl$_3$) δ 7.95 (br s, 1H), 7.19 (dd, 1H, J=8.5, 2.0 Hz), 7.12 (br d, 1H, J=2.0 Hz), 6.71 (d, 1H, J=8.5 Hz), 5.67 (br s, 0.6H), 5.49 (br s, 0.4H), 3.76-3.50 (m, 4H), 2.37-2.18 (m, 2H), 1.48 (br s, 9H).

Step I: 6'-chloro-1'H-spiro[pyrrolidine-3,4'-quinazolin]-2'(3'H)-one hydrochloride To a round bottom flask charged with tert-butyl 6'-chloro-2'-oxo-2',3'-dihydro-1'H-spiro[pyrrolidine-3,4'-quinazoline]-1-carboxylate (100 mg, 0.30 mmol) was added 4N HCl in 1,4-dioxane (3.1 ml, 12.4 mmol) at RT under nitrogen atmosphere and the resulting mixture was stirred at RT for 2 hrs. The reaction mixture was concentrated in vacuo. The crude product was dried under high vacuum and used for the next step without further purification. LC/MS=238 [M+1].

Step J: Tert-butyl ((2S)-1-(6'-chloro-2'-oxo-2',3'-dihydro-1'H-spiro[pyrrolidine-3,4'-quinazolin]-1-yl)-1-oxo-3-phenylpropan-2-yl)carbamate To a stirred solution of 6'-chloro-1'H-spiro[pyrrolidine-3,4'-quinazolin]-2'(3'H)-one hydrochloride (81.1 mg, 0.30 mmol) in DMF (1.0 mL) were added (S)-2-((tert-butoxycarbonyl)amino)-3-phenylpropanoic acid (117 mg, 0.44 mmol), EDC.HCl (85.0 mg, 0.44 mmol), HOBT (59.0 mg, 0.44 mmol) and DIPEA (257 µl, 1.48 mmol) at RT under nitrogen atmosphere. The resulting mixture was stirred at RT for 16 hrs. The reaction mixture was quenched with water and the resulting solid was collected by filtration. The crude product was purified by flash ODS column chromatography (0-40% $CH_3CN$ in $H_2O$) to afford tert-butyl ((2S)-1-(6'-chloro-2'-oxo-2',3'-dihydro-1'H-spiro[pyrrolidine-3,4'-quinazolin]-1-yl)-1-oxo-3-phenylpropan-2-yl)carbamate. LC/MS=485 [M+1].

Step K: 1-((S)-2-amino-3-phenylpropanoyl)-6'-chloro-1'H-spiro[pyrrolidine-3,4'-quinazolin]-2'(3'H)-one hydrochloride To a round bottom flask charged with tert-butyl ((2S)-1-(6'-chloro-2'-oxo-2',3'-dihydro-1'H-spiro[pyrrolidine-3,4'-quinazolin]-1-yl)-1-oxo-3-phenylpropan-2-yl)carbamate (96.0 mg, 0.20 mmol) was added 4N HCl in 1,4-dioxane (3.0 ml, 12.0 mmol) at RT under nitrogen atmosphere and the resulting mixture was stirred at RT for 2 hrs. The reaction mixture was concentrated in vacuo. The crude product was dried under high vacuum and used for the next step without further purification. LC/MS=385 [M+1].

Step L: methyl (4-(((2S)-1-(6'-chloro-2'-oxo-2',3'-dihydro-1'H-spiro[pyrrolidine-3,4'-quinazolin]-1-yl)-1-oxo-3-phenylpropan-2-yl)carbamoyl)phenyl)carbamate To a stirred solution of 1-((S)-2-amino-3-phenylpropanoyl)-6'-chloro-1'H-spiro[pyrrolidine-3,4'-quinazolin]-2'(3'H)-one hydrochloride (83.4 mg, 0.20 mmol) in DMF (2.0 mL) were added 4-((methoxycarbonyl)amino)benzoic acid (57.9 mg, 0.30 mmol), EDC.HCl (56.9 mg, 0.30 mmol), HOBT (40.1 mg, 0.30 mmol) and DIPEA (206 µl, 1.19 mmol) at RT under nitrogen atmosphere. The reaction mixture was stirred at RT for 16 hrs and concentrated in vacuo. The crude product was purified by flash ODS column chromatography (0-50% $CH_3CN$ in $H_2O$) to afford methyl (4-(((2S)-1-(6'-chloro-2'-oxo-2',3'-dihydro-1'H-spiro[pyrrolidine-3,4'-quinazolin]-1-yl)-1-oxo-3-phenylpropan-2-yl)carbamoyl)phenyl)carbamate (Ex-19). LC/MS=562 [M+1]. The mixture of the two stereoisomers was purified by chiral SFC (AS-H column, 30% MeOH (0.2% DEA)/$CO_2$) to afford Ex-19a (fastereluting) and Ex-19b (slower eluting):

| Example | Structure | LCMS [M + 1] | FXIa Ki (nM) |
|---|---|---|---|
| 19a (Isomer B) | methyl (4-(((2S)-1-(6'-chloro-2'-oxo-2',3'-dihydro-1'H-spiro[pyrrolidine-3,4'-quinazolin]-1-yl)-1-oxo-3-phenylpropan-2-yl)carbamoyl)phenyl)carbamate | 562 | 5000 |
| 19b (Isomer A) | methyl (4-(((2S)-1-(6'-chloro-2'-oxo-2',3'-dihydro-1'H-spiro[pyrrolidine-3,4'-quinazolin]-1-yl)-1-oxo-3-phenylpropan-2-yl)carbamoyl)phenyl)carbamate | 562 | 708 |

Intermediate 1 for Example 20

Methyl (4-(((2S)-1-(5-chloro-2-oxospiro[indoline-3,3'-pyrrolidin]-1'-yl)-3-cyclopropyl-1-oxopropan-2-yl)carbamoyl)phenyl)carbamate

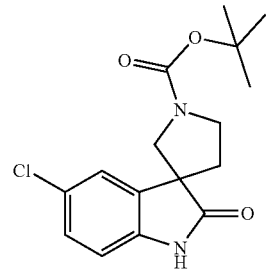 [SMILES: CC(C)(C)OC(=O)N1CCC2(C1)C(=O)Nc1ccc(Cl)cc12]

Step A: tert-butyl 5-chloro-2-oxospiro[indoline-3,3'-pyrrolidine]-1'-carboxylate To a stirred solution tert-butyl 2-oxospiro[indoline-3,3'-pyrrolidine]-1'-carboxylate (800 mg, 2.77 mmol) in dichloromethane (40 mL) and DMF (4 mL) was added N-chlorosuccinimide and the mixture was allowed to stir at room temperature overnight. Aqueous $NaHCO_3$ was added and the mixture was extracted with EtOAc. The organic layer was washed with brine, dried over $MgSO_4$, filtered and concentrated. The crude product was purified by ISCO (40 g, EtOAc/Hex=1/1) to give tert-butyl 5-chloro-2-oxospiro[indoline-3,3'-pyrrolidine]-1'-carboxylate. [M+1]=324.

| Example | Structure | LCMS [M + 1] | FXIa Ki (nM) |
|---|---|---|---|
| 20A (isomer A) | methyl (4-(((2S)-1-(5-chloro-2-oxospiro[indoline-3,3'-pyrrolidin]-1'-yl)-3-cyclopropyl-1-oxopropan-2-yl)carbamoyl)phenyl)carbamate | 511.9 | 8750 |
| 20B (isomer B) | methyl (4-(((2S)-1-(5-chloro-2-oxospiro[indoline-3,3'-pyrrolidin]-1'-yl)-3-cyclopropyl-1-oxopropan-2-yl)carbamoyl)phenyl)carbamate | 511.9 | 539 |

Example 21

Methyl (4-(((2S)-1-(6-chloro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate

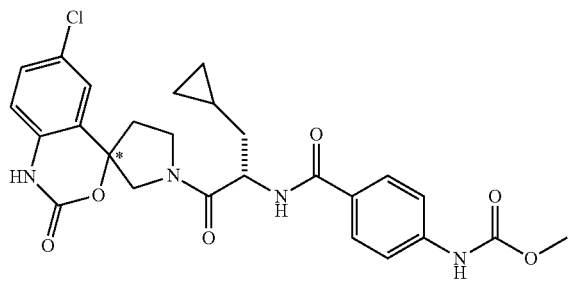

Ex-21a and Ex-21b

Step A: Tert-butyl ((2S)-1-(6-chloro-2-oxo-1,2-dihydrospiro[benzo[d][1,3]oxazine-4,3'-pyrrolidin]-1'-yl)-3-cyclopropyl-1-oxopropan-2-yl)carbamate To a stirred solution of 6-chlorospiro[benzo[d][1,3]oxazine-4,3'-pyrrolidin]-2(1H)-one hydrochloride (487 mg, 1.77 mmol) in DMF (8.8 mL) was added to (S)-2-((tert-butoxycarbonyl)amino)-3-cyclopropylpropanoic acid (812 mg, 3.54 mmol), HATU (1346 mg, 3.54 mmol) and DIPEA (1237 µl, 7.08 mmol) at RT. The reaction mixture was stirred at RT overnight. The reaction mixture was diluted with sat. NaHCO₃ (aq) and EtOAc. The organic layer was washed with brine, dried over MgSO₄, filtered and concentrated in vacuo. The crude product was purified by flash silica gel column chromatography (1/1=EtOAc/Hex) to give tert-butyl ((2S)-1-(6-chloro-2-oxo-1,2-dihydrospiro[benzo[d][1,3]oxazine-4,3'-pyrrolidin]-1'-yl)-3-cyclopropyl-1-oxopropan-2-yl)carbamate. LC/MS=450 [M+1]

Step B: 1'-((S)-2-Amino-3-cyclopropylpropanoyl)-6-chlorospiro[benzo[d][1,3]oxazine-4,3'-pyrrolidin]-2(1H)-one hydrochloride To a round bottom flask charged with tert-butyl ((2S)-1-(6-chloro-2-oxo-1,2-dihydrospiro[benzo[d][1,3]oxazine-4, 3'-pyrrolidin]-1'-yl)-3-cyclopropyl-1-oxopropan-2-yl)carbamate (374 mg, 0.831 mmol) was added 4N HCl in 1,4-dioxane (2.494 ml, 9.97 mmol) at RT. The reaction mixture was stirred at RT for 1.5 hrs. The reaction mixture was stirred for 5 hr at RT. The reaction mixture was concentrated by a rotary evaporator. The crude product was dried over vac. oven overnight and used for the next step without further purification. LC/MS=350 [M+1]

Step C: Methyl (4-(((2S)-1-(6-chloro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate To a stirred solution of 1'-((S)-2-Amino-3-cyclopropylpropanoyl)-6-chlorospiro[benzo[d][1,3]oxazine-4,3'-pyrrolidin]-2(1H)-one hydrochloride (263.2 mg, 0.681 mmol) in DMF (6.8 mL) was added added 4-(methoxycarbonyl)amino)benzoic acid (146 mg, 0.750 mmol), HOBT (115 mg, 0.750 mmol), EDC (144 mg, 0.750 mmol) and DIPEA (536 µl, 3.07 mmol) at RT. The reaction mixture was stirred at RT overnight. The reaction mixture was diluted with sat. NaHCO₃ (aq) and EtOAc. The organic layer was washed with brine and dried over MgSO₄, filtered and concentrated in vacuo. The crude product was purified by flash silica gel column chromatography (0-100% EtOAc in hexanes) to afford methyl (4-(((2S)-1-(6-chloro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate. LC/MS=527 [M+1]. The mixture of the two stereoisomers was purified by chiral SFC (AS-H column, 40% 2:1 MeOH/MeCN/CO₂) to afford Ex-21a (faster eluting) and Ex-21b (slower eluting).

By using procedures similar to those previously described and with appropriate starting materials, including appropriate "Boc-protected amino acid" reagents, the following compounds were synthesized. These compounds were characterized by LC/MS.

| Example | Structure | LCMS [M + 1] | FXIa Ki (nM) |
|---|---|---|---|
| 21a (isomer A) | methyl (4-(((S)-1-((S)-6-chloro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate | 527 | 726 |
| 21b (isomer B) | methyl (4-(((S)-1-((R)-6-chloro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate | 527 | 31.2 |
| 22 | methyl (4-(((S)-1-((R)-6-chloro-2-oxo-1,2-dihydrospiro[benzo[d][1,3]oxazine-4,3'-pyrrolidin]-1'-yl)-3-(4-fluorophenyl)-1-oxopropan-2-yl)carbamoyl)phenyl)carbamate | 581 | 5.3 |
| 23 (racemate) | methyl (4-((2-(6-chloro-2-oxo-1,2-dihydrospiro[benzo[d][1,3]oxazine-4,3'-pyrrolidin]-1'-yl)-2-oxoethyl)carbamoyl)phenyl)carbamate | 473 | 248 |
| 24 (racemate) | methyl (4-(((2S)-1-(6-chloro-2-oxo-1,2-dihydrospiro[benzo[d][1,3]oxazine-4,3'-pyrrolidin]-1'-yl)-2-methyl-1-oxo-3-phenylpropan-2-yl)carbamoyl)phenyl)carbamate | 577 | 5000 |
| 25 (racemate) | methyl (4-(((1S,2R)-1-(6-chloro-2-oxo-1,2-dihydrospiro[benzo[d][1,3]oxazine-4,3'-pyrrolidin]-1'-ylcarbonyl)-2-phenylcyclopropyl)carbamoyl)phenyl)carbamate | 575 | 5000 |
| 26 (racemate) | methyl (4-((2-(6-chloro-2-oxo-1,2-dihydrospiro[benzo[d][1,3]oxazine-4,3'-pyrrolidin]-1'- | 575 | 5000 |

| Example | Structure | LCMS [M + 1] | FXIa Ki (nM) |
|---|---|---|---|
| | ylcarbonyl)-2,3-dihydro-1H-inden-2-yl)carbamoyl)phenyl)carbamate | | |
| 27 (racemate) | methyl (4-(((2S)-1-(6-chloro-2-oxo-1,2-dihydrospiro[benzo[d][1,3]oxazine-4,3'-pyrrolidin]-1'-yl)-3-(3,4-difluorophenyl)-1-oxopropan-2-yl)carbamoyl)phenyl)carbamate | 599 | 14.3 |
| 28 (racemate) | methyl (4-((1-(6-chloro-2-oxo-1,2-dihydrospiro[benzo[d][1,3]oxazine-4,3'-pyrrolidin]-1'-yl)-1-oxo-3-(1H-pyrazol-3-yl)propan-2-yl)carbamoyl)phenyl)carbamate | 553 | 63.7 |
| 29 (racemate) | methyl (4-(((1S)-2-(6-chloro-2-oxo-1,2-dihydrospiro[benzo[d][1,3]oxazine-4,3'-pyrrolidin]-1'-yl)-2-oxo-1-phenylethyl)carbamoyl)phenyl)carbamate | 549 | 5000 |
| 30 (racemate) | methyl (4-(((2S)-1-(6-chloro-2-oxo-1,2-dihydrospiro[benzo[d][1,3]oxazine-4,3'-pyrrolidin]-1'-yl)-3-(1-methyl-1H-imidazol-5-yl)-1-oxopropan-2-yl)carbamoyl)phenyl)carbamate | 567 | 17.60 |
| 31 (racemate) | methyl (4-(((2S)-1-(6-chloro-2-oxo-1,2-dihydrospiro[benzo[d][1,3]oxazine-4,3'-pyrrolidin]-1'-yl)-1-oxo-3-(1H-pyrazol-1-yl)propan-2-yl)carbamoyl)phenyl)carbamate | 553 | 26 |
| 32 (racemate) | methyl (4-(((2S)-1-(6-chloro-2-oxo-1,2-dihydrospiro[benzo[d][1,3]oxazine-4,3'-pyrrolidin]-1'-yl)-1-oxo-3-(thiophen-3-yl)propan-2-yl)carbamoyl)phenyl)carbamate | 569 | 16 |
| 33 (racemate) | methyl (4-(((2S,3R)-1-(6-chloro-2-oxo-1,2-dihydrospiro[benzo[d][1,3]oxazine-4,3'-pyrrolidin]-1'-yl)-1-oxo-3-phenylbutan-2-yl)carbamoyl)phenyl)carbamate | 577 | 4313 |
| 34 (racemate) | methyl (4-(((2S)-1-(6-chloro-2-oxo-1,2-dihydrospiro[benzo[d][1,3]oxazine-4,3'-pyrrolidin]-1'-yl)-3-cyclohexyl-1-oxopropan-2-yl)carbamoyl)phenyl)carbamate | 569 | 90 |
| 35 (racemate) | methyl (4-(((2S)-1-(6-chloro-2-oxo-1,2-dihydrospiro[benzo[d][1,3]oxazine-4,3'-pyrrolidin]-1'-yl)-3-(4-hydroxyphenyl)-1-oxopropan-2-yl)carbamoyl)phenyl)carbamate | 579 | 3.28 |
| 36 | methyl (4-(((S)-1-((R)-6-chloro-5-fluoro-2-oxo-1,2-dihydrospiro[benzo[d][1,3]oxazine-4,3'-piperidin]-1'-yl)-5,5,5-trifluoro-1-oxopentan-2-yl)carbamoyl)phenyl)carbamate | 601.14 | 84.41 |
| 37 | methyl (4-(((S)-1-((R)-6-chloro-2-oxo-1,2-dihydrospiro[benzo[d][1,3]oxazine-4,3'-piperidin]-1'-yl)-4-methoxy-1-oxobutan-2-yl)carbamoyl)phenyl)carbamate | 545.17 | 9.21 |
| 38 | methyl (4-(((S)-1-((R)-6-chloro-2-oxo-1,2-dihydrospiro[benzo[d][1,3]oxazine-4,3'-piperidin]-1'-yl)-3-hydroxy-1-oxopropan-2-yl)carbamoyl)phenyl)carbamate | 517.23 | 49.85 |
| 39 | methyl (4-(((2S)-3-(4-benzoylphenyl)-1-(6-chloro-2-oxo-1,2-dihydrospiro[benzo[d][1,3]oxazine-4,3'-pyrrolidin]-1'-yl)-1-oxopropan-2-yl)carbamoyl)phenyl)carbamate | 667.19 | 39.31 |
| 40 | methyl (4-(((2S)-1-(6-chloro-2-oxo-1,2-dihydrospiro[benzo[d][1,3]oxazine-4,3'-pyrrolidin]-1'-yl)-1-oxo-3-(thiazol-4-yl)propan-2-yl)carbamoyl)phenyl)carbamate | 570.11 | 52.40 |
| 41 | methyl (4-(((2R)-2-benzyl-3-(6-chloro-2-oxo-1,2-dihydrospiro[benzo[d][1,3]oxazine-4,3'-pyrrolidin]-1'-yl)-3-oxopropyl)carbamoyl)phenyl)carbamate | 577.18 | >5000 |
| 42 | methyl (4-((1-(6-chloro-2-oxo-1,2-dihydrospiro[benzo[d][1,3]oxazine-4,3'-pyrrolidin]-1'-yl)-3-(1,1-dioxidotetrahydro-2H-thiopyran-4-yl)-1-oxopropan-2-yl)carbamoyl)phenyl)carbamate | 619.16 | 83.55 |
| 43 | methyl (4-(((2S)-1-(6-chloro-2-oxo-1,2-dihydrospiro[benzo[d][1,3]oxazine-4,3'-pyrrolidin]-1'-yl)-3-(3-fluorothiophen-2-yl)-1-oxopropan-2-yl)carbamoyl)phenyl)carbamate | 587.11 | 17.66 |
| 44 | methyl (4-(((2S)-1-(6-chloro-2-oxo-1,2-dihydrospiro[benzo[d][1,3]oxazine-4,3'-pyrrolidin]-1'-yl)-3-(4-(cyclopentyloxy)phenyl)-1-oxopropan-2-yl)carbamoyl)phenyl)carbamate | 647.22 | 70.00 |
| 45 | methyl (4-(((S)-1-((R)-6-chloro-2-oxo-1,2-dihydrospiro[benzo[d][1,3]oxazine-4,3'-piperidin]-1'-yl)-3-(4-cyanophenyl)-1-oxopropan-2-yl)carbamoyl)phenyl)carbamate | 602.3 | 5.55 |
| 46 | methyl (4-(((S)-1-((R)-6-chloro-2-oxo-1,2-dihydrospiro[benzo[d][1,3]oxazine-4,3'-piperidin]-1'-yl)-3-(4-(methylsulfonamido)phenyl)-1-oxopropan-2-yl)carbamoyl)phenyl)carbamate | 670.17 | 0.39 |
| 47 | methyl (4-(((S)-3-(4-carbamoylphenyl)-1-((R)-6-chloro-2-oxo-1,2-dihydrospiro[benzo[d][1,3]oxazine-4,3'-piperidin]-1'-yl)-1-oxopropan-2-yl)carbamoyl)phenyl)carbamate | 620.18 | 0.55 |

-continued

| Example | Structure | LCMS [M + 1] | FXIa Ki (nM) |
|---|---|---|---|
| 48 | methyl (4-(((S)-3-(4-acetamidophenyl)-1-((R)-6-chloro-2-oxo-1,2-dihydrospiro[benzo[d][1,3]oxazine-4,3'-piperidin]-1'-yl)-1-oxopropan-2-yl)carbamoyl)phenyl)carbamate | 634.2 | 2.01 |
| 49 | methyl (4-(((2S)-4-(6-chloro-2-oxo-1,2-dihydrospiro[benzo[d][1,3]oxazine-4,3'-pyrrolidin]-1'-yl)-4-oxo-1-phenylbutan-2-yl)carbamoyl)phenyl)carbamate | 577.18 | 362 |
| 50 | methyl (4-(((2S)-1-(6-chloro-2-oxo-1,2-dihydrospiro[benzo[d][1,3]oxazine-4,3'-pyrrolidin]-1'-yl)-3-(naphthalen-2-yl)-1-oxopropan-2-yl)carbamoyl)phenyl)carbamate | 613.18 | 33.74 |
| 51 | methyl (4-(((2S)-1-(6-chloro-2-oxo-1,2-dihydrospiro[benzo[d][1,3]oxazine-4,3'-pyrrolidin]-1'-yl)-6-hydroxy-1-oxohexan-2-yl)carbamoyl)phenyl)carbamate | 545.17 | 55.70 |
| 52 | methyl (4-(((2S)-1-(6-chloro-2-oxo-1,2-dihydrospiro[benzo[d][1,3]oxazine-4,3'-pyrrolidin]-1'-yl)-1-oxo-4-phenylbutan-2-yl)carbamoyl)phenyl)carbamate | 577.18 | 17.62 |
| 53 | methyl (4-(((S)-1-((R)-6-chloro-2-oxo-1,2-dihydrospiro[benzo[d][1,3]oxazine-4,3'-piperidin]-1'-yl)-3-(1-methyl-1H-imidazol-5-yl)-1-oxopropan-2-yl)carbamoyl)phenyl)carbamate | 581.18 | 15.51 |
| 54 | methyl (4-(((S)-1-((R)-6-chloro-2-oxo-1,2-dihydrospiro[benzo[d][1,3]oxazine-4,3'-piperidin]-1'-yl)-1-oxo-6-(2,2,2-trifluoroacetamido)hexan-2-yl)carbamoyl)phenyl)carbamate | 654.19 | 51.98 |
| 55 | methyl (4-(((S)-1-((R)-6-chloro-2-oxo-1,2-dihydrospiro[benzo[d][1,3]oxazine-4,3'-piperidin]-1'-yl)-1-oxopropan-2-yl)carbamoyl)phenyl)carbamate | 501.15 | 93.19 |
| 56 | methyl (4-(((2S)-1-((R)-6-chloro-2-oxo-1,2-dihydrospiro[benzo[d][1,3]oxazine-4,3'-piperidin]-1'-yl)-4-(methylsulfinyl)-1-oxobutan-2-yl)carbamoyl)phenyl)carbamate | 577.15 | 101.90 |
| 57 | methyl (4-(((S)-1-((R)-6-chloro-2-oxo-1,2-dihydrospiro[benzo[d][1,3]oxazine-4,3'-piperidin]-1'-yl)-4-(methylthio)-1-oxobutan-2-yl)carbamoyl)phenyl)carbamate | 561.15 | 4.90 |
| 58 | methyl (4-(((S)-1-((R)-6-chloro-2-oxo-1,2-dihydrospiro[benzo[d][1,3]oxazine-4,3'-piperidin]-1'-yl)-1-oxo-3-(thiazol-4-yl)propan-2-yl)carbamoyl)phenyl)carbamate | 584.13 | 4.04 |
| 59 | methyl (4-(((S)-1-((R)-6-chloro-2-oxo-1,2-dihydrospiro[benzo[d][1,3]oxazine-4,3'-piperidin]-1'-yl)-4-(methylsulfonyl)-1-oxobutan-2-yl)carbamoyl)phenyl)carbamate | 593.14 | 97.65 |
| 60 | methyl (4-(((S)-1-((R)-6-chloro-2-oxo-1,2-dihydrospiro[benzo[d][1,3]oxazine-4,3'-piperidin]-1'-yl)-4-methyl-1-oxopentan-2-yl)carbamoyl)phenyl)carbamate | 543.19 | 48.89 |
| 61 | methyl (4-(((S)-1-((R)-6-chloro-5-fluoro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate | 545.26 | 12.70 |
| 62 | methyl (4-(((S)-1-((R)-6-chloro-5-fluoro-2-oxo-1,2-dihydrospiro[benzo[d][1,3]oxazine-4,3'-piperidin]-1'-yl)-1-oxo-3-(pyridin-4-yl)propan-2-yl)carbamoyl)phenyl)carbamate | 595.94 | 0.88 |
| 63 | methyl (4-(((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)carbamoyl)phenyl)carbamate | 559.29 | 5.64 |
| 64 | methyl (4-(((S)-1-((R)-6-chloro-2-oxo-1,2-dihydrospiro[benzo[d][1,3]oxazine-4,3'-piperidin]-1'-yl)-4,4,4-trifluoro-1-oxobutan-2-yl)carbamoyl)phenyl)carbamate | 569.9 | 1933 |
| 65 | methyl (4-(((S)-1-((R)-6-chloro-2-oxo-1,2-dihydrospiro[benzo[d][1,3]oxazine-4,3'-piperidin]-1'-yl)-1-oxo-3-(tetrahydro-2H-pyran-4-yl)propan-2-yl)carbamoyl)phenyl)carbamate | 586.0 | 41.5 |
| 66 | methyl (4-(((S)-3-cyclopropyl-1-((R)-6-methyl-2-oxo-1,2-dihydrospiro[benzo[d][1,3]oxazine-4,3'-piperidin]-1'-yl)-1-oxopropan-2-yl)carbamoyl)phenyl)carbamate | 521.5 | 30 |
| 67A (isomer A) | methyl (4-(((2S)-1-((R)-6-chloro-5-fluoro-2-oxo-1,2-dihydrospiro[benzo[d][1,3]oxazine-4,3'-piperidin]-1'-yl)-3-(2,2-difluorocyclopropyl)-1-oxopropan-2-yl)carbamoyl)phenyl)carbamate | 595.9 | 11.6 |
| 67B (isomer B) | methyl (4-(((2S)-1-((R)-6-chloro-5-fluoro-2-oxo-1,2-dihydrospiro[benzo[d][1,3]oxazine-4,3'-piperidin]-1'-yl)-3-(2,2-difluorocyclopropyl)-1-oxopropan-2-yl)carbamoyl)phenyl)carbamate | 595.9 | 7.88 |
| 68 | methyl (4-(((S)-2-((R)-6-chloro-5-fluoro-2-oxo-1,2-dihydrospiro[benzo[d][1,3]oxazine-4,3'-piperidin]-1'-yl)-1-cyclopropyl-2-oxoethyl)carbamoyl)phenyl)carbamate | 545.9 | 56.4 |
| 69 | methyl (4-(((S)-1-((R)-6-chloro-5-fluoro-2-oxo-1,2-dihydrospiro[benzo[d][1,3]oxazine-4,3'-piperidin]-1'-yl)-1- | 647.56 | 36.20 |

| Example | Structure | LCMS [M + 1] | FXIa Ki (nM) |
|---|---|---|---|
| | oxo-3-(quinoxalin-2-yl)propan-2-yl)carbamoyl)phenyl)carbamate | | |
| 70 | methyl (4-(((S)-1-((R)-6-chloro-5-fluoro-2-oxo-1,2-dihydrospiro[benzo[d][1,3]oxazine-4,3'-piperidin]-1'-yl)-3-(1H-indol-3-yl)-1-oxopropan-2-yl)carbamoyl)phenyl)carbamate | 634.56 | 20.69 |
| 71 | methyl (4-(((S)-1-((R)-6-chloro-2-oxo-1,2-dihydrospiro[benzo[d][1,3]oxazine-4,3'-piperidin]-1'-yl)-3-cyclobutyl-1-oxopropan-2-yl)carbamoyl)phenyl)carbamate | 555.55 | 50.95 |
| 72 | methyl (4-(((S)-1-((R)-6-chloro-2-oxo-1,2-dihydrospiro[benzo[d][1,3]oxazine-4,3'-piperidin]-1'-yl)-3-cyclohexyl-1-oxopropan-2-yl)carbamoyl)phenyl)carbamate | 583.55 | 3.58 |
| 73 | methyl (4-(((S)-1-((R)-6-chloro-2-oxo-1,2-dihydrospiro[benzo[d][1,3]oxazine-4,3'-piperidin]-1'-yl)-3-cyclopentyl-1-oxopropan-2-yl)carbamoyl)phenyl)carbamate | 569.57 | 31.96 |

Intermediate 2 for Example 74

Methyl 2-amino-3-(5-fluoropyridin-2-yl)propanoate

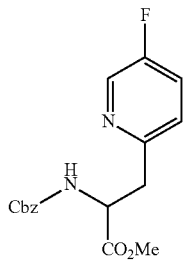 [SMILES: COC(=O)C(Cc1ccc(F)cn1)NC(=O)OCc1ccccc1]

Step A: Synthesis of methyl (Z)-2-(((benzyloxy)carbonyl)amino)-3-(5-fluoropyridin-2-yl)acrylate To a 250 ml round bottom flask containing methyl 2-(((benzyloxy)carbonyl)amino)-2-(dimethoxyphosphoryl)acetate (2.165 g, 6.54 mmol) in tetrahydrofuran (30 ml) was added 1,1,3,3-tetramethylguanidine (0.943 ml, 7.52 mmol) dropwise at −20° C. The reaction mixture was stirred at a temperature below 0° C. for 1 h. After which 5-fluoropicolinaldehyde (0.940 g, 7.52 mmol) in THF was added to the flask and stirred until the completion of the reaction (judged by LCMS). The crude was loaded on 40 g silica column and purified by ISCO using 0-100% EtOAc in hexanes to afford the desired compound.

Step B: Example Synthesis of methyl 2-amino-3-(5-fluoropyridin-2-yl)propanoate

To a 250 ml round bottom flask containing (Z)-methyl 2-(((benzyloxy)carbonyl)amino)-3-(5-fluoropyridin-2-yl)acrylate (2.160 g, 6.54 mmol), in MeOH (20 ml) was added palladium hydroxide on carbon (0.367 g, 0.523 mmol). The system was evacuated and refilled with Hydrogen. The process was repeated two times and the resulting suspension was stirred under an atmosphere of $H_2$ until the completion of the reaction. The solids were filtered out and washed with methanol. The filtrate was concentrated to afford the title compound.

By using procedures similar to those described previously and using appropriate starting materials, the following compounds were synthesized. These compounds were characterized by LC/MS.

| Example | Structure | LCMS [M + 1] | FXIa Ki (nM) |
|---|---|---|---|
| 74 | methyl (4-(((S)-1-((R)-6-chloro-5-fluoro-2-oxo-1,2-dihydrospiro[benzo[d][1,3]oxazine-4,3'-piperidin]-1'-yl)-3-(5-fluoropyridin-2-yl)-1-oxopropan-2-yl)carbamoyl)phenyl)carbamate | 614.31 | 2.82 |
| 75 | methyl (4-(((S)-1-((R)-6-chloro-5-fluoro-2-oxo-1,2-dihydrospiro[benzo[d][1,3]oxazine-4,3'-piperidin]-1'-yl)-3-(5-methoxypyridin-2-yl)-1-oxopropan-2-yl)carbamoyl)phenyl)carbamate | 626.16 | 1.90 |
| 76 | methyl (4-(((S)-1-((R)-6-chloro-5-fluoro-2-oxo-1,2-dihydrospiro[benzo[d][1,3]oxazine-4,3'-piperidin]-1'-yl)-3-(3-fluoropyridin-4-yl)-1-oxopropan-2-yl)carbamoyl)phenyl)carbamate | 614.10 | 1.39 |

Examples 77-83

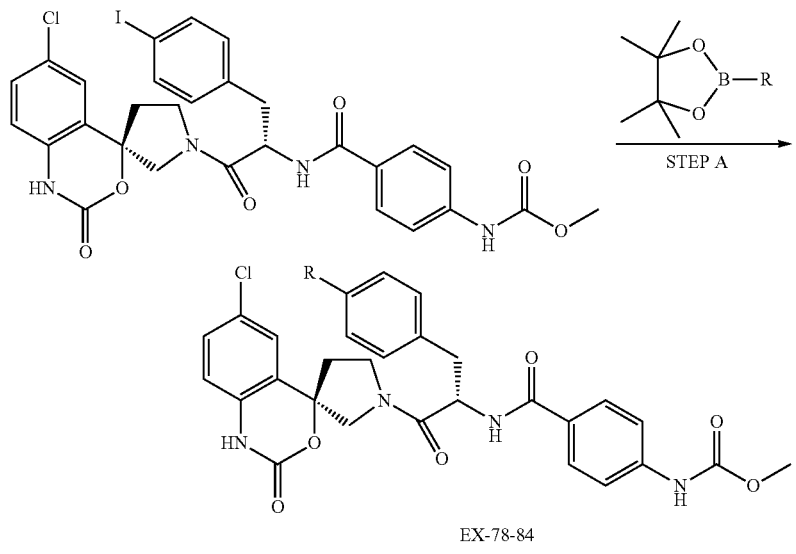

EX-78-84

Step A:

Under an inert $N_2$ atmosphere in a glove box, methyl (4-(((S)-1-((R)-6-chloro-2-oxo-1,2-dihydrospiro[benzo[d][1,3]oxazine-4,3'-pyrrolidin]-1'-yl)-3-(4-iodophenyl)-1-oxopropan-2-yl)carbamoyl)phenyl)carbamate (25 mg, 0.036 mmol) was added, it was degassed, then anhydrous THF (1 ml), boronic acid (0.073 mmol), 2$^{nd}$ generation XPhos precatalyst (3.63 umol) and potassium phosphate 1M aqueous solution (75 μL, 0.075 mmol) were added. It was capped tightly and heated to 60° C. overnight outside the box. The solvent was removed in vacuo. 3 mL EtOAc and 1 mL water were added, and the fractions were extracted 2× with EtOAc. The combined organic layers were put into a 20 mL scintillation vial and silica-DMT Pd scavenging resin was added. The mixture was allowed to mix for 1 hour, then it was filtered through a frit to remove the resin and dried en vacuo. The residue was taken up in DMSO and purified by reverse phase chromatography using a TFA (0.1%) modifier eluting with 20-60% gradient $CH_3CN$/water.

By using procedures similar to those described previously, and using appropriate starting materials, the following compounds were synthesized. These compounds were characterized by LC/MS.

| Example | Structure | LCMS [M + 1] | FXIa Ki (nM) |
|---|---|---|---|
| 77 | methyl (4-(((S)-3-(4-(1H-pyrazol-3-yl)phenyl)-1-((R)-6-chloro-2-oxo-1,2-dihydrospiro[benzo[d][1,3]oxazine-4,3'-pyrrolidin]-1'-yl)-1-oxopropan-2-yl)carbamoyl)phenyl)carbamate | 629.2 | 3.48 |
| 78 | methyl (4-(((S)-3-(4-(1H-pyrazol-4-yl)phenyl)-1-((R)-6-chloro-2-oxo-1,2-dihydrospiro[benzo[d][1,3]oxazine-4,3'-pyrrolidin]-1'-yl)-1-oxopropan-2-yl)carbamoyl)phenyl)carbamate | 629.18 | 2.37 |
| 79 | methyl (4-(((S)-3-(4-(1H-pyrrol-3-yl)phenyl)-1-((R)-6-chloro-2-oxo-1,2-dihydrospiro[benzo[d][1,3]oxazine-4,3'-pyrrolidin]-1'-yl)-1-oxopropan-2-yl)carbamoyl)phenyl)carbamate | 628.13 | 9.98 |
| 80 | methyl (4-(((S)-1-((R)-6-chloro-2-oxo-1,2-dihydrospiro[benzo[d][1,3]oxazine-4,3'-pyrrolidin]-1'-yl)-3-(4-((E)-3-methoxyprop-1-en-1-yl)phenyl)-1-oxopropan-2-yl)carbamoyl)phenyl)carbamate | 633.2 | 75.0 |
| 81 | methyl (4-(((S)-1-((R)-6-chloro-2-oxo-1,2-dihydrospiro[benzo[d][1,3]oxazine-4,3'-pyrrolidin]-1'-yl)-3-(4-(1-methyl-3-(trifluoromethyl)-1H-pyrazol-5-yl)phenyl)-1-oxopropan-2-yl)carbamoyl)phenyl)carbamate | 711.19 | 29.87 |
| 82 | methyl (4-(((S)-1-((R)-6-chloro-2-oxo-1,2-dihydrospiro[benzo[d][1,3]oxazine-4,3'-pyrrolidin]-1'-yl)-3-(4-(3-methylisoxazol-4-yl)phenyl)-1-oxopropan-2-yl)carbamoyl)phenyl)carbamate | 644.18 | 7.12 |
| 83 | methyl (4-(((S)-1-((R)-6-chloro-2-oxo-1,2-dihydrospiro[benzo[d][1,3]oxazine-4,3'-pyrrolidin]-1'-yl)-3-(4-(1-methyl-1H-pyrazol-4-yl)phenyl)-1-oxopropan-2-yl)carbamoyl)phenyl)carbamate | 643.2 | 2.65 |

Example 84

Methyl(4-(((2S)-1-(6-chloro-2-oxo-1,2-dihydrospiro[benzo[d][1,3]oxazine-4,3'-pyrrolidin]-1'-yl)-3-(3-cyclopropylisoxazol-5-yl)-1-oxopropan-2-yl)carbamoyl)phenyl)carbamate

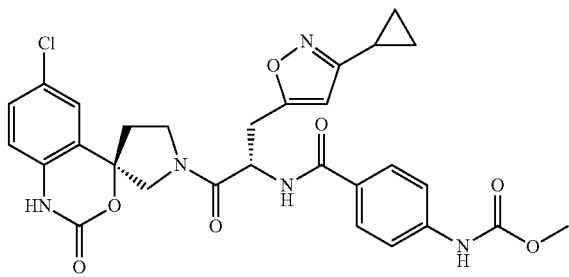 [SMILES: COC(=O)Nc1ccc(C(=O)N[C@@H](Cc2cc(C3CC3)no2)C(=O)N2CC[C@@]3(C2)OC(=O)Nc2ccc(Cl)cc23)cc1]

STEP A: methyl (4-(((2S)-1-(6-chloro-2-oxo-1,2-dihydrospiro[benzo[d][1,3]-oxazine-4,3'-pyrrolidin]-1'-yl)-3-(3-cyclopropylisoxazol-5-yl)-1-oxopropan-2-yl)carbamoyl)phenyl)carbamate Anhydrous DCM (1 ml) was added to methyl (4-(((2S)-1-(6-chloro-2-oxo-1,2-dihydrospiro[benzo[d][1,3]oxazine-4,3'-pyrrolidin]-1'-yl)-1-oxopent-4-yn-2-yl)carbamoyl)phenyl)carbamate (25 mg, 0.049 mmol) and (E)-cyclopropanecarbaldehyde oxime (8.33 mg, 0.098 mmol). The mixture was stirred then cooled in ice to 0° C. Sodium hypochlorite (0.093 ml, 0.196 mmol) was added slowly to the reaction. The reaction was allowed to stir for ~30 min, and then removed the ice bath. After 16 hrs, the solvent was removed and the residue was taken up in DMSO. It was filtered and purified by reverse phase chromatography using an ammonium hydroxide modifier eluting with 20-50% gradient CH₃CN/water to provide methyl (4-(((2S)-1-(6-chloro-2-oxo-1,2-dihydrospiro[benzo[d][1,3]oxazine-4,3'-pyrrolidin]-1'-yl)-3-(3-cyclopropylisoxazol-5-yl)-1-oxopropan-2-yl)carbamoyl)phenyl)carbamate.

| Example | Structure | LCMS [M + 1] | FXIa Ki (nM) |
|---|---|---|---|
| 84 | methyl (4-(((S)-1-((R)-6-chloro-2-oxo-1,2-dihydrospiro[benzo[d][1,3]oxazine-4,3'-pyrrolidin]-1'-yl)-3-(3-cyclopropylisoxazol-5-yl)-1-oxopropan-2-yl)carbamoyl)phenyl)carbamate | 594.17 | 28.15 |

Example 85

Methyl (4-(((S)-1-((R)-6-chloro-2-oxo-1,2-dihydrospiro[benzo[d][1,3]oxazine-4,3'-piperidin]-1'-yl)-4-(3,3-difluoroazetidin-1-yl)-1,4-dioxobutan-2-yl)carbamoyl)phenyl)carbamate

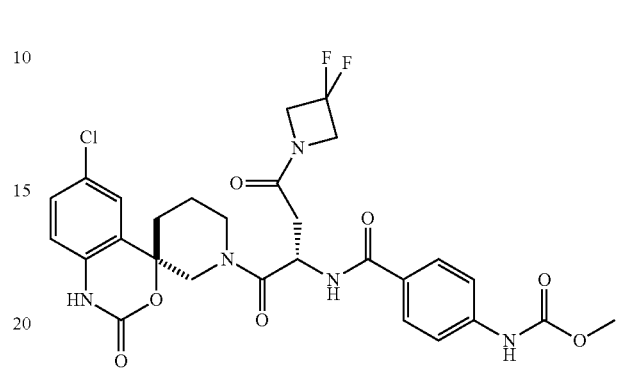

Step A:

Hydrogen chloride (10.63 ml, 42.5 mmol) was added to (R)-tert-butyl 6-chloro-2-oxo-1,2-dihydrospiro[benzo[d][1,3]oxazine-4,3'-piperidine]-1'-carboxylate (1.5 g, 4.25 mmol) in dioxane (2 ml). The reaction mixture was stirred at rt overnight before concentrating under vacuum. (R)-6-chlorospiro[benzo[d][1,3]oxazine-4,3'-piperidin]-2(1H)-one hydrochloride which was used directly in the next step. LCMS: m/z 253 [M+H]⁺.

Step B:

HATU (1.578 g, 4.15 mmol) and (S)-2-((tert-butoxycarbonyl)amino)-4-methoxy-4-oxobutanoic acid (0.855 g, 3.46 mmol), followed by N-ethyl-N-isopropylpropan-2-amine (1.807 ml, 10.37 mmol), were added to (R)-6-chlorospiro[benzo[d][1,3]oxazine-4,3'-piperidin]-2(1H)-one hydrochloride (1.00 g, 3.46 mmol) in DMF (10 ml). The reaction mixture was stirred at rt for 5 min then worked up by adding 50 mL water, extracted 2×50 mL EtOAc. The EtOAc layers were combined and washed 2×50 mL sat. aq. NaCl solution and concentrated. (S)-methyl 3-((tert-butoxycarbonyl)amino)-4-((R)-6-chloro-2-oxo-1,2-dihydrospiro[benzo[d][1,3]oxazine-4,3'-piperidin]-1'-yl)-4-oxobutanoate was used directly in the next step. LCMS: m/z 482.37 [M+H]⁺.

Step C:

Hydrogen chloride (8.04 ml, 32.2 mmol) was added to (S)-methyl 3-((tert-butoxycarbonyl)amino)-4-((R)-6-chloro-2-oxo-1,2-dihydrospiro[benzo[d][1,3]oxazine-4,3'-piperidin]-1'-yl)-4-oxobutanoate (1.55 g, 3.22 mmol) in dioxane (2 ml), and the mixture was stirred overnight at rt. It was concentrated under vacuum. (S)-methyl 3-amino-4-((R)-6-chloro-2-oxo-1,2-dihydrospiro[benzo[d][1,3]oxazine-4,3'-piperidin]-1'-yl)-4-oxobutanoate hydrochloride was used directly in the next step. LCMS: m/z 382.22 [M+H]⁺.

Step D:

HATU (1.091 g, 2.87 mmol) and 4-((methoxycarbonyl)amino)benzoic acid (0.467 g, 2.391 mmol), followed by N-ethyl-N-isopropylpropan-2-amine (1.249 ml, 7.17 mmol) were added to (S)-methyl 3-amino-4-((R)-6-chloro-2-oxo-1,2-dihydrospiro[benzo[d][1,3]oxazine-4,3'-piperidin]-1'-yl)-4-oxobutanoate hydrochloride (1.00 g, 2.391 mmol) in DMF (5 ml). The reaction mixture was stirred at rt for 5 min and worked up by adding 50 mL water, extracted 2×50 mL EtOAc, combined EtOAc layers were washed 2×50 mL sat.

aq. NaCl solution and concentrated. The crude was purified by silica gel chromatography (30-40% of 30% EtOH, EtOAc:Hexanes) to give (S)-methyl 4-((R)-6-chloro-2-oxo-1,2-dihydrospiro[benzo[d][1,3]oxazine-4,3'-piperidin]-1'-yl)-3-(4-((methoxycarbonyl)amino)benzamido)-4-oxobutanoate which was used directly in the next step. LCMS: m/z 559.40 [M+H]$^+$.

Step E:
Lithium hydroxide (4.92 ml, 9.84 mmol) was added to (S)-methyl 4-((R)-6-chloro-2-oxo-1,2-dihydrospiro[benzo[d][1,3]oxazine-4,3'-piperidin]-1'-yl)-3-(4-((methoxycarbonyl)amino)benzamido)-4-oxobutanoate (1.1 g, 1.968 mmol) in MeOH (4 ml) and THF (6 ml), and the mixture was stirred at rt for 10 min. The reaction mixture was extracted with 10 mL water and 10 mL EtOAc. The EtOAc layer was discarded and the aqueous layer was acidified to pH 4-5, extracted with 3×10 mL EtOAc. The combined EtOAc layers were dried on Na$_2$SO$_4$, concentrated on rotovap. (S)-4-((R)-6-chloro-2-oxo-1,2-dihydrospiro[benzo[d][1,3]oxazine-4,3'-piperidin]-1'-yl)-3-(4-((methoxycarbonyl)amino)benzamido)-4-oxobutanoic acid was used directly in the next step. LCMS: m/z 545.38 [M+H]$^+$.

Step F:
HATU (15.35 mg, 0.040 mmol) and 3,3-difluoroazetidine (3.42 mg, 0.037 mmol), followed by N-ethyl-N-isopropylpropan-2-amine (0.019 ml, 0.110 mmol), was added to (S)-4-((R)-6-chloro-2-oxo-1,2-dihydrospiro[benzo[d][1,3]oxazine-4,3'-piperidin]-1'-yl)-3-(4-((methoxycarbonyl)amino)benzamido)-4-oxobutanoic acid (20 mg, 0.037 mmol) in DMF (1 ml). The reaction mixture was stirred at rt for 5 min and purified by reversed phase HPLC using ACN:Water, where both contains 0.05% TFA. The desired fractions were lyophilized. LCMS: m/z 620.33 [M+H]$^+$. $^1$H NMR δ (ppm)(CH$_3$OH-d4): 0.12-0.11 (1H, m), 1.62 (1H, d, J=13.36 Hz), 1.88 (1H, s), 1.91 (1H, s), 2.11 (1H, d, J=13.96 Hz), 2.38 (2H, td, J=13.48, 4.79 Hz), 2.48 (2H, dd, J=15.27, 4.46 Hz), 2.82 (2H, d, J=4.70 Hz), 2.85 (1H, d, J=8.92 Hz), 3.00-2.93 (1H, m), 3.70 (1H, s), 3.77-3.76 (2H, m), 4.04-4.00 (1H, m), 4.13 (1H, d, J=13.71 Hz), 4.28 (2H, t, J=12.06 Hz), 4.63 (2H, t, J=12.54 Hz), 5.67 (2H, dd, J=10.01, 4.47 Hz), 6.94 (2H, dd, J=8.53, 2.92 Hz), 7.59-7.33 (1H, m), 7.75 (1H, d, J=8.44 Hz), 7.92 (1H, d, J=8.51 Hz), 9.57 (1H, s).

By using procedures similar to those described previously, and using appropriate starting materials, the following compounds were synthesized. These compounds were characterized by LC/MS.

| Example | Structure | LCMS [M + H] | hu Factor XIa Ki (nM) |
|---|---|---|---|
| 85 | methyl (4-(((S)-1-((R)-6-chloro-2-oxo-1,2-dihydrospiro[benzo[d][1,3]oxazine-4,3'-piperidin]-1'-yl)-4-(3,3-difluoroazetidin-1-yl)-1,4-dioxobutan-2-yl)carbamoyl)phenyl)carbamate | 620.33 | 33.32 |
| 86 | methyl (4-(((S)-1-((R)-6-chloro-2-oxo-1,2-dihydrospiro[benzo[d][1,3]oxazine-4,3'-piperidin]-1'-yl)-4-(cyclobutylamino)-1,4-dioxobutan-2-yl)carbamoyl)phenyl)carbamate | 598.46 | 33.74 |
| 87 | methyl (4-(((S)-1-((R)-6-chloro-2-oxo-1,2-dihydrospiro[benzo[d][1,3]oxazine-4,3'-pyrrolidin]-1'-yl)-1,4-dioxo-4-(piperidin-1-yl)butan-2-yl)carbamoyl)phenyl)carbamate | 598.47 | 3.65 |
| 88 | methyl (4-(((S)-1-((R)-6-chloro-2-oxo-1,2-dihydrospiro[benzo[d][1,3]oxazine-4,3'-pyrrolidin]-1'-yl)-4-morpholino-1,4-dioxobutan-2-yl)carbamoyl)phenyl)carbamate | 600.33 | 20 |
| 89 | methyl (4-(((S)-1-((R)-6-chloro-2-oxo-1,2-dihydrospiro[benzo[d][1,3]oxazine-4,3'-pyrrolidin]-1'-yl)-1,4-dioxo-4-((tetrahydro-2H-pyran-4-yl)amino)butan-2-yl)carbamoyl)phenyl)carbamate | 614.38 | 59.25 |
| 90 | methyl (4-(((S)-1-((R)-6-chloro-2-oxo-1,2-dihydrospiro[benzo[d][1,3]oxazine-4,3'-pyrrolidin]-1'-yl)-1,4-dioxo-4-(pyridin-2-ylamino)butan-2-yl)carbamoyl)phenyl)carbamate | 607.31 | 57.40 |
| 91 | methyl (4-(((S)-1-((R)-6-chloro-2-oxo-1,2-dihydrospiro[benzo[d][1,3]oxazine-4,3'-pyrrolidin]-1'-yl)-4-((4-fluorophenyl)amino)-1,4-dioxobutan-2-yl)carbamoyl)phenyl)carbamate | 624.02 | 143.60 |
| 92 | methyl (4-(((S)-1-((R)-6-chloro-2-oxo-1,2-dihydrospiro[benzo[d][1,3]oxazine-4,3'-pyrrolidin]-1'-yl)-4-(cyclopropanesulfonamido)-1,4-dioxobutan-2-yl)carbamoyl)phenyl)carbamate | 634.38 | 56.10 |
| 93 | methyl (4-(((S)-1-((R)-6-chloro-2-oxo-1,2-dihydrospiro[benzo[d][1,3]oxazine-4,3'-pyrrolidin]-1'-yl)-4-(oxetan-3-ylamino)-1,4-dioxobutan-2-yl)carbamoyl)phenyl)carbamate | 586.42 | 45.82 |
| 94 | methyl (4-(((2S)-4-(6-azabicyclo[3.2.0]heptan-6-yl)-1-((R)-6-chloro-2-oxo-1,2-dihydrospiro[benzo[d][1,3]oxazine-4,3'-piperidin]-1'-yl)-1,4-dioxobutan-2-yl)carbamoyl)phenyl)carbamate | 624.22 | 5.47 |
| 95 | methyl (4-(((S)-1-((R)-6-chloro-2-oxo-1,2-dihydrospiro[benzo[d][1,3]oxazine-4,3'-piperidin]-1'-yl)-4-((S)-2-(hydroxymethyl)azetidin-1-yl)-1,4-dioxobutan-2-yl)carbamoyl)phenyl)carbamate | 614.19 | 3.59 |
| 96 | methyl (4-(((S)-1-((R)-6-chloro-2-oxo-1,2-dihydrospiro[benzo[d][1,3]oxazine-4,3'-piperidin]-1'-yl)-4- | 627.23 | 202.70 |

| Example | Structure | LCMS [M + H] | hu Factor XIa Ki (nM) |
|---|---|---|---|
| 97 | (3-(dimethylamino)azetidin-1-yl)-1,4-dioxobutan-2-yl)carbamoyl)phenyl)carbamate methyl (4-(((S)-1-((R)-6-chloro-2-oxo-1,2-dihydrospiro[benzo[d][1,3]oxazine-4,3'-piperidin]-1'-yl)-4-(3-methoxyazetidin-1-yl)-1,4-dioxobutan-2-yl)carbamoyl)phenyl)carbamate | 614.19 | 51.15 |
| 98 | methyl (4-(((S)-1-((R)-6-chloro-2-oxo-1,2-dihydrospiro[benzo[d][1,3]oxazine-4,3'-piperidin]-1'-yl)-4-(((1-methyl-1H-pyrazol-5-yl)methyl)amino)-1,4-dioxobutan-2-yl)carbamoyl)phenyl)carbamate | 638.21 | 38.30 |
| 99 | methyl (4-(((S)-1-((R)-6-chloro-2-oxo-1,2-dihydrospiro[benzo[d][1,3]oxazine-4,3'-piperidin]-1'-yl)-4-((cyclopropylmethyl)amino)-1,4-dioxobutan-2-yl)carbamoyl)phenyl)carbamate | 598.2 | 40.36 |
| 100 | methyl (4-(((S)-1-((R)-6-chloro-2-oxo-1,2-dihydrospiro[benzo[d][1,3]oxazine-4,3'-piperidin]-1'-yl)-4-(3-cyclopropyl-3-hydroxyazetidin-1-yl)-1,4-dioxobutan-2-yl)carbamoyl)phenyl)carbamate | 640.21 | 39.89 |
| 101 | methyl (4-(((S)-1-((R)-6-chloro-2-oxo-1,2-dihydrospiro[benzo[d][1,3]oxazine-4,3'-piperidin]-1'-yl)-4-((R)-3-methoxypyrrolidin-1-yl)-1,4-dioxobutan-2-yl)carbamoyl)phenyl)carbamate | 628.21 | 36.37 |
| 102 | methyl (4-(((S)-1-((R)-6-chloro-2-oxo-1,2-dihydrospiro[benzo[d][1,3]oxazine-4,3'-piperidin]-1'-yl)-4-((S)-2-methylazetidin-1-yl)-1,4-dioxobutan-2-yl)carbamoyl)phenyl)carbamate | 598.47 | 0.77 |

Example 103

Methyl (4-(((S)-1-((R)-6-chloro-2-oxo-1,2-dihydrospiro[benzo[d][1,3]oxazine-4,3'-piperidin]-1'-yl)-4-fluoro-1-oxobutan-2-yl)carbamoyl)phenyl)carbamate

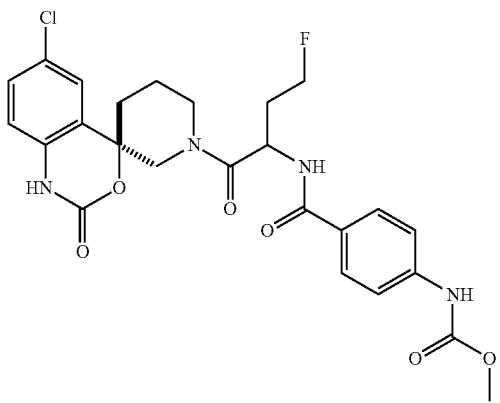

Step A: Synthesis of ethyl 2-amino-4-fluorobutanoate

To a solution of ethyl 2-((diphenylmethylene)amino)acetate (2.106 g, 7.88 mmol) in dry Tetrahydrofuran (10 ml) at −30° C., potassium tert-butoxide (1.061 g, 9.45 mmol) was added and the solution was stirred for 1 h at 0° C. To this mixture was added a solution of 1-bromo-2-fluoroethane (1.0 g, 7.88 mmol) in 5 mL THF and the reaction was stirred overnight at rt while slowly allowing it to warm to rt. The reaction was quenched by the addition of 1 mL concentrated HCl, followed by the addition of 30 mL water. The mixture was stirred at rt for 2 h and then solvents were removed. The crude product ethyl 2-amino-4-fluorobutanoate was used directly in the next step.

Step B:

To ethyl 2-amino-4-fluorobutanoate (100 mg, 0.670 mmol) in DMF (1 ml) was added HATU (280 mg, 0.737 mmol), 4-((methoxycarbonyl)amino)benzoic acid (131 mg, 0.670 mmol) followed by N-ethyl-N-isopropylpropan-2-amine (0.350 ml, 2.011 mmol). The reaction mixture was stirred at rt for 5 min and it was purified on reversed phase HPLC using ACN:Water, where both contains 0.05% TFA. Ethyl 4-fluoro-2-(4-((methoxycarbonyl)amino)benzamido)butanoate was obtained. LCMS: m/z 327.36 [M+H]$^+$.

Step C:

Lithium hydroxide (0.659 ml, 1.318 mmol) was added to ethyl 4-fluoro-2-(4-((methoxycarbonyl)amino)benzamido)butanoate (86 mg, 0.264 mmol) in MeOH (4 ml) and THF (6 ml). The reaction mixture was stirred at rt for 5 min and it was extracted with 10 mL water and 10 mL EtOAc. The EtOAc layer was discarded. The aqueous layer was acidified to pH 4-5, extracted with 3×10 mL EtOAc. Combined EtOAc layers were dried on Na$_2$SO$_4$, concentrated on rotovap. 4-fluoro-2-(4((methoxycarbonyl)amino)benzamido)butanoic acid was used directly in the next step. LCMS: m/z 298.28 [M+H]$^+$.

Step D:

To (R)-6-chlorospiro[benzo[d][1,3]oxazine-4,3'-piperidin]-2(1H)-one hydrochloride (70.8 mg, 0.245 mmol) in DMF (2 ml) was added HATU (102 mg, 0.269 mmol), 4-fluoro-2-(4-((methoxycarbonyl)amino)benzamido)butanoic acid (73 mg, 0.245 mmol), followed by N-ethyl-N-isopropylpropan-2-amine (0.128 ml, 0.734 mmol). The reaction mixture was stirred at rt for 5 min and purified by reversed phase HPLC using ACN:Water, where both contains 0.05% TFA. Methyl (4-((1-((R)-6-chloro-2-oxo-1,2-dihydrospiro[benzo[d][1,3]oxazine-4,3'-piperidin]-1'-yl)-4-fluoro-1-oxobutan-2-yl)carbamoyl)phenyl)carbamate resulted. LCMS: m/z 533.51 [M+H]$^+$. $^1$H NMR δ (ppm)

(CH₃OH-d4): 1.56 (1H, s), 1.88 (1H, s), 1.96 (1H, s), 2.12 (1H, d, J=11.72 Hz), 2.22-2.16 (4H, m), 2.41-2.33 (2H, m), 2.67 (1H, s), 2.95 (1H, t, J=13.30 Hz), 3.26 (1H, s), 3.66 (1H, s), 3.68 (1H, s), 3.77 (5H, d, J=1.68 Hz), 3.83 (1H, s), 3.86 (1H, s), 4.33 (1H, d, J=14.32 Hz), 4.48 (1H, d, J=5.58 Hz), 4.51 (1H, s), 4.59-4.57 (1H, m), 4.69-4.65 (1H, m), 5.41-5.33 (1H, m), 6.96-6.89 (2H, m), 7.33 (2H, dt, J=8.46, 2.56 Hz), 7.43-7.39 (2H, m), 7.50 (1H, s), 7.58-7.51 (3H, m), 7.70 (1H, d, J=8.42 Hz), 7.80 (2H, dd, J=25.24, 8.62 Hz), 7.91 (1H, d, J=8.64).

By using procedures similar to those described previously, and using appropriate starting materials, the following compounds were synthesized. These compounds were characterized by LC/MS.

| Example | Structure | LCMS [M + H] | hu Factor XIa Ki (nM) |
|---|---|---|---|
| 103 | methyl (4-(((S)-1-((R)-6-chloro-2-oxo-1,2-dihydrospiro[benzo[d][1,3]oxazine-4,3'-piperidin]-1'-yl)-4-fluoro-1-oxobutan-2-yl)carbamoyl)phenyl)carbamate | 533.31 | 51.96 |
| 104 | methyl (4-(((S)-1-((R)-6-chloro-5-fluoro-2-oxo-1,2-dihydrospiro[benzo[d][1,3]oxazine-4,3'-piperidin]-1'-yl)-4,4-difluoro-1-oxobutan-2-yl)carbamoyl)phenyl)carbamate | 568.13 | 15.00 |
| 105 | methyl (4-(((S)-1-((R)-6-chloro-5-fluoro-2-oxo-1,2-dihydrospiro[benzo[d][1,3]oxazine-4,3'-piperidin]-1'-yl)-4-fluoro-1-oxobutan-2-yl)carbamoyl)phenyl)carbamate | 551.53 | 9.99 |
| 106 | methyl (4-(((S)-1-((R)-6-chloro-2-oxo-1,2-dihydrospiro[benzo[d][1,3]oxazine-4,3'-piperidin]-1'-yl)-3-(4,4-difluorocyclohexyl)-1-oxopropan-2-yl)carbamoyl)phenyl)carbamate | 619.42 | 16.81 |

Example 107

Methyl (4-(((S)-1-((R)-6-chloro-2-oxo-1,2-dihydrospiro[benzo[d][1,3]oxazine-4,3'-piperidin]-1'-yl)-4-(cyclobutanecarboxamido)-1-oxobutan-2-yl)carbamoyl)phenyl)carbamate

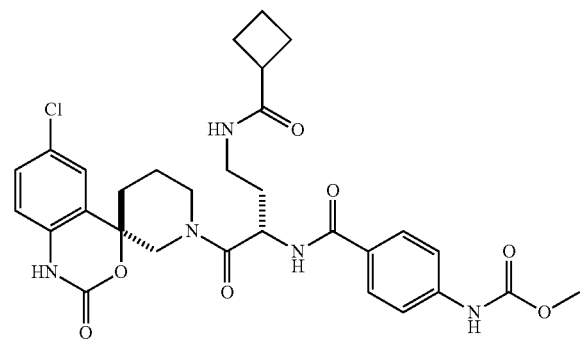

Step A:
HATU (1.556 g, 4.09 mmol) and 4-((methoxycarbonyl)amino)benzoic acid (0.726 g, 3.72 mmol), followed by N-ethyl-N-isopropylpropan-2-amine (1.944 ml, 11.16 mmol) were added to (S)-methyl 2-amino-4-((tert-butoxycarbonyl)amino)butanoate hydrochloride (1 g, 3.72 mmol) in DMF (3 ml). After 5 min of stirring at rt, it was worked up by adding 100 mL water, extracted 2×150 mL EtOAc, combined EtOAc lyers was washed 2×100 mL sat. aq. NaCl solution and concentrated. (S)-methyl 4-((tert-butoxycarbonyl)amino)-2-(4-((methoxycarbonyl)amino)benzamido)butanoate (1.42 g, 3.12 mmol) was used for the next step without purification.

Step B:
Lithium hydroxide (8.55 ml, 17.10 mmol) was added to (S)-methyl 4-((tert-butoxycarbonyl)amino)-2-(4-((methoxycarbonyl)amino)benzamido)butanoate (1.4 g, 3.42 mmol) in MeOH (4 ml) and THF (6 ml). After 5 min of stirring at rt, the reaction mixture was extracted with 100 mL water and 100 mL EtOAc. The EtOAc layer was discarded and the aqueous layer was acidified to pH 4-5, and extracted with 3×100 mL EtOAc. The combined EtOAc layers were dried on Na₂SO₄, concentrated on a rotovap to yield (S)-4-((tert-butoxycarbonyl)amino)-2-(4-((methoxycarbonyl)amino)benzamido)butanoic acid.

Step C:
HATU (212 mg, 0.556 mmol) and (S)-4-((tert-butoxycarbonyl)amino)-2-(4-((methoxycarbonyl)amino)benzamido) butanoic acid (200 mg, 0.506 mmol), followed by N-ethyl-N-isopropylpropan-2-amine (0.264 ml, 1.517 mmol) was added to (R)-6-chlorospiro[benzo[d][1,3]oxazine-4,3'-piperidin]-2(1H)-one hydrochloride (146 mg, 0.506 mmol) in DMF (5 ml). After 5 min of stirring at rt, it was worked up by adding 100 mL water, and extracted 2×100 mL EtOAc. The combined EtOAc layers were washed 3×100 mL sat. aq. NaCl solution and concentrated to yield tert-butyl((S)-4-((R)-6-chloro-2-1,2-dihydrospiro[benzo[d][1,3]oxazine-4,3'-piperidin]-1-yl)-3-(4-((methoxycarbonyl)amino)benzamido)-4-oxobutyl)carbamate.

Step D:
Hydrogen chloride (0.575 ml, 2.301 mmol) was added to tert-butyl((S)-4-((R)-6-chloro-2-1,2-dihydrospiro[benzo[d][1,3]oxazine-4,3'-piperdin]-1-yl)-3-(4-((methoxycarbonyl)amino)benzamido)-4-oxobutyl)carbamate (290 mg, 0.460 mmol) in 1,4-dioxane (5 ml). The reaction was stirred at rt until completion. The solvent was concentrated to dryness. It was purified by reversed phase chromatography using ACN:Water, where both contains 0.05% TFA and yielded methyl (4-(((S)-4-amino-1-((R)-6-chloro-2-oxo-1,2-dihydrospiro[benzo[d][1,3]oxazine-4,3'-piperidin]-1'-yl)-1-oxobutan-2-yl)carbamoyl)phenyl)carbamate 2,2,2-trifluoroacetate.

Step E:
HATU (16.24 mg, 0.043 mmol) and cyclobutanecarboxylic acid (3.89 mg, 0.039 mmol), followed by N-ethyl-N-isopropylpropan-2-amine (0.020 ml, 0.116 mmol) was added to methyl (4-(((S)-4-amino-1-((R)-6-chloro-2-oxo-1,2-dihydrospiro[benzo[d][1,3]oxazine-4,3'-piperidin]-1'-yl)-1-oxobutan-2-yl)carbamoyl)phenyl)carbamate 2,2,2-trifluoroacetate (25 mg, 0.039 mmol) in DMF (1 ml). After 5 min of stirring at rt, it was purified by reversed phase chromatography using ACN:water, where both contains 0.05% TFA, to yield methyl (4-(((S)-1-((R)-6-chloro-2-oxo-1,2-dihydrospiro[benzo[d][1,3]oxazine-4,3'-piperidin]-1'-yl)-4-(cyclobutanecarboxamido)-1-oxobutan-2-yl)carbamoyl) phenyl)carbamate. LCMS: m/z 612.42 [M+H]⁺. ¹H NMR δ (ppm)(CH₃OH-d4): 1.32 (1H, s), 1.87 (3H, d, J=9.11 Hz), 2.01 (2H, t, J=8.33 Hz), 2.16 (9H, dd, J=15.81, 8.14 Hz), 2.26 (5H, dd, J=19.89, 10.43 Hz), 2.94 (1H, dd, J=13.94, 8.24 Hz), 3.16-3.10 (2H, m), 3.24 (1H, d, J=7.53 Hz), 3.72 (1H, s), 3.77-3.76 (5H, m), 5.24 (1H, t, J=6.85 Hz), 6.97-6.90 (2H, m), 7.36-7.33 (2H, m), 7.45-7.41 (2H, m), 7.60-7.54 (4H, m), 7.75 (1H, s), 7.79-7.76 (1H, m), 7.86 (1H, d, J=8.40 Hz), 7.92 (2H, d, J=8.42 Hz).

By using procedures similar to those described previously, and using appropriate starting materials, the following compounds were synthesized. These compounds were characterized by LC/MS.

Step B:
To a stirred solution of methyl (4-(((S)-1-((R)-6-chloro-2-oxo-1,2-dihydrospiro[benzo[d][1,3]oxazine-4,3'-pyrrolidin]-1'-yl)-4-hydroxy-1-oxobutan-2-yl)carbamoyl)phenyl) carbamate (120 mg, 0.232 mmol) in DCM (2 ml) was added Dess-MartinPeriodinane (197 mg, 0.464 mmol) and NaHCO₃ (19.50 mg, 0.232 mmol) and the mixture was stirred at rt overnight under N₂. A drop of DMSO was added to dissolve the water. When the reaction was complete, it was poured into aq. thio and aq. NaOH and extracted with DCM to give the aldehyde which was used in the next step.

Step C:
To a stirred solution of methyl (4-(((S)-1-((R)-6-chloro-2-oxo-1,2-dihydrospiro[benzo[d][1,3]oxazine-4,3'-pyrrolidin]-1'-yl)-1,4-dioxobutan-2-yl)carbamoyl)phenyl)carbamate (14 mg, 0.027 mmol) dissolved in THF (1 ml) at 0° C. was added methylmagnesium bromide (9.06 µl, 0.027

| Example | Structure | LCMS [M + H] | hu Factor XIa Ki (nM) |
|---|---|---|---|
| 107 | methyl (4-(((S)-1-((R)-6-chloro-2-oxo-1,2-dihydrospiro[benzo[d][1,3]oxazine-4,3'-piperidin]-1'-yl)-4-(cyclobutanecarboxamido)-1-oxobutan-2-yl)carbamoyl)phenyl)carbamate | 612.42 | 50.70 |
| 108 | methyl (4-(((S)-1-((R)-6-chloro-2-oxo-1,2-dihydrospiro[benzo[d][1,3]oxazine-4,3'-piperidin]-1'-yl)-4-(methylsulfonamido)-1-oxobutan-2-yl)carbamoyl)phenyl)carbamate | 608.29 | 21.52 |
| 109 | methyl (4-(((S)-1-((R)-6-chloro-2-oxo-1,2-dihydrospiro[benzo[d][1,3]oxazine-4,3'-piperidin]-1'-yl)-4-((cyclobutoxycarbonyl)amino)-1-oxobutan-2-yl)carbamoyl)phenyl)carbamate | 628.34 | 48.31 |

Example 110

Methyl (4-(((2S)-1-((R)-6-chloro-2-oxo-1,2-dihydrospiro[benzo[d][1,3]oxazine-4,3'-pyrrolidin]-1'-yl)-4-hydroxy-1-oxopentan-2-yl)carbamoyl)phenyl)carbamate

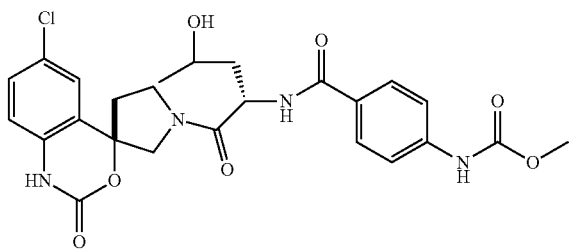

Step A:
Methyl (S)-4-((R)-6-chloro-2-oxo-1,2-dihydrospiro[benzo[d][1,3]oxazine-4,3'-pyrrolidin]-1'-yl)-3-(4-((methoxycarbonyl)amino)benzamido)-4-oxobutanoate (25 mg, 0.046 mmol) was suspended in THF (2 mL) and lithium borohydride (2.498 mg, 0.115 mmol) was added. The mixture was stirred at ambient temperature overnight. The aqueous layer was extracted with EtOAc and the combined organic extracts were washed with brine, dried over MgSO₄, filtered, and concentrated in vacuo. It was purified over Gilson reverse phase chromatography 10-100% acetonitrile/water to give methyl (4-(((S)-1-((R)-6-chloro-2-oxo-1,2-dihydrospiro[benzo[d][1,3]oxazine-4,3'-pyrrolidin]-1'-yl)-4-hydroxy-1-oxobutan-2-yl)carbamoyl)phenyl)carbamate.

mmol) and the mixture was stirred for 1.0 h. The reaction was then quenched and the product was purified with reverse Gilson 10-100% water to acetonitrile to give racemic methyl (4-(((2S)-1-((R)-6-chloro-2-oxo-1,2-dihydrospiro[benzo[d][1,3]oxazine-4,3'-pyrrolidin]-1'-yl)-4-hydroxy-1-oxopentan-2-yl)carbamoyl)phenyl)carbamate.

Example 111

Methyl (4-(((S)-1-((R)-6-chloro-2-oxo-1,2-dihydrospiro[benzo[d][1,3]oxazine-4,3'-pyrrolidin]-1'-yl)-4-hydroxy-4-methyl-1-oxopentan-2-yl)carbamoyl)phenyl)carbamate

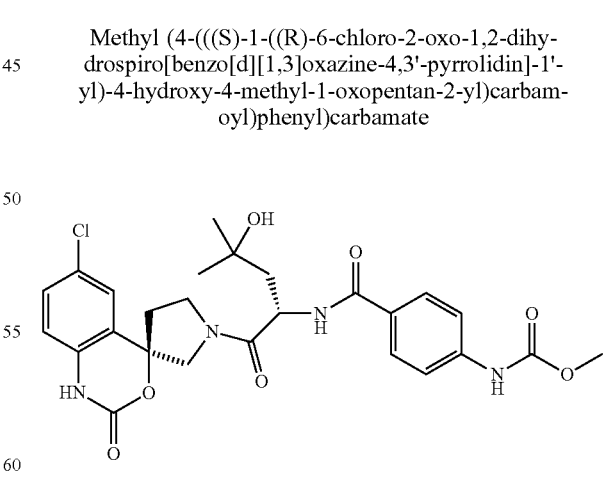

Step A:
To a solution of methyl (S)-4-((R)-6-chloro-2-oxo-1,2-dihydrospiro[benzo[d][1,3]oxazine-4,3'-pyrrolidin]-1'-yl)-3-(4-((methoxycarbonyl)amino)benzamido)-4-oxobutanoate (24 mg, 0.044 mmol) in THF (2 ml) was added methylmagnesium bromide (0.022 ml, 0.066 mmol) at −78°

C. and the mixture was stirred for 1 h. The reaction was warmed up to rt and stirred for 30 min and quenched with satd. NH₄Cl and extracted with ethyl acetate. The organic fractions were concentrated and LCMS indicated mostly the product shown. The reaction was quenched with satd NH₄Cl, extracted 3× with EtOAc, combined organic layer washed with brine, dried over MgSO₄, filtered and evaporated to dryness to give the crude product which was purified by Gilson reverse phase chromatography 10-100% acetonitrile/water to give methyl (4-(((S)-1-((R)-6-chloro-2-oxo-1,2-dihydrospiro[benzo[d][1,3]oxazine-4,3'-pyrrolidin]-1'-yl)-4-hydroxy-4-methyl-1-oxopentan-2-yl)carbamoyl)phenyl)carbamate.

Example 112

Methyl (4-(((S)-4-(azetidin-1-yl)-1-((R)-6-chloro-2-oxo-1,2-dihydrospiro[benzo[d][1,3]oxazine-4,3'-pyrrolidin]-1'-yl)-1-oxobutan-2-yl)carbamoyl)phenyl)carbamate

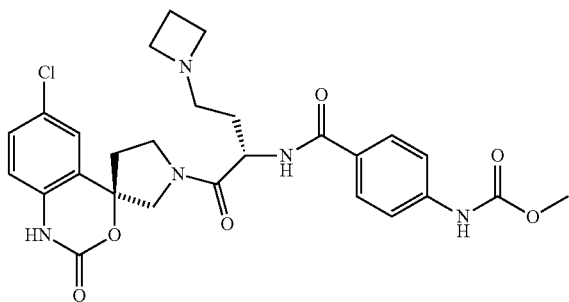 [SMILES: COC(=O)Nc1ccc(C(=O)N[C@@H](CCN2CCC2)C(=O)N2CC[C@@]3(C2)OC(=O)Nc2ccc(Cl)cc23)cc1]

Step A:

To a stirred solution of methyl (4-(((S)-1-((R)-6-chloro-2-oxo-1,2-dihydrospiro[benzo[d][1,3]oxazine-4,3'-pyrrolidin]-1'-yl)-1,4-dioxobutan-2-yl)carbamoyl)phenyl)carbamate (14 mg, 0.027 mmol) and azetidine (3.10 mg, 0.054 mmol) in MeOH (1 ml) was added sodium triacetoxyborohydride (23.05 mg, 0.109 mmol) and the mixture was stirred for 3.0 h. The reaction was quenched with satd NH₄Cl and extracted with DCM. It was purified with reverse phase Gilson 10-100% ACN/water to give methyl (4-(((S)-4-(azetidin-1-yl)-1-((R)-6-chloro-2-oxo-1,2-dihydrospiro[benzo[d][1,3]oxazine-4,3'-pyrrolidin]-1'-yl)-1-oxobutan-2-yl)carbamoyl)phenyl)carbamate.

By using procedures similar to those described previously, and using appropriate starting materials, the following compounds were synthesized. These compounds were characterized by LC/MS.

| Example | Structure | LCMS [M + H] | hu Factor XIa Ki (nM) |
|---|---|---|---|
| 110 | methyl (4-(((2S)-1-((R)-6-chloro-2-oxo-1,2-dihydrospiro[benzo[d][1,3]oxazine-4,3'-pyrrolidin]-1'-yl)-4-hydroxy-1-oxopentan-2-yl)carbamoyl)phenyl)carbamate | 532 | 52 |
| 111 | methyl (4-(((S)-1-((R)-6-chloro-2-oxo-1,2-dihydrospiro[benzo[d][1,3]oxazine-4,3'-pyrrolidin]-1'-yl)-4-hydroxy-4-methyl-1-oxopentan-2-yl)carbamoyl)phenyl)carbamate | 546 | 12 |
| 112 | methyl (4-(((S)-4-(azetidin-1-yl)-1-((R)-6-chloro-2-oxo-1,2-dihydrospiro[benzo[d][1,3]oxazine-4,3'-pyrrolidin]-1'-yl)-1-oxobutan-2-yl)carbamoyl)phenyl)carbamate | 557 | 219 |

Example 113

N—((S)-1-((R)-6-chloro-5-fluoro-2-oxo-1,2-dihydrospiro[benzo[d][1,3]oxazine-4,3'-piperidin]-1'-yl)-1-oxo-3-(pyrimidin-5-yl)propan-2-yl)-2-oxo-1,2-dihydroquinoline-6-carboxamide

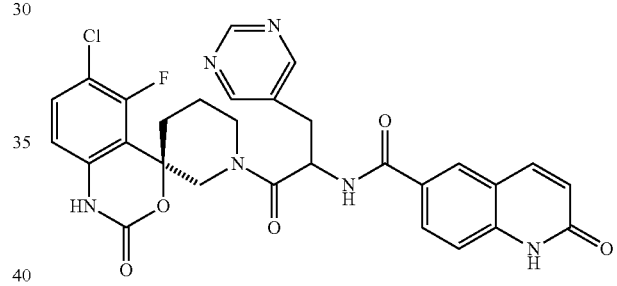

Step 1: 6-(methoxycarbonyl)quinoline 1-oxide

To a stirred solution of methyl quinoline-6-carboxylate (2 g, 10.68 mmol) in CHCl₃ (120 mL) was added m-CPBA (4.61 g, 21.37 mmol) (80%) and the reaction mixture was stirred at 25° C. under N₂ for 16 h. TLC and LCMS showed that the starting material was consumed completely. The mixture was quenched by addition of sat. NaHCO₃ aq. (50 mL), and extract with EtOAc (50 mL×2). The combined organic layers were dried over Na₂SO₄, filtered and the solvent was removed to give the crude product which was purified by flash silica gel chromatography (ISCO®; 40 g SepaFlash® Silica Flash Column, Eluent of 0~10% MeOH/DCM gradient at 40 mL/min) to give the title compound.
¹H NMR (CD₃OD, 400 MHz): δ 8.63-8.80 (m, 1H), 8.39 (d, J=9.0 Hz, 1H), 8.24 (d, J=8.4 Hz, 1H), 7.61 (dd, J=6.4, 7.9 Hz, 1H), 4.00 (s, 3H). MS (ESI) m/z 204.0 (M+H).

Step 2: methyl 2-hydroxyquinoline-6-carboxylate

To a solution of 6-(methoxycarbonyl) quinoline 1-oxide (500 mg, 2.461 mmol) in DMF (5 mL) at 0° C. was added trifluoroacetic anhydride (1.738 mL, 12.30 mmol). The reaction mixture was stirred at 25° C. for 16 h. LCMS showed starting material was consumed completely. Then the reaction mixture was poured into saturated aqueous NaHCO₃ (15 mL). The resulting precipitate was filtered off and triturated with EtOAc to give the title compound which was used directly for the next step without purification.

$^1$H NMR (CDCl$_3$, 400 MHz): δ 11.80-12.14 (m, 1H), 8.25 (s, 1H), 8.10 (d, J=8.2 Hz, 1H), 7.81 (d, J=9.4 Hz, 1H), 7.36 (d, J=8.6 Hz, 1H), 6.70 (d, J=9.4 Hz, 1H), 3.89 (s, 3H).

MS (ESI) m/z 204.2 (M+H).

Step 3: 2-hydroxyquinoline-6-carboxylic acid

To a suspension of methyl 2-hydroxyquinoline-6-carboxylate (400 mg, 1.969 mmol) in THF (10 mL) and MeOH (2 mL) was added a solution of LiOH.H$_2$O (83 mg, 1.969 mmol) in water (2 mL). The mixture was heated to 60° C. for 12 h. LCMS showed starting material was consumed completely. After cooling to room temperature, the mixture was neutralized by concentrated HCl (one drop) to pH 7 and stirred for 15 min. The solvent was then evaporated and the solid was dried in vacuum to give the title compound which was used for the next step directly without further purification. MS (ESI) m/z 190.1 (M+H).

Step 4: (S)-methyl 2-((tert-butoxycarbonyl) amino)-3-(pyrimidin-5-yl)propanoate

To a stirred suspension of zinc (1.851 g, 28.3 mmol) in DMF (5 mL) in a 50 mL one-necked round-bottomed flask fitted with a 3-way tap was added TMSCl (36 mL). After 50 min the solvent was removed by syringe and the zinc was washed with DMF (5 mL). The solvent was removed again via syringe and the activated zinc was dried under vacuum. A solution of (R)-methyl 2-((tert-butoxy carbonyl)amino)-3-iodopropanoate (1.553 g, 4.72 mmol) in DMF (5 mL) was added to the activated zinc and the mixture was stirred for 30 min. TLC showed the starting material was disappeared. Then 5-bromopyrimidine (1 g, 6.29 mmol) followed by Pd(PtBu$_3$)$_2$ (0.064 g, 0.126 mmol) was added and the mixture was stirred for 16 h at 50° C. under nitrogen. TLC showed starting material was consumed completely. The resulting mixture was diluted with EtOAc (50 mL) and washed with NH$_4$Cl (20 mL) and brine (20 mL). The organic layer was dried over Na$_2$SO$_4$ and concentrated to give the crude product which was purified by flash silica gel chromatography (ISCO®; 12 g SepaFlash® Silica Flash Column, Eluent of 0~70% EtOAc/PE gradient at 30 mL/min) to give the title compound.

Step 5: (S)-2-((tert-butoxycarbonyl) amino)-3-(pyrimidin-5-yl)propanoic acid

To a stirred solution of (S)-methyl 2-((tert-butoxycarbonyl)amino)-3-(pyrimidin-5-yl)propanoate (230 mg, 0.818 mmol) in MeOH (2 mL), THF (2 mL) and water (2 mL) was added LiOH.H$_2$O (68.6 mg, 1.635 mmol). Then the mixture was stirred at 25° C. for 2 h. LCMS showed starting material was consumed completely. The mixture was acidified with 2N HCl to pH 6 and extracted with ethyl acetate (2×20 mL). The combined organic fractions were washed with brine (10 mL), dried over anhydrous Na$_2$SO$_4$, filtered and evaporated to give the title compound which was used for the next step directly without further purification. MS (ESI) m/z 268.0 (M+H).

Step 6: tert-butyl ((S)-1-((R)-6-chloro-5-fluoro-2-oxo-1,2-dihydrospiro[benzo[d][1,3]oxazine-4,3'-piperidin]-1'-yl)-1-oxo-3-(pyrimidin-5-yl)propan-2-yl)carbamate To a stirred solution of (R)-6-chloro-5-fluorospiro[benzo[d][1,3]oxazine-4,3'-piperidin]-2(1H)-one hydrochloride (115 mg, 0.374 mmol) in DMF (5 mL) was added (S)-2-((tert-butoxycarbonyl)amino)-3-(pyrimidin-5-yl)propanoic acid (100 mg, 0.374 mmol), HATU (171 mg, 0.449 mmol) and DIPEA (0.261 mL, 1.497 mmol) at 25° C. The reaction mixture was stirred at 25° C. for 4 h. LCMS showed the starting material was consumed completely. The reaction mixture was diluted with EtOAc (30 mL) and sat. NaHCO$_3$ (20 mL). The organic layer was washed with brine (20 mL), dried over Na$_2$SO$_4$, filtered and concentrated to give the crude product which was purified by prep-HPLC (preparative HPLC on a GILSON 281 instrument fitted with Waters Diamonsil 150×20 mm×5 um using water and acetonitrile as the eluents. Mobile phase A: water (containing 0.1% TFA-CH$_3$CN), mobile phase B: acetonitrile. Gradient: 22-52% B, 0-11 min; 100% B, 9-11 min) to give the title compound. MS (ESI) m/z 520.1 (M+H).

Step 7: (R)-1'-((S)-2-amino-3-(pyrimidin-5-yl)propanoyl)-6-chloro-5-fluorospiro[benzo[d][1,3]oxazine-4,3'-piperidin]-2(1H)-one To a round bottom flask charged with tert-butyl ((S)-1-((R)-6-chloro-5-fluoro-2-oxo-1,2-dihydrospiro[benzo[d][1,3]oxazine-4,3'-piperidin]-1'-yl)-1-oxo-3-(pyrimidin-5-yl)propan-2-yl)carbamate (90 mg, 0.173 mmol) was added 4M HCl in dioxane (5 mL) and stirred at 25° C. for 2-3 h. LCMS showed the starting material was consumed completely. The reaction mixture was concentrated and the residue was dried in vacuum to give the title compound which was used for the next step without further purification.

MS (ESI) m/z 420.1 (M+H).

Step 8: N—((S)-1-((R)-6-chloro-5-fluoro-2-oxo-1,2-dihydrospiro[benzo[d][1,3]oxazine-4,3'-piperidin]-1'-yl)-1-oxo-3-(pyrimidin-5-yl)propan-2-yl)-2-oxo-1,2-dihydroquinoline-6-carboxamide (Example 113)

To a stirred solution of (3'R)-1'-(2-amino-3-(pyrimidin-5-yl)propanoyl)-6-chloro-5-fluorospiro [benzo[d][1,3]oxazine-4,3'-piperidin]-2(1H)-one hydrochloride (70 mg, 0.153 mmol) in DMF (10 mL) was added 2-oxo-1,2-dihydroquinoline-6-carboxylic acid (58.0 mg, 0.307 mmol), HATU (70.0 mg, 0.184 mmol) and DIPEA (0.107 mL, 0.614 mmol) at 25° C. The reaction mixture was stirred at 25° C. for 4 h. LCMS showed most of starting material was consumed completely. The reaction mixture was diluted with EtOAc (30 mL) and sat. NaHCO$_3$ (aq) (30 mL). The organic layer was washed with brine (30 mL), dried over Na$_2$SO$_4$, filtered and concentrated to give the crude product which was purified by prep-HPLC (preparative HPLC on a GILSON 281 instrument fitted with Waters XSELECT C18 150×30 mm×5 um using water and acetonitrile as the eluents. Mobile phase A: water (containing 0.05% ammonia-CH$_3$CN), mobile phase B: acetonitrile. Gradient: 45-75% B, 0-11 min; 100% B, 9-11 min) to give the title compound.

$^1$H NMR (CD$_3$OD, 400 MHz): δ 8.94-9.06 (m, 1H), 8.78 (br. s., 2H), 8.27 (s, 1H), 7.95-8.12 (m, 2H), 7.83 (d, J=8.5 Hz, 1H), 7.30-7.51 (m, 2H), 6.74-6.86 (m, 1H), 6.62-6.70 (m, 1H), 5.54 (t, J=7.3 Hz, 1H), 5.37 (dd, J=3.5, 10.0 Hz, 1H), 4.58-4.77 (m, 1H), 4.17 (d, J=14.1 Hz, 1H), 3.88 (d, J=14.6 Hz, 1H), 3.34-3.45 (m, 1H), 3.18-3.31 (m, 2H), 3.07-3.18 (m, 1H), 2.83-2.94 (m, 1H), 2.29-2.52 (m, 1H), 2.22 (d, J=16.6 Hz, 1H), 2.02-2.14 (m, 1H), 1.84-1.98 (m, 1H), 1.76 (d, J=12.5 Hz, 1H), 1.57 (d, J=12.0 Hz, 1H). MS (ESI) m/z 591.1 (M+H).

By using procedures similar to those described previously, and using appropriate starting materials, the following compounds were synthesized. These compounds were characterized by LC/MS.

| EXAMPLE | Structure | LCMS [M + 1] | FXIa Ki (nM) |
|---|---|---|---|
| 113 | N-((S)-1-((R)-6-chloro-5-fluoro-2-oxo-1,2-dihydrospiro[benzo[d][1,3]oxazine-4,3'-piperidin]-1'-yl)-1-oxo-3-(pyrimidin-5-yl)propan-2-yl)-2-oxo-1,2-dihydroquinoline-6-carboxamide | 591.1 | 15.61 |
| 114 | N-((S)-1-((R)-6-chloro-5-fluoro-2-oxo-1,2-dihydrospiro[benzo[d][1,3]oxazine-4,3'-piperidin]-1'-yl)-1-oxo-3-(pyrazin-2-yl)propan-2-yl)-2-oxo-1,2-dihydroquinoline-6-carboxamide | 591.1 | 74.4 |

Example 115

Methyl (4-(((S)-1-((R)-6-chloro-5-fluoro-2-oxo-1,2-dihydrospiro[benzo[d][1,3]oxazine-4,3'-piperidin]-1'-yl)-3-(1-methoxycyclopropyl)-1-oxopropan-2-yl)carbamoyl)phenyl)carbamate

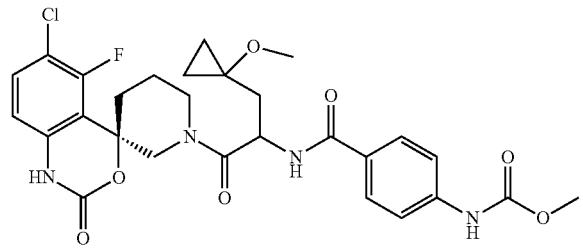 [SMILES: COC(=O)Nc1ccc(C(=O)NC(CC2(OC)CC2)C(=O)N2CCC[C@@]3(C2)OC(=O)Nc2ccc(Cl)c(F)c23)cc1]

Step A: Ethyl 1-methoxycyclopropane-1-carboxylate

To a stirred solution of ethyl 1-hydroxycyclopropanecarboxylate (1.2 g, 8.30 mmol) in THF (41.5 ml) was added NaH (0.231 g, 9.13 mmol) at 0° C. After 30 min at 0° C., iodomethane (0.571 ml, 9.13 mmol) was added dropwise. The reaction mixture was slowly warmed to RT and stirred overnight. The reaction mixture was quenched by adding sat. aq. NH$_4$Cl and dissolved in EtOAc. The organic layer was washed with brine and dried over MgSO$_4$, filtered and concentrated. The crude product was purified by flash silica gel column chromatography (100% Hex to 50/50=Hex/EtOAc) to provide ethyl 1-methoxycyclopropane-1-carboxylate. LCMS [M+1] 145

Step B: (1-methoxycyclopropyl)methanol

To a stirred solution of ethyl 1-methoxycyclopropane-1-carboxylate (434 mg, 3.01 mmol) in CH$_2$Cl$_2$ (15 ml) was added DIBAL-H (9.03 ml, 9.03 mmol) (1M in toluene) at −78° C. After the addition was complete, the reaction was warmed to RT and stirred for an additional 18 hours. The reaction was quenched with anhydrous methanol (4 mL) and stirred for an additional 30 min. The resulting mixture filtered through a short pad of Celite and washed with methanol, followed by DCM. The filtrate was dried over MgSO$_4$, filtered and concentrated in vacuo to provide the compound which was used in next step without further purification.

Step C: 1-Methoxycyclopropane-1-carbaldehyde

To a stirred solution of (1-methoxycyclopropyl)methanol (301 mg, 2.95 mmol) and molecule sieve 4A (powder) in DCM (1.47E+04 μl) at 0° C. was added PCC (953 mg, 4.42 mmol) at 0° C. The reaction mixture was stirred at 0° C. for 1 hr. The mixture was stirred at RT overnight. The reaction mixture was diluted with Et$_2$O, then filtered through Celite®, and rinsed with ether. The residue was concentrated (water bath temperature<15° C.) to ~2 mL of volume.

Step D: methyl (Z)-2-(((benzyloxy)carbonyl)amino)-3-(1-methoxycyclopropyl)acrylate To a stirred solution of (+/−)-benzyloxycarbonyl-alpha-phosphonoglycine trimethyl ester (976 mg, 2.95 mmol) in Tetrahydrofuran (12 ml) was added 1,1,3,3-tetramethylguanidine (0.370 ml, 2.95 mmol) at 0° C. After 1 hr at 0° C., a solution of (1-methoxycyclopropyl)methanol (295 mg, 2.95 mmol) in THF (3 mL) was added at 0° C. The reaction mixture was warmed to RT after 30 min at 0° C. The reaction mixture was stirred at RT overnight. Sat. NH$_4$Cl (aq) was added and the reaction mixture was extracted with DCM. The organic layer was dried over MgSO$_4$, filtered and concentrated. The crude product was purified by flash silica gel column chromatography (40 g, 100% Hex to 1/1 Hex/EtOAc) to afford 1-methoxycyclopropane-1-carbaldehyde. LCMS [M+1]=306

Step E: Methyl 2-amino-3-(1-methoxycyclopropyl)propanoate

To a stirred solution of 1-methoxycyclopropane-1-carbaldehyde (325 mg, 1.064 mmol) in MeOH (3548 μl) was added Pd—C (113 mg, 0.106 mmol) −10% activated at RT. An H$_2$ balloon was installed and the reaction mixture was stirred at RT overnight. The reaction mixture was diluted with DCM (20 mL) and filtered through a short pad of Celite. The filtrate was carefully concentrated at 0° C. in a water bath to afford methyl 2-amino-3-(1-methoxycyclopropyl)propanoate which was used for the next step without further purification. LCMS [M+1]=174

Step F: Methyl 2-(4-((methoxycarbonyl)amino)benzamido)-3-(1-methoxycyclopropyl)propanoate To a stirred solution of methyl 2-amino-3-(1-methoxycyclopropyl)propanoate (183 mg, 1.057 mmol) in DMF (5283 μl) was added 4-((methoxycarbonyl)amino)benzoic acid (227 mg, 1.162 mmol), HATU (442 mg, 1.162 mmol) and DIPEA (738 μl, 4.23 mmol) at RT. The reaction mixture was stirred at RT for 3 hr. Sat. NaHCO$_3$ (aq) was added and the reaction mixture was extracted with EtOAc. The organic layer was dried over MgSO$_4$, filtered and concentrated. The crude product was purified by flash silica gel column chromatography (40 g, 1/1 Hex/EtOAc) to provide methyl 2-(4-((methoxycarbonyl)amino)benzamido)-3-(1-methoxycyclopropyl)propanoate. LCMS [M+1]=351

Step G: 2-(4-((Methoxycarbonyl)amino)benzamido)-3-(1-methoxycyclopropyl)propanoic acid To a stirred solution of methyl 2-(4-((methoxycarbonyl)amino)benzamido)-3-(1-methoxycyclopropyl)propanoate (344 mg, 0.982 mmol) in THF (5 ml) was added a solution of lithium hydroxide monohydrate (41.2 mg, 0.982 mmol) in water (1 mL) and MeOH (2 mL) at RT. The reaction mixture was stirred at RT overnight. 4N HCl in dioxane was added to generate pH=4. The solvent was evaporated and the crude product was dried in vac. oven to provide 2-(4-((methoxycarbonyl)amino)benzamido)-3-(1-methoxycyclopropyl)propanoic acid. LCMS [M+1]=337

Step H: Methyl (4-((1-((R)-6-chloro-5-fluoro-2-oxo-1,2-dihydrospiro[benzo[d][1,3]oxazine-4,3'-piperidin]-1'-yl)-3-(1-methoxycyclopropyl)-1-oxopropan-2-yl)carbamoyl)phenyl)carbamate To a stirred solution of (R)-6-chloro-5-fluorospiro[benzo[d][1,3]oxazine-4,3'-piperidin]-2(1H)-one hydrochloride (280 mg, 0.912 mmol) in DMF (4558 µl) was added 2-(4-((methoxycarbonyl)amino)benzamido)-3-(1-methoxycyclopropyl)propanoic acid (337 mg, 1.003 mmol), HATU (381 mg, 1.003 mmol) and DIPEA (637 µl, 3.65 mmol) at RT. The reaction mixture was stirred at RT for 3 hr.

Sat. NaHCO₃ (aq) was added and the reaction mixture was extracted with EtOAc. The organic layer was washed with brine, dried over MgSO₄, filtered and concentrated. The crude product was purified by flash silica gel column chromatography (40 g, 1/1 EtOAc/Hex to 100% EtOAc) to afford methyl (4-((1-((R)-6-chloro-5-fluoro-2-oxo-1,2-dihydrospiro[benzo[d][1,3]oxazine-4,3'-piperidin]-1'-yl)-3-(1-methoxycyclopropyl)-1-oxopropan-2-yl)carbamoyl)phenyl)carbamate (racemic). The diastereomeric mixtures were resolved under 30% ethanol (0.1% DEA)/CO₂, 100 bar (254 nm) with AS-H (2×25 cm) chiral column.

| Example | Structure | LCMS [M + 1] | FXIa Ki (nM) |
|---|---|---|---|
| 115 | methyl (4-(((S)-1-((R)-6-chloro-5-fluoro-2-oxo-1,2-dihydro-spiro[benzo[d][1,3]oxazine-4,3'-piperidin]-1'-yl)-3-(1-methoxycyclopropyl)-1-oxopropan-2-yl)carbamoyl)phenyl)carbamate | 590.0 | 0.6 |

Example 116

Methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate

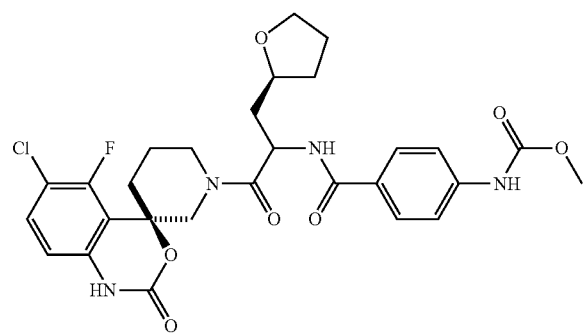

EX-116A

-continued

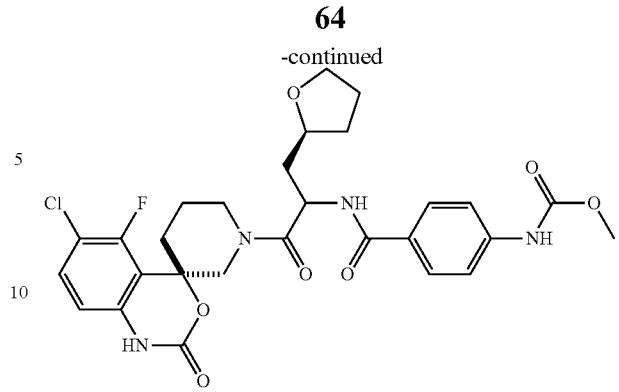

EX-116B

Step 1: (S)-(tetrahydrofuran-2-yl)methanol

To a stirred mixture of (S)-tetrahydrofuran-2-carboxylic acid (3.5 g, 30.1 mmol) in THF (100 mL) at 0° C. was added borane dimethyl sulfide complex (5.72 mL, 60.3 mmol) and the mixture was stirred at 20° C. for 15 h. TLC showed the reaction was complete. The mixture was cooled to 0° C. and MeOH (20 mL) was added dropwise. Then the mixture was allowed to warm to 30° C. and stirred for 30 min. After that, the reaction mixture was concentrated to give the title compound, which was used in the next step reaction without further purification.

¹H NMR (CD₃OD, 400 MHz): 3.93-4.01 (m, 1H), 3.83-3.91 (m, 1H), 3.70-3.83 (m, 1H), 3.53 (dq, J=5.0, 11.5 Hz, 2H), 1.84-2.03 (m, 3H), 1.56-1.75 (m, 1H).

Step 2: (S)-tetrahydrofuran-2-carbaldehyde

To a solution of oxalyl dichloride (2.79 mL, 29.4 mmol) in dry DCM (30 mL) at −78° C. under nitrogen atmosphere was DMSO (4.17 mL, 58.7 mmol). After stirring for a few min, a solution of (S)-(tetrahydrofuran-2-yl)methanol (1.5 g, 14.69 mmol) in DCM (5 mL) was added and the reaction mixture was stirred at −78° C. for 30 min. Et₃N (20.47 mL, 147 mmol) was then added dropwise and the mixture was further stirred at −78° C. for 2 h. TLC showed the reaction was complete. The mixture was quenched with aqueous ammonium chloride (saturated, 20 mL) and extracted with dichloromethane (3×20 mL). The combined organic fractions were washed with brine (20 mL), dried (Na₂SO₄), filtered and evaporated to give the title compound, which was used in the next step reaction directly.

Step 3: (S,E)-methyl 2-(((benzyloxy)carbonyl) amino)-3-(tetrahydrofuran-2-yl)acrylate To a solution of methyl 2-(((benzyloxy)carbonyl)amino)-2-(dimethoxyphosphoryl)acetate (5.28 g, 15.94 mmol) in tetrahydrofuran (15 mL) at 0° C. was added 1,1,3,3-tetramethylguanidine (2.02 mL, 15.94 mmol) and the mixture was stirred at 0° C. for 1.5 h. After that (S)-tetrahydrofuran-2-carbaldehyde (1.33 g, 13.28 mmol) in THF (5 mL) was added dropwise and the resulting solution was allowed to warm up to 20° C. and stirred for 15 h until TLC showed the reaction was complete. The mixture was quenched with aqueous ammonium chloride (saturated, 50 mL) and extracted with EtOAc (3×50 mL). The combined organic fractions were washed with brine (50 mL), dried (Na₂SO₄), filtered and evaporated. The crude product was purified by flash silica gel chromatography (ISCO®; 20 g SepaFlash®

Silica Flash Column, Eluent of 0~40% EtOAc/PE gradient at 30 mL/min) to give the title compound.

$^1$H NMR (CD$_3$OD, 400 MHz): 7.21-7.43 (m, 5H), 6.45 (d, J=7.94 Hz, 1H), 5.11 (s, 2H), 4.60 (q, J=7.50 Hz, 1H), 3.87 (q, J=7.20 Hz, 1H), 3.64-3.80 (m, 4H), 2.07-2.23 (m, 1H), 1.83-2.01 (m, 2H), 1.52-1.72 (m, 1H). MS (ESI) m/z 306.2 (M+H).

Step 4: methyl 2-amino-3-((S)-tetrahydrofuran-2-yl)propanoate

A mixture of (S,E)-methyl 2-(((benzyloxy)carbonyl) amino)-3-(tetrahydrofuran-2-yl)acrylate (280 mg, 0.917 mmol), 10% Pd—C (48.8 mg, 0.046 mmol) in MeOH (20 mL) was evacuated and back-filled with H$_2$ three times and then stirred at 20° C. for 3 h under H$_2$ balloon. TLC showed the reaction was complete. The mixture was filtered, washing with methanol (150 mL) and concentrated to give the title compound, which was used in the next step reaction directly.

$^1$H NMR (CD$_3$OD, 400 MHz): 3.91-4.02 (m, 1H), 3.81 (q, J=7.28 Hz, 1H), 3.65-3.75 (m, 4H), 3.53-3.61 (m, 1H), 2.03 (dd, J=7.39, 11.36 Hz, 1H), 1.84-1.97 (m, 3H), 1.67-1.83 (m, 1H), 1.44-1.56 (m, 1H).

Step 5: methyl 2-(4-((methoxycarbonyl)amino)benzamido)-3-((S)-tetrahydrofuran-2-yl)propanoate A mixture of 4-((methoxycarbonyl)amino)benzoic acid (124 mg, 0.635 mmol), HATU (290 mg, 0.762 mmol), DIPEA (0.222 mL, 1.270 mmol), methyl 2-amino-3-((S)-tetrahydrofuran-2-yl)propanoate (110 mg, 0.635 mmol) in DMF (3 mL) was stirred at 20° C. for 2 h. LCMS showed the reaction was complete. The mixture was diluted with water (15 mL) and extracted with EtOAc (3×30 mL). The combined organic fractions were washed with brine (30 mL), dried (Na$_2$SO$_4$), filtered and evaporated. The crude product was purified by flash silica gel chromatography (ISCO®; 12 g SepaFlash® Silica Flash Column, Eluent of 0-60% EtOAc/PE gradient at 30 mL/min) to give the title compound.

MS (ESI) m/z 351.2 (M+H).

Step 6: 2-(4-((methoxycarbonyl)amino)benzamido)-3-((S)-tetrahydrofuran-2-yl)propanoic acid A mixture of methyl 2-(4-((methoxycarbonyl)amino)benzamido)-3-((S)-tetrahydrofuran-2-yl)propanoate (180 mg, 0.514 mmol), lithium hydroxide monohydrate (43.1 mg, 1.027 mmol) in a co-solvent of MeOH (2 mL)/tetrahydrofuran (2 mL)/water (2 mL) was stirred at 20° C. for 3 h. LCMS showed the reaction was complete. The mixture was acidified with hydrochloric acid (2M) until pH 3.0 and extracted with EtOAc (3×30 mL). The combined organic fractions were washed with brine (30 mL), dried (Na$_2$SO$_4$), filtered and evaporated to give the title compound, which used in the next step reaction directly.

MS (ESI) m/z 337.1 (M+H).

Step 7: methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate (Example 116)

A mixture of 2-(4-((methoxycarbonyl)amino)benzamido)-3-((S)-tetrahydrofuran-2-yl)propanoic acid (20 mg, 0.059 mmol), (R)-6-chloro-5-fluorospiro[benzo[d][1,3]oxazine-4,3'-piperidin]-2(1H)-one (16.10 mg, 0.059 mmol), HATU (27.1 mg, 0.071 mmol), DIPEA (0.031 mL, 0.178 mmol) in DMF (2 mL) was stirred at 20° C. for 1 hour. LCMS showed the reaction was complete. The reaction mixture was diluted with water (10 mL) and extracted with ethyl acetate (3×15 mL). The combined organic fractions were washed with brine (20 mL), dried (Na$_2$SO$_4$), filtered and evaporated. The residue was purified by reversed prep. HPLC (preparative HPLC on an EB instrument fitted with a Phenomenex Synergi C18 150×30 mm×4 um using water and acetonitrile as the eluents. Mobile phase A: water (containing 0.1% TFA, v/v), B: acetonitrile. Gradient: 40-55% B, 0-10 min; 100% B, 10.5-12.5 min; 5% B, 13-15 min) to give the title compound.

$^1$H NMR (CD$_3$OD, 400 MHz): 7.67-7.89 (m, 2H), 7.45-7.58 (m, 2H), 7.35-7.45 (m, 1H), 6.73 (dd, J=3.20, 7.83 Hz, 1H), 4.99-5.39 (m, 1H), 4.52-4.76 (m, 1H), 4.03-4.42 (m, 1H), 3.60-3.99 (m, 6H), 3.17 (dd, J=3.53, 13.89 Hz, 1H), 2.44-2.85 (m, 1H), 2.28 (d, J=8.16 Hz, 1H), 1.81-2.21 (m, 7H), 1.43-1.74 (m, 2H). MS (ESI) m/z 589.3 (M+H).

Step 8: methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate (EX-116A)

Compound methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate (55 mg, 0.093 mmol) was separated with preparative chiral HPLC (Column: OD(250 mm×30 mm, 5 um), Mobile phase: Base-EtOH in CO$_2$, Flow rate: 60 mL/min Wave length: 220 nm t$_{R1}$=5.223 min, t$_{R2}$=5.927) to give crude Example 116 (first peak isomer with shorter retention time in chiral HPLC) and crude Example 116 diasteromer (second peak isomer with longer retention time). The crude Example 116 was purified by reversed prep.HPLC (preparative HPLC on an EB instrument fitted with a Phenomenex Synergi C18 150×30 mm×4 um using water and acetonitrile as the eluents. Mobile phase A: water (containing 0.1% TFA, v/v), B: acetonitrile. Gradient: 43-58% B, 0-10 min; 100% B, 10.5-12.5 min; 5% B, 13-15 min) to give EX-116A. The crude Example 116 diasteromer was purified by reversed prep.HPLC (preparative HPLC on an EB instrument fitted with a Phenomenex Synergi C18 150×30 mm×4 um using water and acetonitrile as the eluents. Mobile phase A: water (containing 0.1% TFA, v/v), B: acetonitrile. Gradient: 43-58% B, 0-10 min; 100% B, 10.5-12.5 min; 5% B, 13-15 min) to give EX-116B.

Example 116A $^1$H NMR (CD$_3$OD, 400 MHz): 7.87 (d, J=8.82 Hz, 1H), 7.74 (d, J=8.60 Hz, 1H), 7.48-7.59 (m, 2H), 7.37-7.47 (m, 1H), 6.75 (dd, J=2.54, 8.49 Hz, 1H), 5.01-5.40 (m, 1H), 4.61-4.86 (m, 1H), 3.91-4.28 (m, 1H), 3.78-3.90 (m, 2H), 3.74 (s, 3H), 3.64-3.73 (m, 1H), 3.15-3.27 (m, 1H), 2.46-2.86 (m, 1H), 1.98-2.39 (m, 5H), 1.79-1.96 (m, 3H), 1.47-1.75 (m, 2H) MS (ESI) m/z 589.3 (M+H).

Example 116B $^1$H NMR (CD$_3$OD, 400 MHz): 7.68-7.83 (m, 2H), 7.53 (d, J=8.60 Hz, 2H), 7.41 (t, J=8.05 Hz, 1H), 6.74 (d, J=8.60 Hz, 1H), 5.23-5.38 (m, 1H), 4.56-4.86 (m, 1H), 4.35 (d, J=13.45 Hz, 1H), 3.98-4.17 (m, 1H), 3.90 (q, J=7.20 Hz, 1H), 3.76-3.83 (m, 1H), 3.74 (s, 3H), 3.32-3.44 (m, 1H), 3.18 (d, J=13.89 Hz, 1H), 2.43-2.89 (m, 1H), 2.29 (d, J=13.89 Hz, 1H), 2.06-2.22 (m, 3H), 1.87-2.05 (m, 3H), 1.81 (d, J=13.89 Hz, 1H), 1.43-1.71 (m, 1H). MS (ESI) m/z 589.3 (M+H).

By using procedures similar to those described previously, and using appropriate starting materials, the following compounds were synthesized. These compounds were characterized by LC/MS.

| Examples | Structure | LCMS [M + 1] | FXIa Ki (nM) |
|---|---|---|---|
| 116A (isomer A) | methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate | 589.3 | 7.51 |
| 116B (Isomer B) | methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate | 589.3 | 4.21 |
| 117A (Isomer A) | methyl (4-((1-((R)-6-chloro-5-fluoro-2-oxo-1,2-dihydrospiro[benzo[d][1,3]oxazine-4,3'-piperidin]-1'-yl)-1-oxo-3-((R)-tetrahydrofuran-2-yl)propan-2-yl)carbamoyl)phenyl)carbamate | 589.1 | 18.73 |
| 117B (Isomer B) | methyl (4-((1-((R)-6-chloro-5-fluoro-2-oxo-1,2-dihydrospiro[benzo[d][1,3]oxazine-4,3'-piperidin]-1'-yl)-1-oxo-3-((R)-tetrahydrofuran-2-yl)propan-2-yl)carbamoyl)phenyl)carbamate | 589.1 | 99.93 |

Example 118

Methyl (4-(((2S,4S)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate

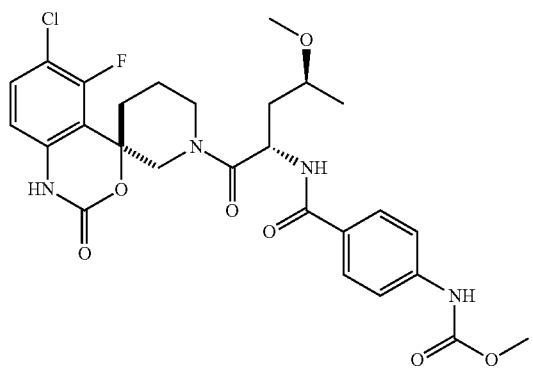

Step 1: (S)-tert-butyl 4-(2-hydroxyethyl)-2,2-dimethyloxazolidine-3-carboxylate

To a solution of (S)-tert-butyl (1,4-dihydroxybutan-2-yl)carbamate (3.8 g, 18.51 mmol) in DCM (50 mL) was added 2,2-dimethoxypropane (28.9 g, 278 mmol) and p-toluenesulfonic acid monohydrate (0.352 g, 1.851 mmol) at 18° C. The resulting mixture was stirred for 2 h at 18° C. TLC (PE/EtOAc=3:1) indicated the reaction was complete. Saturated NaHCO₃ (50 mL) was added and the mixture was extracted with DCM (40 mL×3). The combined organic layers were washed with water (20 mL) and brine (20 mL), dried over anhydrous sodium sulfate, filtered and concentrated. The crude product was purified with combi flash (flash column silica-CS (12 g) PE/EtOAc=100:1-5:1) to give the title compound.

Step 2: (S)-tert-butyl 2,2-dimethyl-4-(2-oxoethyl)oxazolidine-3-carboxylate

To a solution of DMSO (1.591 mL, 22.42 mmol) in dry DCM (15 mL) at −78° C. was added dropwise oxalyl chloride (1.366 g, 10.76 mmol) in a schlenk tube and stirred for 30 min. A solution of (S)-tert-butyl 4-(2-hydroxyethyl)-2,2-dimethyloxazolidine-3-carboxylate (2.2 g, 8.97 mmol) in 25 mL of DCM was added dropwise. After further stirring at −78° C. for 30 min, Et₃N (7.50 mL, 53.8 mmol) was added dropwise, and then the mixture was warmed to 18° C. and stirred for 1.6 h. TLC showed the reaction was complete. The mixture was diluted with water (50 mL) and extracted with DCM (60 mL×3). The combined organic layers were washed with water (50 mL) and brine (40 mL), dried over anhydrous sodium sulfate, filtered and concentrated to give the title compound.

Step 3: (S)-tert-butyl 4-((S)-2-hydroxypropyl)-2,2-dimethyloxazolidine-3-carboxylate To a solution of (S)-tert-butyl 2,2-dimethyl-4-(2-oxoethyl)oxazolidine-3-carboxylate (2.15 g, 8.84 mmol) in dry THF (20 mL) at 18° C. was added 3M methylmagnesium bromide (4.42 ml, 13.26 mmol) in a schlenk tube. The mixture was stirred for 16 h. TLC showed the reaction was complete. The mixture was diluted with sat. NH₄Cl solution (40 mL) and extracted with EtOAc (70 mL×3). The combined organic layers were washed with water (40 mL) and brine (50 mL), dried over anhydrous sodium sulfate, filtered and concentrated. The crude product was purified with combi flash (flash column silica-CS (40 g) PE/EtOAc=100:1-5:1) to give the title compound. MS (ESI) m/z 260.1 (M+H).

Step 4: (S)-tert-butyl 4-((S)-2-methoxypropyl)-2,2-dimethyloxazolidine-3-carboxylate To a cooled solution of (S)-tert-butyl 4-((S)-2-hydroxypropyl)-2,2-dimethyloxazolidine-3-carboxylate (550 mg, 2.121 mmol) in dry tetrahydrofuran (5 mL) was added NaH (187 mg, 4.67 mmol). The mixture was warmed to 20° C. and iodomethane (452 mg, 3.18 mmol) was added. The mixture was stirred at 20° C. for 16 h. TLC indicated the reaction was complete. The mixture was diluted with sat. NH$_4$Cl aqueous solution (10 mL) and extracted with EtOAc (40 mL×3). The combined organic layers were washed with water (30 mL) and brine (20 mL), dried over anhydrous sodium sulfate, filtered and concentrated to give the title compound which was carried to the next step without further purification. MS (ESI) m/z 274.2 (M+H).

Step 5: tert-butyl ((2S,4S)-1-hydroxy-4-methoxypentan-2-yl)carbamate

To a solution of (S)-tert-butyl 4-((S)-2-methoxypropyl)-2,2-dimethyloxazolidine-3-carboxylate (550 mg, 2.012 mmol) in MeOH/THF 10:1 (8 mL) was added p-toluenesulfonic acid monohydrate (19.14 mg, 0.101 mmol) at 0° C. The resulting mixture was stirred for 12 h at 18° C. and TLC showed the reaction was complete. Solvents were evaporated and the residue was diluted with aq. NaHCO$_3$ and extracted with EtOAc (40 mL×3). The combined organic layers were washed with water (40 mL) and brine (50 mL), dried over anhydrous sodium sulfate, filtered and concentrated to give the crude title compound. MS (ESI) m/z 234.1 (M+H).

Step 6: (2S,4S)-2-((tert-butoxycarbonyl)amino)-4-methoxypentanoic acid

To a mixture of tert-butyl ((2S,4S)-1-hydroxy-4-methoxypentan-2-yl)carbamate (350 mg, 1.500 mmol) in acetonitrile (5 mL) and phosphate buffer (2 mL, pH=7) was added TEMPO (23.44 mg, 0.150 mmol) and a solution of sodium chlorite (271 mg, 3.00 mmol) in water (1 mL). The solution was warmed to 30° C. and catalytic amount of diluted bleach (0.36% in water, 1 mL) was added. The mixture was further stirred for 2 h at 30° C. and LCMS indicated the reaction was complete. The mixture was cooled to 0° C. and adjusted to pH 9 with dilute sodium hydroxide solution. Sodium sulfite solution (2 g) in water (10 mL) was added and the mixture was stirred for 20 min. The resulting mixture was washed with methyl butyl ether and the organic layer was discarded. The aqueous layer was acidified with aqueous hydrochloric acid to pH ~2 and extracted with methyl butyl ether (40 mL×4). The combined organic layers were washed with water (20 mL) and brine (20 mL), dried over anhydrous sodium sulfate, filtered and concentrated to give the title compound. MS (ESI) m/z 248.1 (M+H).

Step 7: tert-butyl ((2S,4S)-1-((R)-6-chloro-5-fluoro-2-oxo-1,2-dihydrospiro[benzo[d][1,3]-oxazine-4,3'-piperidin]-1'-yl)-4-methoxy-1-oxopentan-2-yl)carbamate To a solution of (R)-6-chloro-5-fluorospiro[benzo[d][1,3]oxazine-4,3'-piperidin]-2(1H)-one hydrochloride (124 mg, 0.404 mmol), (2S,4S)-2-((tert-butoxycarbonyl)amino)-4-methoxypentanoic acid (100 mg, 0.404 mmol) and HATU (231 mg, 0.607 mmol) in DMF (2 mL) was added DIPEA (0.177 ml, 1.011 mmol) at 18° C. The resulting mixture was stirred at 18° C. for 12 h. TLC indicated the reaction was complete. The mixture was diluted with water (10 mL) and extracted with EtOAc (20 mL×3). The combined organic layers were washed with water (20 mL) and brine (15 mL), dried over anhydrous sodium sulfate, filtered and concentrated. The crude product was purified with combi flash (flash column silica-CS (4 g) PE/EtOAc=100:1-5:1) to give the title compound. MS (ESI) m/z 500.2 (M+H).

Step 8: (R)-1'-((2S,4S)-2-amino-4-methoxypentanoyl)-6-chloro-5-fluorospiro[benzo[d][1,3]-oxazine-4,3'-piperidin]-2(1H)-one 2,2,2-trifluoroacetate To a solution of tert-butyl ((2S,4S)-1-((R)-6-chloro-5-fluoro-2-oxo-1,2-dihydrospiro[benzo-[d][1,3]oxazine-4,3'-piperidin]-1'-yl)-4-methoxy-1-oxopentan-2-yl)carbamate (100 mg, 0.200 mmol) in DCM (3 mL) was added TFA (1.5 mL, 19.47 mmol) at 20° C. The resulting mixture was stirred at 20° C. for 2 h. TLC indicated the reaction was complete. The mixture was concentrated to give the title compound. MS (ESI) m/z 400.1 (M+H).

Step 9: methyl (4-(((2S,4S)-1-((R)-6-chloro-5-fluoro-2-oxo-1,2-dihydrospiro[benzo[d][1,3]-oxazine-4,3'-piperidin]-1'-yl)-4-methoxy-1-oxopentan-2-yl)carbamoyl)phenyl)carbamate To a solution of 4-((methoxycarbonyl)amino)benzoic acid (38.0 mg, 0.195 mmol), (R)-1'-((2S,4S)-2-amino-4-methoxypentanoyl)-6-chloro-5-fluorospiro[benzo[d][1,3]oxazine-4,3'-piperidin]-2(1H)-one 2,2,2-trifluoroacetate (100 mg, 0.195 mmol), HATU (111 mg, 0.292 mmol) in DMF (2 mL) was added DIPEA (0.085 mL, 0.487 mmol) at 20° C. The resulting mixture was stirred for 12 h at 20° C. LCMS indicated the reaction was complete. The mixture was diluted with MeCN (3 mL) and filtered. The filtrate was purified with pre-HPLC (TFA condition) to give the title compound.

$^1$H NMR (CD$_3$OD, 400 MHz): =9.50 (br. s., 1H), 7.86 (d, J=8.6 Hz, 1H), 7.77 (d, J=8.6 Hz, 1H), 7.52 (t, J=8.5 Hz, 2H), 7.42 (q, J=8.4 Hz, 1H), 6.73 (dd, J=4.7, 8.0 Hz, 1H), 5.49-5.36 (m, 1H), 5.14 (d, J=7.9 Hz, 1H), 4.71-4.57 (m, 1H), 4.27 (d, J=13.9 Hz, 1H), 3.85 (d, J=13.9 Hz, 1H), 3.73 (s, 3H), 3.24-3.08 (m, 3H), 2.84-2.69 (m, 1H), 2.55-2.43 (m, 1H), 2.35-2.17 (m, 1H), 2.10-1.76 (m, 3H), 1.14 (d, J=6.2 Hz, 3H). MS (ESI) m/z 577.2 (M+H).

| Example | Structure | LCMS [M + 1] | FXIa Ki (nM) |
|---|---|---|---|
| 118A (isomer A) | methyl (4-(((2S,4S)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate | 577.2 | 2.52 |
| 118B (isomer B) | methyl (4-(((2S,4R)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate | 577.2 | 0.72 |
| 118C (isomer C) | methyl (4-(((2R,4R)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate | 577.2 | 246 |

| Example | Structure | LCMS [M + 1] | FXIa Ki (nM) |
|---|---|---|---|
| 118D (isomer D) | methyl (4-(((2R,4S)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate | 577.2 | 95.38 |

Example 119

Methyl (4-(((S)-1-((R)-6-chloro-5-fluoro-2-oxo-1,2-dihydrospiro[benzo[d][1,3]oxazine-4,3'-piperidin]-1'-yl)-4-methoxy-4-methyl-1-oxopentan-2-yl)carbamoyl)phenyl)carbamate

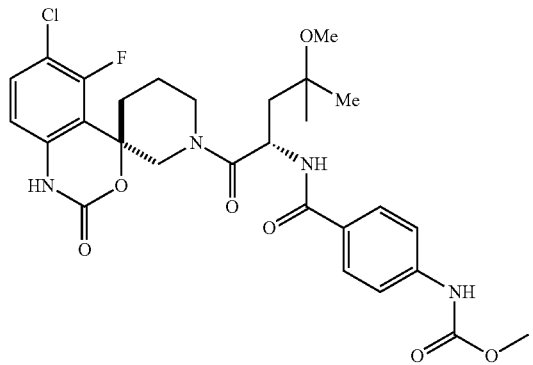

Step 1: (S)-tert-butyl 2,2-dimethyl-4-(2-oxopropyl)oxazolidine-3-carboxylate

To a solution of DMSO (0.376 mL, 5.30 mmol) in dry DCM (15 mL) at −78° C. was added oxalyl chloride (323 mg, 2.54 mmol) in a schlenk tube and stirred for 30 min. A solution of (S)-tert-butyl 4-((S)-2-hydroxypropyl)-2,2-dimethyloxazolidine-3-carboxylate (550 mg, 2.121 mmol) in 25 mL of DCM was added dropwise. After stirring −78° C. for 90 min. TEA (1.774 mL, 12.72 mmol) was added dropwise and the mixture was slowly warmed to 18° C. and further stirred for 1.6 h. TLC showed the reaction was complete. The mixture was diluted with water (50 mL) and extracted with DCM (60 mL×3). The combined organic layers were washed with water (50 mL) and brine (40 mL), dried over anhydrous sodium sulfate, filtered and concentrated to give the title compound. MS (ESI) m/z 258.1 (M+H).

Step 2: (S)-tert-butyl 4-(2-hydroxy-2-methylpropyl)-2,2-dimethyloxazolidine-3-carboxylate To a solution of (S)-tert-butyl 2,2-dimethyl-4-(2-oxopropyl)oxazolidine-3-carboxylate (500 mg, 1.943 mmol) in dry THF (5 mL) at 18° C. was added methylmagnesium bromide (0.972 ml, 2.91 mmol) in a schlenk tube. The mixture was stirred for 16 h. TLC showed the reaction was complete. The mixture was diluted with sat. NH₄Cl solution (40 mL) and extracted with EtOAc (70 mL×3). The combined organic layers were washed with water (40 mL) and brine (50 mL), dried over anhydrous sodium sulfate, filtered and concentrated. The crude product was purified with combi flash (flash column silica-CS (40 g) PE/EtOAc=100:1-5:1) to give the title compound. MS (ESI) m/z 274.1 (M+H).

Step 3: (S)-tert-butyl 4-(2-methoxy-2-methylpropyl)-2,2-dimethyloxazolidine-3-carboxylate To a cooled solution of (S)-tert-butyl 4-(2-hydroxy-2-methylpropyl)-2,2-dimethyloxazolidine-3-carboxylate (400 mg, 1.463 mmol) in dry tetrahydrofuran (5 mL) was added NaH (129 mg, 3.22 mmol). The suspension was warmed to 20° C. and iodomethane (312 mg, 2.195 mmol) was added. The mixture was stirred at 20° C. for 16 h. TLC indicated the reaction was complete. The mixture was diluted with sat. NH₄Cl aqueous solution (10 mL) and extracted with EtOAc (40 mL×3). The combined organic layers were washed with water (30 mL) and brine (20 mL), dried over anhydrous sodium sulfate, filtered and concentrated to give the title compound which was carried to the next step without further purification. MS (ESI) m/z 288.1 (M+H).

Step 4: (S)-tert-butyl (1-hydroxy-4-methoxy-4-methylpentan-2-yl)carbamate

To a solution of (S)-tert-butyl 4-(2-methoxy-2-methylpropyl)-2,2-dimethyloxazolidine-3-carboxylate (200 mg, 0.696 mmol) in MeOH/THF 10:1 (8 mL) was added p-toluenesulfonic acid monohydrate (6.62 mg, 0.035 mmol) at 0° C. The resulting mixture was stirred for 12 h at 18° C. and TLC showed the reaction was complete. Solvents were evaporated and the residue was diluted with aq. NaHCO₃ and extracted with EtOAc (40 mL×3). The combined organic layers were washed with water (40 mL) and brine (50 mL), dried over anhydrous sodium sulfate, filtered and concentrated to give the title compound.

Step 5: (S)-2-((tert-butoxycarbonyl)amino)-4-methoxy-4-methylpentanoic acid

To a mixture of (S)-tert-butyl (1-hydroxy-4-methoxy-4-methylpentan-2-yl)carbamate (150 mg, 0.606 mmol) in acetonitrile (5 mL) and phosphate buffer (2 mL, pH=7) was added TEMPO (9.48 mg, 0.061 mmol) and a solution of sodium chlorite (110 mg, 1.213 mmol) in water (1 mL). The mixture was warmed to 30° C. and catalytic amount of diluted bleach (0.36% in water, 1 mL) was added. The mixture was stirred for 2 h at 30° C. and LCMS indicated the reaction was complete. The mixture was cooled to 0° C. and adjusted to pH 9 with dilute sodium hydroxide solution. Sodium sulfite solution (2 g) in water (10 mL) was added and the mixture was stirred for 20 min. The resulting solution was extracted with methyl butyl ether and the organic layer was discarded. The aqueous layer was acidified with 1N aqueous hydrochloric acid to ~pH 2 and extracted with methyl butyl ether (40 mL×4). The combined organic layers were washed with water (20 mL) and brine (20 mL), dried over anhydrous sodium sulfate, filtered and concentrated to give the title compound. MS (ESI) m/z 262.1 (M+H).

Step 6: tert-butyl ((S)-1-((R)-6-chloro-5-fluoro-2-oxo-1,2-dihydrospiro[benzo[d][1,3]oxazine-4,3'-piperidin]-1'-yl)-4-methoxy-4-methyl-1-oxopentan-2-yl)carbamate To a solution of (R)-6-chloro-5-fluorospiro[benzo[d][1,3] oxazine-4,3'-piperidin]-2(1H)-one hydrochloride (118 mg, 0.383 mmol), (S)-2-((tert-butoxycarbonyl)amino)-4-methoxy-4-methylpentanoic acid (100 mg, 0.383 mmol) and HATU (218 mg, 0.574 mmol) in DMF (1 mL) was added DIPEA (0.167 mL, 0.957 mmol) at 18° C. The resulting mixture was stirred for 12 h at 18° C. TLC indicated the reaction was complete. The mixture was diluted with water (10 mL) and extracted with EtOAc (20 mL×3). The combined organic layers were washed with water (20 mL) and brine (15 mL), dried over anhydrous sodium sulfate, filtered and concentrated. The crude product was purified with combi flash (flash column silica-CS (4 g) PE/EtOAc=100:1-5:1) to give the title compound. MS (ESI) m/z 514.2 (M+H).

Step 7: (R)-1'-((S)-2-amino-4-methoxy-4-methylpentanoyl)-6-chloro-5-fluorospiro[benzo[d][1,3]oxazine-4,3'-piperidin]-2(1H)-one 2,2,2-trifluoroacetate To a solution of tert-butyl ((S)-1-((R)-6-chloro-5-fluoro-2-oxo-1,2-dihydrospiro[benzo[d][1,3]-oxazine-4,3'-piperidin]-1'-yl)-4-methoxy-4-methyl-1-oxopentan-2-yl)carbamate (120 mg, 0.233 mmol) in DCM (3 mL) was added TFA (1.5 mL, 19.47 mmol) at 20° C. The resulting mixture was stirred at 20° C. for 2 h. LCMS indicated the reaction was complete. The mixture was concentrated to give the title compound, which was carried to the next step without further purification. MS (ESI) m/z 414.2 (M+H).

Step 8: methyl (4-(((S)-1-((R)-6-chloro-5-fluoro-2-oxo-1,2-dihydrospiro[benzo[d][1,3]oxazine-4,3'-piperidin]-1'-yl)-4-methoxy-4-methyl-1-oxopentan-2-yl)carbamoyl)phenyl)carbamate (Example 119)

To a solution of 4-((methoxycarbonyl)amino)benzoic acid (44.4 mg, 0.227 mmol), (R)-1'-((S)-2-amino-4-methoxy-4-methylpentanoyl)-6-chloro-5-fluorospiro[benzo[d][1,3]oxazine-4,3'-piperidin]-2(1H)-one 2,2,2-trifluoroacetate (120 mg, 0.227 mmol), HATU (130 mg, 0.341 mmol) in DMF (2 mL) was added DIPEA (0.099 mL, 0.568 mmol) at 20° C. The resulting mixture was stirred for at 20° C. for 12 h. LCMS indicated the reaction was completed. The mixture was diluted with MeCN (3 mL) and filtered. The filtrate was purified with pre-HPLC (TFA condition) to give the title compound.
$^1$H NMR (CD$_3$OD, 400 MHz): 7.86 (d, J=8.6 Hz, 1H), 7.76 (d, J=8.8 Hz, 1H), 7.60-7.49 (m, 2H), 7.48-7.35 (m, 1H), 6.74 (d, J=8.6 Hz, 1H), 5.43 (t, J=6.0 Hz, 1H), 5.11 (d, J=9.0 Hz, 1H), 4.85 (d, J=14.1 Hz, 1H), 4.65 (d, J=12.8 Hz, 1H), 3.85-3.72 (m, 4H), 3.19 (s, 1H), 3.02 (s, 2H), 2.84-2.73 (m, 1H), 2.32-2.18 (m, 2H), 2.02 (dd, J=9.9, 15.0 Hz, 1H), 1.78-1.57 (m, 1H), 1.27-1.11 (m, 6H). MS (ESI) m/z 591.3 (M+H).

| Example | Structure | LCMS [M + 1] | FXIa Ki (nM) |
|---|---|---|---|
| 119 | methyl (4-(((2S)-1-(6-chloro-5-fluoro-2-oxo-1,2-dihydro- | 591.3 | 10.21 |

| Example | Structure | LCMS [M + 1] | FXIa Ki (nM) |
|---|---|---|---|
| | spiro[benzo[d][1,3]oxazine-4,3'-piperidin]-1'-yl)-4-methoxy-4-methyl-1-oxopentan-2-yl)carbamoyl)phenyl)carbamate | | |

Example 120

Methyl (4-(2-benzyl-3-(6-chloro-2-oxo-1,2-dihydrospiro[benzo[d][1,3]-oxazine-4,3'-pyrrolidin]-1'-yl)-3-oxopropanamido)phenyl)carbamate

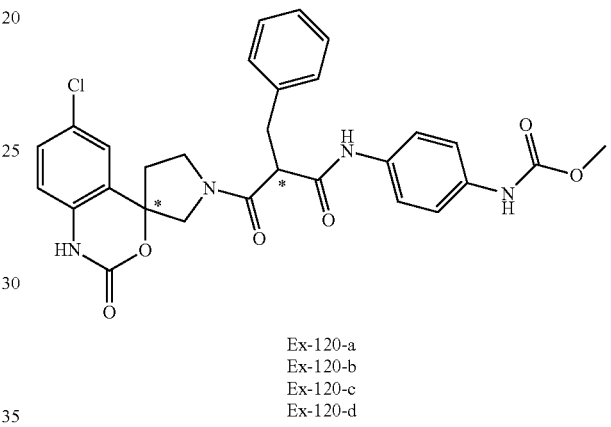

Ex-120-a
Ex-120-b
Ex-120-c
Ex-120-d

Step A: 2-Benzyl-3-ethoxy-3-oxopropanoic acid

To a stirred solution of diethyl 2-benzylmalonate (1.5 g, 5.99 mmol) in ethanol (9.99 ml) was added KOH (0.336 g, 5.99 mmol) at RT. The reaction mixture was stirred at RT for 3 hrs. The solvent was evaporated. Sat. NaHCO$_3$ (aq) was added and extracted with EtOAc. The aq. layer was acidified by adding 1N HCl (pH=1). The acidic aq. layer was extracted with EtOAc (3×) and the organic layer was dried over MgSO$_4$, filtered and concentrated in vacuo. The crude product was used for the next step without further purification. LC/MS=223 [M+1].

Step B: Ethyl 2-benzyl-3-((4-((methoxycarbonyl)amino)phenyl)amino)-3-oxopropanoate To a stirred solution of 2-Benzyl-3-ethoxy-3-oxopropanoic acid (100 mg, 0.450 mmol) in DMF (2.2 mL) was added methyl (4-aminophenyl)carbamate (150 mg, 0.900 mmol), HATU (342 mg, 0.900 mmol) and N-methylmorpholine (148 µl, 1.350 mmol) at RT. The reaction mixture was stirred at RT overnight. The reaction mixture was diluted with sat. NaHCO$_3$ (aq) and EtOAc. The organic layer was washed with brine and dried over MgSO$_4$, filtered and concentrated in vacuo. The crude product was purified by flash silica gel column chromatography (EtOAC/Hex=1/1) to afford Ethyl 2-benzyl-3-((4-((methoxycarbonyl)amino) phenyl)amino)-3-oxopropanoate. LC/MS=371 [M+1].

Step C: Lithium 2-benzyl-3-((4-((methoxycarbonyl)amino)phenyl)amino)-3-oxopropanoate To a stirred solution of Ethyl 2-benzyl-3-((4-((methoxycarbonyl)amino)phenyl)amino)-3-oxopropanoate (110 mg, 0.297 mmol) in THF (1273 µl) and MeOH (849 µl) was added a solution of LiOH-monohydrate (12.46 mg, 0.297 mmol) in water (849 µl) at RT. The reaction mixture was stirred at RT for 3 hrs. The solvent was evaporated and the crude product was dried in vac. oven overnight. The dried crude product was used for the next step without further purification. LC/MS=343 [M+1].

Step D: Methyl (4-(2-benzyl-3-(6-chloro-2-oxo-1,2-dihydrospiro[benzo[d][1,3]oxazine-4,3'-pyrrolidin]-1'-yl)-3-oxopropanamido)phenyl)carbamate To a stirred solution of 6-chlorospiro[benzo[d][1,3]oxazine-4,3'-pyrrolidin]-2(1H)-one hydrochloride (161 mg, 0.586 mmol) and lithium 2-benzyl-3-((4-((methoxycarbonyl)amino)phenyl)amino)-3-oxopropanoate (102 mg, 0.293 mmol) in DMF (1952 µl) was added HATU (223 mg, 0.586 mmol) and DIPEA (179 µl, 1.025 mmol) at RT. The reaction mixture was stirred at RT overnight. The reaction mixture was diluted with sat. NaHCO₃ (aq) and EtOAc. The organic layer was washed with brine and dried over MgSO₄, filtered and concentrated in vacuo. The crude product was purified by flash silica gel column chromatography (1/1 EtOAc/Hex to 10% MeOH in DCM) to afford methyl (4-(2-benzyl-3-(6-chloro-2-oxo-1,2-dihydrospiro[benzo[d][1,3]oxazine-4,3'-pyrrolidin]-1'-yl)-3-oxopropanamido)phenyl)carbamate. LC/MS=563 [M+1]. The mixture of the four stereoisomers was purified by chiral SFC (IC-H column, 65% MeOH (0.2% NH₄OH/CO₂) to afford Ex-120a (faster eluting), Ex-120b (second faster eluting), Ex-120c (third faster eluting), and Ex-120d (slower eluting).

By using procedures similar to those described previously, and using appropriate starting materials, the following compounds were synthesized. These compounds were characterized by LC/MS.

Example 122

Methyl (4-(2-(1-(6-chloro-2-oxo-1,2-dihydrospiro[benzo[d][1,3]oxazine-4,3'-pyrrolidin]-1'-yl)-1-oxo-3-phenylpropan-2-yl)-1H-imidazol-4-yl)phenyl)carbamate

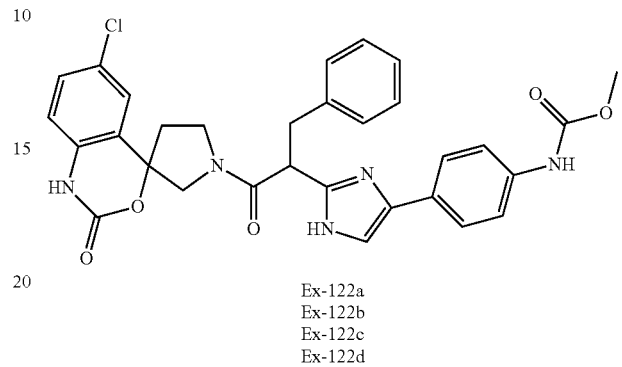

Ex-122a
Ex-122b
Ex-122c
Ex-122d

Step A: 2-Benzyl-3-ethoxy-3-oxopropanoic acid

To a stirred solution of diethyl 2-benzylmalonate (1.5 g, 5.99 mmol) in ethanol (9.99 ml) was added KOH (0.336 g, 5.99 mmol) at RT. The reaction mixture was stirred at RT for 3 hrs. The solvent was evaporated. Sat. NaHCO₃ (aq) was added and extracted with EtOAc. The aq. layer was acidified by adding 1N HCl (pH=1). The acidic aq. layer was extracted with EtOAc (3×) and the organic layer was dried over MgSO₄, filtered and concentrated in vacuo. The crude product was used for the next step without further purification. LC/MS=223 [M+1].

| Example | Structure | LCMS [M + 1] | FXIa Ki (nM) |
|---|---|---|---|
| 120a (isomer A) | methyl (4-((R)-2-benzyl-3-((S)-6-chloro-2-oxo-1,2-dihydrospiro[benzo[d][1,3]oxazine-4,3'-pyrrolidin]-1'-yl)-3-oxopropanamido)phenyl)carbamate | 563 | 4945 |
| 120b (isomer B) | methyl (4-((S)-2-benzyl-3-((S)-6-chloro-2-oxo-1,2-dihydrospiro[benzo[d][1,3]oxazine-4,3'-pyrrolidin]-1'-yl)-3-oxopropanamido)phenyl)carbamate | 563 | 5000 |
| 120c (isomer C) | methyl (4-((R)-2-benzyl-3-((R)-6-chloro-2-oxo-1,2-dihydrospiro[benzo[d][1,3]oxazine-4,3'-pyrrolidin]-1'-yl)-3-oxopropanamido)phenyl)carbamate | 563 | 1444 |
| 120d (isomer D) | methyl (4-((S)-2-benzyl-3-((R)-6-chloro-2-oxo-1,2-dihydrospiro[benzo[d][1,3]oxazine-4,3'-pyrrolidin]-1'-yl)-3-oxopropanamido)phenyl)carbamate | 563 | 5000 |
| 121a (isomer A) | 4-((S)-2-benzyl-3-((S)-6-chloro-2-oxo-1,2-dihydrospiro[benzo[d][1,3]oxazine-4,3'-pyrrolidin]-1'-yl)-3-oxopropanamido)benzoic acid | 534 | 5000 |
| 121b (isomer B) | 4-((R)-2-benzyl-3-((S)-6-chloro-2-oxo-1,2-dihydrospiro[benzo[d][1,3]oxazine-4,3'-pyrrolidin]-1'-yl)-3-oxopropanamido)benzoic acid | 534 | 5000 |
| 121c (isomer C) | 4-((R)-2-benzyl-3-((R)-6-chloro-2-oxo-1,2-dihydrospiro[benzo[d][1,3]oxazine-4,3'-pyrrolidin]-1'-yl)-3-oxopropanamido)benzoic acid | 534 | 438.9 |
| 121d (isomer D) | 4-((S)-2-benzyl-3-((R)-6-chloro-2-oxo-1,2-dihydrospiro[benzo[d][1,3]oxazine-4,3'-pyrrolidin]-1'-yl)-3-oxopropanamido)benzoic acid | 534 | 3783 |

Step B: 1-Ethyl 3-(2-(4-((methoxycarbonyl)amino) phenyl)-2-oxoethyl) 2-benzylmalonate To a stirred solution of 2-Benzyl-3-ethoxy-3-oxopropanoic acid (306 mg, 1.377 mmol) in DMF (1.38E+04 µl) was added cesium carbonate (224 mg, 0.688 mmol) and methyl (4-(2-chloroacetyl)phenyl)carbamate (313 mg, 1.377 mmol) at RT. The reaction mixture was stirred at RT overnight. The reaction mixture was diluted with sat. NaHCO₃ (aq) and EtOAc. The organic layer was washed with brine, dried over MgSO₄, filtered and concentrated in vacuo. The crude product was purified by flash silica gel column chromatography (EtOAc/Hex=1/1) to afford 1-ethyl 3-(2-(4-((methoxycarbonyl)amino)phenyl)-2-oxoethyl) 2-benzylmalonate. LC/MS=414 [M+1]

Step C: Ethyl 2-(4-(4-((methoxycarbonyl)amino) phenyl)-1H-imidazol-2-yl)-3-phenylpropanoate To a microwave tube charged with 1-Ethyl 3-(2-(4-((methoxycarbonyl)amino)phenyl)-2-oxoethyl) 2-benzylmalonate (353 mg, 0.854 mmol) in toluene (8539 µl) was added ammonium acetate (329 mg, 4.27 mmol) at RT. The reaction mixture was capped and microwave irradiated at 150° C. for 40 min. The reaction mixture was transferred to a round bottom flask and rinsed the microwave tube with 10% MeOH in DCM. The solvent was evaporated and the crude was dissolved in EtOAc (100 mL). The organic layer was washed with sat. NaHCO₃ (aq), dried over MgSO₄, filtered and concentrated in vacuo. The crude product was purified by flash silica gel column chromatography (EtOAc/Hex=1/1) to afford ethyl 2-(4-(4-((methoxycarbonyl)amino)phenyl)-1H-imidazol-2-yl)-3-phenylpropanoate. LC/MS=394 [M+1]

Step D: Lithium 2-(4-(4-((methoxycarbonyl)amino) phenyl)-1H-imidazol-2-yl)-3-phenylpropanoate To a stirred solution of ethyl 2-(4-(4-((methoxycarbonyl) amino)phenyl)-1H-imidazol-2-yl)-3-phenylpropanoate (192.6 mg, 0.490 mmol) in THF (1600 µl) and MeOH (500 µl) was added a solution of LiOH-monohydrate (20.54 mg, 0.490 mmol) in water (500 µl) at RT. The reaction mixture was stirred at RT for 4 hrs. The solvent was evaporated and the crude product was dried over vac. oven overnight. The crude product was used for the next step without further purification. LC/MS=366 [M+1].

Step E: Methyl (4-(2-(1-(6-chloro-2-oxo-1,2-dihydrospiro[benzo[d][1,3]oxazine-4,3'-pyrrolidin]-1'-yl)-1-oxo-3-phenylpropan-2-yl)-1H-imidazol-4-yl) phenyl)carbamate To a stirred solution of lithium 2-(4-(4-((methoxycarbonyl)amino)phenyl)-1H-imidazol-2-yl)-3-phenylpropanoate (182 mg, 0.490 mmol) in DMF (2451 µl) was added 6-chlorospiro[benzo[d][1,3]oxazine-4,3'-pyrrolidin]-2(1H)-one hydrochloride (202 mg, 0.735 mmol), HATU (280 mg, 0.735 mmol) and DIPEA (257 µl, 1.470 mmol) at RT. The reaction mixture was stirred at RT for 5 hrs. The reaction mixture was diluted with sat. NaHCO₃ (aq) and EtOAc. The organic layer was washed with brine, dried over MgSO₄, filtered and concentrated in vacuo. The crude product was purified by flash silica gel column chromatography (EtOAc/ Hex=1/1) to afford (40 g, 1/1=EtOAc/Hex) to afford Methyl (4-(2-(1-(6-chloro-2-oxo-1,2-dihydrospiro[benzo[d][1,3] oxazine-4,3'-pyrrolidin]-1'-yl)-1-oxo-3-phenylpropan-2-yl)- 1H-imidazol-4-yl)phenyl)carbamate. LC/MS=586 [M+1]. The mixture of the four stereoisomers was purified by chiral SFC (AS-H column, 40% MeOH (0.2% NH₄OH/CO₂) to afford Ex-122a (faster eluting), Ex-122b (second faster eluting), Ex-122c (third faster eluting), and Ex-122d (slower eluting).

Intermediate 3 for Example 124

Methyl 4-(5-(1-(tert-butoxy)-1-oxo-3-phenylpropan-2-yl)-1H-imidazol-2-yl)-3-fluorothiophene-2-carboxylate

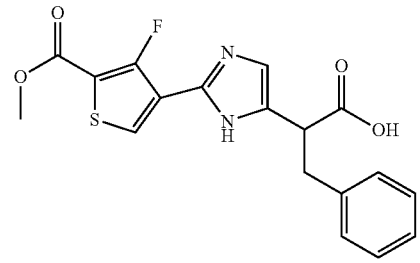 [SMILES: COC(=O)c1scc(-c2ncc(C(Cc3ccccc3)C(=O)O)[nH]2)c1F]

Step A: Synthesis of methyl 4-(1-ethoxyvinyl)-3-fluorothiophene-2-carboxylate To a solution of methyl 4-bromo-3-fluorothiophene-2-carboxylate (2 g, 8.37 mmol) in dioxane (40 ml) was added tributyl(1-ethoxyvinyl)tin (3.39 ml, 10.04 mmol) and tetrakis(triphenylphosphine)palladium(0) (0.483 g, 0.418 mmol). The mixture was heated at reflux under N₂ overnight. LCMS shows loss of SM and clean conversion to less polar desired product. LCMS [M+1]=231

Step B: Synthesis of methyl 4-acetyl-3-fluorothiophene-2-carboxylate

The crude methyl 4-(1-ethoxyvinyl)-3-fluorothiophene-2-carboxylate (1927 mg, 8.37 mmol) was treated with aqueous 1M HCl (1.67E+05 µl, 167 mmol) for about 2 h. After which LCMS showed complete conversion to the desired product. The crude was extracted with DCM, dried over anhydrous MgSO₄, filtered, concentrated in vacuo to afford the title compound.

Step C: Synthesis of methyl 4-(2-bromoacetyl)-3-fluorothiophene-2-carboxylate To a solution of methyl 4-acetyl-3-fluorothiophene-2-carboxylate (1 g, 4.95 mmol) in tetrahydrofuran (19 ml) was added pyridinium tribromide (1.582 g, 4.95 mmol). The reaction mixture was allowed to stir under a N₂ balloon at RT for 8 h. TLC showed little starting material remained and a new spot formed. The reaction was quenched with H₂O (40 mL) and extracted with EtOAc (3×50 mL). The combined organic phases were dried over Na₂SO₄, and concentrated in vacuo. The residue was purified by column chromatography (SiO₂, PE:EtOAc=10:1 to 5:1) to give the title compound methyl 4-(2-bromoacetyl)-3-fluorothiophene-2-carboxylate.

Step D: Synthesis of 1-(tert-butyl) 3-(2-(4-fluoro-5-(methoxycarbonyl)thiophen-3-yl)-2-oxoethyl) 2-benzylmalonate To a solution of 2-benzyl-3-(tert-butoxy)-3-oxopropanoic acid (500 mg, 1.998 mmol) in DMF (20.000 ml) was added Cs$_2$CO$_3$ (325 mg, 0.999 mmol). The resulting mixture was stirred for 5 minutes prior to the addition of methyl 4-(2-bromoacetyl)-3-fluorothiophene-2-carboxylate (562 mg, 1.998 mmol). The resulting reaction mixture was stirred at room-temperature overnight. After which it was diluted with water and extracted with EtOAc. The organics were dried over MgSO$_4$, filtered, and concentrated to afford the crude product which was purified using 0-50% EtOAc in hexanes on ISCO (40 g silica).

Step E: Synthesis of methyl 4-(5-(1-(tert-butoxy)-1-oxo-3-phenylpropan-2-yl)-1H-imidazol-2-yl)-3-fluorothiophene-2-carboxylate To a solution of 1-tert-butyl 3-(2-(4-fluoro-5-(methoxycarbonyl)thiophen-3-yl)-2-oxoethyl) 2-benzylmalonate (300 mg, 0.666 mmol) in toluene (5 mL) was added ammonium acetate (103 mg, 1.332 mmol). The resulting mixture was irradiated using microwave for 40 min at 150° C. After which it was diluted with EtOAc and washed with water. The organics were collected, dried on MgSO$_4$, filtered, and concentrated to afford the crude product as orange brown oil. The crude was purified using 0-100% EtOAc in hexanes to afford the title compound.

Step F: Synthesis of 2,2,2-trifluoroacetic acid compound with 2-(2-(4-fluoro-5-(methoxycarbonyl)thiophen-3-yl)-1H-imidazol-5-yl)-3-phenylpropanoic acid (1:1)

To a 20 ml scintillation vial containing methyl 4-(5-(1-(tert-butoxy)-1-oxo-3-phenylpropan-2-yl)-1H-imidazol-2-yl)-3-fluorothiophene-2-carboxylate (116.9 mg, 0.272 mmol) in DCM (2715 µl) was added TFA (418 µl, 5.43 mmol). The reaction mixture was stirred until the completion of the reaction (checked by LCMS). Solvents were removed in vacuo and crude was taken to next step. LCMS [M+1]=375

Step G: Synthesis of 1-(tert-butyl) 3-methyl 2-benzylmalonate

A 100 mL round-bottom flask equipped with a stir bar was charged with tert-butyl methyl malonate (1.667 g, 9.57 mmol) and DMF (30 mL). To the solution, NaH (0.348 g, 8.70 mmol) was added. The reaction was allowed to stir at 0° C. for 30 min and at room temperature for additional 30 min. To the mixture, (bromomethyl)benzene (1.488 g, 8.7 mmol) was added at 0° C. and the mixture was stirred at room temperature for 12 h. To the reaction mixture, H$_2$O was added, and the mixture was extracted with CH$_2$Cl$_2$ (3×), dried over MgSO$_4$, and concentrated in vacuo. The remaining residue was purified by column chromatography with 5% AcOEt in hexanes to afford the desired product.

Intermediate 4 for Example 125

2-(5-(6-aminopyridin-3-yl)-1H-imidazol-2-yl)-3-phenylpropanoic acid

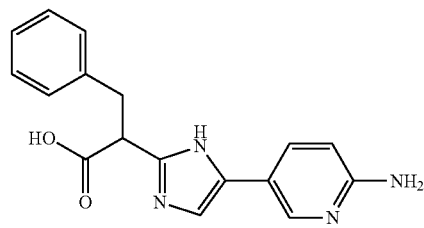 [SMILES: Nc1ccc(-c2cnc(C(Cc3ccccc3)C(=O)O)[nH]2)cn1]

Step A: 2-(5-(6-aminopyridin-3-yl)-1H-imidazol-2-yl)-3-phenylpropanoic acid

To a solution of 2-benzyl-3-ethoxy-3-oxopropanoic acid (1000 mg, 4.50 mmol) and 1-(6-aminopyridin-3-yl)-2-bromoethan-1-one (1500 mg, 4.48 mmol) in DMF (20 ml) was added DIPEA (2950 mg, 22.83 mmol). The reaction was stirred at room temperature overnight. It was quenched with sat. aqueous NaHCO$_3$ and extracted with EtOAc. The organics were combined, washed with water and brined, dried over MgSO$_4$, filtered and concentrated in vacuo. The crude obtained was purified by a silica gel column and the desired product was eluted between 70-95% EtOAc in Hexanes. The fractions were collected and concentrated in vacuo to afford the desired intermediate.

Step B: Ethyl 2-(5-(6-aminopyridin-3-yl)-1H-imidazol-2-yl)-3-phenylpropanoate

Ammonium acetate (774 mg, 10.05 mmol), followed by acetic acid (130 µl), were added to a solution of 1-(2-(6-aminopyridin-3-yl)-2-oxoethyl) 3-ethyl 2-benzylmalonate (358 mg, 1.005 mmol) in toluene (1305 µl). The reaction was stirred at 115° C. for 1 hr, then diluted with EtOAc and sat. aq. NaHCO$_3$. The two resulting phases were separated and the aqueous phase was extracted with EtOAc 3×. The organics were combined, washed with water and brine, dried over MgSO$_4$, filtered and concentrated in vacuo. The crude residue was purified on silica gel column with 0-10% MeOH in DCM to obtain ethyl 2-(5-(6-aminopyridin-3-yl)-1H-imidazol-2-yl)-3-phenylpropanoate.

Step C: 2-(5-(6-aminopyridin-3-yl)-1H-imidazol-2-yl)-3-phenylpropanoic acid

To a suspension of lithium hydroxide monohydrate (40 mg, 0.953 mmol) in water (2.00 ml) was added to a solution of ethyl 2-(5-(6-aminopyridin-3-yl)-1H-imidazol-2-yl)-3-phenylpropanoate (144 mg, 0.428 mmol) in THF (1.50 ml) and MeOH (1.500 ml). The reaction was stirred at RT for 1 h, then dried in vacuo.

Intermediate 5 for Example 126

2-(5-Chloro-4-(4-((methoxycarbonyl)amino)phenyl)-1-((2-(trimethylsilyl)ethoxy)methyl)-1H-imidazol-2-yl)-3-phenylpropanoic acid

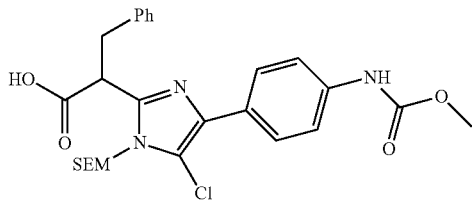 [SMILES: COC(=O)Nc1ccc(-c2nc(C(Cc3ccccc3)C(=O)O)n(COCC[Si](C)(C)C)c2Cl)cc1]

Step 1: 2-Benzyl-3-ethoxy-3-oxopropanoic acid

To a stirred solution of diethyl benzylmalonate (5 g, 19.98 mmol) in 20 mL of ethanol at 0° C. was added a solution of KOH (1.121 g, 19.98 mmol) in 15 mL of ethanol slowly over 15 min. It was allowed to warm to rt and stirred for 16 h. It was concentrated and the residue was partitioned between water (2×100 mL) and diethyl ether (100 mL). The aqueous layer was separated and acidified by addition of 4 M HCl to pH=3. It was extracted with ethyl acetate (3×200 mL). The combined organic layers were washed with brine, dried over sodium sulfate, filtered and concentrated to afford the title compound. MS (m/e): 223.09 [M+H]+.

Step 2: 1-Ethyl 3-(2-(4-((methoxycarbonyl)amino)phenyl)-2-oxoethyl) 2-benzylmalonate To a solution of 2-benzyl-3-ethoxy-3-oxopropanoic acid (1 g, 4.50 mmol) and methyl (4-(2-chloroacetyl)phenyl)carbamate (1.024 g, 4.50 mmol) in DMF (4.50 ml) was added Cs$_2$CO$_3$ (1.466 g, 4.50 mmol) at 0° C. The mixture was stirred for 10 min and allowed to warm up to rt overnight. LC-MS showed the completion of the reaction. It was diluted with ether (50 mL) and washed with water (3×20 mL) then brine (20 mL). The organic layer was separated, dried over sodium sulfate, filtered and concentrated. The residue was purified by ISCO (Gold 80 g, 0-50% ethyl acetate in hexane) to give 1-ethyl 3-(2-(4-((methoxycarbonyl)amino)phenyl)-2-oxoethyl) 2-benzylmalonate. MS (m/e): 414.18 [M+H]+.

Step 3: Ethyl 2-(4-(4-((methoxycarbonyl)amino)phenyl)-1H-imidazol-2-yl)-3-phenylpropanoate A mixture of 1-ethyl 3-(2-(4-((methoxycarbonyl)amino)phenyl)-2-oxoethyl) 2-benzylmalonate (1.5 g, 3.63 mmol) and ammonium acetate (2.80 g, 36.3 mmol) in toluene (6.60 ml) and acetic acid (0.660 ml) were heated to reflux for 15 h. It was cooled to rt and 100 mL ethyl acetate was added. The mixture was washed with water (2×50 mL) and brine. The organic layer was separated and dried over sodium sulfate, filtered and concentrated. The residue was purified by ISCO (Gold 220 g, 0-100% ethyl acetate/ethanol in hexane) to give the title compound. MS (m/e): 394.21 [M+H]+.

Step 4: Ethyl 2-(4-(4-((methoxycarbonyl)amino)phenyl)-1-((2-(trimethylsilyl)ethoxy)methyl)-1H-imidazol-2-yl)-3-phenylpropanoate To a solution of ethyl 2-(4-(4-((methoxycarbonyl)amino)phenyl)-1H-imidazol-2-yl)-3-phenylpropanoate (389 mg, 0.989 mmol) in DMF (2 mL) was added DIEA (0.24 mL, 1.374 mmol) and SEM-Cl (0.23 mL, 1.167 mmol). The solution was stirred at rt overnight. It was diluted with ethyl acetate, washed with water three times and brine once. The organic layer was separated, dried over sodium sulfate, filtered and concentrated under reduced pressure. The residue was purified by ISCO (Gold 24 g, 0-50% ethyl acetate in hexane) to give the title compound. MS (m/e): 524.31 [M+H]+.

Step 5: Ethyl 2-(5-chloro-4-(4-((methoxycarbonyl)amino)phenyl)-1-((2-(trimethylsilyl)ethoxy)methyl)-1H-imidazol-2-yl)-3-phenylpropanoate To a solution of ethyl 2-(4-(4-((methoxycarbonyl)amino)phenyl)-1-((2-(trimethylsilyl)ethoxy)methyl)-1H-imidazol-2-yl)-3-phenylpropanoate (450 mg, 0.859 mmol) in CHCl$_3$ (4296 µl) and acetonitrile (4296 µl) was added NCS (115 mg, 0.859 mmol). The mixture heated at 65° C. for 2 h. It was cooled to rt and purified by ISCO (Gold 24 g, 0-100% ethyl acetate in hexane) to give the title compound. MS (m/e): 557.87 [M+H]+.

Step 6: 2-(5-Chloro-4-(4-((methoxycarbonyl)amino)phenyl)-1-((2-(trimethylsilyl)ethoxy)methyl)-1H-imidazol-2-yl)-3-phenylpropanoic acid To a solution of ethyl 2-(5-chloro-4-(4-((methoxycarbonyl)amino)phenyl)-1-((2-(trimethylsilyl)ethoxy)methyl)-1H-imidazol-2-yl)-3-phenylpropanoate (132 mg, 0.236 mmol) in THF (1.2 mL) and MeOH (1.200 mL) was added LiOH (5 M, 0.057 mL, 0.284 mmol). The mixture was stirred at rt for 2 h. LC-MS showed the completion of the reaction. It was acidified by 1 M HCl (0.3 mL) to adjust pH=5. The mixture was extracted with ethyl acetate (20 mL) and washed with brine (10 mL). The organic layer was dried over sodium sulfate, filtered and concentrated. The residue was purified by ISCO (Gold 24 g, 0-10% MeOH in DCM) to give the title compound. MS (m/e): 529.85 [M+H]+.

By using procedures similar to those described previously, and using appropriate starting materials, the following compounds were synthesized. These compounds were characterized by LC/MS.

| Example | Structure | LCMS [M + 1] | FXIa Ki (nM) |
| --- | --- | --- | --- |
| 122a (isomer A) | methyl (4-(2-((R)-1-((R)-6-chloro-2-oxo-1,2-dihydrospiro[benzo[d][1,3]oxazine-4,3'-pyrrolidin]-1'-yl)-1-oxo-3-phenylpropan-2-yl)-1H-imidazol-4-yl)phenyl)carbamate | 586 | 33.6 |
| 122b (isomer B) | methyl (4-(2-((S)-1-((S)-6-chloro-2-oxo-1,2-dihydrospiro[benzo[d][1,3]oxazine-4,3'-pyrrolidin]-1'-yl)-1-oxo-3-phenylpropan-2-yl)-1H-imidazol-4-yl)phenyl)carbamate | 586 | 4691 |

-continued

| Example | Structure | LCMS [M + 1] | FXIa Ki (nM) |
|---|---|---|---|
| 122c (isomer C) | methyl (4-(2-((R)-1-((S)-6-chloro-2-oxo-1,2-dihydrospiro[benzo[d][1,3]oxazine-4,3'-pyrrolidin]-1'-yl)-1-oxo-3-phenylpropan-2-yl)-1H-imidazol-4-yl)phenyl)carbamate | 586 | 5000 |
| 122d (isomer D) | methyl (4-(2-((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)-1H-imidazol-4-yl)phenyl)carbamate | 586 | 364 |
| 123 (racemic) | 5-(2-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-5-yl)thiophene-2-carboxylic acid | 594.73 | 15.11 |
| 124 (racemic) | 4-(2-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-4-yl)-3-fluorothiophene-2-carboxylic acid | 613.02 | 209.00 |
| 125 (Racemate) | (4R)-1'-(2-(5-(6-aminopyridin-3-yl)-1H-imidazol-2-yl)-3-phenylpropanoyl)-6-chloro-5-fluorospiro[benzo[d][1,3]oxazine-4,3'-piperidin]-2(1H)-one | 562 | 353 |
| 126A (isomer A) | methyl (4-(5-chloro-2-(1-(6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-4-yl)phenyl)carbamate | 652.29 | 1881 |
| 126B (isomerB) | methyl (4-(5-chloro-2-(1-(6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-4-yl)phenyl)carbamate | 652.29 | 153.6 |
| 127 (racemate) | (4R)-6-chloro-1'-(2-(4-chloro-5-(4-fluorophenyl)-1H-imidazol-2-yl)-3-(4-fluorophenyl)propanoyl)spiro[benzo[d][1,3]oxazine-4,3'-piperidin]-2(1H)-one | 598.4 | 5000 |
| 128 (racemate) | 4-(4-chloro-2-(1-((R)-6-chloro-2-oxo-1,2-dihydrospiro[benzo[d][1,3]oxazine-4,3'-piperidin]-1'-yl)-3-(4-fluorophenyl)-1-oxopropan-2-yl)-1H-imidazol-5-yl)benzoic acid | 624.4 | 8750 |

Example 129

Methyl (4-(5-(1-((R)-6-chloro-5-fluoro-2-oxo-1,2-dihydrospiro[benzo[d][1,3]oxazine-4,3'-pyrrolidin]-1'-yl)-1-oxo-3-phenylpropan-2-yl)-1,3,4-oxadiazol-2-yl)phenyl)carbamate

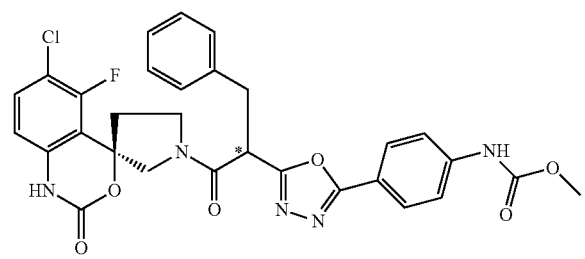

Ex-129A

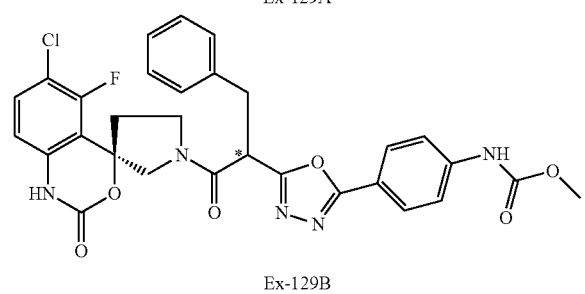

Ex-129B

Step 1: 4-((methoxycarbonyl)amino)benzoic acid

To a stirred solution of 4-aminobenzoic acid (10 g, 72.9 mmol) in acetone (72.9 mL) was added pyridine (5.77 g, 72.9 mmol) and methyl carbonochloridate (7.240 g, 77 mmol) dropwise at 0° C. The reaction mixture was refluxed at 65° C. for 2 h. LCMS showed the starting material was consumed completely. After it was cooled down, the solvent was evaporated and cold water was added. The solid was filtered and washed with water, and dried to give the title compound which was used for the next step without further purification.

$^1$H NMR (CDCl$_3$, 400 MHz): δ 7.97 (d, J=8.6 Hz, 2H), 7.43 (d, J=8.2 Hz, 2H), 3.76 (s, 3H).

Step 2: tert-butyl 2-(4-((methoxycarbonyl)amino) benzoyl)hydrazinecarboxylate

To a stirred solution of 4-((methoxycarbonyl)amino)benzoic acid (5 g, 25.6 mmol) in DMF (50 mL) was added tert-butyl hydrazinecarboxylate (4.06 g, 30.7 mmol), HATU (11.69 g, 30.7 mmol) and DIPEA (17.90 mL, 102 mmol) at 25° C. The reaction mixture was stirred at 25° C. for 16 h. LCMS showed starting material was consumed completely. The reaction mixture was diluted with EtOAc and sat. aq. NaHCO$_3$ (30 mL) was added. The organic layer was washed with brine (30 mL), dried over Na$_2$SO$_4$, filtered and concentrated to give the crude product which was purified by flash silica gel column chromatography (0-100% EtOAc in PE) to give the title compound.

¹H NMR (CD₃OD, 400 MHz): δ 7.79 (d, J=8.2 Hz, 2H), 7.55 (d, J=8.6 Hz, 2H), 3.75 (s, 3H), 3.34 (s, 1H), 1.49 (br. s., 10H). MS (ESI) m/z 210.2 (M-Boc+H).

Step 3: methyl (4-(hydrazinecarbonyl)phenyl)carbamate hydrochloride

A round bottom flask was charged with tert-butyl 2-(4-((methoxycarbonyl) amino)benzoyl) hydrazinecarboxylate (4 g, 12.93 mmol) in HCl/dioxane (40 mL) and the mixture was stirred at 25° C. for 2-3 h. LCMS showed starting material was consumed completely. The reaction mixture was concentrated and the residue was dried in a vacuum to give the title compound which was used for the next step without further purification.
MS (ESI) m/z 210.2 (M+H).

Step 4: ethyl 2-benzyl-3-(2-(4-((methoxycarbonyl) amino)benzoyl)hydrazinyl)-3-oxopropanoate To a stirred solution of 2-benzyl-3-ethoxy-3-oxopropanoic acid (3.31 g, 14.90 mmol) in DMF (30 mL) was added methyl (4-(hydrazinecarbonyl)phenyl)carbamate hydrochloride (3.05 g, 12.42 mmol), HATU (5.66 g, 14.90 mmol) and DIPEA (8.67 mL, 49.7 mmol) at 25° C. The reaction mixture was stirred at 25° C. for 16 h. LCMS showed starting material was consumed completely. The reaction mixture was diluted with EtOAc and sat. NaHCO₃ (30 mL) was added. The organic layer was washed with brine (50 mL), dried over Na₂SO₄, filtered and concentrated to give the crude product which was purified by flash silica gel column chromatography (0-100% EtOAc in PE) to give the title compound.
¹H NMR (CD₃OD, 400 MHz): δ 7.80 (d, J=8.6 Hz, 2H), 7.55 (d, J=8.6 Hz, 2H), 7.12-7.31 (m, 5H), 4.13 (q, J=7.3 Hz, 2H), 3.71-3.79 (m, 4H), 3.34 (s, 1H), 3.12-3.27 (m, 2H), 1.20 (t, J=7.0 Hz, 3H). MS (ESI) m/z 414.2 (M+H).

Step 5: ethyl 2-(5-(4-((methoxycarbonyl)amino) phenyl)-1,3,4-oxadiazol-2-yl)-3-phenylpropanoate A mixture of ethyl 2-benzyl-3-(2-(4-((methoxycarbonyl) amino)benzoyl)hydrazinyl)-3-oxopropanoate (500 mg, 1.209 mmol) in phosphoryl trichloride (13.120 g, 86 mmol) was stirred at 100° C. for 16 h. LCMS showed starting material was consumed completely. The reaction mixture was concentrated to give a crude residue. The residue was diluted with EtOAc (40 mL) and water (20 mL). After extraction, the organic layer was separated and the aqeous was extracted with EtOAc (40 mL×2). The combined organic phases were dried over Na₂SO₄, filtered, concentrated to give the crude product which was purified on a silica-gel column with 0-50% EtOAc/PE to give the title compound. MS (ESI) m/z 396.2 (M+H).

Step 6: 2-(5-(4-((methoxycarbonyl)amino)phenyl)-1,3,4-oxadiazol-2-yl)-3-phenylpropanoic acid To a stirred solution of ethyl 2-(5-(4-((methoxycarbonyl) amino)phenyl)-1,3,4-oxadiazol-2-yl)-3-phenylpropanoate (391 mg, 0.989 mmol) in MeOH (5 mL), THF (5 mL) and water (3 mL) was added LiOH.H₂O (0.396 mL, 1.978 mmol). Then the mixture was stirred at 25° C. for 2 h. LCMS showed starting material was consumed completely. The mixture was acidified with 2N HCl to pH 6, and extracted with ethyl acetate (2×20 mL). The combined organic fractions were washed with brine (10 mL), dried over anhydrous Na₂SO₄, filtered and evaporated under reduced pressure to give the title compound which was used for the next step directly without further purification. MS (ESI) m/z 368.0 (M+H).

Step 7: methyl (4-(5-(1-((R)-6-chloro-5-fluoro-2-oxo-1,2-dihydrospiro[benzo[d][1,3]oxazine-4,3'-pyrrolidin]-1'-yl)-1-oxo-3-phenylpropan-2-yl)-1,3,4-oxadiazol-2-yl)phenyl)carbamate (Example 129)

To a stirred solution of (R)-6-chloro-5-fluorospiro[benzo [d][1,3]oxazine-4,3'-pyrrolidin]-2(1H)-one hydrochloride (120 mg, 0.411 mmol) in DMF (5 mL) was added 2(5-(4-((methoxycarbonyl)amino)phenyl)-1,3,4-oxadiazol-2-yl)-3-phenylpropanoic acid (150 mg, 0.408 mmol), DIPEA (212 mg, 1.642 mmol) and HATU (187 mg, 0.493 mmol) at 25° C. Then the reaction mixture was stirred at 25° C. for 1 h. LCMS showed the starting material was consumed completely. The reaction mixture was diluted with EtOAc (20 mL) and added sat. NaHCO₃ (aq) (5 mL). The organic layer was washed with brine (10 mL), dried over Na₂SO₄, filtered and concentrated to give the crude product which was purified by prep-HPLC (preparative HPLC on a GILSON 281 instrument fitted with Waters Phenomenex Synergi C18 150×30 mm×4 um using water and acetonitrile as the eluents. Mobile phase A: water (containing 0.1% TFA-CH₃CN), mobile phase B: acetonitrile. Gradient: 51-66% B, 0-11 min; 100% B, 9-11 min) to give the title compound. MS (ESI) m/z 606.1 (M+H).

Step 8: methyl (4-(5-(1-((R)-6-chloro-5-fluoro-2-oxo-1,2-dihydrospiro[benzo[d][1,3]oxazine-4,3'-pyrrolidin]-1'-yl)-1-oxo-3-phenylpropan-2-yl)-1,3,4-oxadiazol-2-yl)phenyl)carbamate (Example 129A) and methyl (4-(5-(1-((R)-6-chloro-5-fluoro-2-oxo-1, 2-dihydrospiro[benzo[d][1,3]oxazine-4,3'-pyrrolidin]-1'-yl)-1-oxo-3-phenylpropan-2-yl)-1,3,4-oxadiazol-2-yl)phenyl)carbamate (Example 129B)

Methyl (4-(5-(1-((R)-6-chloro-5-fluoro-2-oxo-1,2-dihydrospiro[benzo[d][1,3]oxazine-4,3'-pyrrolidin]-1'-yl)-1-oxo-3-phenylpropan-2-yl)-1,3,4-oxadiazol-2-yl)phenyl)carbamate (Example 129) (210 mg, 346.53 mmol) was separated with SFC (Column: Chiralpak AS-H 150×4.6 mm I.D., 5 um Mobile phase: 30% methanol (0.05% DEA) in CO₂ Flow rate: 3 mL/min Wavelength: 280 nm) to give methyl (4-(5-(1-((R)-6-chloro-5-fluoro-2-oxo-1,2-dihydrospiro [benzo[d][1,3]oxazine-4,3'-piperidin]-1'-yl)-1-oxo-3-phenylpropan-2-yl)-1,3,4-oxadiazol-2-yl)phenyl)carbamate (first peak, Example 129A) and methyl (4-(5-(1-((R)-6-chloro-5-fluoro-2-oxo-1,2-dihydrospiro[benzo[d][1,3] oxazine-4,3'-piperidin]-1'-yl)-1-oxo-3-phenylpropan-2-yl)-1,3,4-oxadiazol-2-yl)phenyl)carbamate (second peak, Example 129B).

Example 129A (CD₃OD, 400 MHz): δ 7.93-7.96 (m, 2H), 7.63-7.65 (m, 2H), 7.41-7.43 (m, 1H), 7.28-7.32 (m, 5H), 6.71-6.74 (m, 1H), 4.61-4.80 (m, 3H), 4.26-4.29 (m, 0.5H), 3.99-4.02 (m, 1H), 3.78 (s, 4H), 3.39-3.50 (m, 2H), 2.69-2.72 (m, 0.3H), 2.43-2.47 (m, 1H). MS (ESI) m/z 606.1 (M+H).

Example 129B (CD₃OD, 400 MHz): δ 7.92-7.98 (m, 2H), 7.63-7.66 (m, 2H), 7.41-7.43 (m, 1H), 7.26-7.33 (m, 5H), 6.70-6.74 (m, 1H), 4.67-4.75 (m, 3H), 4.26-4.29 (m, 0.3H), 3.99-4.02 (s, 0.6H), 3.83-3.88 (m, 2H), 3.83 (s, 3H), 3.46-3.52 (m, 2H), 2.23-2.43 (m, 1H). MS (ESI) m/z 606.2 (M+H).

| Example | Structure | LCMS [M + 1] | FXIa Ki (nM) |
|---|---|---|---|
| 129A (Isomer A) | methyl (4-(5-((S)-1-((R)-6-chloro-5-fluoro-2-oxo-1,2-dihydro-spiro[benzo[d][1,3]oxazine-4,3'-pyrrolidin]-1'-yl)-1-oxo-3-phenylpropan-2-yl)-1,3,4-oxadiazol-2-yl)phenyl)carbamate | 606.1 | >875 |
| 129B (isomer B) | Isomer 2: methyl (4-(5-(1-((R)-6-chloro-5-fluoro-2-oxo-1,2-dihydro-spiro[benzo[d][1,3]oxazine-4,3'-pyrrolidin]-1'-yl)-1-oxo-3-phenylpropan-2-yl)-1,3,4-oxadiazol-2-yl)phenyl)carbamate | 606.2 | 320.5 |

Example 130

Methyl (4-(5-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-2-yl)phenyl)carbamate

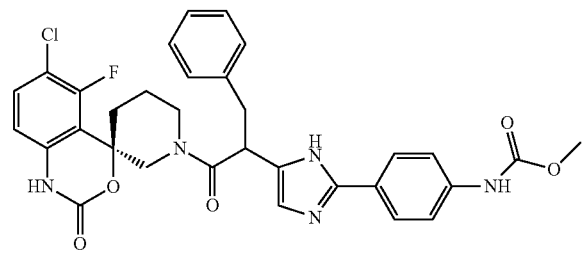

Ex-130A

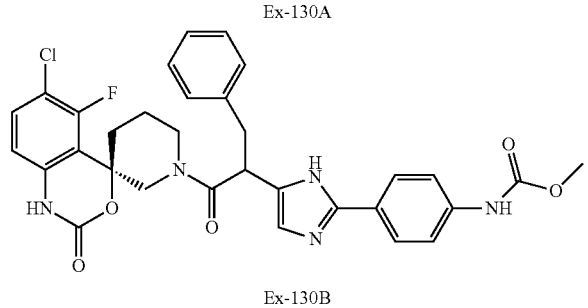

Ex-130B

Step 1: methyl (4-cyanophenyl)carbamate

To a solution of 4-aminobenzonitrile (30 g, 254 mmol) in CH$_3$CN (250 mL) at 0° C. was added methyl carbonochloridate (24.9 g, 264 mmol) and DIPEA (57.7 mL, 330 mmol). After 30 min, the cooling bath was removed and the mixture was stirred for room temperature for 24 h. TLC (SiO$_2$, R$_f$=0.4 PE:EtOAc=5:1) showed starting material was consumed completely. The reaction mixture was concentrated to give the crude product which was purified on a silica-gel column with 0-50% EtOAc/hexane to give the title compound.
$^1$H NMR (CD$_3$OD, 400 MHz): δ 7.60 (s, 4H), 3.73 (s, 3H).

Step 2: ethyl 4-((methoxycarbonyl)amino)benzimidate

To a mixture of methyl (4-cyanophenyl)carbamate (15 g, 85 mmol) in EtOH (50 mL) at 0° C. was added acetyl chloride (48.6 mL, 681 mmol) and the mixture was further stirred at 25° C. for 72 h. LCMS showed starting material was consumed completely. The reaction mixture was concentrated and the residue was then washed with PE (100 mL) to remove residual EtOH to give the title compound which was used directly for the next step without purification. MS (ESI) m/z 223.1 (M+H).

Step 3: methyl (4-carbamimidoylphenyl)carbamate

To a solution of ethyl 4-((methoxycarbonyl)amino)benzimidate (17.6 g, 79 mmol) in EtOH (200 mL) was added ammonium carbonate (38.0 g, 396 mmol) and the reaction was stirred at 25° C. for 12 h. LCMS showed starting material was consumed completely. The solid was filtered and the filtrate was concentrated to give the crude product which was purified on a silica-gel column with 0-20% EtOAc/MeOH to give the title compound.
$^1$H NMR (DMSO-d$_6$, 400 MHz) δ 10.28 (br. s., 1H), 7.85 (d, J=8.6 Hz, 2H), 7.65 (d, J=8.6 Hz, 2H), 3.67 (s, 3H). MS (ESI) m/z 194.2 (M+H).

Step 4: ethyl 4-(benzyloxy)-3-oxobutanoate

To a suspension of NaH (60% dispersion in mineral oil, 7.29 g, 182 mmol) in THF (40 mL) was added dropwise a solution of phenylmethanol (10 g, 92 mmol) in THF (15 mL) at 0° C. under N$_2$. The reaction mixture was stirred for 30 min and a solution of ethyl 4-chloro-3-oxobutanoate (15 g, 91 mmol) in THF (15 mL) was then added dropwise at 0° C. The reaction mixture was further stirred for 16 h while warming to room temperature (25° C.). TLC (SiO$_2$, R$_f$=0.45, PE:EtOAc=10:1) showed the reactant was consumed. The mixture was cooled, aqueous sodium hydrogen carbonate (saturated, 100 mL) was added and the mixture was extracted with EtOAc (2×100 mL). The combined organic fractions were washed with brine (100 mL), dried (Na$_2$SO$_4$), filtered and the solvent was evaporated under reduced pressure. The crude product was purified by flash silica gel chromatography (ISCO®; 80 g SepaFlash® Silica Flash Column, Eluent of 0~20% EtOAc/PE gradient at 80 mL/min) to give the title compound.
$^1$H NMR (CDCl$_3$, 400 MHz) δ 7.31-7.41 (m, 5H), 4.57 (s, 2H), 4.09-4.19 (m, 4H), 3.52 (s, 2H), 1.23 (t, J=7.0 Hz, 3H).

Step 5: ethyl 2-benzyl-4-(benzyloxy)-3-oxobutanoate

To a suspension of NaH (60% dispersion in mineral oil, 6.50 g, 163 mmol) in THF (40 mL) was added a solution of ethyl 4-(benzyloxy)-3-oxobutanoate (5-E) (19.2 g, 81 mmol) in THF (15 mL) at 0° C. under N$_2$. The reaction mixture was stirred for 30 min and a solution of (bromomethyl)benzene (10.13 mL, 85 mmol) in THF (15 mL) was then added dropwise at 0° C. The reaction mixture was further stirred for 16 h while warming to room temperature (25° C.). TLC showed most of the reactant was consumed. The mixture was cooled, aqueous ammonium chloride (saturated, 100 mL) was added and the mixture was extracted with EtOAc (2×150 mL). The combined organic fractions were washed with brine (100 mL), dried (Na$_2$SO$_4$), filtered and the solvent was evaporated under reduced pressure. The crude product was purified by flash silica gel chromatography (ISCO®; 120 g SepaFlash® Silica Flash Column, Eluent of 0~30% EtOAc/PE gradient at 80 mL/min) to give the title compound.

$^1$H NMR (CDCl$_3$, 400 MHz) δ 7.13-7.37 (m, 10H), 4.39-4.52 (m, 2H), 4.04-4.13 (m, 3H), 3.91-4.00 (m, 2H), 3.07-3.25 (m, 2H), 1.08-1.19 (m, 3H).

Step 6: ethyl 2-benzyl-4-hydroxy-3-oxobutanoate

To a stirred solution of ethyl 2-benzyl-4-(benzyloxy)-3-oxobutanoate (8.2 g, 12.56 mmol) in MeOH (50 mL) and EtOAc (15 mL) was added 10% Pd—C (1.337 g, 1.256 mmol) at room temperature (25° C.). The reaction mixture was then heated at 50° C. under 50 psi of H$_2$ for 12 h. TLC showed the reactant was consumed. The mixture was filtered and the solvent was evaporated under reduced pressure. The crude product was purified by flash silica gel chromatography (ISCO®; 80 g SepaFlash® Silica Flash Column, Eluent of 0~50% EtOAc/PE gradient at 40 mL/min) to give the title compound.

$^1$H NMR (CDCl$_3$, 400 MHz) δ 7.19-7.32 (m, 3H), 7.09-7.18 (m, 2H), 4.31-4.42 (m, 1H), 4.09-4.21 (m, 2H), 3.99 (d, J=19.6 Hz, 1H), 3.79 (t, J=7.6 Hz, 1H), 3.20 (d, J=7.4 Hz, 2H), 2.94 (br. s., 1H), 1.25-1.11 (m, 3H).

Step 7: ethyl 2-benzyl-4-bromo-3-oxobutanoate

To a stirred mixture of ethyl 2-benzyl-4-hydroxy-3-oxobutanoate (2.7 g, 11.43 mmol), Ph$_3$P (3.60 g, 13.71 mmol) in DCM (50 mL) at 0° C. was added CBr$_4$ (4.93 g, 14.86 mmol) and the mixture was stirred at 0° C. for 2 h under N$_2$ balloon (15 psi). TLC showed the reactant was consumed. The solvent was evaporated under reduced pressure. The crude product was purified by flash silica gel chromatography (ISCO®; 40 g SepaFlash® Silica Flash Column, Eluent of 0~10% EtOAc/PE gradient at 40 mL/min) to give the title compound.

$^1$H NMR (CDCl$_3$, 400 MHz) δ 7.26 (d, J=7.4 Hz, 2H), 7.16 (d, J=7.0 Hz, 3H), 4.07-4.17 (m, 3H), 3.91 (s, 2H), 3.20 (d, J=7.8 Hz, 2H), 1.18-1.22 (m, 3H).

Step 8: ethyl 2-(2-(4-((methoxycarbonyl)amino)phenyl)-1H-imidazol-5-yl)-3-phenylpropanoate To a solution of methyl (4-carbamimidoylphenyl)carbamate (2.58 g, 13.37 mmol) in DMF (6 mL) and CH$_3$CN (24 mL) was added potassium bicarbonate (2.68 g, 26.7 mmol) at 25° C. The reaction mixture was vigorously stirred for 20 min. A solution of ethyl 2-benzyl-4-bromo-3-oxobutanoate (2.0 g, 6.69 mmol) in acetonitrile (6.00 mL) was then added dropwise via a syringe over a period of 5 min. After completion of the addition, the mixture was heated at 90° C. for 12 h. LCMS and TLC showed the reactant was consumed. The mixture was cooled, filtered and concentrated. The residue was purified by reverse Prep-HPLC (preparative HPLC on a GILSON 281 instrument fitted with a YMC-Actus Triart C18 150×30 mm×5 um) using water and acetonitrile as the eluents. Mobile phase A: water, mobile phase B: acetonitrile (0.1% TFA-CH$_3$CN), 25-45%, 0-10 min; 100% B, 10.5-12.5 min; 5% B, 13-15 min) to give the title compound.

$^1$H NMR (CD$_3$OD, 400 MHz): δ 7.79-7.85 (m, 2H), 7.71-7.78 (m, 2H), 7.20-7.32 (m, 5H), 4.12-4.30 (m, 3H), 3.80 (s, 4H), 3.47 (dd, J=7.71, 13.7 Hz, 1H), 3.21-3.30 (m, 1H), 1.21 (t, J=7.2 Hz, 3H).

MS (ESI) m/z 394.0 (M+H).

Step 9: 2-(2-(4-((methoxycarbonyl)amino)phenyl)-1H-imidazol-5-yl)-3-phenylpropanoic acid To a solution of ethyl 2-(2-(4-((methoxycarbonyl)amino)phenyl)-1H-imidazol-5-yl)-3-phenylpropanoate (90 mg, 0.229 mmol) in THF (1 mL), MeOH (1 mL) and water (1 mL) was added LiOH.H$_2$O (0.458 mL, 2.288 mmol) solution (5M in H$_2$O). The mixture was stirred at 20° C. for 3 h. LCMS showed the reactant was consumed. The resulting mixture was acidified by HCl (1 N) to pH 6, and extracted with EtOAc (20 mL) twice. The combined organic layers were washed with water (10 mL) and brine (10 mL), dried over Na$_2$SO$_4$ and filtered and concentrated to give the crude title compound which was used for the next step directly without further purification. MS (ESI) m/z 366.1 (M+H).

Step 10: methyl (4-(5-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-2-yl)phenyl)carbamate To a stirred solution of 2-(2-(4-((methoxycarbonyl)amino)phenyl)-1H-imidazol-5-yl)-3-phenylpropanoic acid (18 mg, 0.049 mmol) in DMF (1 mL) was added HATU (22.48 mg, 0.059 mmol) at 25° C. The solution was stirred for 10 min and a solution of (R)-6-chloro-5-fluorospiro[benzo[d][1,3]oxazine-4,3'-piperidin]-2(1H)-one hydrochloride (19.67 mg, 0.064 mmol) and DIPEA (0.034 mL, 0.197 mmol) in DMF (1 mL) were added. The reaction mixture was stirred at 25° C. for 12 h. LCMS showed most of starting materials were consumed. The reaction mixture was concentrated to give the crude product which was purified by prep-HPLC (preparative HPLC on a GILSON 281 instrument fitted with Phenomenex Synergi C18×21.2 mm×4 um) using water and acetonitrile as the eluents. Mobile phase A: water mobile phase B: acetonitrile (0.1% TFA-CH$_3$CN), Gradient: 32-52% B, 0-11 min; 100% B, 9-11 min) to give the title compound.

$^1$H NMR (CD$_3$OD, 400 MHz): δ 7.86 (dd, J=9.0, 15.7 Hz, 2H), 7.69-7.78 (m, 3H), 7.41-7.49 (m, 2H), 7.21-7.35 (m, 5H), 6.71-6.82 (m, 1H), 4.64-4.79 (m, 1H), 4.05-4.29 (m, 1H), 3.80 (s, 3H), 3.47-3.63 (m, 1H), 3.20-3.29 (m, 1H), 2.97-3.12 (m, 1H), 2.62-2.79 (m, 1H), 2.42-2.58 (m, 1H), 2.00-2.29 (m, 3H), 1.86-1.98 (m, 1H), 1.55-1.79 (m, 2H). MS (ESI) m/z 618.0 (M+H).

Step 11: methyl (4-(5-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-2-yl)phenyl)carbamate (Example 130A) and methyl (4-(5-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-2-yl)phenyl)carbamate (Example 130B)

Methyl (4-(5-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-imidazol-2-yl)phenyl)carbamate (55 mg, 0.089 mmol) was resolved by SFC (SFC-80-(8)) (Column: OD(250 mm×30 mm, 10 um), Mobile phase: Base-EtOH in CO$_2$, Flow rate: 80 mL/min Wave length: 220 nm $t_{R1}$=1.780 min, $t_{R2}$=2.047) to give crude Example 130A (the first peak isomer with shorter retention time in chiral HPLC) and crude Example 130B (the second peak isomer with longer retention time). The crude Example 130A was then purified by prep-HPLC (preparative HPLC on a GILSON 281 instrument fitted with Phenomenex Synergi C18 100×21.2 mm×4 um) using water and acetonitrile as the eluents. Mobile phase A: water mobile phase B: acetonitrile (0.1% TFA-CH₃CN), Gradient: 26-56% B, 0-11 min; 100% B, 9-11 min) to give Example 130A. The crude product Example 130B was purified by prep-HPLC (preparative HPLC on a GILSON 281 instrument fitted with Phenomenex Synergi C18 100×21.2 mm×4 um) using water and acetonitrile as the eluents. Mobile phase A: water mobile phase B: acetonitrile (0.1% TFA-CH₃CN), Gradient: 25-55% B, 0-11 min; 100% B, 9-11 min) to give Example 130B.

Example 130A

¹H NMR (CD₃OD, 400 MHz): δ 7.85 (d, J=8.8 Hz, 2H), 7.64-7.76 (m, 3H), 7.42 (t, J=8.2 Hz, 1H), 7.04-7.32 (m, 5H), 6.70-6.84 (m, 1H), 4.70 (t, J=7.5 Hz, 1H), 4.48-4.62 (m, 1H), 4.07 (d, J=13.9 Hz, 1H), 3.77 (s, 3H), 3.32-3.42 (m, 1H), 3.16-3.27 (m, 1H), 2.98-3.11 (m, 2H), 2.78-2.90 (m, 1H), 2.41-2.56 (m, 1H), 2.28-2.37 (m, 1H), 2.17 (d, J=13.7 Hz, 1H), 1.54-1.80 (m, 2H). MS (ESI) m/z 618.2 (M+H).

Example 130B

¹H NMR (CD₃OD, 400 MHz): δ 7.76-7.86 (m, 2H), 7.66-7.75 (m, 2H), 7.38-7.48 (m, 2H), 7.18-7.35 (m, 6H), 6.66-6.80 (m, 1H), 4.57-4.77 (m, 2H), 4.08-4.26 (m, 1H), 3.77 (s, 3H), 3.44-3.60 (m, 1H), 3.31-3.39 (m, 1H), 3.11-3.26 (m, 1H), 2.60-2.74 (m, 1H), 2.43-2.56 (m, 1H), 2.03-2.28 (m, 2H), 1.80-1.96 (m, 1H), 1.54-1.76 (m, 1H). MS (ESI) m/z 618.2 (M+H).

| Example | Structure | LCMS [M + 1] | FXIa Ki (nM) |
|---|---|---|---|
| 130A (isomer A) | methyl (4-(5-(1-((R)-6-chloro-5-fluoro-2-oxo-1,2-dihydro-spiro[benzo[d][1,3]oxazine-4,3'-piperidin]-1'-yl)-1-oxo-3-phenylpropan-2-yl)-1H-imidazol-2-yl)phenyl)carbamate | 618.2 | 359.9 |
| 130B (isomer B) | methyl (4-(5-(1-((R)-6-chloro-5-fluoro-2-oxo-1,2-dihydro-spiro[benzo[d][1,3]oxazine-4,3'-piperidin]-1'-yl)-1-oxo-3-phenylpropan-2-yl)-1H-imidazol-2-yl)phenyl)carbamate | 618.2 | >875 |
| 130 (racemate) | methyl (4-(5-(1-((R)-6-chloro-5-fluoro-2-oxo-1,2-dihydro-spiro[benzo[d][1,3]oxazine-4,3'-pyrrolidin]-1'-yl)-1-oxo-3-phenylpropan-2-yl)-1H-imidazol-2-yl)phenyl)carbamate | 604.1 | 91.88 |

Example 131

Methyl (2-(1-(6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazol-5-yl)carbamate

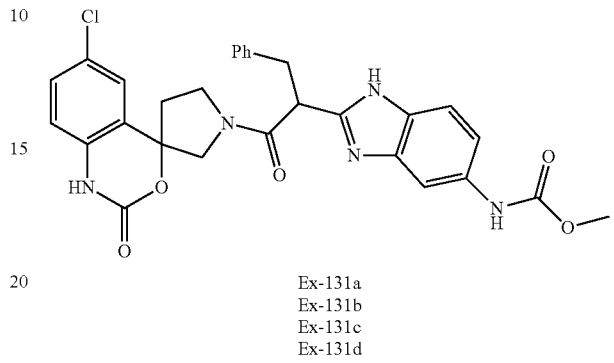

Ex-131a
Ex-131b
Ex-131c
Ex-131d

Step A: 2-Benzyl-3-ethoxy-3-oxopropanoic acid

To a stirred solution of diethyl 2-benzylmalonate (2 g, 7.99 mmol) in ethanol (13.32 ml) was added KOH (0.448 g, 7.99 mmol) at RT. The reaction mixture was stirred at RT for 3 hrs. The solvent was evaporated. Sat. NaHCO₃ (aq) was added and the fractions were extracted with EtOAc. The aqueous layer was acidified by adding 1N HCl (pH=1). The acidic aq. layer was extracted with EtOAc (3×). The organic layer was dried over MgSO₄, filtered and concentrated. The crude product was purified by flash silica gel column chromatography (10% MeOH in DCM) to afford 2-benzyl-3-ethoxy-3-oxopropanoic acid. LC/MS=223 [M+1].

Step B: Ethyl 2-benzyl-3-(6-chloro-2-oxo-1,2-dihydrospiro[benzo[d][1,3]oxazine-4,3'-pyrrolidin]-1'-yl)-3-oxopropanoate To a stirred solution of 2-benzyl-3-ethoxy-3-oxopropanoic acid (457 mg, 2.056 mmol) in DMF (1300 µl) was added 6-chlorospiro[benzo[d][1,3]oxazine-4,3'-pyrrolidin]-2(1H)-one hydrochloride (849 mg, 3.08 mmol), HATU (1173 mg, 3.08 mmol) and DIPEA (1437 µl, 8.23 mmol) at RT. The reaction mixture was stirred at RT for 16 hrs. Sat. NaHCO₃ (aq) was poured into the reaction and the reaction mixture was extracted with EtOAc. The organic layer was washed with brine and dried over MgSO₄, filtered and concentrated. The crude product was purified by flash silica gel column chromatography (EtOAc/Hex=1/1) to provide ethyl 2-benzyl-3-(6-chloro-2-oxo-1,2-dihydrospiro[benzo[d][1,3]oxazine-4,3'-pyrrolidin]-1'-yl)-3-oxopropanoate. LC/MS=443 [M+1].

Step C: 2-Benzyl-3-(6-chloro-2-oxo-1,2-dihydrospiro[benzo[d][1,3]oxazine-4,3'-pyrrolidin]-1'-yl)-3-oxopropanoic acid To a stirred solution of ethyl 2-benzyl-3-(6-chloro-2-oxo-1,2-dihydrospiro[benzo[d][1,3]oxazine-4,3'-pyrrolidin]-1'-yl)-3-oxopropanoate (911 mg, 2.057 mmol) in THF (10 ml) and MeOH (2 mL) was added a solution of lithium hydroxide monohydrate (86 mg, 2.057 mmol) in water (2 ml) at RT.

The reaction mixture was stirred at RT for 16 hrs. The solvent was evaporated and the crude was diluted with water. The aq. layer was extracted with Et$_2$O. The aqueous layer was acidified by 1N HCl and extracted with EtOAc. The organic layer was dried over MgSO$_4$, filtered and concentrated. The crude product was used for the next step without further purification. LC/MS=415 [M+1].

Step D: N-(2-Amino-4-nitrophenyl)-2-benzyl-3-(6-chloro-2-oxo-1,2dihydrospiro[benzo[d][1,3]oxazine-4,3'-pyrrolidin]-1'-yl)-3-oxopropanamide To a stirred solution of 2-benzyl-3-(6-chloro-2-oxo-1,2-dihydrospiro[benzo[d][1,3]oxazine-4,3'-pyrrolidin]-1'-yl)-3-oxopropanoic acid (842 mg, 2.030 mmol) in DMF (2.03E+04 μl) was added 4-nitrobenzene-1,2-diamine (466 mg, 3.04 mmol), HATU (1158 mg, 3.04 mmol) and N-methylmorpholine (669 μl, 6.09 mmol) at RT. The reaction mixture was stirred at RT overnight. The reaction mixture was diluted with sat. NaHCO$_3$ (aq) and extracted with EtOAc. The organic layer was dried over MgSO$_4$, filtered and concentrated. The crude product was purified by flash silica gel column chromatography (1/1 EtOAc/Hex to 100% EtOAc and 10% MeOH in DCM) to provide N-(2-amino-4-nitrophenyl)-2-benzyl-3-(6-chloro-2-oxo-1,2dihydrospiro[benzo[d][1,3]oxazine-4,3'-pyrrolidin]-1'-yl)-3-oxopropanamide. LC/MS=550 [M+1].

Step E: 6-Chloro-1'-(2-(5-nitro-1H-benzo[d]imidazol-2-yl)-3-phenylpropanoyl)spiro[benzo[d][1,3]oxazine-4,3'-pyrrolidin]-2(1H)-one To a round bottom flask of N-(2-amino-4-nitrophenyl)-2-benzyl-3-(6-chloro-2-oxo-1,2 dihydrospiro[benzo[d][1,3]oxazine-4,3'-pyrrolidin]-1'-yl)-3-oxopropanamide (901.7 mg, 1.640 mmol) was added acetic acid (4693 μl, 82 mmol) at RT. The reaction mixture was heated to 65° C. for 3 hrs, and cooled to room temp. Sat. NaHCO$_3$ (aq) was added and the reaction mixture was extracted with DCM. The organic layer was washed with sat. NaHCO$_3$ (aq), dried over MgSO$_4$, filtered and concentrated. The crude product was purified by flash silica gel column chromatography (EtOAc/Hex=1/1) to give 6-chloro-1'-(2-(5-nitro-1H-benzo[d]imidazol-2-yl)-3-phenylpropanoyl)spiro[benzo[d][1,3]oxazine-4,3'-pyrrolidin]-2(1H)-one. LC/MS=532 [M+1].

Step F: 1'-(2-(5-Amino-1H-benzo[d]imidazol-2-yl)-3-phenylpropanoyl)-6-chlorospiro[benzo-[d][1,3]oxazine-4,3'-pyrrolidin]-2(1H)-one To a stirred suspension of 6-chloro-1'-(2-(5-nitro-1H-benzo[d]imidazol-2-yl)-3-phenylpropanoyl)spiro[benzo[d][1,3]oxazine-4,3'-pyrrolidin]-2(1H)-one (472 mg, 0.887 mmol) in EtOAc (30 ml) and MeOH (15 ml) was added platinum(IV) oxide (201 mg, 0.887 mmol) at RT. The reaction mixture was evacuated with a vacuum and purged with H$_2$ gas (balloon). The reaction mixture was stirred at RT for 7 hrs. The reaction mixture was filtered through a short pad of Celite and washed with EtOAc. The solvent was evaporated and the crude product was purified by flash silica gel column chromatography (10% MeOH/DCM) to give 1'-(2-(5-Amino-1H-benzo[d]imidazol-2-yl)-3-phenylpropanoyl)-6-chlorospiro[benzo-[d][1,3]oxazine-4,3'-pyrrolidin]-2(1H)-one. LC/MS=502 [M+1].

Step G: Methyl (2-(1-(6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazol-5-yl)carbamate To a stirred solution of 1'-(2-(5-Amino-1H-benzo[d]imidazol-2-yl)-3-phenylpropanoyl)-6-chlorospiro[benzo-[d][1,3]oxazine-4,3'-pyrrolidin]-2(1H)-one (277.2 mg, 0.552 mmol) in DCM (2 ml)/THF (1 ml) was added pyridine (0.045 ml, 0.552 mmol) and methyl carbonochloridate (0.043 ml, 0.552 mmol) at RT. The reaction mixture was stirred at RT for 4 hrs. The reaction mixture was quenched by aq. NaHCO$_3$, and extracted with DCM. The organic layer was dried over MgSO$_4$, filtered and concentrated. The crude product was purified by flash silica gel column chromatography (40 g, EtOAc/Hex=1/1) to give the desired product. LC/MS=560 [M+1]. The mixture of the four stereoisomers was purified by chiral SFC (OD column, 40% MeOH/CO$_2$ to afford Ex-131a (faster eluting), Ex-131b (second faster eluting), Ex-131c (third faster eluting), and Ex-131d (slower eluting).

By using procedures similar to those described previously, and using appropriate starting materials, the following compounds were synthesized. These compounds were characterized by LC/MS.

| Example | Structure | LCMS [M + 1] | FXIa Ki (nM) |
|---|---|---|---|
| 131a (isomer A) | methyl (2-((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazol-5-yl)carbamate | 560 | 5000 |
| 131b (isomer B) | methyl (2-((S)-1-((S)-6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazol-5-yl)carbamate | 560 | 5000 |
| 131c (isomer C) | methyl (2-((R)-1-((R)-6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazol-5-yl)carbamate | 560 | 354 |
| 131d (isomer D) | methyl (2-((R)-1-((S)-6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazol-5-yl)carbamate | 560 | 5000 |
| 132A (isomer A) | 2-(1-((R)-6-chloro-2-oxo-1,2-dihydrospiro[benzo[d][1,3]oxazine-4,3'-piperidin]-1'-yl)-3-(4-fluorophenyl)-1-oxopropan-2-yl)-1H-benzo[d]imidazole-6-carboxylic acid | 563.9 | 61.7 |

| Example | Structure | LCMS [M + 1] | FXIa Ki (nM) |
|---|---|---|---|
| 132A (isomer B) | 2-(1-((R)-6-chloro-2-oxo-1,2-dihydrospiro[benzo[d][1,3]oxazine-4,3'-piperidin]-1'-yl)-3-(4-fluorophenyl)-1-oxopropan-2-yl)-1H-benzo[d]imidazole-6-carboxylic acid | 563.9 | 449.2 |
| 133 (racemate) | (4R)-6-chloro-1'-(2-(6-fluoro-1H-benzo[d]imidazol-2-yl)-3-(4-fluorophenyl)propanoyl)spiro[benzo[d][1,3]oxazine-4,3'-piperidin]-2(1H)-one | 537.9 | 8750 |

Example 134

Methyl (2-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-indol-5-yl)carbamate

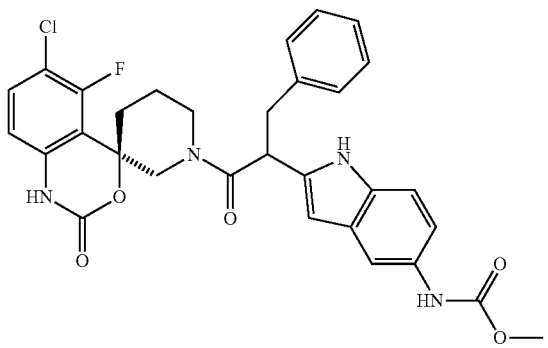 [SMILES: COC(=O)Nc1ccc2[nH]c(C(Cc3ccccc3)C(=O)N3CCC[C@@]4(C3)OC(=O)Nc3ccc(Cl)c(F)c34)cc2c1]

Step 1: methyl 2-amino-5-nitrobenzoate

To a solution of 2-amino-5-nitrobenzoic acid (10 g, 54.9 mmol) in MeOH (150 mL) was added $H_2SO_4$ (4 mL, 75 mmol) at 15° C. The mixture was stirred at 90° C. for 60 h. LCMS showed the reaction was nearly completed. Then the mixture was treated with sat. $NaHCO_3$ solution to pH=8. The precipitate was collected to give the title compound which was used for the next step without further purification.

$^1$H NMR (CDCl3, 400 MHz): δ 8.85 (d, J=2.2 Hz, 1H), 8.14 (dd, J=9.3, 2.2 Hz, 1H), 6.68 (d, J=9.3 Hz, 1H), 3.94 ppm (s, 3H). MS (ESI) m/z 197.2 (M+H).

Step 2: (2-amino-5-nitrophenyl)methanol

To a solution of methyl 2-amino-5-nitrobenzoate (14 g, 71.4 mmol) in THF (200 mL) was added $LiBH_4$ (2.35 g, 112 mmol) at 0° C. and the reaction mixture was sitrred at 10° C. for 5 h. Another batch of $LiBH_4$ (2 g, 88 mmol) was added at 0° C. The mixture was further stirred at 10° C. for 16 h. TLC (PE/EtOAc=2/1) showed the reaction was complete. The reaction was quenched with sat. aq. $NH_4Cl$ (55 mL) and extracted with EtOAc (150 mL×3). The combined organic layers were washed with brine (100×3 mL), dried over $Na_2SO_4$, filtered and concentrated to give the title compound, which was used for the next step without further purification.

MS (ESI) m/z 169.0 (M+H).

Step 3: (2-amino-5-nitrobenzyl)triphenylphosphonium bromide

To solution of (2-amino-5-nitrophenyl)methanol (4 g, 23.79 mmol) in acetonitrile (50 mL) was added triphenylphosphine hydrobromide (8.2 g, 23.79 mmol) at 15° C. and the mixture was stirred at 100° C. for 4 h under $N_2$. LCMS showed the reaction was complete. The mixture was cooled to 15° C. and filtered to give the title compound which was used for the next step without further purification.

$^1$H NMR ($CD_3OD$, 400 MHz): 7.90 (t, J=8.6 Hz, 4H), 7.60-7.79 (m, 14H), 4.80 ppm (d, J=14.3 Hz, 2H).

Step 4: (2-(3-ethoxy-3-oxopropanamido)-5-nitrobenzyl)triphenylphosphonium bromide To solution of (2-amino-5-nitrobenzyl)triphenylphosphonium bromide (10.2 g, 20.68 mmol) in DCM (50 mL) was added ethyl 3-chloro-3-oxopropanoate (3.11 g, 20.68 mmol) at 10° C. under $N_2$ and the mixture was stirred at 10° C. for 4 h under $N_2$. LCMS showed the reaction was complete. The mixture was concentrated in vacuo to give the title compound which was used for the next step without further purification. MS (ESI) m/z 527.2 (M+).

Step 5: ethyl 2-(5-nitro-1H-indol-2-yl)acetate

To a suspension of (2-(3-ethoxy-3-oxopropanamido)-5-nitrobenzyl)triphenylphosphonium bromide (12.6 g, 23.89 mmol) in toluene (10 mL) was added 1M potassium 2-methylpropan-2-olate in THF (35.8 mL, 35.8 mmol) and the mixture was stirred at 110° C. under $N_2$ for 30 min. LCMS showed the reaction was complete. The mixture was then diluted with water (50 mL) and extracted with EtOAc (80 mL×3). The combined organic layers were dried over $Na_2SO_4$, filtered and concentrated. The residue was purified by column chromatography ($SiO_2$, PE/EtOAc=1/0-4/1) to give the title compound.

$^1$H NMR (CDCl$_3$, 400 MHz): δ 8.51 (s, 1H), 8.08 (dd, J=8.9, 1.9 Hz, 1H), 7.38 (d, J=9.0 Hz, 1H), 6.52 (s, 1H), 4.20-4.30 (m, 2H), 3.89 (s, 2H), 1.29-1.37 ppm (m, 3H). MS (ESI) m/z 249.3 (M+H).

Step 6: tert-butyl 2-(2-ethoxy-2-oxoethyl)-5-nitro-1H-indole-1-carboxylate

To solution of ethyl 2-(5-nitro-1H-indol-2-yl)acetate (3.5 g, 14.10 mmol) in DCM (3 mL) was added DMAP (0.345 g, 2.82 mmol) and $Boc_2O$ (3.27 mL, 14.10 mmol) at 15° C. under $N_2$. The mixture was stirred at 15° C. for 2.5 h under $N_2$. LCMS showed the reaction was complete. The mixture was diluted with water (30 mL) and extracted with DCM (30 mL×4). The combined organic layers were dried with Na$_2$SO$_4$, filtered and concentrated. The residue was purified by column chromatography (SiO$_2$, PE/EtOAc=1/0-8/1) to give the title compound.

$^1$H NMR (CDCl$_3$, 400 MHz): δ 8.42 (d, J=1.3 Hz, 1H), 8.14-8.25 (m, 2H), 6.62 (s, 1H), 4.21 (q, J=7.1 Hz, 2H), 4.07 (s, 2H), 1.68 (s, 9H), 1.28 ppm (t, J=7.1 Hz, 3H).

Step 7: tert-butyl 2-(1-ethoxy-1-oxo-3-phenylpropan-2-yl)-5-nitro-1H-indole-1-carboxylate To a solution of tert-butyl 2-(2-ethoxy-2-oxoethyl)-5-nitro-1H-indole-1-carboxylate (2350 mg, 6.75 mmol) in THF (20 mL) was added KHMDS (6.75 mL, 6.75 mmol) at −78° C. under N$_2$. The mixture was stirred at −78° C. for 1 h and then benzyl bromide (0.802 mL, 6.75 mmol) was added at −78° C. The mixture was further stirred at 15° C. for 30 min. LCMS showed the reaction was complete. The mixture was diluted with water (30 mL) and extracted with EtOAc (30 mL×4). The organic layers were combined, dried with Na$_2$SO$_4$, filtered and concentrated. The residue was purified by column chromatography (SiO$_2$, PE/EtOAc=1/0-10/1) to give the title compound. MS (ESI) m/z 339.2 (M-Boc+H).

Step 8: tert-butyl 5-amino-2-(1-ethoxy-1-oxo-3-phenylpropan-2-yl)-1H-indole-1-carboxylate To a solution of tert-butyl 2-(1-ethoxy-1-oxo-3-phenylpropan-2-yl)-5-nitro-1H-indole-1-carboxylate (1 g, 2.281 mmol) in EtOH (30 mL) was added platinum(IV) oxide (0.052 g, 0.228 mmol) and the mixture was stirred at 15° C. under H$_2$ (15 psi) for 3 h. LCMS showed the reaction was complete. The mixture was filtered and the filtrate was concentrated to give the title compound which was used for the next step without further purification.

$^1$H NMR (CDCl$_3$, 400 MHz): δ 7.79 (d, J=8.8 Hz, 1H), 7.16-7.26 (m, 5H), 6.76 (d, J=1.8 Hz, 1H), 6.66 (dd, J=8.7, 2.1 Hz, 1H), 6.39 (s, 1H), 4.79 (br. s., 1H), 4.09 (q, J=7.1 Hz, 2H), 3.33-3.45 (m, 1H), 3.22-3.32 (m, 1H), 1.68 (s, 9H), 1.13 ppm (t, J=7.1 Hz, 3H). MS (ESI) m/z 409.3 (M+H).

Step 9: tert-butyl 2-(1-ethoxy-1-oxo-3-phenylpropan-2-yl)-5-((methoxycarbonyl)amino)-1H-indole-1-carboxylate To a solution of tert-butyl 5-amino-2-(1-ethoxy-1-oxo-3-phenylpropan-2-yl)-1H-indole-1-carboxylate (1250 mg, 2.142 mmol) in DCM (8 mL) was added methyl carbonochloridate (405 mg, 4.28 mmol) and TEA (0.746 mL, 5.36 mmol) and the mixture was stirred at 15° C. under N$_2$ for 3 h. TLC (PE/EtOAc=3/1) showed the reaction was complete. The mixture was concentrated and purified by p-TLC (SiO$_2$, PE/EtOAc=3/1) to give the title compound.

$^1$H NMR (CDCl$_3$, 400 MHz): δ 7.92 (d, J=8.8 Hz, 1H), 7.58 (br. s., 1H), 7.12-7.26 (m, 6H), 6.59 (br. s., 1H), 6.50 (s, 1H), 4.80 (br. s., 1H), 4.10 (q, J=7.1 Hz, 2H), 3.79 (s, 3H), 3.38-3.47 (m, 1H), 3.24-3.33 (m, 1H), 1.68 (s, 9H), 1.14 (t, J=7.1 Hz, 3H).

Step 10: sodium 2-(1-(tert-butoxycarbonyl)-5-((methoxycarbonyl)amino)-1H-indol-2-yl)-3-phenylpropanoate To solution of tert-butyl 2-(1-ethoxy-1-oxo-3-phenylpropan-2-yl)-5-((methoxycarbonyl)amino)-1H-indole-1-carboxylate (530 mg, 1.136 mmol) in MeOH (8) and water (2 mL) was added NaOH (54.5 mg, 1.363 mmol) and the mixture was stirred at 50° C. for 16 h. LCMS showed the reaction was complete. The mixture was concentrated in vacuo to give the crude title compound which was used for the next step without further purification. MS (ESI) m/z 339.1 (M-Boc+H).

Step 11: tert-butyl 2-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-5-((methoxycarbonyl)amino)-1H-indole-1-carboxylate To solution of sodium 2-(1-(tert-butoxycarbonyl)-5-((methoxycarbonyl)amino)-1H-indol-2-yl)-3-phenylpropanoate (crude 150 mg, 0.318 mmol) and (R)-6-chloro-5-fluorospiro[benzo[d][1,3]oxazine-4,3'-piperidin]-2(1H)-one hydrochloride (98 mg, 0.318 mmol) in DCM (5 mL) was added EDC (91 mg, 0.477 mmol), HOBT (73.1 mg, 0.477 mmol) and TEA (0.222 mL, 1.591 mmol) at 15° C. under N$_2$. The mixture was stirred at 15° C. for 18 h under N$_2$. LCMS showed the reaction was complete. The mixture was diluted with water (30 mL) and extracted with DCM (30 mL×4). The organic layer were combined, dried with Na$_2$SO$_4$, filtered and concentrated to give crude title compound which was used for the next step without further purification. MS (ESI) m/z 691.2 (M+H).

Step 12: methyl (2-(1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-1H-indol-5-yl)carbamate (Example 134)

To a solution of tert-butyl 2-(1-((R)-6-chloro-5-fluoro-2-oxo-1,2-dihydrospiro[benzo[d][1,3]-oxazine-4,3'-piperidin]-1'-yl)-1-oxo-3-phenylpropan-2-yl)-5-((methoxycarbonyl)amino)-1H-indole-1-carboxylate (crude 200 mg) in DCM (10 mL) was added TFA (1 mL, 12.98 mmol) and the mixture was stirred at 15° C. for 1 h. It was concentrated and purified by HPLC (TFA condition) to give Example 134. MS (ESI) m/z 591.2 (M+H).

| Example | Structure | LCMS [M + 1] | FXIa Ki (nM) |
|---|---|---|---|
| 134 | methyl (2-(1-((R)-6-chloro-5-fluoro-2-oxo-1,2-dihydro-spiro[benzo[d][1,3]oxazine-4,3'-piperidin]-1'-yl)-1-oxo-3-phenylpropan-2-yl)-1H-indol-5-yl)carbamate | 591.2 | >875 |

Example 135

(4R)-6-chloro-1'-(3-cyclopropyl-2-((6-fluoro-1H-indazol-3-yl)amino)propanoyl)spiro[benzo[d][1,3]oxazine-4,3'-piperidin]-2(1H)-one

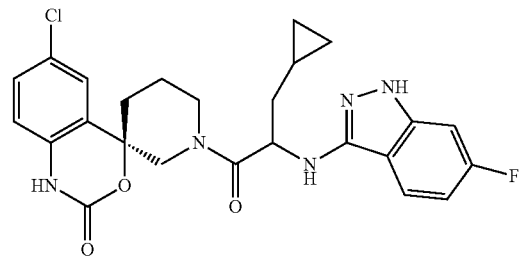 [SMILES: O=C1Nc2ccc(Cl)cc2[C@@]2(CCCN(C(=O)C(CC3CC3)Nc3n[nH]c4cc(F)ccc34)C2)O1]

Step A: Ethyl 2-(cyclopropylmethyl)-1,3-dithiane-2-carboxylate

A solution of (bromomethyl)cyclopropane (3.86 g, 28.6 mmol) and ethyl 1,3-dithiane-2-carboxylate (5 g, 26.0 mmol) in DMF (11 ml) was added dropwise over 5 min to an ice cooled suspension of NaH (1.248 g, 31.2 mmol) in benzene (33.0 ml). The suspension was stirred at 0° C. for 15 min and the reaction was allowed to warm to rt and stirred overnight. It was poured into sat. aq. ammonium chloride (50 mL) and extracted with ethyl acetate (2×50 mL). The combined organic layers were washed with brine, dried over sodium sulfate, filtered and concentrated. The residue was purified by ISCO (Gold 80 g, 0-30% ethyl acetate in hexane) to give ethyl 2-(cyclopropylmethyl)-1,3-dithiane-2-carboxylate.

Step B: Ethyl 3-cyclopropyl-2-oxopropanoate

A solution of ethyl 2-(cyclopropylmethyl)-1,3-dithiane-2-carboxylate (5.7 g, 23.13 mmol) in acetone/water (97/3, v/v, 20 mL) was added by a syringe pump over 30 min to a stirred suspension of NBS (41.2 g, 231 mmol) in acetone/water (97/3, v/v, 300 mL) at −5° C. The reaction mixture was stirred at rt for 1 h, while the progress of the reaction was monitored by TLC. It was quenched by adding sodium thiosulfate until the color faded from the organic layer. Most acetone was removed in vacuo and the mixture was extracted with DCM/Hexane (1/1, v/v, 3×300 mL). The combined organic layers were washed with sodium thiosulfate, water and brine. It was seperated and dried over sodium sulfate, filtered and concentrated. The residue was purified by ISCO (Gold 80 g, 0-60% diethyl ether in hexane) to give ethyl 3-cyclopropyl-2-oxopropanoate.

Step C: Ethyl 3-cyclopropyl-2-((6-fluoro-1-(4-methoxybenzyl)-1H-indazol-3-yl)amino)propanoate A solution of 6-fluoro-1-(4-methoxybenzyl)-1H-indazol-3-amine (100 mg, 0.369 mmol) and ethyl 3-cyclopropyl-2-oxopropanoate (69.1 mg, 0.442 mmol) in DCE (2 mL) and AcOH (0.200 mL) was heated at 50° C. for 30 min. It was cooled to rt and added sodium triacetoxyborohydride (102 mg, 0.479 mmol). The mixture was stirred at 50° C. for 1 h. It was concentrated and diluted with ethyl acetate (50 mL), washed with sodium carbonate (10%, 10 mL), brine (10 mL). The organic layer was dried over sodium sulfate, filtered and concentrated. The residue was purified by ISCO (Gold 24 g, 0-30% ethyl acetate in hexane) to give the title compound. MS (m/e): 411.89 [M+H]$^+$.

Step D: 3-Cyclopropyl-2-((6-fluoro-1-(4-methoxybenzyl)-1H-indazol-3-yl)amino)propanoic acid A solution of ethyl 3-cyclopropyl-2-((6-fluoro-1-(4-methoxybenzyl)-1H-indazol-3-yl)amino)propanoate (70 mg, 0.170 mmol) in THF (1 ml) and MeOH (1.000 mL) was treated with 5 M LiOH (0.5 mL, 2.500 mmol) at rt for 30 min. It was quenched with 4 M HCl to adjust pH=3, extracted with ethyl acetate (20 mL) and washed with brine (10 mL). The organic layer was dried over sodium sulfate, filtered and concentrated. The residue was purified by ISCO (Gold 12 g, 0-10% methanol in DCM) then by TLC (1000 um, 5% methanol in DCM) to give the titled compound. MS (m/e): 384.15 [M+H]$^+$.

Step E: (4R)-6-Chloro-1'-(3-cyclopropyl-2-((6-fluoro-1-(4-methoxybenzyl)-1H-indazol-3-yl)amino)propanoyl)spiro[benzo[d][1,3]oxazine-4,3'-piperidin]-2(1H)-one (R)-6-chloro-2-oxo-1,2-dihydrospiro[benzo[d][1,3]oxazine-4,3'-piperidin]-1'-ium chloride (11 mg, 0.038 mmol), HATU (18 mg, 0.047 mmol) and 3-cyclopropyl-2-((6-fluoro-1-(4-methoxybenzyl)-1H-indazol-3-yl)amino)propanoic acid (14 mg, 0.037 mmol) in DCM (0.5 ml) and DIEA (19 µl, 0.109 mmol) was added. It was stirred at rt for 30 min and purified by ISCO (Gold 4 g, 0-5% methanol in DCM) to give the title compound. MS (m/e): 618.36 [M+H]$^+$.

Step F: (4R)-6-chloro-1'-(3-cyclopropyl-2-((6-fluoro-1H-indazol-3-yl)amino)propanoyl)spiro[benzo[d][1,3]oxazine-4,3'-piperidin]-2(1H)-one (3'R)-6-chloro-1'-(3-cyclopropyl-2-((6-fluoro-1-(4-methoxybenzyl)-1H-indazol-3-yl)amino)propanoyl)spiro[benzo[d][1,3]oxazine-4,3'-piperidin]-2(1H)-one (15.7 mg, 0.025 mmol) was treated with TFA (1 mL, 12.98 mmol) at 70° C. for 45 min. It was cooled to rt and concentrated under reduced pressure. To the residue was added 2 mL DCM and a few drops of triethylamine, then purified by ISCO (Gold 12 g, 0-10% Methanol in DCM) to give the title compound.

Example 136

Methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)benzo[d]isoxazol-6-yl)carbamate

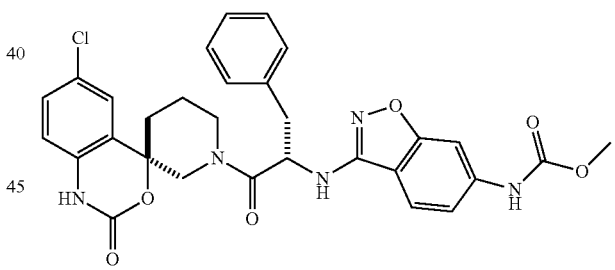

Step A: tert-Butyl (2-fluoro-4-nitrobenzoyl)-L-phenylalaninate

A mixture of 2-fluoro-4-nitrobenzoic acid (1.00 g, 5.40 mmol), (S)-tert-butyl 2-amino-3-phenylpropanoate hydrochloride (2.78 g, 10.80 mmol), N1-((ethylimino)methylene)-N3,N3-dimethylpropane-1,3-diamine hydrochloride (1.553 g, 8.10 mmol), 1-hydroxybenzotriazole (1.095 g, 8.10 mmol) and DIPEA (4.72 ml, 27.0 mmol) in DMF (30.0 ml) was stirred at room temperature for 17 hours. The reaction mixture was concentrated under reduced pressure, diluted with ethyl acetate (250 mL), and washed twice with water (200 mL). The residue was dried over sodium sulfate, filtered and concentrated. The crude compound was purified by flash chromatography (eluted in 30% ethyl acetate in hexane) to give tert-butyl (2-fluoro-4-nitrobenzoyl)-L-phenylalaninate. LCMS [M+1]=389.

Step B: tert-Butyl (E)-((2-fluoro-4-nitrophenyl)(hydroxyimino)methyl)-L-phenylalaninate To a solution of (S)-tert-butyl 2-(2-fluoro-4-nitrobenzamido)-3-phenylpropanoate (100 mg, 0.257 mmol) in THF (3.8 ml) was added Lawesson's Reagent (125 mg, 0.309 mmol) and the reaction mixture was stirred for 2 hours at room temperature. The temperature was raised to 65° C. and the mixture was stirred for 16 hours. The reaction mixture was concentrated under reduced pressure, ethyl acetate (50 mL) was added, and it was washed with aqueous sodium bicarbonate solution (30 mL). It was dried over sodium sulfate, filtered and concentrated. The crude compound was purified by flash chromatography (eluted in 30% ethylacetate in hexane) to give tert-Butyl (E)-((2-fluoro-4-nitrophenyl)(hydroxyimino)methyl)-L-phenylalaninate. LCMS [M+1]=405.

Step C: tert-butyl (6-nitrobenzo[d]isoxazol-3-yl)-L-phenylalaninate

To a solution of (S)-tert-butyl 2-(2-fluoro-4-nitrophenylthioamido)-3-phenylpropanoate (85.8 mg, 0.212 mmol) in methanol (7.0 ml) was added hydroxylamine hydrochloride (442 mg, 6.36 mmol) and sodium bicarbonate (535 mg, 6.36 mmol) at room temperature. The reaction mixture was heated to 80° C. and stirred for 23 hours. The reaction mixture was concentrated under reduced pressure, and the resulting crude compound was dissolved in ethylacetate (50 mL), washed with water (30 mL) and brine (30 mL). It was dried over sodium sulfate, filtered and concentrated. The crude compound was purified by flash chromatography (eluted in 45% ethylcetate in hexane) to give tert-butyl (6-nitrobenzo[d]isoxazol-3-yl)-L-phenylalaninate. LCMS [M+1] 404

Step D: tert-butyl (6-nitrobenzo[d]isoxazol-3-yl)-L-phenylalaninate

To a solution of (S,E)-tert-butyl 2-(2-fluoro-N'-hydroxy-4-nitrobenzimidamido)-3-phenylpropanoate (28.0 mg, 0.069 mmol) in DMF (0.8 ml) was added potassium carbonate (23.98 mg, 0.174 mmol) at room temperature and it was stirred for 2 hours. The reaction mixture was heated d to 60° C. and stirred for 18 hours. The reaction mixture was cooled to room temperature and concentrated under reduced pressure. The residue was purified by flash column chromatography (Silica Redisep 12 g, eluted in 20% EtOAc in hexane) to give tert-butyl (6-aminobenzo[d]isoxazol-3-yl)-L-phenylalaninate. LCMS [M+1] 384.

Step E: tert-butyl (6-aminobenzo[d]isoxazol-3-yl)-L-phenylalaninate

A mixture of (S)-tert-butyl 2-((6-nitrobenzo[d]isoxazol-3-yl)amino)-3-phenylpropanoate (10.8 mg, 0.028 mmol) and tin(II) chloride dihydrate (20.98 mg, 0.093 mmol) in ethanol (0.5 ml) was heated in a sealed tube at 70° C. for 1 hour. The reaction mixture was concentrated under reduced pressure, basified using aqueous sodiumbicarbonate (5 mL) and extracted twice with dichloromethane (20 mL) and washed with brine (10 mL). It was dried over sodium sulfate, filtered and concentrated to give tert-butyl (6-aminobenzo[d]isoxazol-3-yl)-L-phenylalaninate. The crude compound was directly used for next step without purification. LCMS [M+1] 354.

Step F: tert-butyl (6-((methoxycarbonyl)amino)benzo[d]isoxazol-3-yl)-L-phenylalaninate To a solution of (S)-tert-butyl 2-((6-aminobenzo[d]isoxazol-3-yl)amino)-3-phenylpropanoate (107 mg, 0.303 mmol) in pyridine (3.0 ml) was added methyl chloroformate (0.026 ml, 0.333 mmol) at room temperature and stirred at rt for 1 hour. The reaction mixture was concentrated under reduced pressure, water (50 mL) was added and the organic fractions were extracted twice with dichloromethane (2×50 mL). The combined organic layers were washed with brine (30 mL), dried over sodium sulfate, filtered and concentrated. The residue was purified by flash column chromatography (Silica Redisep 24 g, eluted in 50% EtOAc in hexane) to give tert-butyl (6-((methoxycarbonyl)amino)benzo[d]isoxazol-3-yl)-L-phenylalaninate. LCMS [M+1] 412.

Step G: (6-((methoxycarbonyl)amino)benzo[d]isoxazol-3-yl)-L-phenylalanine

Trifluoroacetic acid (1.0 mL, 12.98 mmol) was added to a solution of (S)-tert-butyl 2-((6-((methoxycarbonyl)amino)benzo[d]isoxazol-3-yl)amino)-3-phenylpropanoate (95.6 mg, 0.232 mmol) in DCM (2.0 ml) at room temperature and stirred at rt for 6 hours. The reaction mixture was concentrated under reduced pressure to give (6-((methoxycarbonyl)amino)benzo[d]isoxazol-3-yl)-L-phenylalanine which was used directly for next step. LCMS [M+1] 356.

Step H: methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)benzo[d]isoxazol-6-yl)carbamate A mixture of (S)-2-((6-((methoxycarbonyl)amino)benzo[d]isoxazol-3-yl)amino)-3-phenylpropanoic acid compound with 2,2,2-trifluoroacetic acid (1:1) (100 mg, 0.213 mmol), (R)-6-chlorospiro[benzo[d][1,3]oxazine-4,3'-piperidin]-2 (1H)-one hydrochloride (92 mg, 0.320 mmol), EDC (61.3 mg, 0.320 mmol), 1H-benzo[d][1,2,3]triazol-1-ol (43.2 mg, 0.320 mmol) and DIPEA (0.186 ml, 1.065 mmol) in DMF (2.0 ml) was stirred at room temperature for 16 hours. The reaction mixture was diluted with water (50 mL) and extracted with ethyl acetate (2×50 mL). The combined organic layers were washed with brine (2×30 mL), dried over sodium sulfate, filtered and concentrated. The residue was purified by flash column chromatography (Silica Redisep Rf 24 g, eluted in 8% methanol in dichloromethane) followed by reverse phase chromatography (Redisep C18 gold 26 g, eluted in 55% acetonitrile in water) to give methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)benzo[d]isoxazol-6-yl)carbamate. LCMS [M+1]=591

Example 137

Methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)-1-methyl-1H-indazol-6-yl)carbamate

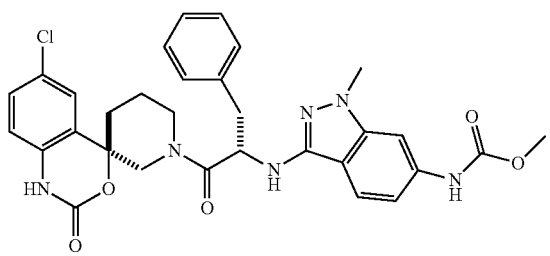

Step A: tert-butyl (1-methyl-6-nitro-1H-indazol-3-yl)-L-phenylalaninate

A solution of (S)-tert-butyl 2-(2-fluoro-4-nitrophenylthioamido)-3-phenylpropanoate (200 mg, 0.494 mmol) and methylhydrazine (0.052 ml, 0.989 mmol) in n-butanol (5.6 ml) was heated in a sealed tube at 100° C. for 23 hours. The reaction mixture was cooled to room temperature, concentrated under reduced pressure at 60° C. The residue was purified by flash chromatography (Silica Redisep 24 g, eluted in 25% EtOAc in hexane) to afford tert-butyl (1-methyl-6-nitro-1H-indazol-3-yl)-L-phenylalaninate. LCMS [M+1] 397.

Step B: tert-butyl (6-amino-1-methyl-1H-indazol-3-yl)-L-phenylalaninate

A mixture of (S)-tert-butyl 2-((1-methyl-6-nitro-1H-indazol-3-yl)amino)-3-phenylpropanoate (78.3 mg, 0.198 mmol) and tin(II) chloride dihydrate (147 mg, 0.652 mmol) in ethanol (3.6 ml) was heated in a sealed tube at 70° C. for 2 hours. The reaction mixture was concentrated under reduced pressure, basified using aqueous sodium bicarbonate (30 mL) and extracted twice with dichloromethane (2×40 mL), and washed with brine (30 mL). It was dried over sodium sulfate, filtered and concentrated to give tert-butyl (6-amino-1-methyl-1H-indazol-3-yl)-L-phenylalaninate which was directly used for next step without purification. LCMS [M+1] 367.

Step C: tert-butyl (6-((methoxycarbonyl)amino)-1-methyl-1H-indazol-3-yl)-L-phenylalaninate To a solution of (S)-tert-butyl 2-((6-amino-1-methyl-1H-indazol-3-yl)amino)-3-phenylpropanoate (61.4 mg, 0.168 mmol) in pyridine (2.0 ml) was added methyl chloroformate (0.014 ml, 0.184 mmol) at room temperature and stirred at RT for 1 hour. The reaction mixture was concentrated under reduced pressure, added water (30 mL) and extracted twice with dichloromethane (2×30 mL). The combined organic layers were washed with brine (30 mL), dried over sodium sulfate, filtered and concentrated. The residue was purified by flash column chromatography (Silica Redisep 24 g, eluted in 40% EtOAc in hexane) to provide tert-butyl (6-((methoxycarbonyl)amino)-1-methyl-1H-indazol-3-yl)-L-phenylalaninate. LCMS [M+1] 425.

Step D: (6-((methoxycarbonyl)amino)-1-methyl-1H-indazol-3-yl)-L-phenylalanine To a solution of (S)-tert-butyl 2-((6-((methoxycarbonyl)amino)-1-methyl-1H-indazol-3-yl)amino)-3-phenylpropanoate (30.4 mg, 0.072 mmol) in DCM (0.5 ml) was added trifluoroacetic acid (0.276 ml, 3.58 mmol) at room temperature and stirred at rt for 6 hours. The reaction mixture was concentrated under reduced pressure to give (6-((methoxycarbonyl)amino)-1-methyl-1H-indazol-3-yl)-L-phenylalanine and directly used for next step. LCMS [M+1] 369.

Step E: methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)-1-methyl-1H-indazol-6-yl)carbamate A mixture of (S)-2-((6-((methoxycarbonyl)amino)-1-methyl-1H-indazol-3-yl)amino)-3-phenylpropanoic acid compound with 2,2,2-trifluoroacetic acid (1:1) (38.2 mg, 0.079 mmol), (R)-6-chlorospiro[benzo[d][1,3]oxazine-4,3'-piperidin]-2(1H)-one hydrochloride (34.3 mg, 0.119 mmol), EDC (22.77 mg, 0.119 mmol), 1H-benzo[d][1,2,3]triazol-1-ol (16.05 mg, 0.119 mmol) and DIPEA (0.069 ml, 0.396 mmol) in DMF (1.0 ml) was stirred at room temperature for 7 hours. The reaction mixture was diluted with water (20 mL) and extracted with ethyl acetate (2×20 mL). Combined organic layers were washed with brine (2×20 mL), dried over sodium sulfate, filtered and concentrated. The residue was purified by flash column chromatography (Silica Redisep Rf 24 g, eluted in 6% methanol in dichloromethane) followed by reverse phase chromatography (Redisep C18 gold 26 g, eluted in 50% acetonitrile in water) to provide methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)-1-methyl-1H-indazol-6-yl)carbamate. LCMS [M+1] 604.

By using procedures similar to those described previously, and using appropriate starting materials, the following compounds were synthesized. These compounds were characterized by LC/MS

| Example | Structure | LCMS [M + 1] | Hu FXIa Ki (nM) |
|---|---|---|---|
| 135 (racemate) | (4R)-6-chloro-1'-(3-cyclopropyl-2-((6-fluoro-1H-indazol-3-yl)amino)propanoyl)spiro[benzo[d][1,3]oxazine-4,3'-piperidin]-2(1H)-one | 497.82 | >8750 |
| 136 | methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)benzo[d]isoxazol-6-yl)carbamate | 591.0 | 522.6 |

| Example | Structure | LCMS [M + 1] | Hu FXIa Ki (nM) |
|---|---|---|---|
| 137 | methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)-1-methyl-1H-indazol-6-yl)carbamate | 604.0 | 8196 |
| 138 | methyl (3-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)benzo[d]isoxazol-5-yl)carbamate | 591 | 8750 |

Example 139

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-sulfamoylbenzamide

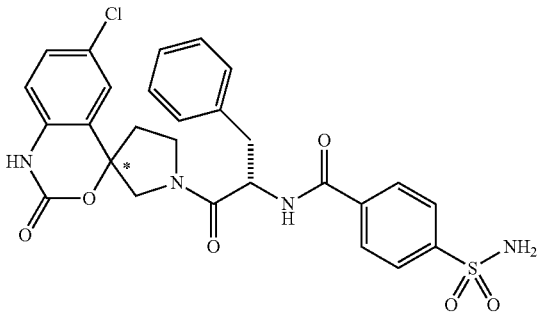 [SMILES: NS(=O)(=O)c1ccc(C(=O)N[C@@H](Cc2ccccc2)C(=O)N2CCC3(C2)OC(=O)Nc2ccc(Cl)cc23)cc1]

Step A: N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-sulfamoylbenzamide To a stirred solution of 1'-((S)-2-amino-3-phenylpropanoyl)-6-chlorospiro[benzo[d][1,3]oxazine-4,3'-pyrrolidin]-2(1H)-one (0.200 g, 0.474 mmol) in DMF (5 mL) was added hydrochloride 4-sulfamoylbenzoic acid (0.12 g, 0.596 mmol), HATU (0.270 g, 0.710 mmol) and DIPEA (0.248 ml, 1.421 mmol) at RT. The reaction mixture was stirred at RT for 3 h. The reaction mixture was concentrated in vacuo and purified by flash silica-gel column chromatography (0-55% EtOAc/CH$_2$Cl$_2$) to afford N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-sulfamoylbenzamide. LC/MS=569 [M+1]

Example 140

4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid

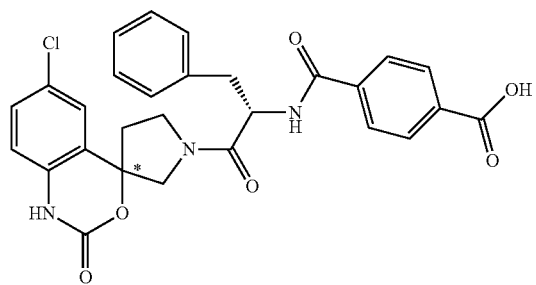 [SMILES: O=C1Nc2ccc(Cl)cc2C2(CCN(C(=O)[C@H](Cc3ccccc3)NC(=O)c3ccc(C(=O)O)cc3)C2)O1]

Step A: tert-butyl 4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoate To a stirred solution of 1'-((S)-2-amino-3-phenylpropanoyl)-6-chlorospiro[benzo[d][1,3]oxazine-4,3'-pyrrolidin]-2(1H)-one (0.500 g, 1.184 mmol) in DMF (6 mL) was added 4-(tert-butoxycarbonyl)benzoic acid (0.395 g, 1.776 mmol), HATU (0.675 g, 1.776 mmol) and DIPEA (0.827 ml, 4.74 mmol) at RT. The reaction mixture was stirred at RT for 6 h. The reaction mixture was diluted with saturated NaHCO$_3$ (aq) and extracted with EtOAc. The organic layer was dried over MgSO$_4$, filtered and concentrated. The crude product was purified by flash silica-gel column chromatography (0-100% EtOAc/Hex) to afford tert-butyl 4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoate. LC/MS=591 [M+1]

Step B: 4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid To a stirred solution of tert-butyl 4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoate (267.6 mg, 0.454 mmol) in DCM (2268 µl) was added TFA (349 µl, 4.54 mmol) at RT. The reaction mixture was stirred at RT overnight. The solvent was evaporated and the clean crude product was dried under vac. oven overnight to give 4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid. LC/MS=534 [M+1]. The mixture of the two stereoisomers was purified by chiral SFC (AD-H column, 60% 2:1 IPA:MeCN) to afford Ex-140a (faster eluting), and Ex-140b (slower eluting).

Intermediate 6 for Ex-186

4-(((2-methoxyethoxy)carbonyl)amino)benzoic acid

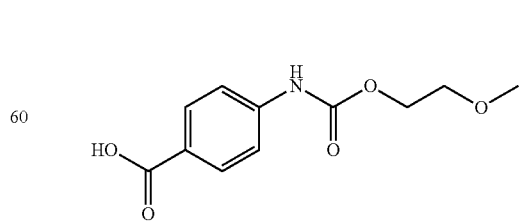

To a stirred solution of 4-aminobenzoic acid (1 g, 7.29 mmol) in acetone (7.29 ml) was added pyridine (0.590 ml, 7.29 mmol) and 2-methoxyethyl carbonochloridate (0.848 ml, 7.29 mmol) dropwise at RT. The reaction mixture was refluxed at 65° C. for 2 hrs. After it cooled down, the solvent was evaporated. Cold water was added and precipitate was generated, filtered and washed with water. It was dried in a vacuum oven overnight to provide 4-(((2-methoxyethoxy) carbonyl)amino)benzoic acid. LCMS=240 [M+1]

Intermediate 7 for Ex-195

3-amino-1H-indazole-6-carboxylic acid hydrochloride

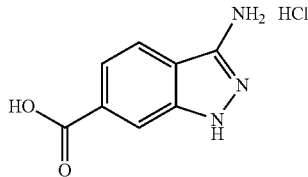 [SMILES: Cl ; Nc1n[nH]c2cc(C(=O)O)ccc12]

To a stirred solution of 4-cyano-3-fluorobenzoic acid (2 g, 12.11 mmol) in butan-1-ol (36.7 ml) was added hydrazine hydrate (3.08 g, 40.0 mmol) at RT. The reaction mixture was heated to 110° C. overnight. The reaction was cooled to RT and the precipitate was collected by filtration. The solid was then dissolved in 1N NaOH (8 ml, 8.00 mmol) (aq) and extracted with EtOAc. The aq. layer was acidified to pH=4 with 1N HCl. The resulting precipitate was collected by filtration and dried under vacuum oven overnight. The solid was redissolved in MeOH and insoluble material was filtered out. The filtrate was evaporated to give 3-amino-1H-indazole-6-carboxylic acid hydrochloride. LCMS=178 [M+1]

Intermediate 8 for Ex-185

3-amino-1H-indazole-5-carboxylic acid hydrochloride

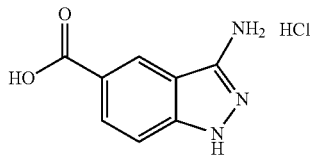 [SMILES: Nc1n[nH]c2ccc(C(=O)O)cc12 ; Cl]

To a solution of 3-cyano-4-fluorobenzoic acid (980.0 mg, 5.94 mmol) in ethanol (6 mL), was added hydrazine hydrate (0.89 mL, 17.8 mmol). The reaction was heated at reflux for 3 hours. The reaction was cooled to room temperature and ethanol was removed under reduced pressure. The resultant oil was taken up in water (50 mL) and basified with 1N aqueous sodium hydroxide (5 mL). The solution was washed once with ethyl acetate (25 mL). The aqueous phase was acidified to pH=3 with 6 N aqueous hydrochloric acid and was allowed to stir at room temperature for 1 hour. The resulting precipitate was collected by filtration and dried under vacuum to give the title compound, 3-Amino-1H-indazole-5-carboxylic acid. LCMS=178 [M+1].

Intermediate 9 for Ex-199

4-hydroxy-2-oxo-1,2-dihydroquinoline-6-carboxylic acid

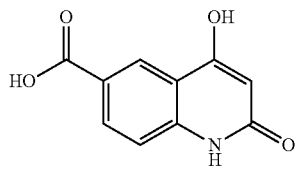 [SMILES: O=C(O)c1ccc2[nH]c(=O)cc(O)c2c1]

Step A: 4-(2-carboxyacetamido)benzoic acid

To a stirred solution of Meldrum's acid (1.10 g, 7.63 mmol) in anhydrous toluene (70 mL) was added 4-aminobenzoic acid (1.05 g, 7.66 mmol) at RT under nitrogen atmosphere. The reaction flask was fitted with Dean-Stark apparatus and the resulting suspension was heated to reflux for 3 hrs. After it cooled down to 0° C., the precipitate that appeared was filtered, washed with toluene (30 mL), and dried to afford 4-(2-carboxyacetamido)benzoic acid. LC/MS=222 [M−1].

Step B: 4-hydroxy-2-oxo-1,2-dihydroquinoline-6-carboxylic acid

To a round bottom flask charged with 4-(2-carboxyacetamido)benzoic acid (1.41 g, 6.32 mmol) was added PPA (10.0 g) at RT. The reaction mixture was heated to 130° C. for 3 hrs. After it cooled down to RT, ice-cold water (10 mL) was added to the reaction mixture. The resulting precipitate was filtered and dried. The crude compound was then recrystallized from hot ethanol (60 mL/g), filtered, and washed with cold ethanol to give 4-hydroxy-2-oxo-1,2-dihydroquinoline-6-carboxylic acid. LC/MS=206 [M+1].

Intermediate 10 for Ex-188

4-(1H-imidazol-2-ylamino)benzoic acid hydrochloride

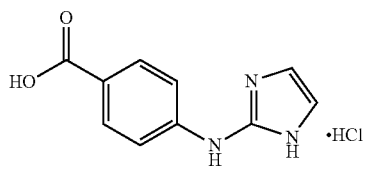 [SMILES: O=C(O)c1ccc(Nc2ncc[nH]2)cc1 ; Cl]

Step A: tert-butyl 4-(1H-imidazol-2-ylamino)benzoate

A 30 ml, microwave reaction vessel was flushed with nitrogen gas and charged with Pd$_2$(dba)$_3$ (9.2 mg, 0.0100 mmol), tBuBrettPhos (9.6 mg, 0.0198 mmol) and tert-BuOH (1.00 mL). The reaction vessel was sealed and the mixture was stirred at 120° C. for 3 minutes. A second 30 mL microwave reaction vessel was flushed with nitrogen gas and charged with tert-butyl 4-bromobenzoate (515 mg, 2.00 mmol), 2-aminoimidazole sulfate (291 mg, 2.20 mmol) and K$_3$PO$_4$ (1.28 g, 6.03 mmol). To the mixture was added the preheated catalyst solution described above followed by addition of N,N-dimethylformamide (4.00 mL). The reaction vessel was sealed and the reaction mixture was heated at 120° C. for 5 hrs. The reaction mixture was cooled to RT and concentrated in vacuo. To the resulting residue was added saturated aqueous NaHCO$_3$ (15 mL) and the pH was adjusted to 9. The mixture was extracted with DCM (30 mL×3). The combined organic layers were washed with brine, dried over Na$_2$SO$_4$ and concentrated in vacuo. The crude product was purified by flash silica gel column chromatography (0-20% MeOH in DCM) to afford tert-butyl 4-(1H-imidazol-2-ylamino)benzoate. LC/MS=260 [M+1].

Step B: 4-(1H-imidazol-2-ylamino)benzoic acid hydrochloride

To a round bottom flask charged with tert-butyl 4-(1H-imidazol-2-ylamino)benzoate (102 mg, 0.393 mmol) was added 4 M HCl in 1,4-dioxane (4.00 mL, 16.0 mmol) at RT. The reaction mixture was stirred at RT for 15 hrs. The reaction mixture was concentrated in vacuo and dried under high vacuum overnight to afford 4-(1H-imidazol-2-ylamino) benzoic acid hydrochloride, which was used for the next step without further purification. LC/MS=202 [M−1].

Intermediate 11 for Ex-189

4-(3-methylureido)benzoic acid

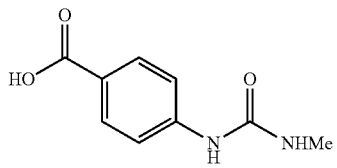 [SMILES: CNC(=O)Nc1ccc(C(=O)O)cc1]

Step A: tert-butyl 4-(3-methylureido)benzoate

To a stirred solution of tert-butyl 4-aminobenzoate (207 mg, 1.07 mmol) and NaOH (42.8 mg, 1.07 mmol) in 1,4-dioxane (2.1 mL) and H$_2$O (2.1 mL) at 0° C. was added methylaminoformyl chloride (100 mg, 1.07 mmol) and the reaction mixture was stirred at RT for 16 hrs. The reaction mixture was quenched with H$_2$O and extracted with EtOAc. The organic extracts were washed with brine, dried over Na$_2$SO$_4$, filtered and concentrated in vacuo. The crude product was purified by flash silica gel column chromatography (0-100% EtOAc in Hexanes) to afford tert-butyl 4-(3-methylureido)benzoate. LC/MS=251 [M+1].

Step B: 4-(3-methylureido)benzoic acid

To a round bottom flask charged with tert-butyl 4-(3-methylureido)benzoate (81.0 mg, 0.324 mmol) was added 4 M HCl in 1,4-dioxane (3.4 mL, 13.6 mmol) at RT under nitrogen atmosphere and the resulting mixture was stirred at RT for 6 hrs. The reaction mixture was concentrated in vacuo and dried under high vacuum to afford 4-(3-methylureido)benzoic acid. LC/MS=195 [M+1].

Example 190

2-(Piperazin-1-yl)ethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl) phenyl)carbamate 2 trifluoroacetic acid salt

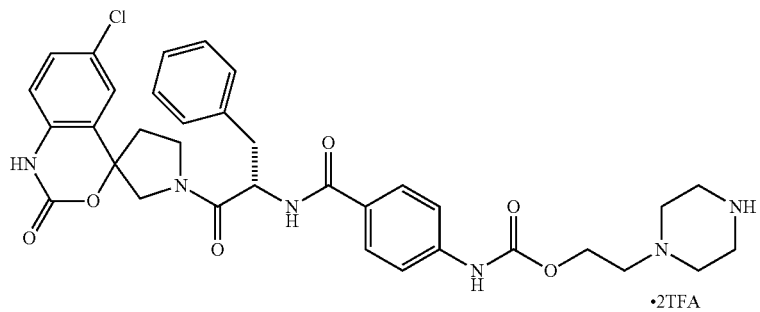 [SMILES: O=C(Nc1ccc(C(=O)N[C@@H](Cc2ccccc2)C(=O)N2CCC3(C2)OC(=O)Nc2ccc(Cl)cc23)cc1)OCCN1CCNCC1]

Step A: ethyl 4-(((2-bromoethoxy)carbonyl)amino)benzoate

To a microwave vial charged with ethyl 4-isocyanatobenzoate (1.00 g, 5.23 mmol) in hexane (10.5 mL) was added 2-bromoethanol (654 mg, 5.23 mmol) at RT under nitrogen atmosphere. The reaction vessel was sealed and stirred at 70° C. for 5 hrs and cooled to RT. The reaction mixture was filtered and the resulting residue was washed with hexanes to afford ethyl 4-(((2-bromoethoxy)carbonyl)amino)benzoate. LC/MS=316 [M+1].

Step B: tert-butyl 4-(2-(((4-(ethoxycarbonyl)phenyl) carbamoyl)oxy)ethyl)piperazine-1-carboxylate To a microwave vial charged with ethyl 4-(((2-bromoethoxy)carbonyl)amino)benzoate (500 mg, 1.58 mmol) in acetonitrile (7.9 mL) was added tert-butyl piperazine-1-carboxylate (1.47 g, 7.91 mmol) at RT under nitrogen atmosphere. The reaction vessel was sealed and stirred at 80° C. for 14 hrs and concentrated under reduced pressure. The crude product was purified by flash silica gel column chromatography (0-100% EtOAc in Hexanes) to afford tert-butyl 4-(2-(((4-(ethoxycarbonyl)phenyl)carbamoyl) oxy)ethyl)piperazine-1-carboxylate. LC/MS=422 [M+1].

Step C: lithium 4-(((2-(4-(tert-butoxycarbonyl)piperazin-1-yl)ethoxy)carbonyl)amino)benzoate To a microwave vial charged with tert-butyl 4-(2-(((4-(ethoxycarbonyl)phenyl)carbamoyl)oxy)ethyl)piperazine-1-carboxylate (533 mg, 1.27 mmol) in THF (6.3 mL) and H₂O (6.3 mL) at RT was added lithium hydroxide monohydrate (53.1 mg, 1.27 mmol). The reaction vessel was sealed and stirred at 50° C. for 22 hrs and concentrated in vacuo. The crude product was triturated with DCM in hexanes to afford 204 mg of lithium 4-(((2-(4-(tert-butoxycarbonyl)piperazin-1-yl)ethoxy)carbonyl)amino)benzoate, which was used for next step without further purification. LC/MS=394 [M+1].

Step D: Tert-butyl 4-(2-(((4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamoyl)oxy)ethyl)piperazine-1-carboxylate To a stirred solution of 1'-((S)-2-amino-3-phenylpropanoyl)-6-chlorospiro[benzo[d][1,3]oxazine-4,3'-pyrrolidin]-2(1H)-one (100 mg, 0.259 mmol) in DMF (1.1 mL) were added lithium 4-(((2-(4-(tert-butoxycarbonyl)piperazin-1-yl)ethoxy)carbonyl)amino)benzoate (155 mg, 0.389 mmol), EDC.HCl (74.5 mg, 0.389 mmol), HOBT (52.5 mg, 0.389 mmol) and DIPEA (136 µl, 0.778 mmol) at RT. The reaction mixture was stirred at RT overnight. The reaction mixture was diluted with EtOAc and washed with H₂O. The organic layer was washed with brine, dried over Na₂SO₄, filtered and concentrated in vacuo. The crude product was purified by flash silica gel column chromatography (0-10% MeOH in DCM) followed by reverse phase chromatography (10-100% CH₃CN in H₂O) to afford tert-butyl 4-(2-(((4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamoyl)oxy)ethyl)piperazine-1-carboxylate. LC/MS=761 [M+1].

STEP E: 2-(piperazin-1-yl)ethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate 2 trifluoroacetic acid salt To a stirred solution of tert-butyl 4-(2-(((4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamoyl)oxy)ethyl)piperazine-1-carboxylate (76.0 mg, 0.099 mmol) in DCM (1.3 mL) at 0° C. was added trifluroacetic acid (0.7 mL, 9.14 mmol). The reaction mixture was stirred at 0° C. for 2 hrs. The reaction mixture was concentrated in vacuo, triturated with DCM in hexanes, and dried under high vacuum to afford 2-(piperazin-1-yl)ethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate 2 trifluoroacetic acid salt. LC/MS=661 [M+1].

Intermediate 12 for Ex-191

4-(((2-morpholinoethoxy)carbonyl)amino)benzoic acid

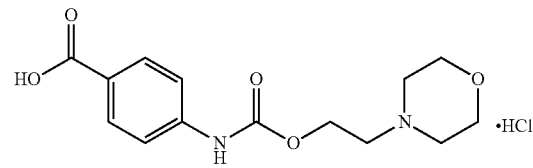 [SMILES: O=C(Nc1ccc(C(=O)O)cc1)OCCN1CCOCC1 ; Cl]

Step A: ethyl 4-(((2-morpholinoethoxy)carbonyl)amino)benzoate

To a microwave vial charged with ethyl 4-(((2-bromoethoxy)carbonyl)amino)benzoate (500 mg, 1.58 mmol) in acetonitrile (7.9 mL) was added morpholine (0.69 mL, 7.9 mmol) at RT under nitrogen atmosphere. The reaction vessel was sealed and stirred at 80° C. for 14 hrs and concentrated under reduced pressure. The crude product was purified by flash silica gel column chromatography (0-100% EtOAc in Hexanes) to afford ethyl 4-(((2-morpholinoethoxy)carbonyl)amino)benzoate. LC/MS=322 [M+1].

Step B: 4-(((2-morpholinoethoxy)carbonyl)amino)benzoic acid hydrochloride

To a microwave vial charged with ethyl 4-(((2-morpholinoethoxy)carbonyl)amino)benzoate (300 mg, 0.931 mmol) in THF (4.5 mL) and H₂O (4.5 mL) at RT was added lithium hydroxide monohydrate (39.0 mg, 0.929 mmol). The reaction vessel was sealed and stirred at 50° C. for 41 hrs and concentrated in vacuo. The resulting residue was diluted with H₂O and washed with DCM. The aqueous layer was acidified to pH 2 by addition of 1 M HCl (aq.) and concentrated under reduced pressure to afford 4-(((2-morpholinoethoxy)carbonyl)amino)benzoic acid hydrochloride. LC/MS=295 [M+1].

Example 192

N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide 1-oxide

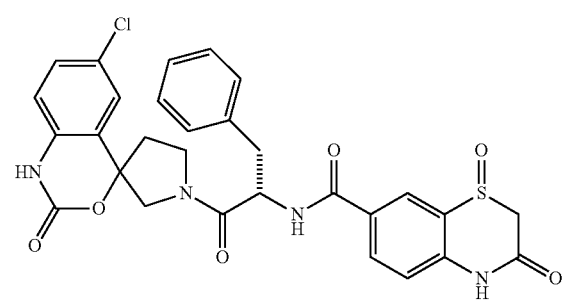 [SMILES: O=C1CS(=O)c2cc(C(=O)N[C@@H](Cc3ccccc3)C(=O)N3CCC4(C3)OC(=O)Nc3ccc(Cl)cc34)ccc2N1]

Step A: 3-oxo-3,4-dihydro-2H-benzo[b][1,4]thiazine-7-carbonitrile

A 30 mL microwave reaction vessel was flushed with nitrogen gas and charged with 7-bromo-2H-[1,4]-benzothiazin-3(4H)-one (502 mg, 2.06 mmol), zinc cyanide (729 mg, 6.21 mmol), N,N-diisopropylethylamine (0.75 mL, 4.31 mmol) and 1,1'-[bis(diphenylphosphino)ferrocene]dichloropalladium(II) (84.6 mg, 0.116 mmol). The resulting mixture was irradiated in a microwave apparatus (Biotage) at 150° C. for 75 minutes and cooled to RT. The cooled mixture was concentrated under reduced pressure. The crude product was roughly purified by flash silica gel column chromatography (0-20% MeOH in DCM) to afford 3-oxo-3,4-dihydro-2H-benzo[b][1,4]thiazine-7-carbonitrile which was used for the next step without further purification. LC/MS=189 [M−1].

Step B: 3-oxo-3,4-dihydro-2H-benzo[b][1,4]thiazine-7-carboxylic acid

A mixture of 3-oxo-3,4-dihydro-2H-benzo[b][1,4]thiazine-7-carbonitrile (127 mg, <0.668 mmol), hydrochloric acid (6.0 M in water; 10.0 mL, 60.0 mmol) and acetic acid (10.0 mL) in a sealed tube was stirred at 100° C. for 71 hours and cooled to RT. The cooled mixture was filtered and the filtrate was concentrated under reduced pressure. The resulting solids were collected by filtration, washed with water (10 mL) and dried under high vacuum to afford 3-oxo-3,4-dihydro-2H-benzo[b][1,4]thiazine-7-carboxylic acid. LC/MS=208 [M−1].

Step C: N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide To a stirred solution of 1'-((S)-2-amino-3-phenylpropanoyl)-6-chlorospiro[benzo[d][1,3]oxazine-4,3'-pyrrolidin]-2(1H)-one (25.2 mg, 0.0653 mmol) in DMF (0.30 mL) was added 3-oxo-3,4-dihydro-2H-benzo[b][1,4]thiazine-7-carboxylic acid (18.1 mg, 0.0865 mmol), EDC.HCl (16.6 mg, 0.0866 mmol), HOBT (11.7 mg, 0.0866 mmol) and DIPEA (0.060 mL, 0.344 mmol) at RT. The reaction mixture was stirred at RT overnight and concentrated under reduced pressure. The crude product was purified by preparative thin layer chromatography (10% MeOH in DCM) to afford N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide. LC/MS=577 [M+1].

Step D: N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide 1-oxide To a stirred solution of N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide (9.6 mg, 0.0166 mmol) in 1,4-dioxane (0.50 mL) at RT was added 3-chloroperbenzoic acid (<77%; 3.7 mg, <0.0165 mmol). The resulting mixture was stirred at RT for 5 hrs and concentrated under reduced pressure. The crude product was purified by preparative thin layer chromatography (10% MeOH in DCM) followed by high-performance liquid chromatography (HPLC) using reverse-phase column [Luna® 10µ Prep C18(2) 100A AXIA (10 µm particle size, 50 mm×150 mm), gradient: successively with 10-10% B over 5 minutes, 10-60% B over 10 minutes, and 60-60% B over 10 minutes, mobile phases A: water; B: acetonitrile, flow rate: 35 mL/min, detection at UV 254 nm] to afford N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide 1-oxide. LC/MS=591 [M−1].

Example 193

N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide 1,1-dioxide

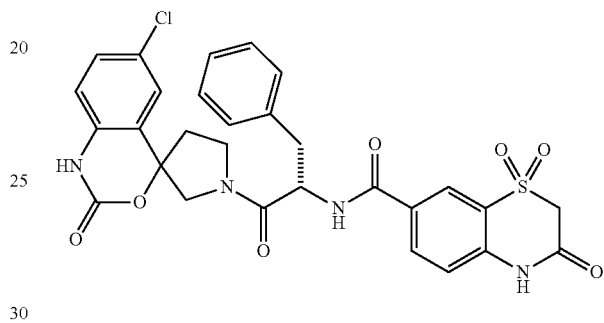

To a stirred solution of N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide (9.6 mg, 0.0166 mmol) in 1,4-dioxane (0.50 mL) at RT was added 3-chloroperbenzoic acid (<77%; 11.2 mg, <0.0500 mmol). The resulting mixture was stirred at RT for 7 hrs and concentrated under reduced pressure. The crude product was purified by preparative thin layer chromatography (10% MeOH in DCM) to afford N-((2S)-1-(6-chloro-2-oxo-1,2-dihydrospiro[benzo[d][1,3]oxazine-4,3'-pyrrolidine]-1'-yl)-1-oxo-3-phenylpropan-2-yl)-3-oxo-3,4-dihydro-2H-benzo[b][1,4]thiazine-7-carboxamide 1,1-dioxide. LC/MS=607 [M−1].

Intermediate 13 for Ex-194

(S)-4-(((((Tetrahydrofuran-2-yl)methoxy)carbonyl)amino)benzoic acid

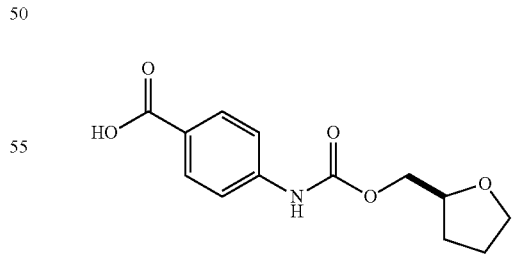

Step A: tert-butyl 4-(((4-nitrophenoxy)carbonyl)amino)benzoate

To a stirred solution of tert-butyl 4-aminobenzoate (1.00 g, 5.17 mmol) in anhydrous DCM (25 mL) were added 4-nitrophenyl chloroformate (1.04 g, 5.17 mmol) and pyridine (0.5 mL, 6.20 mmol) at RT under nitrogen atmosphere. The reaction mixture was stirred at RT for 14 hrs and concentrated under reduced pressure. The crude product was purified by flash silica gel column chromatography (0-100% EtOAc in Hexanes) to afford of tert-butyl 4-(((4-nitrophenoxy)carbonyl)amino)benzoate. LC/MS=359 [M+1].

Step B: (S)-tert-butyl 4-(((((tetrahydrofuran-2-yl)methoxy)carbonyl)amino)benzoate To a microwave vial charged with tert-butyl 4-(((4-nitrophenoxy)carbonyl)amino)benzoate (644 mg, ca. 60% purity) in THF (7.2 mL) was added (S)-(tetrahydrofuran-2-yl)methanol (370 mg, 3.62 mmol) at RT under nitrogen atmosphere. The reaction vessel was sealed and stirred at 60° C. for 14 hrs and concentrated under reduced pressure. The crude product was purified by flash silica gel column chromatography (0-100% EtOAc in Hexanes) followed by reverse phase chromatography (10-100% CH$_3$CN in H$_2$O) to afford (S)-tert-butyl 4-(((((tetrahydrofuran-2-yl)methoxy)carbonyl)amino)benzoate. LC/MS=322 [M+1].

Step C: (S)-4-(((((tetrahydrofuran-2-yl)methoxy)carbonyl)amino)benzoic acid

To a round bottom flask charged with (S)-tert-butyl 4-(((((tetrahydrofuran-2-yl)methoxy)carbonyl)amino)benzoate (275 mg, 0.856 mmol) was added 4 M HCl in 1,4-dioxane (10 mL, 40 mmol) at RT under nitrogen atmosphere and the resulting mixture was stirred at RT for 16 hrs. The reaction mixture was concentrated in vacuo, triturated with hexanes and dried under high vacuum to afford (S)-4-(((((tetrahydrofuran-2-yl)methoxy)carbonyl)amino)benzoic acid. LC/MS=266 [M+1].

Example 196

Methyl (5-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)thiophen-2-yl)carbamate

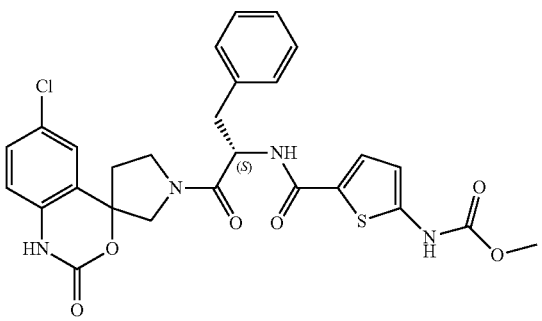

Step A: N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-5-nitrothiophene-2-carboxamide To a stirred solution of 1'-((S)-2-amino-3-phenylpropanoyl)-6-chlorospiro[benzo[d][1,3]oxazine-4,3'-pyrrolidin]-2(1H)-one hydrochloride (500 mg, 1.184 mmol) in DMF (11.800 mL) was added 5-nitrothiophene-2-carboxylic acid (226 mg, 1.302 mmol), EDC (250 mg, 1.302 mmol), HOBT (199 mg, 1.302 mmol) and neat DIPEA (0.931 mL, 5.33 mmol) at RT. The reaction mixture was stirred at RT for 16 hrs. The reaction mixture was diluted with EtOAc and sat. NaHCO$_3$ (aq). The aqueous phase was extracted with EtOAc. The organic layer was washed with brine, dried over MgSO$_4$, filtered and concentrated. The crude product was purified by flash silica gel column chromatography (0-100% EtOAc in Hexanes) to provide N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-5-nitrothiophene-2-carboxamide. LCMS=541 [M+1]

Step B: 5-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)thiophene-2-carboxamide To a stirred solution of N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-5-nitrothiophene-2-carboxamide (100 mg, 0.185 mmol) in 2:1 EtOAc (6162 µl):MeOH (3081 µl) was added platinum(IV) oxide (25.2 mg, 0.111 mmol). The reaction mixture was evacuated with vacuum and purged with nitrogen gas (3×) and placed under hydrogen balloon and stirred at RT for 3 hrs. The reaction mixture was filtered through Celite and washed with EtOAc and DCM. The filtrate was evaporated and the crude product was purified by flash silica gel column chromatography (0-100% EtOAc in Hex followed by 0-10% MeOH in DCM) to afford 5-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)thiophene-2-carboxamide. LCMS=511 [M+1].

Step C: Methyl (5-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)thiophen-2-yl)carbamate To a solution of 5-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)thiophene-2-carboxamide (60 mg, 0.117 mmol) in DCM (1174 µl) was added pyridine (18.99 µl, 0.235 mmol) and methyl chloroformate (9.07 µl, 0.117 mmol) at 0° C. The reaction mixture was warmed to RT and stirred for 30 min. The reaction mixture was quenched with sat. NH$_4$Cl (aq) and DCM was added. The aqueous phase was extracted 3× with DCM. The organic layer was washed with water, sat. NaHCO$_3$ (aq) and brine and dried over MgSO$_4$, filtered, and concentrated. The crude product was purified by flash silica gel column chromatography (0-100% EtOAc in Hex) to afford methyl (5-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)thiophen-2-yl)carbamate. LCMS=569 [M+1]

Example 217

3-amino-N—((S)-1-(R)-6-chloro-2-oxo-1,2-dihydrospiro[benzo[d][1,3]oxazine-4,3'-pyrrolidin]-1'-yl)-1-oxo-3-phenylpropan-2-yl)benzo[d]isoxazole-6-carboxamide

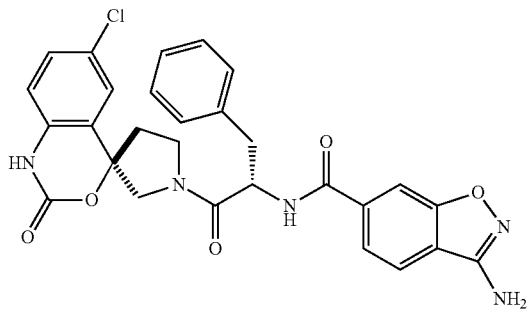

Step A: tert-Butyl (6-cyanobenzo[d]isoxazol-3-yl)carbamate

To a stirred solution of 3-aminobenzo[d]isoxazole-6-carbonitrile (400 mg, 2.5 mmol) in DMPU (4 mL) was added BOC-anhydride (1.6 g, 7.5 mmol), and DMAP (30.7 mg, 0.25 mmol). The reaction mixture was stirred at 70° C. for 14 hrs under an atmosphere of nitrogen gas. The reaction mixture was diluted with EtOAc (60 mL) and washed with water (50 mL×three times). The organic extract was dried over $Na_2SO_4$ and concentrated under reduced pressure to give the crude compound which was purified by flash chromatography (24 g ISCO column taken, 0-20% EtOAc/hexanes, 30 min, elution of 10% gave desired comp) to give tert-butyl (6-cyanobenzo[d]isoxazol-3-yl)carbamate (669 mg) which was 1:1 mixture of mono and bis-boc protected product. This mix. of compounds were carried forward for following steps without further purification. LCMS [M−55] =204

Step B: 3-((tert-Butoxycarbonyl)amino)benzo[d]isoxazole-6-carboxylic acid

To a stirred solution of tert-butyl (6-cyanobenzo[d]isoxazol-3-yl)carbamate (654 mg, 2.52 mmol) in EtOH (7.5 mL) and water (7.5 mL) was added NaOH (353 mg) at RT. The reaction mixture was heated to 80° C. for 16 hrs. The reaction mixture was diluted with sat. $NaHCO_3$ solution (15 mL) and extracted with MTBE (three times, 30 mL each). The aq. part was acidified to pH 3 by using 10% citric acid solution when precipitate appeared. The precipitate was filtered, and dried to give 3-((tert-Butoxycarbonyl)amino)benzo[d]isoxazole-6-carboxylic acid. LCMS [M+1] 279

Step C: tert-butyl (6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzo[d]isoxazol-3-yl)carbamate To a stirred solution of (R)-1'-((S)-2-amino-3-phenylpropanoyl)-6-chlorospiro[benzo[d][1,3]-oxazine-4,3'-pyrrolidin]-2(1H)-one (52.8 mg) in DMF (1.3 mL) was added 3-((tert-Butoxycarbonyl)amino)benzo[d]isoxazole-6-carboxylic acid (57 mg), EDC (39.3 mg), HOBT (31.4 mg) and DIPEA (71 uL) at RT under nitrogen atmosphere and stirred at rt for 18 h. The reaction mixture was quenched with water (5 mL) and extracted with EtOAc (10 mL, three times). The combined organic extracts were dried over sodium sulfate, and concentrated under reduced pressure to get the crude compound which was purified by flash chromatography (12 g column taken, 0-100% EA/hexanes, 20 min run, elution of 60% gave tert-butyl (6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzo[d]isoxazol-3-yl)carbamate. LCMS [M−55]=590.

Step D: 3-amino-N—((S)-1-(R)-6-chloro-2-oxo-1,2-dihydrospiro[benzo[d][1,3]oxazine-4,3'-pyrrolidin]-1'-yl)-1-oxo-3-phenylpropan-2-yl)benzo[d]isoxazole-6-carboxamide To a stirred solution of tert-butyl (6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzo[d]isoxazol-3-yl)carbamate (54.3 mg) in DCM (2 mL) was added TFA (0.9 mL) at 0° C. and the reaction mixture was slowly warmed to RT and stirred for 2 hrs. The reaction mixture was concentrated, purified by reverse phase chromatography (C18 100 g col taken, 10-100% $CH_3CN$/water, elution of 62% gave desired compound) to give 3-amino-N—((S)-1-(R)-6-chloro-2-oxo-1,2-dihydrospiro[benzo[d][1,3]oxazine-4,3'-pyrrolidin]-1'-yl)-1-oxo-3-phenylpropan-2-yl)benzo[d]isoxazole-6-carboxamide. LCMS [M+1] =546.9

Intermediate 14 for Ex-218

3-cyano-1H-indazole-6-carboxylic acid

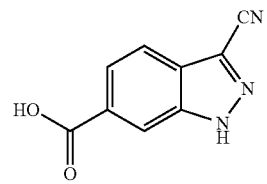 [SMILES: N#Cc1n[nH]c2cc(C(=O)O)ccc12]

Step A: Methyl 3-iodo-1H-indazole-6-carboxylate

To a solution of methyl 1H-indazole-6-carboxylate (865 mg, 4.91 mmol) in N,N-dimethylformamide (12 mL) was added potassium hydroxide (840 mg, 3.05 mmol) followed by iodine (1.5 g, 5.9 mmol). The mixture was stirred at room temperature for 3 hours. Aqueous sodium bisulfate was added and the mixture was extracted with ethyl acetate twice. The combined organic layers were washed with brine, dried over sodium sulfate, filtered and concentrated in vacuo. The residue was purified via flash column chromatography (5-65% ethyl acetate/hexanes) to afford methyl 3-iodo-1H-indazole-6-carboxylate. LCMS [M+1]=303.

Step B: methyl 3-cyano-1H-indazole-6-carboxylate

A mixture of methyl 3-iodo-1H-indazole-6-car-boxylate, zinc dust, zinc cyanide, [1,1'-bis(diphenylphos-phino)ferrocene]-dichloropalladium(II), complex with dichloromethane, and copper (I) iodide in dimethylacetamide (12 mL) was purged with nitrogen for 5 minutes. The mixture was stirred at 120° C. for 6 hours. The reaction mixture was cooled, diluted with ethyl acetate (250 mL), and filtered through Celite, rinsing with ethyl acetate (100 mL). To the filtrate was added 400 mL of a solution of saturated aqueous ammonium chloride and diluted ammonium hydroxide. The mixture was stirred for 1 hour. The layers were then separated. The organic layer was washed with water and brine, dried over sodium sulfate, filtered and concentrated in vacuo. The residue was triturated with hexane and DCM to give methyl 3-cyano-1H-indazole-6-carboxylate. LCMS [M+1]=202

Step C: 3-cyano-1H-indazole-6-carboxylic acid

Methyl 3-cyano-1H-indazole-5-carboxylate was dissolved in methanol (6 mL), and THF (3 ml) and lithium hydroxide (73 mg in 3 ml) was added. The reaction was stirred at room temperature overnight. The reaction mixture was concentrated to remove the methanol and the residue was acidified to pH=4 with 1 N aqueous hydrochloric acid. The resulting precipitate was collected by filtration, washed with water, and dried in a vacuum oven to provide 3-cyano-1H-indazole-6-carboxylic acid. LCMS [M+1]=188.

Intermediate 15 for Ex-219

3-carbamoyl-1H-indazole-6-carboxylic acid

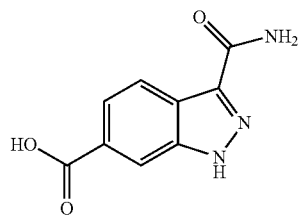 [SMILES: NC(=O)c1n[nH]c2cc(C(=O)O)ccc12]

Step A: 3-carbamoyl-1H-indazole-6-carboxylic acid

A suspension of 3-cyano-1H-indole-6-carboxylic acid ethyl ester (100 mg, 1.4 mmol) in methanol (5 mL) was added to a solution of urea hydrogen peroxide (477 mg) in 2.0 sodium hydroxide (2.54 mL) at 0° C. The suspension was allowed to warm to room temperature and was stirred for 12 h. The reaction was concentrated under reduced pressure. Water was added and the solution was acidified with 2 N aqueous hydrochloric acid to pH=2. A precipitate formed. The reaction mixture was stirred for 1 minute at room temperature and was then filtered. The solid was washed with water and heptanes and was dried in a vacuum oven to give 3-carbamoyl-1H-indole-6-carboxylic acid. LCMS [M+1]=206.

Example 222

Methyl (4-((((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)methyl)phenyl)carbamate

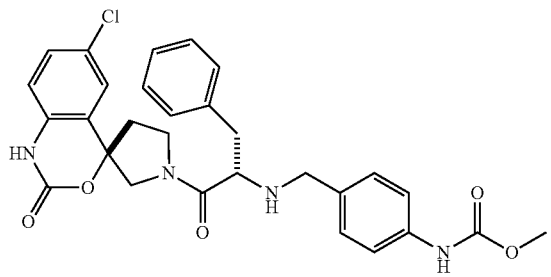

Step A: Methyl (4-(hydroxymethyl)phenyl)carbamate

To a stirred mixture of 4-[(methoxycarbonyl)amino]benzoic acid (586 mg, 3.00 mmol) and tetrahydrofuran (15.0 mL) at ambient temperature was added borane tetrahydrofuran complex (1.0 M in tetrahydrofuran; 9.00 mL, 9.00 mmol). The resulting mixture was stirred at ambient temperature for 14 hours under a nitrogen gas atmosphere. To the reaction mixture was added saturated aqueous ammonium chloride (100 mL) and the pH was adjusted to 7-8. The resulting mixture was extracted with dichloromethane (250 mL×3). The combined organic extracts were washed with brine (100 mL), dried over sodium sulfate, and concentrated under reduced pressure. The resulting residue was purified by column chromatography (silica gel 50 g, step gradient eluting with 10:1, 5:1, 4:1, 3:1, 2:1, and 1:1 hexane/ethyl acetate) to give methyl (4-(hydroxymethyl)phenyl)carbamate. LCMS [M+1]=182

Step B: Methyl (4-formylphenyl)carbamate

To a stirred mixture of methyl (4-(hydroxymethyl)phenyl)carbamate (215 mg, 1.19 mmol) and dichloromethane (7.50 mL) at ambient temperature was added Dess-Martin periodinane (556 mg, 1.31 mmol). The resulting mixture was stirred at ambient temperature for 14 hours under a nitrogen gas atmosphere and concentrated under reduced pressure. The resulting residue was purified by column chromatography (silica gel 30 g, step gradient eluting with 10:1, 5:1, 4:1, 3:1, and 2:1 hexane/ethyl acetate) to give methyl (4-formylphenyl)carbamate. LCMS [M+1]=180

Step C: Methyl (4-((((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)methyl)phenyl)carbamate To a stirred solution of methyl (4-formylphenyl)carbamate (18.0 mg, 0.100 mmol) and (R)-1'-(L-phenylalanyl)-6-chlorospiro[benzo[d][1,3]oxazine-4,3'-pyrrolidin]-2(1H)-one (38.8 mg, 0.101 mmol) in methanol (1.00 mL) was added titanium(IV) isopropoxide (0.060 mL, 0.203 mmol). The resulting mixture was stirred at ambient temperature for 2 hours under a nitrogen gas atmosphere. To the reaction mixture was added sodium borohydride (19.2 mg, 0.508 mmol). The resulting mixture was stirred at ambient temperature for 1 hour under a nitrogen gas atmosphere and concentrated under reduced pressure. The resulting residue was basified to pH 12 with 1.0 M potassium carbonate (K₂CO₃) in water (5.0 mL). The resulting mixture was extracted with dichloromethane (40 mL, 20 mL×3). The combined organic extracts were dried over sodium sulfate and concentrated under reduced pressure. The resulting residue was purified by preparative thin layer chromatography (silica gel, 200 mm×200 mm×0.5 mm×6 plates, dichloromethane/acetone (3:1)) to give methyl (4-((((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)methyl)phenyl)carbamate. LCMS [M+1]=550.

Example 223

Methyl (4-(1-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)-2,2,2-trifluoroethyl)phenyl)carbamate

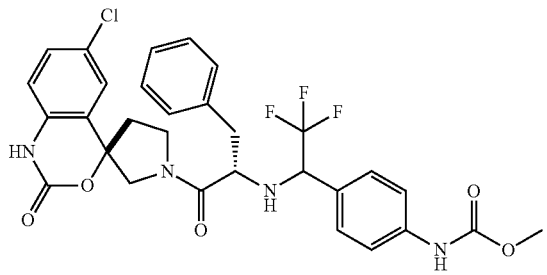

Step A: Methyl (4-(2,2,2-trifluoroacetyl)phenyl)carbamate

To a stirred mixture of 1-(4-aminophenyl)-2,2,2-trifluoro-1-ethanone (570 mg, 3.01 mmol), pyridine (0.70 mL, 8.65 mmol), and dichloromethane (15.0 mL) at ambient temperature was added methyl chloroformate (0.30 mL, 3.88 mmol). The resulting mixture was stirred at ambient temperature for 17 hours under a nitrogen gas atmosphere and concentrated under reduced pressure. The resulting residue was purified by column chromatography (silica gel 50 g, step gradient eluting with 40:1, 30:1, 20:1, and 10:1 dichloromethane/acetone) to give methyl (4-(2,2,2-trifluoroacetyl)phenyl)carbamate. LCMS [M+1]=248.

Step B: Methyl (4-(2,2,2-trifluoro-1-hydroxyethyl)phenyl)carbamate

To a stirred solution of methyl (4-(2,2,2-trifluoroacetyl)phenyl)carbamate (24.8 mg, 0.100 mmol) in methanol (0.50 mL) was added titanium(IV) isopropoxide (0.060 mL, 0.203 mmol). The resulting mixture was stirred at ambient temperature for 5 hours under a nitrogen gas atmosphere. To the reaction mixture was added sodium borohydride (19.2 mg, 0.508 mmol). The resulting mixture was stirred at ambient temperature for 13 hours under a nitrogen gas atmosphere. To the reaction mixture was added saturated aqueous sodium bicarbonate (NaHCO₃) (1 mL). The resulting mixture was extracted with dichloromethane (10 mL×3) and the combined organic layers were washed with brine (5 mL), dried over sodium sulfate, and concentrated under reduced pressure. The resulting residue was purified by preparative thin layer chromatography (silica gel, 200 mm×200 mm×0.5 mm×4 plates, hexane/ethyl acetate (2:1)) to give methyl (4-(2,2,2-trifluoro-1-hydroxyethyl)phenyl)carbamate. LCMS [M+1]=250.

Step C: Methyl (4-(1-chloro-2,2,2-trifluoroethyl)phenyl)carbamate

To a stirred mixture of methyl (4-(2,2,2-trifluoro-1-hydroxyethyl)phenyl)carbamate (21.1 mg, 0.0847 mmol), N,N-diisopropylethylamine (0.12 mL, 0.689 mmol), and dichloromethane (1.00 mL) at ambient temperature was added methanesulfonyl chloride (0.030 mL, 0.388 mmol). The resulting mixture was stirred at ambient temperature for 24 hours under a nitrogen gas atmosphere. To the reaction mixture were added N,N-diisopropylethylamine (0.080 mL, 0.459 mmol) and methanesulfonyl chloride (0.020 mL, 0.258 mmol). The resulting mixture was stirred at ambient temperature for 15 hours under a nitrogen gas atmosphere and concentrated under reduced pressure. The resulting residue was purified by preparative thin layer chromatography (silica gel, 200 mm×200 mm×0.5 mm×4 plates, hexane/ethyl acetate (4:1)) give methyl (4-(1-chloro-2,2,2-trifluoroethyl)phenyl)carbamate. LCMS [M+1]=268

Step D: methyl (4-(1-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)-2,2,2-trifluoroethyl)phenyl)carbamate A mixture of methyl (4-(1-chloro-2,2,2-trifluoroethyl)phenyl)carbamate (10.2 mg, 0.0381 mmol), (R)-1'-(L-phenylalanyl)-6-chlorospiro[benzo[d][1,3]oxazine-4,3'-pyrrolidin]-2(1H)-one (22.5 mg, 0.0583 mmol), N,N-diisopropylethylamine (0.020 mL, 0.115 mmol), and 1-methyl-2-pyrrolidinone (0.20 mL) was stirred at ambient temperature for 3 hours and at 60° C. for 9 hours under a nitrogen gas atmosphere, and concentrated under reduced pressure. The resulting residue was basified to pH 12 with 1.0 M potassium carbonate (K₂CO₃) in water (1.0 mL). The resulting mixture was extracted with dichloromethane (10 mL, 5 mL×3). The combined organic extracts were dried over sodium sulfate and concentrated under reduced pressure. The resulting residue was purified by preparative thin layer chromatography (silica gel, 200 mm×200 mm×0.5 mm×4 plates, dichloromethane/acetone (6:1)) to give methyl (4-(1-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)-2,2,2-trifluoroethyl)phenyl)carbamate. LCMS [M+1]=618.

Example 224

(4R)-1'-((1-(3-amino-1H-indazol-6-yl)ethyl)-L-phenylalanyl)-6-chlorospiro[benzo[d][1,3]oxazine-4,3'-pyrrolidin]-2(1H)-one dihydrochloride

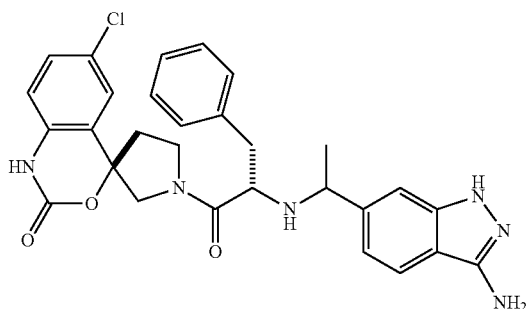

Step A: 1-(3-Amino-1H-indazol-6-yl)ethan-1-one

A mixture of 3-amino-6-bromo-1H-indazole (2.13 g, 10.0 mmol), 1-ethoxy-1-(tributylstannyl)ethylene (5.10 mL, 15.1 mmol), tetrakis(triphenylphosphine)palladium(0) (1.16 g, 1.00 mmol), and degassed N,N-dimethylformamide (20.0 mL) in a sealed tube was stirred at 120° C. for 4 hours under a nitrogen gas atmosphere and cooled to ambient temperature. To the cooled mixture was added hydrochloric acid (1.0 M in water; 170 mL, 170 mmol). The resulting mixture was stirred at ambient temperature for 4 hours and concentrated under reduced pressure. To the resulting residue was added saturated aqueous sodium bicarbonate and the pH was adjusted to 9. The precipitated solids were filtered and washed with water and hexane. The solids were purified by column chromatography (silica gel 50 g, step gradient eluting with 1:0 and 10:1 ethyl acetate/methanol) to give 1-(3-amino-1H-indazol-6-yl)ethan-1-one. LCMS [M+1]= 176

Step B: Boc-protected 1-(3-amino-1H-indazol-6-yl)ethan-1-one

A mixture of 1-(3-amino-1H-indazol-6-yl)ethan-1-one (748 mg, <4.27 mmol), di-tert-butyl dicarbonate (4.68 g, 21.4 mmol), N,N-diisopropylethylamine (7.50 mL, 43.1 mmol), 4-(dimethylamino)pyridine (266 mg, 2.18 mmol), and tetrahydrofuran (40.0 mL) was stirred at ambient temperature for 15 hours and concentrated under reduced pressure. The resulting residue was purified by column chromatography (silica gel 100 g, step gradient eluting with 10:1 and 5:1 hexane/ethyl acetate) to give Boc-protected 1-(3-amino-1H-indazol-6-yl)ethan-1-one. LCMS [M+1]=476

Step C: tert-butyl (6-(1-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)ethyl)-1H-indazol-3-yl)carbamate To a stirred solution of Boc-protected 1-(3-amino-1H-indazol-6-yl)ethan-1-one (238 mg, 0.500 mmol) and (R)-1'-(L-phenylalanyl)-6-chlorospiro[benzo[d][1,3]oxazine-4,3'-pyrrolidin]-2(1H)-one (194 mg, 0.503 mmol) in methanol (4.00 mL) was added titanium(IV) isopropoxide (0.30 mL, 1.01 mmol). The resulting mixture was stirred at ambient temperature for 5 hours under a nitrogen gas atmosphere. To the reaction mixture was added sodium borohydride (95.0 mg, 2.51 mmol). The resulting mixture was stirred at ambient temperature for 2 hours under a nitrogen gas atmosphere. To the reaction mixture was added potassium carbonate ($K_2CO_3$) (700 mg, 5.06 mmol) and concentrated under reduced pressure. The resulting residue was extracted with dichloromethane (100 mL×3). The combined organic layers were washed with brine (50 mL), dried over sodium sulfate, and concentrated under reduced pressure. The resulting residue was purified by preparative thin layer chromatography (silica gel, 200 mm×200 mm×0.5 mm×24 plates, dichloromethane/methanol (10:1)) to give tert-butyl (6-(1-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)ethyl)-1H-indazol-3-yl)carbamate. LCMS [M+1]= 646

Step D: (4R)-1'-((1-(3-amino-1H-indazol-6-yl)ethyl)-L-phenylalanyl)-6-chlorospiro[benzo[d][1,3]oxazine-4,3'-pyrrolidin]-2(1H)-one dihydrochloride A mixture of tert-butyl (6-(1-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)ethyl)-1H-indazol-3-yl)carbamate (10.1 mg, 0.0157 mmol) and hydrogen chloride (HCl) (4.0 M in 1,4-dioxane; 0.50 mL, 2.00 mmol) was stirred at ambient temperature for 14 hours. The mixture was concentrated under reduced pressure. The resulting residue was purified by trituration with hexane/dichloromethane to give (4R)-1'-((1-(3-amino-1H-indazol-6-yl)ethyl)-L-phenylalanyl)-6-chlorospiro[benzo[d][1,3]oxazine-4,3'-pyrrolidin]-2(1H)-one dihydrochloride. LCMS [M+1]=548

Intermediate 16 for Ex-232

4-(5-oxo-4,5-dihydro-1,2,4-oxadiazol-3-yl)benzoic acid

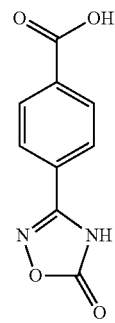

Step A: Synthesis of methyl (Z)-4-(N'-hydroxycarbamimidoyl)benzoate

To a 250 ml round bottom flask was added methyl 4-cyanobenzoate (2.06 g, 12.78 mmol), hydroxylamine hydrochloride (4.44 g, 63.9 mmol) and MeOH (32.0 ml). To the resulting solution was then added $Et_3N$ (8.91 ml, 63.9 mmol). The formation of precipitate was observed and the reaction was stirred at RT for 24 h. Water and DCM were added to the reaction mixture to precipitate the product. Then, extra solvent was evaporated to induce precipitation.

The precipitate was filtered, washed with water, ether and hexanes, and dried to afford the title product. LCMS [M+1]=195

Step B: Synthesis of methyl 4-(5-oxo-4,5-dihydro-1,2,4-oxadiazol-3-yl)benzoate To a 100 ml round bottom flask was added methyl (Z)-4-(N'-hydroxycarbamimidoyl)benzoate, di(1H-imidazol-1-yl)methanone (1.182 g, 7.29 mmol), and dioxane (8.68 ml). The resulting suspension was then stirred at 110° C. for 1 h, after which all the solvent was removed and the residue was washed with water and then treated with HCl (3 M) to induce precipitation. The precipitate was then washed with water and ether and dried in vacuum to afford the title compound. LCMS [M+1]=221

Step C: Synthesis of methyl 4-(5-oxo-4,5-dihydro-1,2,4-oxadiazol-3-yl)benzoate To a 100 ml round bottom flask was added methyl 4-(5-oxo-4,5-dihydro-1,2,4-oxadiazol-3-yl)benzoate (1.1372 g, 5.16 mmol), MeOH (4 ml), tetrahydrofuran (4 ml) and LiOH (0.495 g, 20.66 mmol) in water (2 ml). The resulting solution was then stirred at RT overnight, after which it was treated with HCl to give the benzoic acid product. The solid was filtered and washed with ether and hexanes to afford the desired product which was further dried in a vacuum oven to yield the title product. LCMS [M+1]=207

Intermediate 17 for Ex-235

4-(1H-imidazol-2-yl)thiophene-2-carboxylic acid

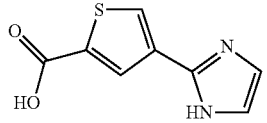 [SMILES: O=C(O)c1cc(-c2ncc[nH]2)cs1]

Step A: Synthesis of tert-butyl 2-iodo-1H-imidazole-1-carboxylate

To a 100 ml round bottom flask containing 2-iodo-1H-imidazole (708 mg, 3.65 mmol), BOC-anhydride (0.890 ml, 3.83 mmol) in DMF (7.5 ml) and acetonitrile (7.5 ml) was added Et₃N (0.636 ml, 4.56 mmol) and stirred overnight. It was then quenched with NH₄Cl and chromatographed on ISCO using 0-30% EtOAc in hexanes to afford the title compound.

Step B: Synthesis of methyl 4-(1H-imidazol-2-yl)thiophene-2-carboxylate

To a 20 ml scintillation vial containing tert-butyl 2-iodo-1H-imidazole-1-carboxylate (360 mg, 1.224 mmol), (5-(methoxycarbonyl)thiophen-3-yl)boronic acid (342 mg, 1.836 mmol), Reactant 2 (39.9 mg, 0.061 mmol), Dioxane (3 ml) was added POTASSIUM PHOSPHATE TRIBASIC (0.918 ml, 1.836 mmol) under nitrogen. It was then stirred at 90° C. until the completion of the reaction. The product was purified by ISCO to afford the title compound as a solid that was carried over to next step. LCMS [M+1]=209

Step C: Synthesis of 4-(1H-imidazol-2-yl)thiophene-2-carboxylic acid

To a 20 ml scintillation vial containing methyl 4-(1H-imidazol-2-yl)thiophene-2-carboxylate (254 mg, 1.22 mmol) in tetrahydrofuran (2 ml), and MeOH (2 ml) was added LiOH (1.220 ml, 6.10 mmol), and the mixture was stirred at RT until the completion of the reaction. The solvents were removed in vacuo and the residue was suspended in ether and acidified using dilute HCl. After addition of hexanes, the reaction mixture was allowed to stand at RT. The resulting suspension was collected, and dried in vacuum oven to afford the title compound. LCMS [M+1]=195

Intermediate 18 for Ex-238

3-((methoxycarbonyl)amino)bicyclo[1.1.1]pentane-1-carboxylic acid

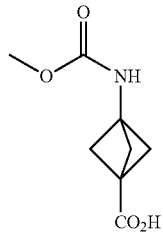

Step A: Synthesis of methyl 3-((methoxycarbonyl)amino)bicyclo[1.1.1]pentane-1-carboxylate To a solution of 3-(methoxycarbonyl)bicyclo[1.1.1]pentane-1-carboxylic acid (500 mg, 2.94 mmol) and Et₃N (0.430 ml, 3.09 mmol) in benzene (4 ml) was added diphenylphosphoryl azide (0.665 ml, 3.09 mmol) at rt. After stirring for 2 h at reflux temperature, methanol (141 mg, 4.41 mmol) was added and the mixture was stirred overnight. Then, it was quenched by the addition of water. The crude product was extracted with DCM and dried over anhydrous MgSO₄. It was filtered, concentrated in vacuo and purified by ISCO 40 g using 0-100% EtOAc in hexanes to afford the title compound that was carried over to next step.

Step B: Synthesis of 3-((methoxycarbonyl)amino)bicyclo[1.1.1]pentane-1-carboxylic acid To a 20 ml scintillation vial containing methyl 3-((methoxycarbonyl)amino)bicyclo[1.1.1]pentane-1-carboxylate (586 mg, 2.94 mmol) in MeOH (2.5 ml) and tetrahydrofuran (2.5 ml) was added LiOH (5.88 ml, 29.4 mmol) and stirred at RT until the completion of the reaction. The solvents were removed in vacuo and the reaction was quenched with dilute HCl and the product was extracted with DCM, dried over MgSO₄, filtered, concentrated to afford the title compound. LCMS [M+1]=186

Intermediate 19 for Ex-247

4-(5-oxo-1,5-dihydro-4H-1,2,4-triazol-4-yl)benzoic acid

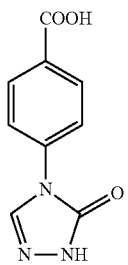

Step A: Synthesis of methyl 4-((phenoxycarbonyl)amino)benzoate

To a 250 ml round bottom flask was added methyl 4-((phenoxycarbonyl)amino)benzoate (0.00 g, 0.00 mmol) in THF (20 ml). The resulting solution was then cooled to 0° C. and then an aqueous solution of sodium bicarbonate (1.334 g, 15.88 mmol) in 8 ml of water was added. To this suspension was then introduced phenyl carbonochloridate (1.743 ml, 13.89 mmol) in 2 ml THF and it was stirred overnight at RT. The reaction mixture was extracted with EtOAc and washed with dilute HCl and water respectively. The organic extract was dried over anhydrous MgSO$_4$, filtered and evaporated to afford the title compound.

Step B: Synthesis of methyl 4-(hydrazinecarboxamido)benzoate

To a 500 ml round bottom flask containing phenyl formate (3.59 g, 13.23 mmol) in acetonitrile (50 ml) was added hydrazine (2.076 ml, 66.2 mmol). The resulting suspension was stirred at RT. The precipitate was filtered and washed with water and DCM. It was then washed with hexanes and Et$_2$O and dried in a vacuum oven for 2 h to afford the title compound. LCMS [M+1]=210

Step C: Synthesis of methyl 4-(5-oxo-1,5-dihydro-4H-1,2,4-triazol-4-yl)benzoate To a microwave reaction vial was added methyl 4-(hydrazinecarboxamido)benzoate (1 g, 4.78 mmol), formamidine acetate (3.48 g, 33.5 mmol), and 1-propanol (15 ml). The reaction was heated in microwave at 100° C. for 1 h. After which water was added to the reaction mixture and the product was filtered which was further washed with hexanes and ether. The resulting solid was then dried in a vacuum oven to afford the title compound. LCMS [M+1]=220

Step D: Synthesis of 4-(5-oxo-1,5-dihydro-4H-1,2,4-triazol-4-yl)benzoic acid To a 250 ml round bottom flask was added the ester (1.1242 g, 5.13 mmol), MeOH (4 ml), tetrahydrofuran (4 ml), and LiOH (0.491 g, 20.51 mmol) in water (2 ml). The resulting mixture was then stirred at RT overnight. It was quenched with HCl to give the benzoic acid. The solid was filtered and dried in vacuum. LCMS [M+1]=206

Intermediate 20 for Ex-241

4-(((methoxycarbonyl)amino)methyl)benzoic acid

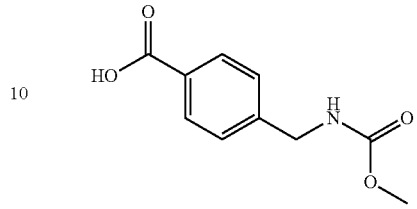

To a suspension of 4-(aminomethyl)benzoic acid (443.2 mg, 2.93 mmol) in dioxane (10 ml) was added methyl carbonochloridate (0.261 ml, 3.37 mmol) and DMA (0.2 ml). The reaction mixture was heated to 70° C. overnight. The reaction mixture was evaporated to dryness and the residue was triturated with water. The solids were filtered and dried to give the product.

Intermediate 21 for Ex-242

6-((methoxycarbonyl)amino)pyridazine-3-carboxylic acid

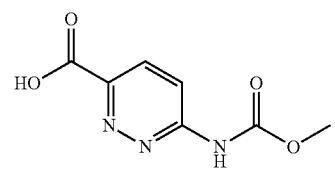

Step A: Synthesis of methyl 6-((methoxycarbonyl)amino)pyridazine-3-carboxylate To a 100 ml round bottom flask containing methyl 6-aminopyridazine-3-carboxylate (367 mg, 2.397 mmol) and THF (10 ml), was added K$_2$CO$_3$ (497 mg, 3.59 mmol) in 10 ml water. Then methyl carbonochloridate (0.204 ml, 2.64 mmol) was added. The resulting mixture was stirred overnight. Water was added to the reaction mixture and the organics were extracted using DCM. The solution was then filtered, and concentrated to afford the title compound which was carried over to next step. LCMS [M+1]=212

Step B: Synthesis of 6-((methoxycarbonyl)amino)pyridazine-3-carboxylic acid

To a 100 ml round bottom flask containing methyl 6-((methoxycarbonyl)amino)pyridazine-3-carboxylate (506 mg, 2.396 mmol), THF (5 ml) and MeOH (5) was added LiOH (4.79 ml, 23.96 mmol), and the mixture was stirred at RT until the completion of the reaction. 1M HCl was added to adjust the pH to <4. The product was extracted using DCM and dried over anhydrous MgSO$_4$. The solvent was removed in a vacuum to afford a solid which was washed with ether and hexanes to afford the title compound which was dried overnight in a vacuum oven. LCMS [M+1]=198

Intermediate 22 for Ex-204

2-((methoxycarbonyl)amino)isonicotinic acid

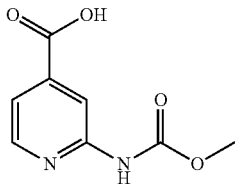

Step A: Synthesis of methyl 2-((methoxycarbonyl)amino)isonicotinate

To a 100 ml pear shaped flask containing methyl 2-aminoisonicotinate (500 mg, 3.29 mmol) in pyridine (5 ml, 61.8 mmol) was added methyl carbonochloridate (0.305 ml, 3.94 mmol) at 0° C. The suspension was then slowly warmed to room temperature and stirred overnight. The reaction was quenched with NaHCO$_3$ (aq) and the organics were extracted using DCM. The organic extract was dried over anhydrous MgSO$_4$, filtered and concentrated. It was then treated with ether and filtered to afford the title compound which was carried over to next step. LCMS [M+1]=211

Step B: Synthesis of 2-((methoxycarbonyl)amino)isonicotinic acid

To a 100 ml round bottom flask containing methyl 2-((methoxycarbonyl)amino)isonicotinate (0.692 g, 3.29 mmol), MeOH (3 ml) and THF (3 ml) was added LiOH (6.58 ml, 32.9 mmol). The resulting solution was stirred at RT until the completion of the reaction. All of the solvents were removed and the reaction mixture was treated with 1M HCl. The solvents were again removed under a vacuum. The solid was filtered, washed with ether and hexanes, and dried in a vacuum oven for 2 h prior to use. The filtrate was concentrated. LCMS [M+1]=197

Intermediate 23 for Ex-243

Methyl 4-((methoxycarbonyl)amino)bicyclo[2.2.2]octane-1-carboxylate

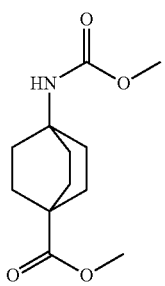 [SMILES: COC(=O)NC12CCC(C(=O)OC)(CC1)CC2]

Step A: Synthesis of methyl 4-((methoxycarbonyl)amino)bicyclo[2.2.2]octane-1-carboxylate To a solution of methyl 4-aminobicyclo[2.2.2]octane-1-carboxylate (260.4 mg, 1.421 mmol) was added K$_2$CO$_3$ (589 mg, 4.26 mmol) in 5 ml water. Methyl carbonochloridate (0.143 ml, 1.847 mmol) was added at 0° C. and then the reaction was allowed to warm to RT and stirred overnight. Water was added and the crude product was extracted with DCM, dried over anhydrous MgSO$_4$, filtered, and concentrated to afford the desired compound. A small amount of DCM and hexane was used to three or four times to precipitate the product. LCMS [M+1]=242

Intermediate 24 for Ex-228

2,4-dioxo-1,2,3,4-tetrahydroquinazoline-6-carboxylic acid

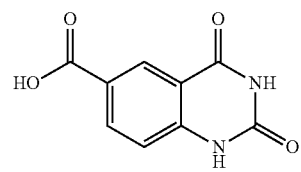 [SMILES: O=C(O)c1ccc2[nH]c(=O)[nH]c(=O)c2c1]

Step A: Synthesis of 2,4-dioxo-1,2,3,4-tetrahydroquinazoline-6-carbonitrile A suspension of 6-bromo-2,4(1h,3h)-quinazolinedione (300 mg, 1.245 mmol), zinc cyanide (175 mg, 1.494 mmol), and tetrakis(triphenylphosphine)palladium(0) (115 mg, 0.100 mmol) in DMF (12.400 ml) was irradiated in microwave reactor at 220° C. for 60 min. The reaction was quenched with sat. aq. NaHCO$_3$ and extracted with EtOAc. The organic phase was washed with water and brine, dried over MgSO$_4$, filtered and evaporated. The title compound was collected by filtration out of DCM. LCMS [M+1]=188.

Step B: 2,4-dioxo-1,2,3,4-tetrahydroquinazoline-6-carboxylic acid

A suspension of 2,4-dioxo-1,2,3,4-tetrahydroquinazoline-6-carbonitrile in equal parts HCl (0.22 ml) and water (0.22 ml) was stirred at 100° C. 24 hr. The reaction mixture was basified with 1M NaOH to pH and extracted with EtOAc. Then, the aqueous phase was re-acidified to pH 2 with 1M HCl and extracted with EtOAc. The organics were combined and concentrated in vacuo to afford the title compound. LCMS [M+1]=207.

Examples 226 and 227

Methyl 3-amino-6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)-1H-indazole-1-carboxylate and methyl (6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)-1H-indazol-3-yl)carbamate

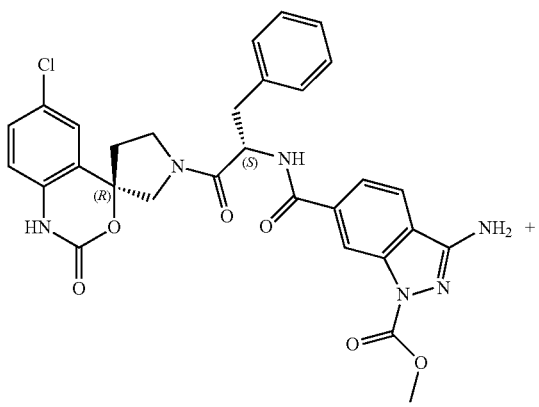

EX-226

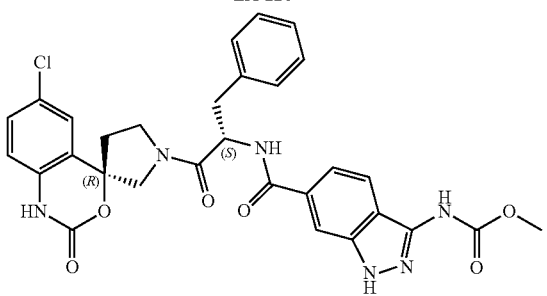

EX-227

To a stirred suspension of 3-amino-N—((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)-1H-indazole-6-carboxamide (0347798-0152-01 (65 mg, 0.119 mmol) in DCM (1 ml) was added 100 µL of 1.19M solution of methyl chloroformate in anhydrous DCM at 0° C. The reaction was quenched with saturated aqueous NH₄Cl after stirring for 20 min at 0° C. and extracted with EtOAc. The organics were combined, washed with water and brine, dried over MgSO₄, filtered, and concentrated in vacuo. The crude was purified by silica gel column and a mixture of isomers was eluted at 7% MeOH in DCM. The isomers were seperated by a chiral column to obtain methyl 3-amino-6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)-1H-indazole-1-carboxylate, LCMS [M+1]=604 and methyl (6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)-1H-indazol-3-yl)carbamate, LCMS [M+1]=604.

Intermediate 25 for Ex-248

3-(tert-Butoxycarbonyl)-2-methyl-1H-indole-5-carboxylic acid

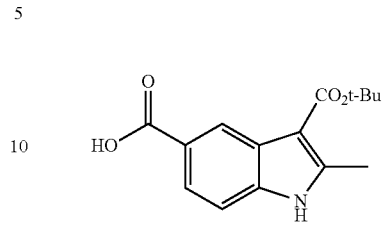

Step 1: 3-(tert-Butyl) 5-methyl 2-methyl-1H-indole-3,5-dicarboxylate

To a microwave tube was added methyl 4-amino-3-iodobenzoate (1 g, 3.61 mmol), cuprous iodide (0.137 g, 0.722 mmol), L-proline (0.166 g, 1.444 mmol) and cesium carbonate (2.352 g, 7.22 mmol). It was purged with nitrogen three times and DMSO (10 ml) was added (degassed by sparging nitrogen for 15 min), and then tert-butyl 3-oxobutanoate (0.685 g, 4.33 mmol) was added. The mixture was stirred at 90° C. for 4 h and was allowed to cool to rt. It was diluted with ethyl acetate (50 mL) and filtered through a pad of Celite. The filtrate was washed with water (3×20 mL) and brine. The organic layer was seperated and dried over sodium sulfate, filtered and concentrated. The residue was purified by ISCO (silica gel 40 g, 0-100% ethyl acetate in hexane) to give the title compound. MS (m/e): 233.93 [M-tert-butyl+H]⁺. ¹HNMR (500 MHz, DMSO-d₆) δ (ppm)=8.89 (1H, s), 7.93 (1H, dd, J=8.5, 1.7 Hz), 7.32 (2H, m), 3.96 (3H, s), 2.78 (3H, s), 1.71 (9H, s).

Step 2: 3-(tert-Butoxycarbonyl)-2-methyl-1H-indole-5-carboxylic acid

To 3-tert-Butyl 5-methyl 2-methyl-1H-indole-3,5-dicarboxylate (53 mg, 0.183 mmol) in THF (1.0 ml) and MeOH (1.0 ml) was added LiOH (5 M, 1.0 ml, 5.00 mmol). The mixture was heated at 70° C. for 3 h. It was cooled to rt and acidified with 4 M HCl to pH 5. The mixture was extracted with ethyl acetate (2×20 mL). The combined organic layers were washed with brine, dried over sodium sulfate, filtered and concentrated. MS (m/e): 220.03 [M-tert-butyl+H]⁺.

Intermediate 26 for Ex-255

2-Oxo-1,2-dihydroquinoline-6-carboxylic acid

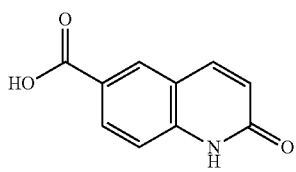 [SMILES: O=C(O)c1ccc2[nH]c(=O)ccc2c1]

Step 1: methyl 2-oxo-1,2,3,4-tetrahydroquinoline-6-carboxylate

To a suspension of 2-oxo-1,2,3,4-tetrahydroquinoline-6-carboxylic acid (0.86 g, 4.50 mmol) in MeOH (10 ml), SOCl$_2$ (0.492 ml, 6.75 mmol) at 0° C. was added dropwise. It was heated to reflux for 3 h and cooled to rt overnight. Crystals were formed and collected by filtration to afford the title compound. MS (m/e): 206.03 [M+H]$^+$.

Step 2: Methyl 2-oxo-1,2-dihydroquinoline-6-carboxylate

To a solution of methyl 2-oxo-1,2,3,4-tetrahydroquinoline-6-carboxylate (200 mg, 0.975 mmol) in chloroform (4 mL) was added NBS (226 mg, 1.267 mmol) and benzoyl peroxide (11.80 mg, 0.049 mmol). The mixture was heated at 60° C. for 8 h. Solids slowly precipitated during the process. It was cooled to rt. The solids were collected by filtration and washed with methanol. MS (m/e): 204.03 [M+H]$^+$.

Step 3: 2-Oxo-1,2-dihydroquinoline-6-carboxylic acid

A suspension of methyl 2-oxo-1,2-dihydroquinoline-6-carboxylate (50 mg, 0.246 mmol) in THF (1 ml) and MeOH (1.000 mL) was added LiOH (1 mL, 5.00 mmol). It was heated at 60° C. for 1.5 h and cooled to rt overnight. The solution was acidified by 4 M HCl to pH 3. The solids were aged for 15 min and collected by filtration to give the title compound. MS (m/e): 190.05 [M+H]$^+$.

Example 256

N—((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-3-(trifluoromethyl)-1H-indazole-5-carboxamide

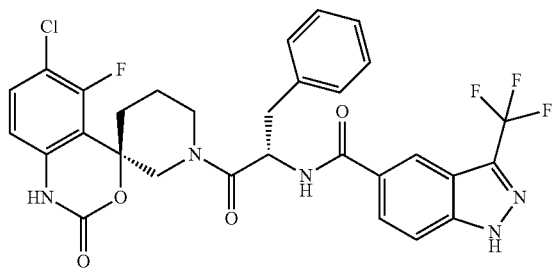 [SMILES: O=C1Nc2ccc(Cl)c(F)c2[C@@]2(CCCN(C(=O)[C@H](Cc3ccccc3)NC(=O)c3ccc4[nH]nc(C(F)(F)F)c4c3)C2)O1]

Step 1: methyl 3-(trifluoromethyl)-1H-indazole-5-carboxylate

To a solution of 5-(4,4,5,5-tetramethyl-1,3,2-dioxaborolan-2-yl)-3-(trifluoromethyl)-1H-indazole (200 mg, 0.641 mmol) in MeOH (10 mL) at −78° C. was added diacetoxypalladium (14.39 mg, 0.064 mmol), benzoquinone (72.7 mg, 0.673 mmol) and triphenylphosphine (33.6 mg, 0.128 mmol). The reaction mixture was degassed and refilled with CO 3 times. The mixture was stirred at 22° C. for 16 h under a CO balloon. The TLC showed new spots formed. The reaction was quenched by adding 30 mL of H$_2$O and extracted with EtOAc (15 mL×3). The organic layer was concentrated and purified by TLC (PE:EtOAc=5:1) to give the title compound.

$^1$H NMR (CDCl$_3$, 400 MHz): δ 10.64 (br.s, 1H), 8.63 (s, 1H), 8.19 (d, J=9.2 Hz, 1H), 7.61 (d, J=8.8 Hz, 1H), 3.98 (s, 3H).

Step 2: 3-(trifluoromethyl)-1H-indazole-5-carboxylic acid

To a solution of methyl 3-(trifluoromethyl)-1H-indazole-5-carboxylate (70 mg, 0.287 mmol) in MeOH (1 mL), water (1 mL) and THF (1 mL) was added LiOH (34.3 mg, 1.433 mmol), then the reaction mixture was stirred at 40° C. for 16 h. TLC showed a new spot formed. The reaction was quenched by adding 5 mL of H$_2$O and extracted with EtOAc (10 mL×3), the combined organic layers were dried and filtered, concentrated to give the title compound.

$^1$H NMR (CD$_3$OD, 400 MHz): δ 8.51 (s, 1H), 8.12 (d, J=8.8 Hz, 1H), 7.68 (d, J=8.4 Hz, 1H).

Step 3: N—((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-3-(trifluoromethyl)-1H-indazole-5-carboxamide To a solution of (R)-1'-((S)-2-amino-3-phenylpropanoyl)-6-chloro-5-fluorospiro[benzo[d][1,3]-oxazine-4,3'-piperidin]-2(1H)-one hydrochloride (80 mg, 0.176 mmol) in DMF (3 mL) was added 3-(trifluoromethyl)-1H-indazole-5-carboxylic acid (40.5 mg, 0.176 mmol), HATU (80 mg, 0.211 mmol) and Et$_3$N (0.074 mL, 0.528 mmol), and the mixture was stirred for 4 h at 25° C. under N$_2$ atmosphere (balloon). LCMS showed the desired product and that the starting material was consumed. The residue was purified by prep-HPLC (Neutral method) to give the title compound.

$^1$H NMR (CD$_3$OD, 400 MHz): δ 8.32 (s, 1H), 8.10 (s, 0.5H), 7.91 (d, J=8.8 Hz, 1H), 7.67-7.65 (m, 1.5H), 7.63-7.59 (m, 0.5H), 7.39-7.28 (m, 1.6H), 7.23-7.17 (m, 8H), 6.80-6.72 (m, 1.5H), 5.46 (t, J=7.2 Hz, 1H), 5.26-5.23 (m, 0.5H), 4.82-4.61 (m, 3.5H), 4.19 (d, J=13.2 Hz, 1H), 3.89 (d, J=15.2 Hz, 0.5H), 3.24-3.03 (m, 5H), 2.83-2.79 (m, 0.5H), 2.47-2.33 (m, 2H), 2.18-2.15 (m, 1H), 2.01-1.93 (m, 4H), 1.58-1.55 (m, 0.5H), 1.26-1.24 (m, 1H).

MS (ESI) m/z 630.0 (M+H).

Intermediate 27 for Ex-265

3-(3-oxomorpholino)benzoic acid

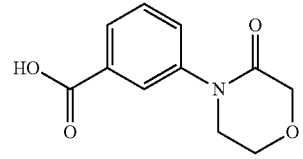 [SMILES: O=C(O)c1cccc(N2CCOCC2=O)c1]

Step A: 3-(3-oxomorpholino)benzoate

Morpholin-3-one (238 mg, 2.354 mmol), ethyl 3-iodobenzoate (0.515 ml, 3.06 mmol), (1R,2R)-N1,N2-dimethylcyclohexane-1,2-diamine (0.074 ml, 0.471 mmol), copper(I) iodide (90 mg, 0.471 mmol), and potassium phosphate (999 mg, 4.71 mmol) in DMSO (4 ml) were stirred at RT under nitrogen in the dark. After 1 hr UPLC was very clean and had the desired mass. The mixture was diluted with 100 mL EtOAc, washed with 3×25 mL water, 1×25 mL brine. The EtOAc layer was dried over Na$_2$SO$_4$, filtered and concentrated under reduced pressure. The crude was purified by silica gel chromatography (30-40% of 30% EtOH, EtOAc: Hexanes) to give ethyl 3-(3-oxomorpholino)benzoate (465 mg, 1.772 mmol).

Step B: 3-(3-oxomorpholino)benzoic acid

Ethyl 3-(3-oxomorpholino)benzoate (465 mg, 1.866 mmol) in MeOH (4 ml) and THF (6 ml) was added to lithium hydroxide (4.66 ml, 9.33 mmol). After 5 min of stirring at rt, the reaction mixture was extracted with 10 mL water and 10 mL EtOAc. The EtOAc layer was discarded and the aqueous layer was acidified to pH 4-5 and extracted with 3×10 mL EtOAc. The combined EtOAc layers were dried on $Na_2SO_4$, and concentrated on a rotovap. It was purified by reverse phased chromatography using ACN:Water, where both contain 0.05% TFA.

Example 267

2-(5-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)-3-fluorothiophen-2-yl)-2-oxoacetic acid

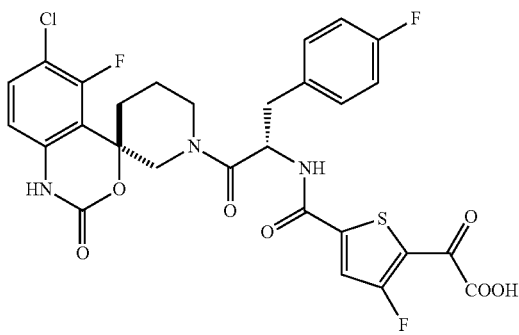

Step A:
To methyl 2-mercaptoacetate (1.287 ml, 14.10 mmol) in tetrahydrofuran (10 ml) at 0° C. was added 2,3,4,6,7,8,9,10-octahydropyrimido[1,2-a]azepine (1.063 ml, 7.05 mmol) followed by diethyl but-2-ynedioate (1.129 ml, 7.05 mmol). After 30 minutes, it was warmed to rt and stirred overnight at rt. LC/MS showed the desired mass. 50 mL water and 100 mL EtOAc were added and the compound precipitated out, which was filtered off by suction filtration.

Step B:
5-ethyl 2-methyl 3-hydroxythiophene-2,5-dicarboxylate (225 mg, 0.977 mmol) (prepared as in experiment 3), cesium fluoride (445 mg, 2.93 mmol) and 1,3-bis(2,6-diisopropylphenyl)-2,2-difluoro-2,3-dihydro-1h-imidazole (500 mg, 1.173 mmol) in toluene (9 ml) were heated at 110° C. overnight. The desired mass was observed by LC/MS. It was filtered through a fritted disposable funnel, and washed with 2×10 mL toluene. The filtrate was concentrated until dryness. The compound was purified on a silica gel column using 20-30% 3:1 EtOAc:EtOH with Hexanes to give 5-ethyl 2-methyl 3-fluorothiophene-2,5-dicarboxylate (130 mg, 0.532 mmol).

Step C:
Lithium hydroxide (0.420 ml, 0.840 mmol) was added to 5-ethyl 2-methyl 3-fluorothiophene-2,5-dicarboxylate (130 mg, 0.560 mmol) in MeOH (4 ml) and THF (6 ml). After 5 min of stirring at rt, LC/MS showed the desired compound. 10 mL water was added, and it was extracted with 2×10 mL EtOAc. The EtOAc layer was discarded and the aqueous layer was acidified to pH 4-5, and extracted with 3×10 mL EtOAc. The combined EtOAc layers were dried on $Na_2SO_4$, and concentrated on a rotovap.

Step D:
HATU (67.0 mg, 0.176 mmol) and 4-fluoro-5-(methoxycarbonyl)thiophene-2-carboxylic acid (30 mg, 0.147 mmol) wer added to (R)-1'-((S)-2-amino-3-(4-fluorophenyl)propanoyl)-6-chloro-5-fluorospiro[benzo[d][1,3]oxazine-4,3'-piperidin]-2(1H)-one hydrochloride (69.4 mg, 0.147 mmol) in DMF (1 ml), followed by N-ethyl-N-isopropylpropan-2-amine (0.077 ml, 0.441 mmol). After 5 min of stirring at rt, LC/MS showed the desired compound. It was purified by reverse phase chromatography using ACN:water, where both contain 0.05% TFA. Methyl 5-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)-3-fluorothiophene-2-carboxylate was obtained. LCMS: m/z 622.43 [M+H]$^+$. H NMR δ (ppm)($CH_3OH$-d4): 0.12(1H, s), 1.61(1H, d, J=13.58 Hz), 1.96 (1H, s), 2.22 (2H, d, J=14.53 Hz), 2.35 (1H, s), 2.49 (1H, td, J=13.44, 4.63 Hz), 2.86 (1H, d, J=12.90 Hz), 3.01 (1H, dd, J=13.71, 7.62 Hz), 3.90 (7H, t, J=16.08 Hz), 4.10 (2H, d, J=13.99 Hz), 4.62 (1H, d, J=14.84 Hz), 4.68 (1H, s), 5.21-5.19 (1H, m), 5.37 (1H, q, J=7.83 Hz), 6.79 (2H, dd, J=20.11, 8.68 Hz), 6.96 (4H, dt, J=25.25, 8.57 Hz), 7.28 (4H, t, J=6.66 Hz), 7.49-7.42 (3H, m), 7.56 (1H, s), 7.60 (1H, s), 7.71 (1H, s), 8.88 (1H, d, J=8.86 Hz), 9.14 (1H, d, J=9.07 Hz).

Step E:
lithium hydroxide (0.193 ml, 0.385 mmol) was added to methyl 5-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)-3-fluorothiophene-2-carboxylate (45 mg, 0.077 mmol) in MeOH (4 ml) and THF (6 ml). After 48 hrs of stirring at rt, LC/MS showed the desired compound. 500 uL TFA was added, and it was purified on reverse phase chromatography using ACN:Water, where both contain 0.05% TFA. 5-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)-3-fluorothiophene-2-carboxylic acid was obtained. LCMS: m/z 608.4 [M+H]$^+$. H NMR δ (ppm) ($CH_3OH$-d4): 0.12 (1H, s), 1.61 (1H, d, J=13.58 Hz), 1.96 (1H, s), 2.22 (2H, d, J=14.53 Hz), 2.35 (1H, s), 2.49 (1H, td, J=13.44, 4.63 Hz), 2.86 (1H, d, J=12.90 Hz), 3.01 (1H, dd, J=13.71, 7.62 Hz), 3.90 (7H, t, J=16.08 Hz), 4.10 (2H, d, J=13.99 Hz), 4.62 (1H, d, J=14.84 Hz), 4.68 (1H, s), 5.21-5.19 (1H, m), 5.37 (1H, q, J=7.83 Hz), 6.79 (2H, dd, J=20.11, 8.68 Hz), 6.96 (4H, dt, J=25.25, 8.57 Hz), 7.28 (4H, t, J=6.66 Hz), 7.49-7.42 (3H, m), 7.56 (1H, s), 7.60 (1H, s), 7.71 (1H, s), 8.88 (1H, d, J=8.86 Hz), 9.14 (1H, d, J=9.07 Hz).

Example 271

(2-(((4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)phenyl)carbamoyl)oxy)ethyl)phosphonic acid

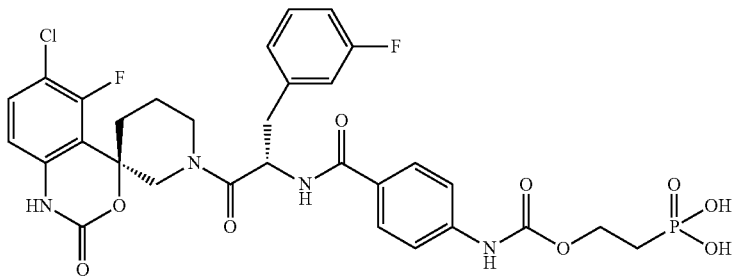 [SMILES: O=C(Nc1ccc(C(=O)N[C@@H](Cc2cccc(F)c2)C(=O)N2CCC[C@@]3(C2)OC(=O)Nc2ccc(Cl)c(F)c23)cc1)OCCP(=O)(O)O]

Step A:

Et3N (1266 μl, 9.08 mmol) was added to dimethyl (2-hydroxyethyl)phosphonate (588 μl, 4.54 mmol) in acetonitrile (3.03E+04 μl) followed by N,N'-disuccinimidyl carbonate (1745 mg, 6.81 mmol). The reaction mixture was stirred at rt for 3 h before concentrating under vacuum. Sat. aqueous NaHCO3 was then added, and the mixture was extracted with EtOAc (2×, 40.0 mL). The combined organic layers were dried over Na2SO4, filtered and concentrated under vacuum. The crude was used directly in the next step. 2-(dimethoxyphosphoryl)ethyl (2,5-dioxopyrrolidin-1-yl) carbonate in DCM (30.0 mL) was added Et3N (950 μl, 6.81 mmol) followed by tert-butyl 4-aminobenzoate (614 mg, 3.18 mmol). The reaction mixture was stirred at rt overnight before water was added. The two layers were then separated, and the organic layer was dried over Na2SO4, filtered and concentrated under vacuum. The crude was purified by silica gel chromatography, eluting with 0-100% EtOAc/Hexanes, to give tert-butyl 4-(((2-(dimethoxyphosphoryl)ethoxy)carbonyl)amino)benzoate. LCMS: m/z 374 [M+H]+.

STEP B: TFA (5000 μl, 64.9 mmol) was added dropwise at rt to tert-butyl 4-(((2-(dimethoxyphosphoryl)ethoxy)carbonyl)amino)benzoate (684 mg, 1.832 mmol) in DCM (5000 μl). The reaction mixture was stirred at the same temperature for 1 h before being concentrated under vacuum. The residue was re-dissolved in DCM and washed with water. The organic layer was dried over Na2SO4, filtered and concentrated under vacuum. The crude residue was put in a high vacuum overnight to give 4-(((2-(dimethoxyphosphoryl)ethoxy)carbonyl)amino)benzoic acid. LCMS: m/z 318 [M+H]+.

Step C:

2,4,6-Tripropyl-1,3,5,2,4,6-trioxatriphosphorinane-2,4,6-trioxide (250 μl, 0.402 mmol) was added to (R)-1'-((S)-2-amino-3-(3-fluorophenyl)propanoyl)-6-chloro-5-fluorospiro[benzo[d][1,3]oxazine-4,3'-piperidin]-2(1H)-one hydrochloride (95.0 mg, 0.201 mmol), 4-(((2-(dimethoxyphosphoryl)ethoxy)carbonyl)amino)benzoic acid (63.8 mg, 0.201 mmol) and TEA (168 μl, 1.207 mmol) in DCM (2011 μl). The reaction mixture was stirred at rt overnight and concentrated under vacuum. The crude was purified by silica gel chromatography, eluting with 0-80% EtOAC:EtOH mixture/Hexanes, to give 2-(dimethoxyphosphoryl)ethyl (4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)phenyl)carbamate. The product was further purified by RP HPLC (Gilson on a 19×100 mm, Waters Sunfire C18 column, 5μ particle size, linear gradient, standard 29% ACN/H2O to 59% ACN/H2O buffering with 0.1% TFA at flow rate 25 mL/min over 12 min). LCMS: m/z 735 [M+H]+.

Step D:

TMS-Br (95 μl, 0.730 mmol) was added dropwise at rt to 2-(dimethoxyphosphoryl)ethyl (4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)phenyl)carbamate (122 mg, 0.166 mmol) in DCM (8299 μl), followed by 2,6-lutidine (38.7 μl, 0.332 mmol). The reaction mixture was stirred at the same temperature for 5 h. MeOH was then added, and the mixture was stirred for another 30 min before being concentrated under vacuum. The crude was purified by RP HPLC (Gilson on a 19×100 mm, Waters XBridge C18 column, 5μ particle size, linear gradient, standard 10% ACN/H2O to 100% ACN/H2O buffering with 0.05% TFA at flow rate 30 mL/min over 10 min) to give (2-(((4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)phenyl)carbamoyl)oxy)ethyl)phosphonic acid. LCMS: m/z 707 [M+H]+.

Example 273

(2-(4-(((S)-1-((R)-6-Chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)benzamido)ethyl)phosphonic acid

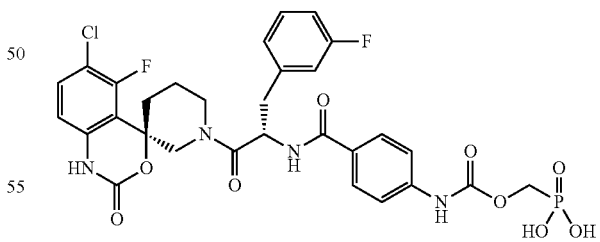

Step A:

HATU (630 mg, 1.656 mmol) was added to 4-(tert-butoxycarbonyl)benzoic acid (368 mg, 1.656 mmol), diethyl (2-aminoethyl)phosphonate (300 mg, 1.656 mmol) and DIPEA (868 μl, 4.97 mmol) in a THF (1.38E+04 μl):DMF (2760 μl) mixture. The reaction mixture was stirred at rt for 2 h and concentrated under vacuum. The crude was purified by silica gel chromatography, eluting with 0-100% EtOAc/Hexanes, to give the amide-coupling product. LCMS: m/z 386 [M+H]+.

TFA (4000 μl, 51.9 mmol) was added at rt to the amide-coupling product in DCM (4.00 mL). The reaction mixture was stirred at the same temperature for 1 h before being concentrated under vacuum. The residue was diluted with DCM and washed with water. The organic layer was dried over Na₂SO₄, filtered and concentrated under vacuum. The crude was used directly in the next step. LCMS: m/z 330 [M+H]⁺.

Step B:

2,4,6-tripropyl-1,3,5,2,4,6-trioxatriphosphorinane-2,4,6-trioxide (341 μl, 0.550 mmol) was added to (R)-1'-((S)-2-amino-3-(3-fluorophenyl)propanoyl)-6-chloro-5-fluorospiro[benzo[d][1,3]oxazine-4,3'-piperidin]-2(1H)-one hydrochloride (130 mg, 0.275 mmol), 4-((2-(diethoxyphosphoryl)ethyl)carbamoyl)benzoic acid (91 mg, 0.275 mmol) and TEA (230 μl, 1.651 mmol) in DCM (2752 μl). The reaction mixture was stirred at rt overnight and concentrated under vacuum. The crude was purified by silica gel chromatography (eluting with 0-80% 3:1 EtOAC:EtOH mixture/Hexanes) to give diethyl (2-(4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)benzamido)ethyl)phosphonate. Further purification by RP HPLC (Gilson on a 19×100 mm, Waters XBridge C18 column, 5μ particle size, linear gradient, standard 10% ACN/H2O to 100% ACN/H₂O buffering with 0.05% TFA at flow rate 30 mL/min over 10 min). LCMS: m/z 747 [M+H]⁺.

Step C:

TMS-Br (95 μl, 0.730 mmol) was added dropwise at rt to diethyl (2-(4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)benzamido)ethyl)phosphonate (124 mg, 0.166 mmol) in DCM (4149 μl), followed by 2,6-lutidine (38.7 μl, 0.332 mmol). The reaction mixture was stirred at the same temperature for 5 h. MeOH was added, and the mixture was stirred for another 30 min before being concentrated under vacuum. The crude was purified by RP HPLC (Gilson on a 19×100 mm, Waters Sunfire C18 column, 5μ particle size, linear gradient, standard 20% ACN/H2O to 55% ACN/H2O buffering with 0.1% TFA at flow rate 25 mL/min over 12 min) to give (2-(4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)benzamido)ethyl)phosphonic acid. LCMS: m/z 691 [M+H]⁺.

Example 274

2-(1H-tetrazol-5-yl)ethyl (4-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)phenyl)carbamate Step A:

HATU (97 mg, 0.254 mmol) was added to (R)-1'-((S)-2-amino-3-(4-fluorophenyl)propanoyl)-6-chloro-5-fluorospiro[benzo[d][1,3]oxazine-4,3'-piperidin]-2(1H)-one hydrochloride (120 mg, 0.254 mmol), 4-((tert-butoxycarbonyl)amino)benzoic acid (60.3 mg, 0.254 mmol) and DIPEA (222 μl, 1.270 mmol) in THF (2541 μl) were. The reaction mixture was stirred at rt for 2 h before being concentrated under vacuum. The crude was purified by silica gel chromatography, eluting with 0-90% EtOAc/Hexanes, to give the amide-coupling product. LCMS: m/z 655 [M+H]⁺.

Step B:

To the amide-coupling product in DCM (2000 μL) was added TFA (1000 μl, 12.98 mmol), and the reaction was stirred at rt for 1 h before sat aqueous NaHCO₃ was added carefully. The mixture was extracted with DCM (2×, 30.0 mL), and the combined organic layers were then dried over Na₂SO₄, filtered and concentrated under vacuum. The crude 4-amino-N—((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)benzamide (147 mg, 0.265 mmol) was used directly in the next step. LCMS: m/z 555 [M+H]⁺.

Step C:

To a solution of 4-amino-N—((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)benzamide (147 mg, 0.265 mmol) in DCM (2649 μl) was added Et₃N (73.8 μl, 0.530 mmol) and triphosgene (79 mg, 0.265 mmol) at −20° C. The reaction mixture was stirred for 30 min, and then 2-(1H-tetrazol-5-yl)ethanol (91 mg, 0.795 mmol) was added followed by Et₃N (73.8 μl, 0.530 mmol). The resulting mixture was allowed to warm to rt and stirred overnight. Water was added then followed by DCM extractions (2×, 20.0 mL). The combined organic layers were dried over Na₂SO₄, filtered and concentrated under vacuum. The crude was purified by RP HPLC (Gilson on a 19×100 mm, Waters Sunfire C18 column, 5μ particle size, linear gradient, standard 20% ACN/H2O to 55% ACN/H2O buffering with 0.1% TFA at flow rate 25 mL/min over 12 min) and another further purification (Gilson on a 19×100 mm, Waters XBridge C18 column, 5μ particle size, linear gradient, standard 5% ACN/H2O to 100% ACN/H2O buffering with 0.05% TFA at flow rate 30 mL/min over 12 min) to give 2-(1H-tetrazol-5-yl)ethyl (4-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)phenyl)carbamate.

By using procedures similar to those described previously, with appropriate starting materials and "right-side" reagents, the following compounds were synthesized. These compounds were characterized by LC/MS.

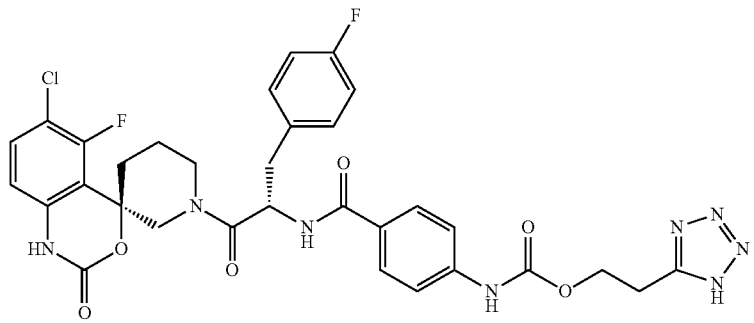 [SMILES: O=C(Nc1ccc(C(=O)N[C@@H](Cc2ccc(F)cc2)C(=O)N2CCC[C@@]3(C2)OC(=O)Nc2ccc(Cl)c(F)c23)cc1)OCCc1nnn[nH]1]

| Example | Structure | LCMS [M + 1] | FXIa Ki (nM) |
| --- | --- | --- | --- |
| 139 (racemate) | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-sulfamoylbenzamide | 569 | 928 |
| 140a (isomer A) | 4-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid | 534 | 1600 |
| 140b (isomer B) | 4-(((S)-1-((S)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid | 534 | 5000 |
| 141a (isomer A) | 3-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid | 534 | 44.7 |
| 142 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-1H-indazole-5-carboxamide | 530 | 48.4 |
| 143 | methyl (3-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 563 | 1253 |
| 144 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-methylpyrimidine-5-carboxamide | 506 | 5000 |
| 145 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-methylpyrazine-2-carboxamide | 506 | 3316 |
| 146 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-methyloxazole-4-carboxamide | 495 | 5000 |
| 147 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-5-methoxypicolinamide | 521 | 4030 |
| 148 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-5-(methylsulfonyl)picolinamide | 570 | 1871 |
| 149 | 2-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)pyrimidine-5-carboxamide | 506 | 5000 |
| 150 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-cyanobenzamide | 515 | 430 |
| 151 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(1H-tetrazol-5-yl)benzamide | 558 | 1783 |
| 152 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-6-cyanonicotinamide | 516 | 1024 |
| 153 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-1H-pyrrolo[3,2-b]pyridine-5-carboxamide | 530 | 488 |
| 154 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-(1H-pyrazol-1-yl)benzamide | 556 | 2517 |
| 155 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-hydroxyisonicotinamide | 507 | 169 |
| 156 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)isoxazole-3-carboxamide | 481 | 2148 |
| 157 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(hydroxymethyl)cyclohexanecarboxamide | 526 | 3350 |
| 158 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-6-(hydroxymethyl)nicotinamide | 521 | 752 |
| 159 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-6-(1H-imidazol-1-yl)nicotinamide | 557 | 743.5 |
| 160 | 1-(4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)cyclopropanecarboxylic acid | 575 | 5000 |
| 161 | 4-(1-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)cyclopropyl)benzoic acid | 575 | 4488 |

| Example | Structure | LCMS [M + 1] | FXIa Ki (nM) |
|---|---|---|---|
| 162 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(2,2,2-trifluoroacetamido)benzamide | 603 | 594 |
| 163 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(methylsulfonamido)benzamide | 584 | 63.2 |
| 164 | 2-methoxyethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 607 | 9.4 |
| 165 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-oxo-3,4-dihydro-2H-benzo[b][1,4]thiazine-7-carboxamide | 577 | 14.6 |
| 166 | methyl (6-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)pyridin-3-yl)carbamate | 564 | 184.4 |
| 167 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-oxo-2,3-dihydrooxazolo[4,5-b]pyridine-6-carboxamide | 548 | 4163 |
| 168 | 2-acetamido-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)isonicotinamide | 548 | 576.5 |
| 169 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-(2-oxoimidazolidin-1-yl)benzamide | 574 | 774 |
| 170 | 2-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-methylthiazole-5-carboxamide | 526 | 508 |
| 171 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-oxo-3,4-dihydro-2H-benzo[b][1,4]oxazine-7-carboxamide | 561 | 21.8 |
| 172 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-oxoisoindoline-5-carboxamide | 545 | 328 |
| 173 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-((4S,5S)-4-methyl-2-oxooxazolidin-5-yl)benzamide | 589 | 385 |
| 174 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-oxoindoline-6-carboxamide | 545 | 261 |
| 175 | 2-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)thiazole-4-carboxamide | 512 | 212 |
| 176 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazole-5-carboxamide | 530 | 59.8 |
| 177 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-6-hydroxypyrimidine-4-carboxamide | 508 | 559 |
| 178 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-fluoro-4-hydroxybenzamide | 524 | 251 |
| 179 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-guanidinobenzamide | 547 | 454 |
| 180 | 2-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazole-5-carboxamide | 545 | 56.7 |
| 181 | 2-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)benzo[d]thiazole-6-carboxamide | 562 | 18.7 |
| 182 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-1H-indazole-6-carboxamide | 530 | 136.8 |
| 183 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-oxo-2,3-dihydrobenzo[d]oxazole-5-carboxamide | 547 | 86.9 |

| Example | Structure | LCMS [M + 1] | FXIa Ki (nM) |
|---|---|---|---|
| 184 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-oxo-2,3-dihydrobenzo[d]isothiazole-6-carboxamide 1,1-dioxide | 595 | 5000 |
| 185 | 3-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-1H-indazole-5-carboxamide | 545 | 96 |
| 186 | 2-methoxyethyl (5-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)pyridin-2-yl)carbamate | 608 | 166 |
| 187 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-oxo-2,3,4,5-tetrahydro-1H-benzo[b]azepine-7-carboxamide | 573 | 151 |
| 188 | 4-((1H-imidazol-2-yl)amino)-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)benzamide | 571 | 42 |
| 189 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(3-methylureido)benzamide | 562 | 17.6 |
| 190 | 2-(piperazin-1-yl)ethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 661.1 | 76.7 |
| 191 | 2-morpholinoethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 662 | 33.5 |
| 192 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-oxo-3,4-dihydro-2H-benzo[b][1,4]thiazine-7-carboxamide 1-oxide | 593 | 99.7 |
| 193 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-oxo-3,4-dihydro-2H-benzo[b][1,4]thiazine-7-carboxamide 1,1-dioxide | 609 | 145.1 |
| 194 | ((S)-tetrahydrofuran-2-yl)methyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate | 633 | 5.48 |
| 195 | 3-amino-N-((S)-1-((R)-6-chloro-5-fluoro-2-oxo-1,2-dihydrospiro[benzo[d][1,3]oxazine-4,3'-pyrrolidin]-1'-yl)-1-oxo-3-phenylpropan-2-yl)-1H-indazole-6-carboxamide | 563 | 1.0 |
| 196 | methyl (5-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)thiophen-2-yl)carbamate | 569 | 63.4 |
| 197 | 3-amino-N-((S)-1-((R)-6-chloro-2-oxo-1,2-dihydrospiro[benzo[d][1,3]oxazine-4,3'-piperidin]-1'-yl)-1-oxo-3-phenylpropan-2-yl)-1H-indazole-6-carboxamide | 559.0 | 0.62 |
| 198 | N-((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)-2,3-dioxo-1,2,3,4-tetrahydroquinoxaline-6-carboxamide | 574 | 2.77 |
| 199 | N-((S)-1-((R)-6-chloro-2-oxo-1,2-dihydrospiro[benzo[d][1,3]oxazine-4,3'-piperidin]-1'-yl)-1-oxo-3-phenylpropan-2-yl)-4-hydroxy-2-oxo-1,2-dihydroquinoline-6-carboxamide | 588.0 | 0.6 |
| 200 | 3-amino-N-((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)-1H-indazole-6-carboxamide | 523.9 | 4.4 |
| 201 | methyl (3-chloro-4-(((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)carbamoyl)phenyl)carbamate | 576 | 91.3 |
| 202 | N-((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)-3,4-difluorobenzamide | 504.9 | 925 |
| 203 | 5-(((S)-1-((R)-6-chloro-2-oxo-1,2-dihydrospiro[benzo[d][1,3]oxazine-4,3'-piperidin]-1'-yl)-1-oxo-3-phenylpropan-2-yl)carbamoyl)thiophene-2-carboxylic acid | 555.0 | 10.3 |
| 204 | methyl (5-(((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)carbamoyl)pyridin-2-yl)carbamate | 542.9 | 244 |
| 205 | 6-amino-N-((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)nicotinamide | 484.9 | 72.2 |

-continued

| Example | Structure | LCMS [M + 1] | FXIa Ki (nM) |
|---|---|---|---|
| 206 | N-((S)-1-((R)-6-chloro-2-oxo-1,2-dihydrospiro[benzo[d][1,3]oxazine-4,3'-piperidin]-1'-yl)-1-oxo-3-phenylpropan-2-yl)-2-(methylamino)isonicotinamide | 535.0 | 14.5 |
| 207 | N-((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)-2,3-dihydro-1H-pyrrolo[2,3-b]pyridine-5-carboxamide | 510.9 | 8750 |
| 208 | 2-amino-5-(((S)-1-((R)-6-chloro-2-oxo-1,2-dihydrospiro[benzo[d][1,3]oxazine-4,3'-piperidin]-1'-yl)-3-(4-fluorophenyl)-1-oxopropan-2-yl)carbamoyl)benzoic acid | 582.0 | 1.63 |
| 209 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-hydroxy-2-oxo-1,2-dihydroquinoline-6-carboxamide | 606.0 | 0.11 |
| 210 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-4-hydroxy-2-oxo-1,2-dihydroquinoline-6-carboxamide | 569.9 | 0.22 |
| 211 | 6-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)-2-oxo-1,2-dihydroquinolin-4-yl acetate | 648.0 | 39.6 |
| 212 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-6-((2,2,2-trifluoroethyl)amino)nicotinamide | 621.0 | 132.6 |
| 213 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-2-oxo-2,3-dihydro-1H-benzo[d]imidazole-5-carboxamide | 542.9 | 10.4 |
| 214 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-3-hydroxy-1H-indazole-5-carboxamide | 542.9 | 0.7 |
| 215 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-3-hydroxy-1H-indazole-6-carboxamide | 542.9 | 13.8 |
| 216 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-5-hydroxy-1H-indole-2-carboxamide | 541.9 | 37.6 |
| 217 | 3-amino-N-((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)benzo[d]isoxazole-6-carboxamide | 546.9 | 2.3 |
| 218 | N-((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)-3-cyano-1H-indazole-6-carboxamide | 555.9 | 246 |
| 219 | N6-((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)-1H-indazole-3,6-dicarboxamide | 574.0 | 2309 |
| 220 | methyl ((1S,4r)-4-(((S)-1-((R)-6-chloro-2-oxo-1,2-dihydrospiro[benzo[d][1,3]oxazine-4,3'-piperidin]-1'-yl)-1-oxo-3-phenylpropan-2-yl)carbamoyl)cyclohexyl)carbamate | 584.0 | 33.7 |
| 221 | N-((S)-1-((R)-6-chloro-2-oxo-1,2-dihydrospiro[benzo[d][1,3]oxazine-4,3'-piperidin]-1'-yl)-1-oxo-3-phenylpropan-2-yl)-4-hydroxy-2-oxo-1,2-dihydroquinoline-7-carboxamide | 588.0 | 518.0 |
| 222 | methyl (4-((((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)methyl)phenyl)carbamate | 550.0 | 8750 |
| 223 | methyl (4-(1-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)-2,2,2-trifluoroethyl)phenyl)carbamate | 618.0 | 8750 |
| 224 | (4R)-1'-((1-(3-amino-1H-indazol-6-yl)ethyl)-1-phenylalanyl)-6-chlorospiro[benzo[d][1,3]oxazine-4,3'-pyrrolidin]-2(1H)-one | 548.0 | 8750 |
| 225 | 3-amino-N-((2S)-1-(6-chloro-5-fluoro-2-oxo-1,2-dihydrospiro[benzo[d][1,3]oxazine-4,3'-piperidin]-1'-yl)-1-oxo-3-phenylpropan-2-yl)-1H-indazole-6-carboxamide | 578 | 0.4 |
| 226 | methyl (6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)-1H-indazol-3-yl)carbamate | 604 | 18.1 |

| Example | Structure | LCMS [M + 1] | FXIa Ki (nM) |
|---|---|---|---|
| 227 | methyl 3-amino-6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)-1H-indazole-1-carboxylate | 604 | 9.0 |
| 228 | N-((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)-2,4-dioxo-1,2,3,4-tetrahydroquinazoline-6-carboxamide | 574 | 17.1 |
| 229 | diethyl (4-(((R)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)phosphonate | 658.19 | 8750 |
| 230 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-(2-methoxyacetamido)benzamide | 609.38 | 17.31 |
| 231 | isopropyl (4-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate | 623.28 | 35.08 |
| 232 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-(5-oxo-2,5-dihydro-1,2,4-oxadiazol-3-yl)benzamide | 606.35 | 257.90 |
| 233 | (5-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)thiophen-2-yl)boronic acid | 572.24 | 7.88 |
| 234 | methyl (2-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)pyrimidin-5-yl)carbamate | 597.15 | 16.90 |
| 235 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-5-(1H-imidazol-2-yl)thiophene-2-carboxamide | 594.36 | 1.26 |
| 236 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-(1H-imidazol-2-yl)thiophene-2-carboxamide | 593.81 | 65.28 |
| 237 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-5-(1H-imidazol-2-yl)thiophene-2-carboxamide | 558.33 | 5.85 |
| 238 | methyl (3-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)bicyclo[1.1.1]pentan-1-yl)carbamate | 585.32 | 103.60 |
| 239 | 4-(((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)carbamoyl)thiazole-2-carboxylic acid | 519.26 | 404.90 |
| 240 | 4-acetamido-N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)benzamide | 579.37 | 4.28 |
| 241 | methyl (4-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)benzyl)carbamate | 609.33 | 53.94 |
| 242 | methyl (6-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)pyridazin-3-yl)carbamate | 597.36 | 177.20 |
| 243 | methyl (4-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)bicyclo[2.2.2]octan-1-yl)carbamate | 627.39 | 95.99 |
| 245 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)thiophene-2,5-dicarboxamide | 571.28 | 0.97 |
| 246 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-6-oxo-1,6-dihydropyridine-3-carboxamide | 539.28 | 77.77 |
| 247 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-(5-oxo-1,5-dihydro-4H-1,2,4-triazol-4-yl)benzamide | 605.30 | 66.75 |

-continued

| Example | Structure | LCMS [M + 1] | FXIa Ki (nM) |
|---|---|---|---|
| 248 | tert-butyl 5-(((S)-1-((R)-6-chloro-2-oxo-1,2-dihydrospiro[benzo[d][1,3]oxazine-4,3'-piperidin]-1'-yl)-1-oxo-3-phenylpropan-2-yl)carbamoyl)-2-methyl-1H-indole-3-carboxylate | 656.89 | 303.5 |
| 249 | 5-(((S)-1-((R)-6-chloro-2-oxo-1,2-dihydrospiro[benzo[d][1,3]oxazine-4,3'-piperidin]-1'-yl)-1-oxo-3-phenylpropan-2-yl)carbamoyl)-2-methyl-1H-indole-3-carboxylic acid | 601.40 | 2.02 |
| 250 | N-((S)-1-((R)-6-chloro-2-oxo-1,2-dihydrospiro[benzo[d][1,3]oxazine-4,3'-piperidin]-1'-yl)-1-oxo-3-phenylpropan-2-yl)-2-methyl-1H-indole-5-carboxamide | 557.35 | 41.9 |
| 251 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-2-oxo-1,2,3,4-tetrahydroquinoline-6-carboxamide | 555.32 | 5.72 |
| 252 | 4-(((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)carbamoyl)-N-methylpyridin-2-aminium 2,2,2-trifluoroacetate | 516.32 | 9.11 |
| 253 | 5-(((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)carbamoyl)pyridin-2-aminium 2,2,2-trifluoroacetate | 501.77 | 14.00 |
| 254 | 3-amino-N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-1H-indazole-6-carboxamide | 541.34 | 2.11 |
| 255 | N-((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)-2-oxo-1,2-dihydroquinoline-6-carboxamide | 553.24 | 4.00 |
| 256 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-3-(trifluoromethyl)-1H-indazole-5-carboxamide | 630.0 | >875 |
| 257 | N-((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-2-oxo-1,2-dihydroquinoline-6-carboxamide | 589.16 | 0.78 |
| 258 | 3-amino-N-((S)-1-((R)-6-chloro-2-oxo-1,2-dihydrospiro[benzo[d][1,3]oxazine-4,3'-pyrrolidin]-1'-yl)-1-oxo-3-(pyridin-4-yl)propan-2-yl)-1H-indazole-6-carboxamide | 546.16 | 1.73 |
| 259 | 6-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)-2-naphthoic acid | 584 | 298.2 |
| 260 | 4-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-1H-benzo[d]imidazole-6-carboxamide | 545 | 77.87 |
| 261 | 2-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)quinoline-6-carboxamide | 556 | 4047 |
| 262 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-hydroxyquinoxaline-6-carboxamide | 558 | 511.8 |
| 263 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4H-benzo[e][1,2,4]thiadiazine-7-carboxamide 1,1-dioxide | 594 | 1973 |
| 264 | N-((S)-1-((R)-6-chloro-5-fluoro-2-oxo-1,2-dihydrospiro[benzo[d][1,3]oxazine-4,3'-piperidin]-1'-yl)-1,4-dioxo-4-(pyrrolidin-1-yl)butan-2-yl)-2,4-dioxo-1,2,3,4-tetrahydroquinoline-6-carboxamide | 626.54 | 0.39 |
| 265 | N-((S)-1-((R)-6-chloro-2-oxo-1,2-dihydrospiro[benzo[d][1,3]oxazine-4,3'-piperidin]-1'-yl)-1-oxo-3-phenylpropan-2-yl)-3-(3-oxomorpholino)benzamide | 603.56 | 661.20 |
| 266 | 3-amino-N-((S)-4-(azetidin-1-yl)-1-((R)-6-chloro-2-oxo-1,2-dihydrospiro[benzo[d][1,3]oxazine-4,3'-piperidin]-1'-yl)-1,4-dioxobutan-2-yl)-1H-indazole-6-carboxamide | 566.25 | 3.82 |
| 267 | 5-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)-3-fluorothiophene-2-carboxylic acid | 608.40 | 0.70 |

-continued

| Example | Structure | LCMS [M + 1] | FXIa Ki (nM) |
|---|---|---|---|
| 268 | 3-amino-N-((S)-1-((R)-6-chloro-2-oxo-1,2-dihydrospiro[benzo[d][1,3]oxazine-4,3'-piperidin]-1'-yl)-1,4-dioxo-4-(pyrrolidin-1-yl)butan-2-yl)-1H-indazole-6-carboxamide | 580.48 | 0.85 |
| 269 | 3-amino-N-((S)-1-((R)-6-chloro-2-oxo-1,2-dihydrospiro[benzo[d][1,3]oxazine-4,3'-piperidin]-1'-yl)-4-hydroxy-4-methyl-1-oxopentan-2-yl)-1H-indazole-6-carboxamide | 542 | 5 |
| 270 | N-((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)-3-(2H-tetrazol-5-yl)benzamide | 608.5 | 45.5 |
| 272 | (2-(((4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)phenyl)carbamoyl)oxy)ethyl)phosphonic acid | 707.6 | 1.24 |
| 272 | (2-(((4-(((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)carbamoyl)phenyl)carbamoyl)oxy)ethyl)phosphonic acid | 653.5 | 7.92 |
| 273 | (2-(4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)benzamido)ethyl)phosphonic acid | 691.4 | 367 |
| 274 | 2-(1H-tetrazol-5-yl)ethyl (4-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)phenyl)carbamate | 695.5 | 3.22 |

Example 275

Methyl (4-(3-((2S)-1-(6-chloro-2-oxo-1,2-dihydrospiro[benzo[d][1,3]oxazine-4,3'-pyrrolidin]-1'-yl)-1-oxo-3-phenylpropan-2-yl)ureido)phenyl)carbamate

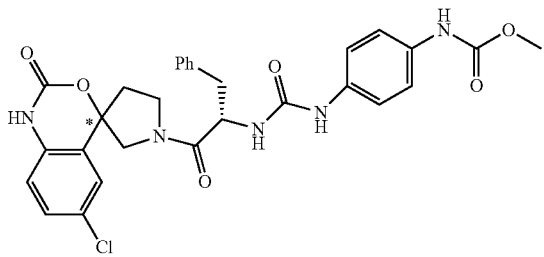 [SMILES: COC(=O)Nc1ccc(NC(=O)N[C@@H](Cc2ccccc2)C(=O)N2CCC3(C2)OC(=O)Nc2ccc(Cl)cc23)cc1]

Step A:
To a stirred solution of 1'-((S)-2-amino-3-phenylpropanoyl)-6-chlorospiro[benzo[d][1,3]oxazine-4,3'-pyrrolidin]-2(1H)-one, HCl (25 mg, 0.059 mmol), di(1H-imidazol-1-yl)methanone (14.40 mg, 0.089 mmol), and DIPEA (22.95 mg, 0.178 mmol) in THF (1 ml). The resulting solution was stirred for 2 hours at room temperature. The imidazole urea intermediate was formed and the reaction conversion was complete. The methyl (4-aminophenyl)carbamate (0.095 mmol) was added to the resulting solution and stirred for overnight at RT. Water was added to the resulting reaction and extracted with EtOAc (2×1 mL). The combined organic layer was dried over $Na_2SO_4$, concentrated in vacuum. The crude product was purified by flash silica gel column chromatography (10% MeOH in DCM) to afford methyl (4-(3-((2S)-1-(6-chloro-2-oxo-1,2-dihydrospiro[benzo[d][1,3]oxazine-4,3'-pyrrolidin]-1'-yl)-1-oxo-3-phenylpropan-2-yl)ureido)phenyl)carbamate. LCMS=578 [M+1].

By using procedures similar to those described previously, with appropriate starting materials and "right-side" reagents, the following compounds were synthesized. These compounds were characterized by LC/MS.

| Example | Structure | LCMS [M + 1] | FXIa Ki (nM) |
|---|---|---|---|
| 275 | methyl (4-(3-((2S)-1-(6-chloro-2-oxo-1,2-dihydrospiro[benzo[d][1,3]oxazine-4,3'-pyrrolidin]-1'-yl)-1-oxo-3-phenylpropan-2-yl)ureido)phenyl)carbamate | 578 | 5000 |
| 276 | 3-amino-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4,6-dihydropyrrolo[3,4-c]pyrazole-5(2H)-carboxamide | 536 | 5000 |
| 277 | 4-(3-((2S)-1-(6-chloro-2-oxo-1,2-dihydrospiro[benzo[d][1,3]oxazine-4,3'-pyrrolidin]-1'-yl)-1-oxo-3-phenylpropan-2-yl)ureido)benzoic acid | 549 | 5000 |

-continued

| Example | Structure | LCMS [M + 1] | FXIa Ki (nM) |
|---|---|---|---|
| 278 | N5-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4,6-dihydropyrrolo[3,4-c]pyrazole-3,5(1H)-dicarboxamide | 564 | 5000 |
| 279 | 3-((3-((2S)-1-(6-chloro-2-oxo-1,2-dihydrospiro[benzo[d][1,3]oxazine-4,3'-pyrrolidin]-1'-yl)-1-oxo-3-phenylpropan-2-yl)ureido)methyl)benzoic acid | 563 | 5000 |

Example 280

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-cyanobenzenesulfonamide

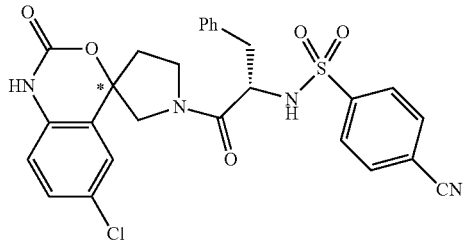 [SMILES: N#Cc1ccc(S(=O)(=O)N[C@@H](Cc2ccccc2)C(=O)N2CCC3(C2)OC(=O)Nc2ccc(Cl)cc23)cc1]

Step A:

To a stirred solution of 1'-((S)-2-amino-3-phenylpropanoyl)-6-chlorospiro[benzo[d][1,3]oxazine-4,3'-pyrrolidin]-2(1H)-one and HCl (50 mg, 0.130 mmol) in DMF (2 mL) was added 4-cyanobenzene-1-sulfonyl chloride (0.194 mmol), and DIPEA (50.2 mg, 0.389 mmol). The reaction mixture was stirred for 24 hours at room temperature. Water was added to the resulting reaction and the aqueous layer was extracted with EtOAc (2×1 mL). The combined organic layer was dried over $Na_2SO_4$, and concentrated in vacuum. The crude product was purified by flash silica gel column chromatography (10% MeOH in DCM) to afford N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-cyanobenzenesulfonamide. LCMS=551 [M+1].

By using procedures similar to those described previously, with appropriate starting materials and "middle and right-side right-side" reagents, the following compounds were synthesized. These compounds were characterized by LC/MS.

| Example | Structure | LCMS [M + 1] | FXIa Ki (nM) |
|---|---|---|---|
| 280 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-cyanobenzenesulfonamide | 551 | 5000 |
| 281 | 2-chloro-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(3-methylureido)benzenesulfonamide | 633 | 5000 |
| 282 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-oxo-3,4-dihydro-2H-benzo[b][1,4]oxazine-6-sulfonamide | 597 | 5000 |
| 283 | 4-(N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)sulfamoyl)benzoic acid | 570 | 5000 |
| 284 | N-(4-(N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)sulfamoyl)phenyl)acetamide | 583 | 5000 |
| 285 | N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-hydroxybenzo[d]oxazole-5-sulfonamide | 583 | 5000 |
| 290 | (R)-1'-((2S,4R)-1-(2-aminobenzo[d]thiazole-6-carbonyl)-4-methoxypyrrolidine-2-carbonyl)-6-chlorospiro[benzo[d][1,3]oxazine-4,3'-pyrrolidin]-2(1H)-one | 542 | 2404 |
| 291 | (R)-1'-((2S,4R)-1-(2-aminobenzo[d]thiazole-6-carbonyl)-4-fluoropyrrolidine-2-carbonyl)-6-chlorospiro[benzo[d][1,3]oxazine-4,3'-pyrrolidin]-2(1H)-one | 530 | 4623 |
| 292 | (R)-1'-((2S,4R)-1-(2-aminobenzo[d]thiazole-6-carbonyl)-4-benzylpyrrolidine-2-carbonyl)-6-chlorospiro[benzo[d][1,3]oxazine-4,3'-pyrrolidin]-2(1H)-one | 602 | 1866 |

Example 293

N-(4-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)phenyl)acetamide

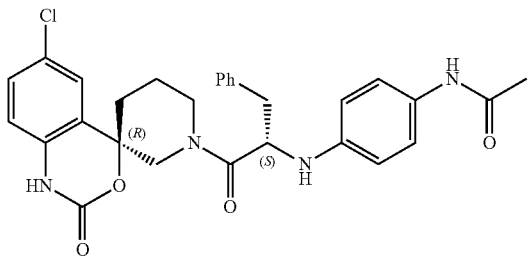

To a 1 dram vial was added (R)-1'-((S)-2-amino-3-phenylpropanoyl)-6-chlorospiro[benzo[d][1,3]oxazine-4,3'-piperidin]-2(1H)-one, TFA (30 mg, 0.058 mmol), N-(4-bromophenyl)acetamide (24.99 mg, 0.117 mmol), cesium carbonate (57.1 mg, 0.175 mmol), and RockPhos G3 Biaryl Precat (4.98 mg, 5.84 μmol) in dioxane (584 μl). The resulting reaction was stirred for 16 hours at 90° C. The reaction was filtered to remove $Cs_2CO_3$ and the solvent was removed in a vacuum, and the residue was dissolved in 1 mL of DMSO and purified by HPLC (Column, XBridge C18, 5u, 19×100 mm, Part #186002978. Mobile Phase A: Water; Mobile Phase B: Acetonitrile. Modifier: 0.16% Ammonium Hydroxide). The desired compound, N-(4-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)phenyl)acetamide was obtained. LC/MS=534 [M+1].

Example 296

(R)-1'-((S)-2-((5-(1H-pyrazol-3-yl)pyridin-2-yl)amino)-3-phenylpropanoyl)-6-chlorospiro[benzo[d][1,3]oxazine-4,3'-piperidin]-2(1H)-one

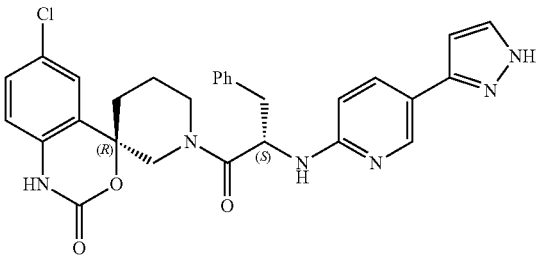

Step A: (R)-1'-((S)-2-((5-bromopyridin-2-yl)amino)-3-phenylpropanoyl)-6-chlorospiro[benzo[d][1,3]oxazine-4,3'-piperidin]-2(1H)-one To a 8 mL vial was added (R)-1'-((S)-2-amino-3-phenylpropanoyl)-6-chlorospiro[benzo[d][1,3]oxazine-4,3'-piperidin]-2(1H)-one, TFA (320 mg, 0.623 mmol), and 5-bromo-2-fluoropyridine (121 mg, 0.685 mmol) in THF (2 ml). 2 mL of 1M of LiHMDS (313 mg, 1.868 mmol) in THF was added drop by drop to the solution at room temperature. The resulting solution was stirred for overnight at the same temperature. 2 ml of water was added to wash the solution and extracted with EtOAc (3×2 mL). The combined organic later was dried over $Na_2SO_4$, and concentrated to give the residue, which was purified by flash chromatography on silica gel (EtOAc/Hexane, ISCO). The desired compound (R)-1'-((S)-2-((5-bromopyridin-2-yl)amino)-3-phenylpropanoyl)-6-chlorospiro[benzo[d][1,3]oxazine-4,3'-piperidin]-2(1H)-one was obtained. LC/MS=556 [M+1].

Step B:

(R)-1'-((S)-2-((5-(1H-pyrazol-3-yl)pyridin-2-yl)amino)-3-phenylpropanoyl)-6-chlorospiro[benzo[d][1,3]oxazine-4,3'-piperidin]-2(1H)-one (L-005469340-000N)

To a 2 mL microwave vial was added (R)-1'-((S)-2((5-bromopyridin-2-yl)amino)-3-phenylpropanoyl)-6-chlorospiro[benzo[d][1,3]oxazine-4,3'-piperidin]-2(1H)-one (25 mg, 0.045 mmol) and (1H-pyrazol-3-yl)boronic acid (10.07 mg, 0.09 mmol). (1H-pyrazol-3-yl) boronic acid (10.07 mg, 0.09 mmol), [[1,1'-bis(diphenylphosphino) ferrocene] dichloropalladium(II) (3.29 mg, 4.50 μmol) and tripotassium phosphate (28.6 mg, 0.135 mmol) in a mixed solvent of dioxane (1 ml) and water (0.25 ml). The reaction vial was irradiated in a microwave Initiator (Biotage) for 15 min at 120° C. The reaction was separated and the organic layer was filtered and concentrated to give a residue which was dissolved in 1 mL of DMSO and purified by HPLC (Column, XBridge C18, 5u, 19×100 mm, Part #186002978. Mobile Phase A: Water; Mobile Phase B: Acetonitrile. Modifier: 0.16% Ammonium Hydroxide). (R)-1'-((S)-2-((5-(1H-pyrazol-3-yl)pyridin-2-yl)amino)-3-phenylpropanoyl)-6-chlorospiro[benzo[d][1,3]oxazine-4,3'-piperidin]-2(1H)-one was obtained. LC/MS=544 [M+1].

By using procedures similar to those described previously, and using appropriate starting materials, the following compounds were synthesized. These compounds were characterized by LC/MS.

| Example | Structure | LCMS [M + 1] | Hu FXIa Ki (nM) |
|---|---|---|---|
| 293 | N-(4-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)phenyl)acetamide | 534 | 10000 |
| 294 | 6-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)amino)-5-fluoronicotinic acid | 525 | 10000 |
| 295 | (R)-6-chloro-1'-((6'-hydroxy-[3,3'-bipyridin]-6-yl)-L-phenylalanyl)spiro[benzo[d][1,3]oxazine-4,3'-piperidin]-2(1H)-one | 570 | 10000 |

-continued

| Example | Structure | LCMS [M + 1] | Hu FXIa Ki (nM) |
|---|---|---|---|
| 296 | (R)-1'-((5-(1H-pyrazol-3-yl)pyridin-2-yl)-L-phenylalanyl)-6-chlorospiro[benzo[d][1,3]oxazine-4,3'-piperidin]-2(1H)-one | 543 | 10000 |
| 297 | 3-(6-(((S)-1-((R)-6-chloro-2-oxo-1,2-dihydrospiro[benzo[d][1,3]oxazine-4,3'-piperidin]-1'-yl)-1-oxo-3-phenylpropan-2-yl)amino)pyridin-3-yl)benzoic acid | 597 | 10000 |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and he synthetic substrate, Z-Gly-Pro-Arg-AFC, TFA salt (Sigma #C0980) at a concentration of 100 µM.

Activity assays were performed by diluting a stock solution of substrate at least tenfold to a final concentration≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K-P-R-AFC (Sigma #C6608) at a concentration of 100 mM.

Activity assays were performed by diluting a stock solution of substrate at least tenfold to a final concentration≤0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). IC50 was determined by inflection point from a four parameter logistic curve fit. Ki was calculated using the Cheng Prusoff equation, Ki=IC50/(1+([S]/Km)).

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Plasma Kallikrein data for selected compounds is as follows:

| Examples | Kallikrein (nM) |
|---|---|
| 3b (isomer B) | 1.55 |
| 6 | 4.02 |
| 7 | 3.51 |

-continued

| Examples | Kallikrein (nM) |
|---|---|
| 8a (Isomer A) | 9.78 |
| 9 | 2.6 |
| 13 | 1.4 |
| 14b (isomer B) | 47.8 |
| 15 | 2.8 |
| 16 | 1.36 |
| 22 | 21.9 |
| 27 (racemate) | 32.6 |
| 30 (racemate) | 37.0 |
| 31 (racemate) | 77.3 |
| 32 (racemate) | 42.2 |
| 35 (racemate) | 24.6 |
| 37 | 2.68 |
| 38 | 9.45 |
| 39 | 86.6 |
| 40 | 116.4 |
| 43 | 42.5 |
| 44 | <1.30 |
| 45 | <1.30 |
| 47 | <1.30 |
| 48 | 1.27 |
| 50 (racemate) | 226.8 |
| 52 (racemate) | 92.8 |
| 53 | 2.21 |
| 57 | 1.43 |
| 58 | <1.36 |
| 60 | 3.31 |
| 61 | 11.17 |
| 62 | 0.54 |
| 63 | 1.73 |
| 65 | 5.4 |
| 66 | 3.8 |
| 67A (isomer A) | 2.9 |
| 67B (isomer B) | 1.80 |
| 72 | 17.66 |
| 74 | 2.53 |
| 75 | 1.56 |
| 76 | 1.20 |
| 77 | 32.6 |
| 78 | 24.5 |
| 79 | 14.5 |
| 81 | 7.98 |
| 82 | 11.7 |
| 83 | 31.1 |
| 84 | 28.4 |
| 87 | 11.0 |
| 94 | 1.42 |
| 95 | 1.81 |
| 97 | 15.3 |
| 98 | 25.4 |
| 99 | 17.6 |
| 100 | 19.7 |
| 101 | 10.26 |
| 102 | <1.36 |
| 104 | 5.28 |
| 105 | 3.04 |
| 110 | 147 |
| 111 | 76 |
| 115 | 0.6 |
| 116A | 4.78 |
| 117A | 10.6 |
| 118A | 1.79 |
| 118B | 1.06 |
| 119 | 4.92 |
| 123 (racemic) | 4.65 |
| 143 | 2.63 |
| 144 | 7.72 |
| 164 | 36.0 |
| 165 | 27.5 |
| 171 | 58.0 |
| 181 | 50.7 |
| 188 | 155 |
| 189 | 51.3 |
| 191 | 123 |
| 194 | 30.9 |
| 195 | 1.90 |
| 197 | 1.30 |
| 198 | 30.1 |
| 199 | 0.6 |
| 200 | 1.0 |
| 203 | 2.1 |
| 206 | 1.7 |
| 208 | 1.95 |
| 209 | 0.33 |
| 213 | 0.54 |
| 214 | 1.4 |
| 215 | 2.6 |
| 216 | 1.7 |
| 217 | 3.2 |
| 225 | 0.95 |
| 226 | 23.2 |
| 227 | 5.0 |
| 228 | 19.3 |
| 230 | 2.72 |
| 231 | 4.74 |
| 233 | 2.44 |
| 234 | 3.03 |
| 235 | 0.87 |
| 237 | 0.96 |
| 240 | 1.49 |
| 241 | 2.13 |
| 245 | 0.65 |
| 249 | <1.36 |
| 250 | 13.3 |
| 251 | <1.36 |
| 252 | <1.36 |
| 253 | 1.79 |
| 254 | 0.83 |
| 255 | 0.45 |
| 256 | 31.0 |
| 257 | 0.57 |
| 258 | 4.08 |
| 260 | 130.2 |
| 264 | 0.94 |
| 266 | 1.22 |
| 267 | 0.29 |
| 268 | 0.90 |
| 269 | 3.0 |
| 270 | 0.65 |
| 270 | 0.65 |
| 271 | 0.60 |
| 272 | 0.81 |
| 274 | 0.65 |

What is claimed is:
1. A compound of Formula I:

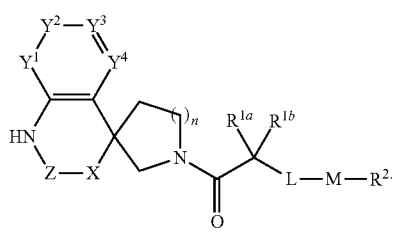

wherein X is absent, $CH_2$, $CH_2O$, O or NH;
$Y^1$ is $CR^3$ or N,
$Y^2$ is $CR^3$ or N,
$Y^3$ is $CR^3$ or N,
$Y^4$ is $CR^3$ or N,
with the proviso that three of $Y^1$, $Y^2$, $Y^3$ and $Y^4$ are not simultaneously N, and all four of $Y^1$, $Y^2$, $Y^3$ and $Y^4$ are not simultaneously N;
Z is S, SO, $SO_2$ or C=O;

L is NHC(=O);

M is phenyl, wherein said phenyl group is optionally substituted with one to three substituents independently selected from halo, cyano, hydroxy, oxo, $C_{1-6}$ alkyl or $NR^6R^7$;

$R^{1a}$ is hydrogen, halo, cyano, hydroxy, $C_{1-4}$ alkyl, $C_{3-6}$ cycloalkyl, aryl, heteroaryl, heterocyclyl, $C_{1-4}$ alkyl-$C_{3-6}$ cycloalkyl, $C_{1-4}$ alkyl-aryl, $C_{1-4}$ alkyl-heteroaryl or $C_{1-4}$ alkyl-heterocyclyl, wherein said alkyl groups are optionally substituted with one to three substituents independently selected from halo, hydroxy, methoxy, $SR^4$, $SOR^4$, $SO_2R^4$, $C(=O)R^9$, $C(=O)NHR^9$, $C(=O)NHCH_2R^9$, $C(=O)NHSO_2R^9$ or $NHC(=O)R^4$, and said cycloalkyl, aryl, heteraryl and heterocyclyl groups are optionally substituted with one to three groups independently selected from halo, hydroxy, oxo, cyano, $C_{1-4}$ alkyl, $C_{2-4}$ alkenyl-$OR^4$, $OR^4$, $C(=O)NR^6R^7$, $NHC(=O)R^4$, $NHC(=O)R^9$, $NHC(=O)OR^9$, $C(=O)R^9$, $R^9$, $OR^9$, $NHSO_2R^4$, $SO_2R^4$ or $NR^6R^7$;

$R^{1b}$ is hydrogen, halo, cyano, hydroxy or $C_{1-4}$ alkyl, wherein said alkyl is optionally substituted with one to three groups independently selected from halo or hydroxy;

or $R^{1a}$ and $R^{1b}$ can be taken together with the atom between them to form a $C_{3-6}$ cycloalkyl, aryl, heteroaryl or heterocyclyl ring system wherein said cycloalkyl, aryl, heteroaryl or heterocyclyl ring systems are optionally substituted with one to three groups independently selected from halo, hydroxy or aryl;

$R^2$ is hydrogen, halo, cyano, $OR^4$, $R^4$, $R^9$, $C(=O)OR^4$, $C_{1-3}$ alkyl-$C(=O)OR^5$, $NR^4R^7$, $NR^6R^9$, $NHC(=O)R^4$, $NHC(=O)OR^4$, $NHC(=O)O-C_{1-3}$ alkyl-$OR^5$, $NHC(=O)O(C_{1-3}$ alkyl)$R^9$, $NHC(=O)O(R^4)C(=O)OH$, $C_{1-3}$ alkyl-$NHC(=O)OR^5$, $NHC(=O)NR^6R^7$, $NH(C=NH)NR^6R^7$, $C(=O)NR^6R^7$, $CH_2C(=O)NR^6R^7$, $C(CH_3)(NR^6R^7)C(=O)R^4$, $NHC(=O)NH-C_{1-3}$ alkyl-$R^9$, $SO_2R^4$, $NHSO_2R^4$, $NHSO_2R^9$, $SO_2NR^6R^7$, $P(=O)(OCH_2CH_3)_2$, $P(=O)(OH)_2$; or $B(OH)_2$;

each $R^3$ is independently hydrogen, $R^4$, $C_{3-6}$ cycloalkyl, halo, cyano or $OR^4$, wherein said alkyl and cycloalkyl groups are optionally substituted with one to three groups independently selected from halo or hydroxy;

each $R^4$ is independently hydrogen or $C_{1-6}$ alkyl, wherein said alkyl is optionally substituted with one to three halo or hydroxy;

each $R^5$ is independently hydrogen or $C_{1-6}$ alkyl, wherein said alkyl is optionally substituted with one to three halo;

each $R^6$ is independently hydrogen or $C_{1-6}$ alkyl;

each $R^7$ is independently hydrogen or $C_{1-6}$ alkyl;

each $R^8$ is independently hydrogen, halo or methyl;

each $R^9$ is independently aryl, heteroaryl, heterocyclyl or $C_{3-8}$ cycloalkyl, wherein said aryl, heteroaryl, heterocyclyl and cycloalkyl groups are optionally substituted with one to three substituents independently selected from the group consisting of halo, cyano, oxo, cyclopropyl, $R^4$, $OR^4$, $C(=O)OR^4$ or $NR^6R^7$;

n is an integer from zero to three;

or a pharmaceutically acceptable salt thereof.

2. The compound of claim 1 wherein X is O; or a pharmaceutically acceptable salt thereof.

3. The compound of claim 1 wherein $R^{1a}$ is $C_{1-4}$ alkyl-aryl and $R^{1b}$ is hydrogen; or a pharmaceutically acceptable salt thereof.

4. The compound of claim 3 wherein $R^{1a}$ is $CH_2$-phenyl and $R^{1b}$ is hydrogen; or a pharmaceutically acceptable salt thereof.

5. The compound of claim 1 wherein $R^2$ is NHC(=O)$OR^4$; or a pharmaceutically acceptable salt thereof.

6. The compound of claim 1 wherein $R^3$ is halo; or a pharmaceutically acceptable salt thereof.

7. A compound selected from:

methyl (4-(((S)-1-((S)-6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate;

methyl (4-(((S)-1-((R)-6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate;

methyl (4-(((S)-1-oxo-1-((R)-2-oxo-1,2-dihydrospiro[benzo[d][1,3]oxazine-4,3'-pyrrolidin]-1'-yl)-3-phenylpropan-2-yl)carbamoyl)phenyl)carbamate;

methyl (4-(((S)-1-((S)-6-chloro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((2S)-1-(6'-chloro-2'-oxo-1',2'-dihydrospiro[azepane-3,4'-benzo[d][1,3]oxazin]-1-yl)-1-oxo-3-phenylpropan-2-yl)carbamoyl)phenyl)carbamate;

(S)-methyl (4-((1-(6'-chloro-2'-oxo-1',2'-dihydrospiro[azetidine-3,4'-benzo[d][1,3]oxazin]-1-yl)-1-oxo-3-phenylpropan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

methyl (4-(((S)-1-((R)-6-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-((S)-6-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-((R)-6-methoxy-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-oxo-1-((R)-2-oxo-6-(trifluoromethyl)-1,2-dihydrospiro[benzo[d][1,3]oxazine-4,3'-piperidin]-1'-yl)-3-phenylpropan-2-yl)carbamoyl)phenyl)carbamate;

methyl (4-(((S)-1-((R)-6-chloro-5,7-difluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-((R)-6-chloro-8-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((2S)-1-(6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-((S)-6-methyl-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

methyl (4-(((S)-1-((R)-6-methyl-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

methyl (4-(((S)-1-((R)-6-methyl-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-((R)-5-fluoro-6-methyl-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((S)-1-((R)-6-cyclopropyl-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

methyl (4-(((2S)-1-(6'-chloro-2'-oxo-2',3'-dihydro-1'H-spiro[pyrrolidine-3,4'-quinolin]-1-yl)-1-oxo-3-phenylpropan-2-yl)carbamoyl)phenyl)carbamate;

methyl (4-(((2S)-1-(6'-chloro-2'-oxo-2',3'-dihydro-1'H-spiro[pyrrolidine-3,4'-quinazolin]-1-yl)-1-oxo-3-phenylpropan-2-yl)carbamoyl)phenyl)carbamate;

methyl (4-(((2S)-1-(5-chloro-2-oxospiro[indoline-3,3'-pyrrolidin]-1'-yl)-3-cyclopropyl-1-oxopropan-2-yl)carbamoyl)phenyl)carbamate;

methyl (4-(((2S)-1-(6'-chloro-2'-oxo-2',3'-dihydro-1'H-spiro[pyrrolidine-3,4'-quinazolin]-1-yl)-1-oxo-3-phenylpropan-2-yl)carbamoyl)phenyl)carbamate;

methyl (4-(((2S)-1-(5-chloro-2-oxospiro[indoline-3,3'-pyrrolidin]-1'-yl)-3-cyclopropyl-1-oxopropan-2-yl)carbamoyl)phenyl)carbamate;

methyl (4-(((S)-1-((S)-6-chloro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-3-(4-fluorophenyl)-1-oxopropan-2-yl)carbamoyl)phenyl)carbamate;

methyl (4-((2-(6-chloro-2-oxo-1,2-dihydrospiro[benzo[d][1,3]oxazine-4,3'-pyrrolidin]-1'-yl)-2-oxoethyl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-2-methyl-1-oxo-3-phenylpropan-2-yl)carbamoyl)phenyl)carbamate;

methyl (4-(((1S,2R)-1-(6-chloro-2-oxo-1,2-dihydrospiro[benzo[d][1,3]oxazine-4,3'-pyrrolidin]-1'-ylcarbonyl)-2-phenylcyclopropyl)carbamoyl)phenyl)carbamate;

methyl (4-((2-(6-chloro-2-oxo-1,2-dihydrospiro[benzo[d][1,3]oxazine-4,3'-pyrrolidin]-1'-ylcarbonyl)-2,3-dihydro-1H-inden-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-3-(3,4-difluorophenyl)-1-oxopropan-2-yl)carbamoyl)phenyl)carbamate;

methyl (4-((1-(6-chloro-2-oxo-1,2-dihydrospiro[benzo[d][1,3]oxazine-4,3'-pyrrolidin]-1'-yl)-1-oxo-3-(1H-pyrazol-3-yl)propan-2-yl)carbamoyl)phenyl)carbamate;

methyl (4-(((1S)-2-(6-chloro-2-oxo-1,2-dihydrospiro[benzo[d][1,3]oxazine-4,3'-pyrrolidin]-1'-yl)-2-oxo-1-phenylethyl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-3-(1-methyl-1H-imidazol-5-yl)-1-oxopropan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-1-oxo-3-(1H-pyrazol-1-yl)propan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-1-oxo-3-(thiophen-3-yl)propan-2-yl)carbamoyl)phenyl)carbamate;

methyl (4-(((2S,3R)-1-(6-chloro-2-oxo-1,2-dihydrospiro[benzo[d][1,3]oxazine-4,3'-pyrrolidin]-1'-yl)-1-oxo-3-phenylbutan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-3-cyclohexyl-1-oxopropan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-3-(4-hydroxyphenyl)-1-oxopropan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-5,5,5-trifluoro-1-oxopentan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-methoxy-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-hydroxy-1-oxopropan-2-yl)carbamoyl)phenyl)carbamate;

methyl (4-(((2S)-3-(4-benzoylphenyl)-1-(6-chloro-2-oxo-1,2-dihydrospiro[benzo[d][1,3]oxazine-4,3'-pyrrolidin]-1'-yl)-1-oxopropan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-1-oxo-3-(thiazol-4-yl)propan-2-yl)carbamoyl)phenyl)carbamate;

methyl (4-(((2R)-2-benzyl-3-(6-chloro-2-oxo-1,2-dihydrospiro[benzo[d][1,3]oxazine-4,3'-pyrrolidin]-1'-yl)-3-oxopropyl)carbamoyl)phenyl)carbamate;

methyl (4-((1-(6-chloro-2-oxo-1,2-dihydrospiro[benzo[d][1,3]oxazine-4,3'-pyrrolidin]-1'-yl)-3-(1,1-dioxidotetrahydro-2H-thiopyran-4-yl)-1-oxopropan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-3-(3-fluorothiophen-2-yl)-1-oxopropan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-3-(4-(cyclopentyloxy)phenyl)-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-(4-cyanophenyl)-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-(4-(methylsulfonamido)phenyl)-1-oxopropan-2-yl)carbamoyl)phenyl)carbamate;

methyl (4-(((S)-3-(4-carbamoylphenyl)-1-((R)-6-chloro-2-oxo-1,2-dihydrospiro[benzo[d][1,3]oxazine-4,3'-piperidin]-1'-yl)-1-oxopropan-2-yl)carbamoyl)phenyl)carbamate;

methyl (4-(((S)-3-(4-acetamidophenyl)-1-((R)-6-chloro-2-oxo-1,2-dihydrospiro[benzo[d][1,3]oxazine-4,3'-piperidin]-1'-yl)-1-oxopropan-2-yl)carbamoyl)phenyl)carbamate;

methyl (4-(((2S)-4-(6-chloro-2-oxo-1,2-dihydrospiro[benzo[d][1,3]oxazine-4,3'-pyrrolidin]-1'-yl)-4-oxo-1-phenylbutan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-3-(naphthalen-2-yl)-1-oxopropan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-6-hydroxy-1-oxohexan-2-yl)carbamoyl)phenyl)carbamate;

methyl (4-(((2S)-1-(6-chloro-2-oxo-1,2-dihydrospiro[benzo[d][1,3]oxazine-4,3'-pyrrolidin]-1'-yl)-1-oxo-4-phenylbutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-(1-methyl-1H-imidazol-5-yl)-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-1-oxo-6-(2,2,2-trifluoroacetamido)hexan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-1-oxopropan-2-yl)carbamoyl)phenyl)carbamate;

methyl (4-(((2S)-1-((R)-6-chloro-2-oxo-1,2-dihydrospiro[benzo[d][1,3]oxazine-4,3'-piperidin]-1'-yl)-4-(methylsulfinyl)-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(methylthio)-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-1-oxo-3-(thiazol-4-yl)propan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(methylsulfonyl)-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-methyl-1-oxopentan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-pyrrolidin]-1'-yl)-3-cyclopropyl-1-oxopropan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-1-oxo-3-(pyridin-4-yl)propan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4,4,4-trifluoro-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-1-oxo-3-(tetrahydro-2H-pyran-4-yl)propan-2-yl)carbamoyl)phenyl)carbamate;

methyl (4-(((S)-3-cyclopropyl-1-((R)-6-methyl-2-oxo-1,2-dihydrospiro[benzo[d][1,3]oxazine-4,3'-piperidin]-1'-yl)-1-oxopropan-2-yl)carbamoyl)phenyl)carbamate;

methyl (4-(((2S)-1-((R)-6-chloro-5-fluoro-2-oxo-1,2-dihydrospiro[benzo[d][1,3]oxazine-4,3'-piperidin]-1'-yl)-3-(2,2-difluorocyclopropyl)-1-oxopropan-2-yl)carbamoyl)phenyl)carbamate;

methyl (4-(((2S)-1-((R)-6-chloro-5-fluoro-2-oxo-1,2-dihydrospiro[benzo[d][1,3]oxazine-4,3'-piperidin]-1'-yl)-3-(2,2-difluorocyclopropyl)-1-oxopropan-2-yl)carbamoyl)phenyl)carbamate;

methyl (4-(((S)-2-((R)-6-chloro-5-fluoro-2-oxo-1,2-dihydrospiro[benzo[d][1,3]oxazine-4,3'-piperidin]-1'-yl)-1-cyclopropyl-2-oxoethyl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-1-oxo-3-(quinoxalin-2-yl)propan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-3-(1H-indol-3-yl)-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-cyclobutyl-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-cyclohexyl-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-cyclopentyl-1-oxopropan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-3-(5-fluoropyridin-2-yl)-1-oxopropan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-3-(5-methoxypyridin-2-yl)-1-oxopropan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-3-(3-fluoropyridin-4-yl)-1-oxopropan-2-yl)carbamoyl)phenyl)carbamate;

methyl (4-(((S)-3-(4-(1H-pyrazol-3-yl)phenyl)-1-((R)-6-chloro-2-oxo-1,2-dihydrospiro[benzo[d][1,3]oxazine-4,3'-pyrrolidin]-1'-yl)-1-oxopropan-2-yl)carbamoyl)phenyl)carbamate;

methyl (4-(((S)-3-(4-(1H-pyrazol-4-yl)phenyl)-1-((R)-6-chloro-2-oxo-1,2-dihydrospiro[benzo[d][1,3]oxazine-4,3'-pyrrolidin]-1'-yl)-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-3-(3-cyclopropylisoxazol-5-yl)-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(3,3-difluoroazetidin-1-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(cyclobutylamino)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-1,4-dioxo-4-(piperidin-1-yl)butan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-4-morpholino-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-1,4-dioxo-4-((tetrahydro-2H-pyran-4-yl)amino)butan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-1,4-dioxo-4-(pyridin-2-ylamino)butan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-4-((4-fluorophenyl)amino)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-4-(cyclopropanesulfonamido)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-4-(oxetan-3-ylamino)-1,4-dioxobutan-2-yl)carbamoyl)phenyl)carbamate;

methyl (4-(((2S)-4-(6-azabicyclo[3.2.0]heptan-6-yl)-1-((R)-6-chloro-2-oxo-1,2-dihydrospiro[benzo[d][1,3]oxazine-4,3'-piperidin]-1'-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-((S)-2-(hydroxymethyl)azetidin-1-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(3-(dimethylamino)azetidin-1-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(3-methoxyazetidin-1-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(((1-methyl-1H-pyrazol-5-yl)methyl)amino)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-((cyclopropylmethyl)amino)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(3-cyclopropyl-3-hydroxyazetidin-1-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-((R)-3-methoxypyrrolidin-1-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-((S)-2-methylazetidin-1-yl)-1,4-dioxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-fluoro-1-oxobutan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3 piperidin]-1'-yl)-4,4-difluoro-1-oxobutan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-4-fluoro-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-3-(4,4-difluorocyclohexyl)-1-oxopropan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(cyclobutanecarboxamido)-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-(methylsulfonamido)-1-oxobutan-2-yl)carbamoyl)phenyl)carbamate;

methyl (4-(((S)-1-((R)-6-chloro-2-oxo-1,2-dihydrospiro[benzo[d][1,3]oxazine-4,3'-piperidin]-1'-yl)-4-((cyclobutoxycarbonyl)amino)-1-oxobutan-2-yl)carbamoyl)phenyl)carbamate;

methyl (4-(((2S)-1-((R)-6-chloro-2-oxo-1,2-dihydrospiro[benzo[d][1,3]oxazine-4,3'-pyrrolidin]-1'-yl)-4-hydroxy-1-oxopentan-2-yl)carbamoyl)phenyl)carbamate;

methyl (4-(((S)-1-((R)-6-chloro-2-oxo-1,2-dihydrospiro[benzo[d][1,3]oxazine-4,3'-pyrrolidin]-1'-yl)-4-hydroxy-4-methyl-1-oxopentan-2-yl)carbamoyl)phenyl)carbamate;

methyl (4-(((S)-4-(azetidin-1-yl)-1-((R)-6-chloro-2-oxo-1,2-dihydrospiro[benzo[d][1,3]oxazine-4,3'-pyrrolidin]-1'-yl)-1-oxobutan-2-yl)carbamoyl)phenyl)carbamate;

methyl (4-(((S)-1-((R)-6-chloro-5-fluoro-2-oxo-1,2-dihydrospiro[benzo[d][1,3]oxazine-4,3'-piperidin]-1'-yl)-3-(1-methoxycyclopropyl)-1-oxopropan-2-yl)carbamoyl)phenyl)carbamate;

methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate;

methyl (4-((1-((R)-6-chloro-5-fluoro-2-oxo-1,2-dihydrospiro[benzo[d][1,3]oxazine-4,3'-piperidin]-1'-yl)-1-oxo-3-((S)-tetrahydrofuran-2-yl)propan-2-yl)carbamoyl)phenyl)carbamate;

methyl (4-((1-((R)-6-chloro-5-fluoro-2-oxo-1,2-dihydrospiro[benzo[d][1,3]oxazine-4,3'-piperidin]-1'-yl)-1-oxo-3-((R)-tetrahydrofuran-2-yl)propan-2-yl)carbamoyl)phenyl)carbamate;

methyl (4-((1-((R)-6-chloro-5-fluoro-2-oxo-1,2-dihydrospiro[benzo[d][1,3]oxazine-4,3'-piperidin]-1'-yl)-1-oxo-3-((R)-tetrahydrofuran-2-yl)propan-2-yl)carbamoyl)phenyl)carbamate;

methyl (4-(((2S,4S)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate;

methyl (4-(((2S,4R)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate;

methyl (4-(((2R,4R)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate;

methyl (4-(((2R,4S)-1-((R)-6-chloro-5-fluoro-2-oxo-1,2-dihydrospiro[benzo[d][1,3]oxazine-4,3'-piperidin]-1'-yl)-4-methoxy-1-oxopentan-2-yl)carbamoyl)phenyl)carbamate;

methyl (4-(((2S)-1-(6-chloro-5-fluoro-2-oxo-1,2-dihydrospiro[benzo[d][1,3]oxazine-4,3'-piperidin]-1'-yl)-4-methoxy-4-methyl-1-oxopentan-2-yl)carbamoyl)phenyl)carbamate;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-sulfamoylbenzamide;

4-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid;

4-(((S)-1-((S)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid;

3-(((S)-1-((R)-6-chloro-2-oxo-1,2-dihydrospiro[benzo[d][1,3]oxazine-4,3'-pyrrolidin]-1'-yl)-1-oxo-3-phenylpropan-2-yl)carbamoyl)benzoic acid;

methyl (3-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-cyanobenzamide;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(1H-tetrazol-5-yl)benzamide;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-2-(1H-pyrazol-1-yl)benzamide;

1-(4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)cyclopropanecarboxylic acid;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(2,2,2-trifluoroacetamido)benzamide;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(methylsulfonamido)benzamide;

2-methoxyethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-(2-oxoimidazolidin-1-yl)benzamide;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-((4S,5S)-4-methyl-2-oxooxazolidin-5-yl)benzamide;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-3-fluoro-4-hydroxybenzamide;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-guanidinobenzamide;

4((1H-imidazol-2-yl)amino)-N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)benzamide;

N-((2S)-1-(6-chloro-2-oxo-1,2-dihydrospiro[benzo[d][1,3]oxazine-4,3'-pyrrolidin]-1'-yl)-1-oxo-3-phenylpropan-2-yl)-4-(3-methylureido)benzamide;

2-(piperazin-1-yl)ethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

2-morpholinoethyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

((S)-tetrahydrofuran-2-yl)methyl (4-(((2S)-1-(6-chloro-2-oxo-1,2-dihydrospiro[benzo[d][1,3]oxazine-4,3'-pyrrolidin]-1'-yl)-1-oxo-3-phenylpropan-2-yl)carbamoyl)phenyl)carbamate;

methyl (3-chloro-4-(((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)carbamoyl)phenyl)carbamate;

N—((S)-1-((R)-6-chloro-2-oxo-1,2-dihydrospiro[benzo[d][1,3]oxazine-4,3'-piperidin]-1'-yl)-3-cyclopropyl-1-oxopropan-2-yl)-3,4-difluorobenzamide;

2-amino-5-(((S)-1-((R)-6-chloro-2-oxo-1,2-dihydrospiro[benzo[d][1,3]oxazine-4,3'-piperidin]-1'-yl)-3-(4-fluorophenyl)-1-oxopropan-2-yl)carbamoyl)benzoic acid;

diethyl (4-(((R)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)phosphonate;

N—((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-(2-methoxyacetamido)benzamide;

isopropyl (4-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)phenyl)carbamate;

N—((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-(5-oxo-2,5-dihydro-1,2,4-oxadiazol-3-yl)benzamide;

4-acetamido-N—((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)benzamide;

methyl (4-(((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)carbamoyl)benzyl)carbamate;

N—((S)-1-((R)-6-chloro-5-fluoro-2-oxo-1,2-dihydrospiro[benzo[d][1,3]oxazine-4,3'-piperidin]-1'-yl)-1-oxo-3-phenylpropan-2-yl)-4-(5-oxo-1,5-dihydro-4H-1,2,4-triazol-4-yl)benzamide;

N—((S)-1-((R)-6-chloro-2-oxo-1,2-dihydrospiro[benzo[d][1,3]oxazine-4,3'-piperidin]-1'-yl)-1-oxo-3-phenylpropan-2-yl)-3-(3-oxomorpholino)benzamide;

N—((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)-3-(2H-tetrazol-5-yl)benzamide;

(2-(((4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)phenyl)carbamoyl)oxy)ethyl)phosphonic acid;

(2-(((4-(((S)-1-((R)-6-chloro-5-fluoro-2-oxo-1,2-dihydrospiro[benzo[d][1,3]oxazine-4,3'-piperidin]-1'-yl)-3-cyclopropyl-1-oxopropan-2-yl)carbamoyl)phenyl)carbamoyl)oxy)ethyl)phosphonic acid;

(2-(4-(((S)-1-((R)-6-chloro-5-fluoro-2-oxo-1,2-dihydrospiro[benzo[d][1,3]oxazine-4,3'-piperidin]-1'-yl)-3-(3-fluorophenyl)-1-oxopropan-2-yl)carbamoyl)benzamido)ethyl)phosphonic acid;

2-(1H-tetrazol-5-yl)ethyl (4-(((S)-1-((R)-6-chloro-5-fluoro-2-oxo-1,2-dihydrospiro[benzo[d][1,3]oxazine-4,3'-piperidin]-1'-yl)-3-(4-fluorophenyl)-1-oxopropan-2-yl)carbamoyl)phenyl)carbamate;

or a pharmaceutically acceptable salt thereof.

8. A pharmaceutical composition comprising a compound of claim 1 and a pharmaceutically acceptable carrier.

9. A method for inhibiting thrombus formation in blood or treating thrombus formation in blood comprising administering a composition of claim 8 to a mammal in need of thereof.

10. A method for preventing thrombus formation in blood comprising administering a composition of claim 8 to a mammal in need thereof.

11. A method of treating venous thromboembolism and pulmonary embolism in a mammal comprising administering a composition of claim 8 to a mammal in need thereof.

12. A method of treating deep vein thrombosis in a mammal comprising administering a composition of claim 8 to a mammal in need thereof.

13. A method of treating thromboembolic stroke in a human comprising administering a composition of claim 8 to a mammal in need thereof.

* * * * *